US006689363B1

(12) United States Patent
Sette et al.

(10) Patent No.: US 6,689,363 B1
(45) Date of Patent: *Feb. 10, 2004

(54) INDUCING CELLULAR IMMUNE RESPONSES TO HEPATITIS B VIRUS USING PEPTIDE AND NUCLEIC ACID COMPOSITIONS

(75) Inventors: Alessandro Sette, La Jolla, CA (US); John Sidney, La Jolla, CA (US); Scott Southwood, Santee, CA (US); Maria A. Vitiello, La Jolla, CA (US); Brian D. Livingston, San Diego, CA (US); Esteban Celis, Rochester, MN (US); Ralph T. Kubo, Carlsbad, CA (US); Howard M. Grey, La Jolla, CA (US); Robert W. Chesnut, Cardiff-by-the-Sea, CA (US)

(73) Assignee: Epimmune Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/239,043

(22) Filed: Jan. 27, 1999

Related U.S. Application Data

(63) Continuation-in-part of application No. 09/189,702, filed on Nov. 10, 1998, and a continuation-in-part of application No. 08/978,291, filed on Nov. 25, 1997, and a continuation-in-part of application No. 08/820,360, filed on Mar. 12, 1997, and a continuation-in-part of application No. 08/344,824, filed on Dec. 23, 1994, and a continuation-in-part of application No. 08/347,610, filed on Dec. 1, 1994, and a continuation-in-part of application No. 08/205,713, filed on Mar. 4, 1994, and a continuation-in-part of application No. 08/197,484, filed on Feb. 16, 1994, now Pat. No. 6,419,931, which is a continuation-in-part of application No. 07/935,811, filed on Aug. 26, 1992, now abandoned, which is a continuation-in-part of application No. 07/874,491, filed on Apr. 27, 1992, now abandoned, which is a continuation-in-part of application No. 07/827,682, filed on Jan. 29, 1992, now abandoned, said application No. 08/347,610, is a continuation-in-part of application No. 08/159,339, filed on Nov. 29, 1993, now Pat. No. 6,037,135, which is a continuation-in-part of application No. 08/103,396, filed on Aug. 6, 1993, now abandoned, which is a continuation-in-part of application No. 08/027,746, filed on Mar. 5, 1993, now abandoned, which is a continuation-in-part of application No. 07/926,666, filed on Aug. 7, 1992, now abandoned, said application No. 08/344,824, is a continuation-in-part of application No. 08/278,634, filed on Jul. 21, 1994, now abandoned, said application No. 08/205,713, is a continuation-in-part of application No. 08/159,184, filed on Nov. 29, 1993, now abandoned, which is a continuation-in-part of application No. 08/073,205, filed on Jun. 4, 1993, now abandoned, which is a continuation-in-part of application No. 08/027,146, filed on Mar. 5, 1993, now abandoned, said application No. 09/189,702, is a continuation-in-part of application No. 08/205,713, said application No. 08/978,291, is a continuation of application No. 08/461,603, filed on Jun. 5, 1995, which is a continuation of application No. 07/935,811.

(60) Provisional application No. 60/013,363, filed on Mar. 13, 1996.

(51) Int. Cl.⁷ .................. A61K 38/00; A61K 38/04; A61K 37/00; A61K 39/12; A61K 39/29; C07K 16/00; C07K 17/00; C07K 5/00; C07K 7/00

(52) U.S. Cl. ................ 424/189.1; 424/185.1; 424/186.1; 530/324; 530/327; 530/328

(58) Field of Search .................. 530/328, 327, 530/324, 325; 435/355, 372, 372.3; 424/185.1, 186.1, 189.1

(56) References Cited

U.S. PATENT DOCUMENTS

| | | | |
|---|---|---|---|
| 4,428,941 A | | 1/1984 | Galibert et al. |
| 4,599,230 A | | 7/1986 | Milich et al. |
| 4,599,231 A | | 7/1986 | Milich et al. |
| 4,818,527 A | | 4/1989 | Thornton et al. |
| 4,882,145 A | | 11/1989 | Thornton et al. |
| 5,017,558 A | | 5/1991 | Vyas |
| 5,019,386 A | | 5/1991 | Machida et al. |
| 5,039,522 A | | 8/1991 | Neurath |
| 5,143,726 A | | 9/1992 | Thornton et al. |
| 5,196,194 A | * | 3/1993 | Rutter et al. |
| 5,780,036 A | * | 7/1998 | Chisari |
| 5,788,969 A | * | 8/1998 | Chisari |
| 5,840,303 A | * | 11/1998 | Chisari et al. |
| 5,932,224 A | | 8/1999 | Chisari |
| 6,037,135 A | | 3/2000 | Kubo et al. |
| 6,235,288 B1 | | 5/2001 | Chisari |

FOREIGN PATENT DOCUMENTS

| | | |
|---|---|---|
| EP | 0 429 816 A1 | 6/1991 |
| EP | 0 469 281 A1 | 2/1992 |
| EP | 0 491 077 A1 | 6/1992 |
| WO | WO 93/03753 | 3/1993 |
| WO | WO 93/03764 | 3/1993 |
| WO | WO 94/03205 | 2/1994 |
| WO | WO 94/19011 | 9/1994 |
| WO | WO 94/20127 | 9/1994 |
| WO | WO 95/03777 | 2/1995 |
| WO | WO 95/22317 | 8/1995 |

OTHER PUBLICATIONS

Compugen Ltd. Sequence Search Report, Database Issued Patents, Results #13 for SEQ ID No.:2524, Mar. 2001.*

Alexander et al., Immunologic Research, 18/2:79–92, 1998.*

(List continued on next page.)

*Primary Examiner*—James Housel
*Assistant Examiner*—Zachariah Lucas
(74) *Attorney, Agent, or Firm*—Sterne, Kessler, Goldstein & Fox P.L.L.C.

(57) ABSTRACT

This invention uses our knowledge of the mechanisms by which antigen is recognized by T cells to develop epitope-based vaccines directed towards HBV. More specifically, this application communicates our discovery of pharmaceutical compositions and methods of use in the prevention and treatment of HBV infection.

55 Claims, 1 Drawing Sheet

OTHER PUBLICATIONS

Figure 1:
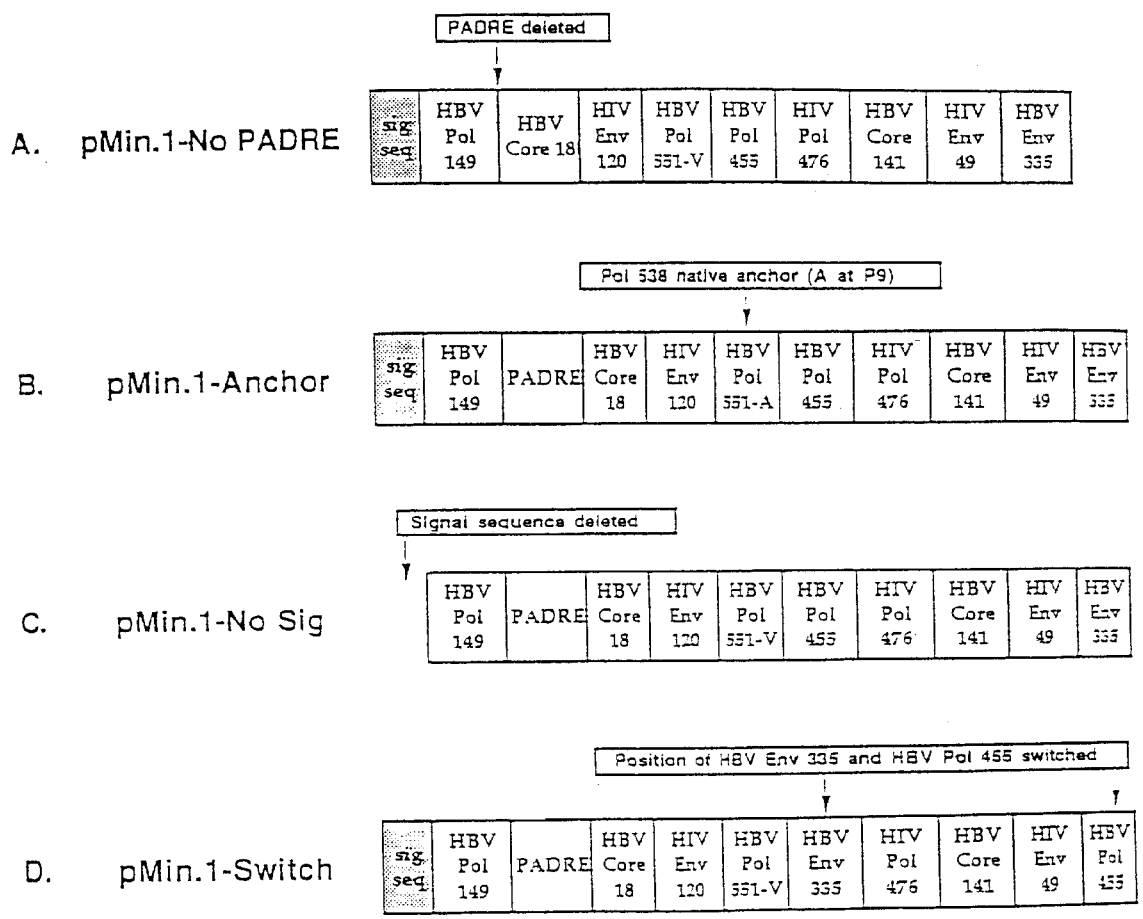

Shimizu et al., The Journal of Immunology, 161:4520–4529, 1998.*

Vitiello et al., J. Clin. Invest., 95:341–349, Jan. 1995.*

Henry, J.B., Clinical & Laboratory Diagnosis & Management by Laboratory Methods, 18th eds., W.B. Saunders Company, Philadelphia, p. 785, 1991.*

Alexander, et al. "The Optimization of Helper T Lymphocyte (HTL) Function in Vaccine Development" *Immunological Research* (1988) 18(2) 79–92.

Toes, et al. "Enhancement of Tumor Outgrowth Through CTL Tolerization After Peptide VAccination is Avoided by Peptide Presentation on Dendritic Cells" *Journal of Immunology* (1998) 160:4449–4456.

Pending Non–Provisional U.S. patent application No. 09/350,401, Sette et al., filed Jul. 8, 1999, Cover page, Tables and Claims only (Not Published).

Alexander et al., *The Journal of Immunology* (1997) 159: 4753–4761.

Ando et al., *J. Exp. Med.* (1993) 178: 1541–1554.

Barnaba et al., *Nature* (1990) 345 258–260.

Bertoletti et al., *Journal of Virology* (1993) 67(4): 2376–2380.

Bertoletti et al., *Nature* (1994) 369:407–410.

Bertoletti et al., *Proc. Natl. Acad. Sci. USA* (1991) 88: 10445–10449.

Bertoni et al., *J. Clin. Invest.* (1997) 100(3): 503–513.

Borras–Cuesta et al., *Eur. J. Immunol.* (1987) 17: 1213–1215.

Bhatnagar et al., *Proc. Natl. Acad. Sci. USA* (1982) 79: 4400–4404.

Celis et al., *The Journal of Immunology* (1988) 140: 1808–1815.

Chisari, *Annu. Rev. Immunol.* (1995) 13: 29–60.

del Guercio et al., *The Journal of Immunology* (1995) 154: 685–693.

Deres et al., *Nature* (1989) 342: 561–564.

Fayolle et al., *The Journal of Immunology* (1991) 147 4069–4073.

Ferrari et al., *J. Clin. Invest.* (1991) 88: 214–222.

Fujii, et al., *Peptide Chemistry* (1983), E. Munekata(Ed.) 215–220.

Hayashi et al., *Chem. Pharm. Bull.* (1988) 36(12): 4993–4999.

Hopp, *Molecular Immunology* (1984) 21(1): 13–26.

Ishioka et al., *Vaccines 90* (1990) Cold Springs Harbor Laboratory Press pp. 7–11.

Kondo et al., *The Journal of Immunology* (1995) 155: 4307–4312.

Lerner et al., *Proc. Natl. Acad. Sci. USA* (1981) 78(6) 3403–34–7.

Milich, *Peptide Research* (1990) 3(2): 85–96.

Milich et al., *The Journal of Immunology* (1987) 139(4): 1223–1231.

Nayersina et al., *The Journal of Immunology* (1993) 150(10): 4659–4671.

Penna et al., *Journal of Virology* (1992) 66(2): 1193–1198.

Penna et al., *J. Exp. Med.* (1991) 174: 1565–2570.

Reherbaum et al., *The Journal of Experimental Medicine* (1995) 181: 1047–1058.

Ruppert et al., *Cell* (1993) 74: 929–937.

Sallberg et al., *Molecular Immunology* (1991) 28(7): 719–726.

Sette et al., *The Journal of Immunology* (1994) 153:5586–5592.

Sidney et al., *The Journal of Immunology* (1996) 157: 3480–3490.

Sidney et al., *Human Immunology* (1996) 45: 79–93.

Wakita et al., *Digestion* (1990) 47: 149–155.

* cited by examiner

INDUCING CELLULAR IMMUNE RESPONSES TO HEPATITIS B VIRUS USING PEPTIDE AND NUCLEIC ACID COMPOSITIONS

CROSS-REFERENCES TO RELATED APPLICATIONS

This application is a continuation-part of U.S. appl. Ser. No. 08/347,610, filed Dec. 1, 1994, which is herein incorporated by reference; and is a continuation-in-part of U.S. appl. Ser. No. 08/344,824, filed Nov. 23, 1994, which is herein incorporated by reference; and is a continuation-in-part of U.S. appl. Ser. No. 08/205,713, filed Mar. 4, 1994, which is herein incorporated by reference; and is a continuation-in-part of U.S. appl. Ser. No. 09/189,702, filed Nov. 10, 1998, which is herein incorporated by reference; and is a continuation-in-part of U.S. appl. Ser. No. 08/820,360, filed Mar. 12, 1997, which is herein incorporated by reference; and is a continuation-in-part of U.S. appl. Ser. No. 08/197,484, filed Feb. 16, 1994, U.S. Pat. No. 6,419,931, which is herein incorporated by reference; which is a continuation-in-part of U.S. appl. Ser. No. 07/935,811, filed Aug. 26, 1992, abandoned, which is herein incorporated by reference; which is a continuation-in-part of U.S. appl. Ser. No. 07/874,491, filed Apr. 27, 1992, abandoned, which is herein incorporated by reference; which is a continuation-in-part of 07/827,682, filed Jan. 29, 1992, abandoned, which is herein incorporated by reference; said appl. Ser. No. 08/347,610 is a continuation-in-part of appl. Ser. No. 08/159,339, filed Nov. 29, 1993, U.S. Pat. No. 6,037,135, which is herein incorporated by reference; which is a continuation-in-part of appl. Ser. No. 08/103,396, filed Aug. 6, 1993, abandoned, which is herein incorporated by reference; which is a continuation-in-part of U.S. appl. Ser. No. 08/027,746, filed Mar. 5, 1993, abandoned, which is herein incorporated by reference; which is a continuation-in-part of U.S. appl. Ser. No. 07/926,666, filed Aug. 7, 1992, abandoned, which is herein incorporated by reference; said appl. Ser. No. 08/344,824 is a continuation-in-part of appl. Ser. No. 08/278,634, filed Jul. 21, 1994, abandoned, which is herein incorporated by reference; said appl. Ser. Ser. No. 08/205,713 is a continuation-in-part of appl. Ser. No. 08/159,184, filed Nov. 29, 1993, abandoned, which is herein incorporated by reference; which is a continuation-in-part of appl. Ser. No. 08/073,205, filed Jun. 4, 1993, abandoned, which is herein incorporated by reference; which is a continuation-in-part of appl. Ser. No. 08/027,146, filed Mar. 5, 1993, abandoned, which is herein incorporated by reference; said appl. Ser. No. 09/189,702 is a continuation-in-part of said appl. Ser. No. 08/205,713; said appl. Ser. No. 08/820,360 claims the benefit of U.S. Provisional Application No. 60/013,363, filed Mar. 13, 1996, which is herein incorporated by reference; the present application is also a continuation-in-part of U.S. appl. Ser. No. 08/978,291, filed Nov. 25, 1997; which is a continuation of U.S. appl. Ser. No. 08/461,603, filed Jun. 5, 1995, which is herein incorporated by reference; which is a continuation of said appl. Ser. No. 07/935,811.

The present application is also related to U.S. Ser. No. 08/197,484, U.S. Ser. No. 08/464,234, U.S. Ser. No. 08/464,496, U.S. Ser. No. 08/464,031, abandoned U.S. Ser. No. 08/464,433, and U.S. Ser. No. 08/461,603, which is a continuation of abandoned U.S. Ser. No. 07/935,811, which is a CIP of abandoned U.S. Ser. No. 07/874,491, which is a CIP of abandoned U.S. Ser. No. 07/827,682, which is a CIP of abandoned Ser. No. 07/749,568. The present application is also related to U.S. Ser. No. 09/226,675, filed Jan. 6, 1999, which is a CTP of U.S. Ser. No. 08/815,396, which is a CIP of abandoned U.S. Ser. No. 60/013,113. Furthermore, the present application is related to U.S. Ser. No. 09/017,735, which is a CIP of abandoned U.S. Ser. No. 08/589,108; U.S. Ser. No. 08/753,622, U.S. Ser. No. 08/822,382, abandoned U.S. Ser. No. 60/013,980, U.S. Ser. No. 08/454,033, U.S. Ser. No. 09/116,424, U.S. Ser. No. 08/205,713, and U.S. Ser. No. 08/349,177, which is a CIP of abandoned U.S. Ser. No. 08/159,184, which is a CIP of abandoned U.S. Ser. No. 08/073,205, which is a CIP of abandoned U.S. Ser. No. 08/027,146. The present application is also related to U.S. Ser. No. 09/017,524, U.S. Ser. No. 08/821,739, abandoned U.S. Ser. No. 60/013,833, U.S. Ser. No. 08/758,409, U.S. Ser. No. 08/589,107, U.S. Ser. No. 08/451,913, U.S. Ser. No. 08/186,266, U.S. Ser. No. 09/116,061, and U.S. Ser. No. 08/347,610, which is a CIP of U.S. Ser. No. 08/159,339, which is a CIP of abandoned U.S. Ser. No. 08/103,396, which is a CIP of abandoned U.S. Ser. No. 08/027,746, which is a CIP of abandoned U.S. Ser. No. 07/926,666. The present application is also related to U.S. Ser. No. 09/017,743, U.S. Ser. No. 08/753,615; U.S. Ser. No. 08/590,298, U.S. Ser. No. 09/115,400, and U.S. Ser. No. 08/452,843, which is a CIP of U.S. Ser. No. 08/344,824, which is a CIP of abandoned U.S. Ser. No. 08/278,634. The present application is also related to provisional U.S. Ser. No. 60/087,192 and U.S. Ser. No. 09/009,953, which is a CIP of abandoned U.S. Ser. No. 60/036,713 and abandoned U.S. Ser. No. 60/037,432. In addition, the present application is related to U.S. Ser. No. 09/098,584 and to U.S. Ser. No. 60/117,486, filed Jan. 27, 1999. All of the above applications in this paragraph are incorporated herein by reference.

FEDERALLY SPONSORED RESEARCH AND DEVELOPMENT

This invention was funded, in part, by the United States government under grants with the National Institutes of Health. The U.S. government has certain rights in this invention.

INDEX

I. Background of the Invention
II. Summary of the Invention
III. Brief Description of the Figures
IV. Detailed Description of the Invention
  A. Definitions
  B. Stimulation of CTL and HTL responses against HBV
  C. Immune Response Stimulating Peptides
    1. Binding Affinity of the Peptides for HLA Molecules
    2. Peptide Binding Motifs and Supermotifs
      a) HLA-A1 supermotif
      b) HLA-A2 supermotif
      c) HLA-A3 supermotif
      d) HLA-A24 supermotif
      e) HLA-B7 supermnotif
      f) H LA-B27 supermotif
      g) HLA-B44 supermotif
      h) HLA-B58 supermotif
      i) HLA-B62 supermotif
      j) HLA-A1 motif
      k) HLA-A3 motif
      l) HLA-A11 motif
      m) HLA-A24 motif
      n) HLA-A2.1 motif
      o) HLA-DR-1-4-7 supermotif
      p) HLA-DR3 motifs
    3. Enhancing Population Coverage of the Vaccine D. Immune Response Stimulating Peptide Analogs
E. Computer Screening of Protein Sequences from Disease-Related Antigens for Supermotif or Motif Containing Peptides
F. Assays to Detect T-Cell Responses
G. Preparation of Peptides
H. Use of Peptide Epitopes for Evaluating Immune Responses
I. Vaccine Compositions
  1. Minigene Vaccines
  2. Combinations with Helper Peptides
J. Administration of Vaccines for Therapeutic or Prophylactic Purposes
K. Kits
V. Examples

I. BACKGROUND OF THE INVENTION

Chronic infection by hepatitis B virus (HBV) affects at least 5% of the world's population and is a major cause of cirrhosis and hepatocellular carcinoma (Hoofnagle, J., *N. Engl. J. Med.* 323:337, 1990; Fields, B. and Knipe, D., In: *Fields Virology* 2:2137, 1990). The World Health Organization lists hepatitis B as a leading cause of death worldwide, close behind chronic pulmonary disease, and more prevalent than AIDS. Chronic HBV infection can range from an asymptomatic carrier state to continuous hepatocellular necrosis and inflammation, and can lead to hepatocellular carcinoma.

The immune response to HBV is believed to play an important role in controlling hepatitis B infection. A variety of humoral and cellular responses to different regions of the HBV nucleocapsid core and surface antigens have been identified. T cell mediated immunity, particularly involving class I human leukocyte antigen-restricted cytotoxic T lymphocytes (CTL), is believed to be crucial in combatting established HBV infection.

Class I human leukocyte antigen (HLA) molecules are expressed on the surface of almost all nucleated cells. CTL recognize peptide fragments, derived from intracellular processing of various antigens, in the form of a complex with class I HLA molecules. This recognition event then results in the destruction of the cell bearing the HLA-peptide complex directly or the activation of non-destructive mechanisms e.g., the production of interferon, that inhibit viral replication.

Several studies have emphasized the association between self-limiting acute hepatitis and multispecific CTL responses (Penna, A. et al., *J. Exp. Med.* 174:1565, 1991; Nayersina, R. et al., *J. Immunol.* 150:4659, 1993). Spontaneous and interferon-related clearance of chronic HBV infection is also associated with the resurgence of a vigorous CTL response (Guidotti, L. G. et al., *Proc. Natl. Acad. Sci. USA* 91:3764, 1994). In all such cases the CTL responses are polyclonal, and specific for multiple viral proteins including the HBV envelope, core and polymerase antigens. By contrast, in patients with chronic hepatitis, the CTL activity is usually absent or weak, and antigenically restricted.

The crucial role of CTL in resolution of HBV infection has been further underscored by studies using HBV transgenic mice. Adoptive transfer of HBV-specific CTL into mice transgenic for the HBV genome resulted in suppression of virus replication. This effect was primarily mediated by a non-lytic, lymphokine-based mechanism (Guidotti, L. G. et al., *Proc. Natl. Acad. Sci. USA* 91:3764, 1994; Guidotti, L. G., Guilhot, S., and Chisari, F. V. *J. Virol.* 68:1265, 1994; Guidotti, L. G. et al., *J. Virol.* 69:6158, 1995; Gilles, P. N., Fey, G., and Chisari, F. V., *J. Virol.* 66:3955, 1992).

As is the case for HLA class I restricted responses, HLA class II restricted T cell responses are usually detected in patients with acute hepatitis, and are absent or weak in patients with chronic infection (Chisari, F. V. and Ferrari, C., *Annu. Rev. Immunol.* 13:29, 1995). HLA Class II responses are tied to activation of helper T cells (HTLs) Helper T lymphocytes, which recognize Class II HLA molecules, may directly contribute to the clearance of HBV infection through the secretion of cytokines which suppress viral replication (Franco, A. et al., *J. Immunol.* 159:2001, 1997). However, their primary role in disease resolution is believed to be mediated by inducing activation and expansion of virus-specific CTL and B cells.

In view of the heterogeneous immune response observed with HBV infection, induction of a multi-specific cellular immune response directed simultaneously against multiple epitopes appears to be important for the development of an efficacious vaccine against HBV. There is a need to establish vaccine embodiments that elicit immune responses that correspond to responses seen in patients that clear HBV infection. Epitope-based vaccines appear useful.

Upon development of appropriate technology, the use of epitope-based vaccines has several advantages over current vaccines. The epitopes for inclusion in such a vaccine are to be selected from conserved regions of viral or tumor-associated antigens, in order to reduce the likelihood of escape mutants. The advantage of an epitope-based approach over the use of whole antigens is that there is evidence that the immune response to whole antigens is directed largely toward variable regions of the antigen, allowing for immune escape due to mutations. Furthermore, immunosuppressive epitopes that may be present in whole antigens can be avoided with the use of epitope-based vaccines.

Additionally, with an epitope-based vaccine approach, there is an ability to combine selected epitopes (CTL and HTL) and additionally to modify the composition of the epitopes, achieving, for example, enhanced immunogenicity. Accordingly, the immune response can be modulated, as appropriate, for the target disease. Similar engineering of the response is not possible with traditional approaches.

Another major benefit of epitope-based immune-stimulating vaccines is their safety. The possible pathological side effects caused by infectious agents or whole protein antigens, which might have their own intrinsic biological activity, is eliminated.

An epitope-based vaccine also provides the ability to direct and focus an immune response to multiple selected antigens from the same pathogen. Thus, patient-by-patient variability in the immune response to a particular pathogen may be alleviated by inclusion of epitopes from multiple antigens from that pathogen in a vaccine composition. A "pathogen" may be an infectious agent or a tumor associated molecule.

However, one of the most formidable obstacles to the development of broadly efficacious epitope-based immuno-therapeutics has been the extreme polymorphism of HLA molecules. To date, effective non-genetically biased coverage of a population has been a task of considerable complexity; such coverage has required that epitopes be used specific for HLA molecules corresponding to each individual HLA allele, therefore, impractically large numbers of epitopes would have to be used in order to cover ethnically diverse populations. There has existed a need to develop peptide epitopes that are bound by multiple HLA antigen molecules for use in epitope-based vaccines. The greater the number of HLA antigen molecules bound, the greater the breadth of population coverage by the vaccine.

Furthermore, as described herein in greater detail, a need has existed to modulate peptide binding properties, for example so that peptides that are able to bind to multiple HLA antigens do so with an affinity that will stimulate an immune response. Identification of epitopes restricted by more than one HLA allele at an affinity that correlates with immunogenicity is important to provide thorough population coverage, and to allow the elicitation of responses of sufficient vigor whereby the natural immune responses noted in self-limiting acute hepatitis, or of spontaneous clearance of chronic HBV infection is induced in a diverse segment of the population. Such a response can also target a broad array of epitopes. The technology disclosed herein provides for such favored immune responses.

The information provided in this section is intended to disclose the presently understood state of the art as of the filing date of the present application. Information is included in this section which was generated subsequent to the priority date of this application. Accordingly, background in this section is not intended, in any way, to delineate the priority date for the invention.

II. SUMMARY OF THE INVENTION

This invention applies our knowledge of the mechanisms by which antigen is recognized by T cells, for example, to develop epitope-based vaccines directed towards HBV. More specifically, this application communicates our discovery of specific epitope pharmaceutical compositions and methods of use in the prevention and treatment of HBV infection.

An embodiment of the present invention includes a peptide composition of less than 100 amino acid residues comprising a peptide epitope useful for inducing an immune response against hepatitis B virus (HBV) said epitope (a) having an amino acid sequence of about 8 to about 13 amino acid residues that have at least 65% identity with a native amino acid sequence for HBV, and, (b) binding to at least one MHC class I HLA allele with a dissociation constant of less than about 500 nM. Further, the peptide composition may comprise an amino acid sequence of at least 77% identity, or at least 100% identity with a native HBV amino acid sequence. In a preferred embodiment, the peptide is one of the peptides designated as being from the envelope, polymerase, protein X, or nucleocapsid core regions of HBV. Preferred peptides are described in Tables VI through XVII or XXI.

An additional embodiment of the present invention comprises a composition of less than 100 amino acid residues comprising a peptide epitope useful for inducing an immune response against hepatitis B virus (HBV) said peptide (a) having an amino acid sequence of about 8 to about 13 amino acid residues and (b) bearing one of the HLA supermotifs or motifs set out in Tables I and II. Furthermore, the composition may comprise a peptide wherein the peptide is one of those described in Tables VI through XVII or Table XXI which bear an HLA A1, A2, A3, A24, B7, B27, B44, B58, or B62 supermotif; or an HLA A1, A3, A11, A24, or A2.1 motif or an HLA A*3301, A*3101, A*6801, B*0702, B*3501, B51, B*5301, B*5401 motif.

In one embodiment of a peptide comprising an HLA A2.1 motif, the peptide does not bear an L or M at position 2 and V at the C-terminal position 9 of a 9 amino acid peptide.

An alternative embodiment of the invention comprises an analog of an HBV peptide of less than 100 amino acid residues in length that bears an HLA binding motif, the analog bearing the same HLA binding motif as the peptide but comprising at least one anchor residue that is different from that of the peptide. In a preferred embodiment, said peptide is an analog of a peptide described in Table VI through Table XVII bearing an HLA A1, A2, A3, A24, B7, B27, B44, B58, or B62 supermotif; or an HLA A1, A3, A11, A24, or A2.1 motif or an A3301, A3101, A6801, B0702, B3501, B51, B5301, B5401 motif.

Embodiments of the invention further include a composition of less than 100 amino acid residues comprising a peptide epitope useful for inducing an immune response against hepatitis B virus (HBV) said peptide (a) having an amino acid sequence of about 9 to about 25 amino acid residues that have at least 65% identity with a native amino acid sequence for HBV and (b) binding to at least one MHC class II HLA allele with a dissociation constant of less than about 1000 nM. In a preferred embodiment, the composition comprises a peptide that has at least 77%, or, 100% identity with a native HBV amino acid sequence. Further, the composition may comprise a peptide wherein said peptide is one of those peptides described in Table XVIII or Table XIX.

The invention also includes a peptide composition of less than 100 amino acid residues, said composition comprising an epitope useful for inducing an immune response against hepatitis B virus (HBV) said epitope (a) having an amino acid sequence of about 10 to about 20 amino acid residues and (b) bearing one of the class II HLA motifs set out in Table III. In a preferred embodiment, said peptide is one of those peptides described in Table XVIII or XIX.

Additional embodiments of the invention include a composition that comprises an isolated nucleic acid sequence that encodes one of the peptides set out in Tables VI through XIX or XXI or XXIII.

Alternatively, an embodiment of the invention comprises a composition that comprises at least two peptides, at least one of said at least two peptides selected from Tables VI–XIX or XXI or XXIII. In a preferred embodiment, two or more of the at least two peptides are depicted in Tables VI–XIX or XXI or XXIII. The composition may further comprise at least one nucleic acid sequence. In a preferred embodiment each of said at least two peptides are encoded by a nucleic acid sequence, wherein each of the nucleic acid sequences are located on a single vector.

Embodiments of the invention additionally include a peptide composition of less than 100 amino acid residues, said composition comprising an epitope useful for inducing an immune response against HBV, said epitope having at least one of the amino acid sequences set out in Table XXIII.

An alternative modality for defining the peptides in accordance with the invention is to recite the physical properties, such as length; primary, secondary and/or tertiary structure; or charge, which are correlated with binding to a particular allele-specific HLA molecule or group of allele-specific HLA molecules. A further modality for defining peptides is to recite the physical properties of an HLA binding pocket, or properties shared by several allele-specific HLA binding pockets (e.g. pocket configuration and charge distribution) and reciting that the peptide fits and binds to said pocket or pockets.

An additional embodiment of the invention comprises a method for inducing a cytotoxic T cell response to HBV in a mammal comprising administering to said mammal at least one peptide from Tables VI to XIX or Table XXI.

Further embodiments of the invention include a vaccine for treating HBV infection that induces a protective immune response, wherein said vaccine comprises at least one peptide selected from Tables VI to Table XIX or Table XXI in a pharmaceutically acceptable carrier.

Also included as an embodiment of the invention is a vaccine for preventing HBV infection that induces a protective immune response, wherein said vaccine comprises at least one peptide selected from Tables VI to XIX or Table XXI in a pharmaceutically acceptable carrier.

The invention further includes an embodiment comprising a method for inducing a cytotoxic T cell response to HBV in a mammal, comprising administering to said mammal a nucleic acid sequence encoding a peptide selected from Tables VI to XIX or Table XXI.

A further embodiment of the invention comprises a kit for a vaccine for treating or preventing HBV infection, wherein the vaccine induces a protective immune response, said vaccine comprising at least one peptide selected from Tables VI to XIX or Table XXI in a pharmaceutically acceptable carrier and instructions for administration to a patient.

Lastly, the invention includes an embodiment comprising a method for monitoring immunogenic activity of a vaccine for HBV in a patient having a known HLA-type, the method comprising incubating a T lymphocyte sample from the patient with a peptide selected from Tables VI to XIX or Table XXI which binds the product of at least one HLA allele present in said patient, and detecting for the presence of a T lymphocyte that binds to the peptide. In a preferred embodiment, the peptide comprises a tetrameric complex.

As will be apparent from the discussion below, other methods and embodiments are also contemplated. Further, novel synthetic peptides produced by any of the methods described herein are also part of the invention.

III. BRIEF DESCRIPTION OF THE FIGURES

FIG. 1: FIG. 1 Illustrates the Position of Peptide Epitopes in Experimental Model Minigene Constructs

IV. DETAILED DESCRIPTION OF THE INVENTION

The peptides and corresponding nucleic acid compositions of the present invention are useful for stimulating an immune response to HBV either by stimulating the production of CTL or HTL responses. The peptides, which are derived directly or indirectly from native HBV amino acid sequences, are able to bind to HLA molecules and stimulate an immune response to HBV. The complete polyprotein sequence from HBV and its variants can be obtained from Genbank. Peptides can also be readily determined from sequence information that may subsequently be discovered for heretofore unknown variants of HBV as will be clear from the disclosure provided below.

The peptides of the invention have been identified in a number of ways, as will be discussed below. Further, analog peptides have been derived and the binding activity for HLA molecules modulated by modifying specific amino acid residues to create peptide analogs exhibiting altered immunogenicity. Further, the present invention provides compositions and combinations of compositions that enable epitope-based vaccines that are capable of interacting with multiple HLA antigens to provide broader population coverage than prior vaccines.

The invention can be better understood with reference to the following definitions:

IV.A. Definitions

"Cross-reactive binding" indicates that a peptide is bound by more than one HLA molecule; a synonym is degenerate binding.

A "cryptic epitope" elicits a response by immunization with an isolated peptide, but the response is not cross-reactive in vitro when intact whole protein which comprises the epitope is used as an antigen.

A "dominant epitope" is an epitope that induces an immune response upon immunization with a whole native antigen. (See, e.g., Sercarz, et al., *Annu. Rev. Immunol.* 11:729766 (1993)) Such a response is cross-reactive in vitro with an isolated peptide epitope.

With regard to a particular amino acid sequence, an "epitope" is a set of amino acid residues which is involved in recognition by a particular immunoglobulin, or in the context of T cells, those residues necessary for recognition by T cell receptor proteins and/or Major Histocompatibility Complex (MHC) receptors. In an immune system setting, in vivo or in vitro, an epitope is the collective features of a molecule, such as primary, secondary and tertiary peptide structure, and charge, that together form a site recognized by an immunoglobulin, T cell receptor or HLA molecule.

As used herein, "high affinity" with respect to HLA class I molecules is defined as binding with an $IC_{50}$ (or $K_D$) of less than 50 nM. "Intermediate affinity" is binding with an $IC_{50}$ (or $K_D$) of between about 50 and about 500 nM. "High affinity" with respect to binding to HLA class II molecules is defined as binding with an $K_D$ of less than 100 nM. "Intermediate affinity" is binding with a $K_D$ of between about 100 and about 1000 nM. Assays for determining binding are described in detail in PCT publications WO 94/20127 and WO 94/03205. Alternatively, binding is expressed relative to a reference peptide. As a particular assay becomes more, or less, sensitive, the $IC_{50}$'s of the peptides tested may change somewhat. However, the binding relative to the reference peptide will not significantly change. For example, in an assay run under conditions such that the $IC_{50}$ of the reference peptide increases 10-fold, the $IC_{50}$ values of the test peptides will also shift approximately 10-fold. Therefore, to avoid ambiguities, the assessment of whether a peptide is a good, intermediate, weak, or negative binder is generally based on its $IC_{50}$, relative to the $IC_{50}$ of a standard peptide.

"Human Leukocyte Antigen" or "HLA" is a human class I or class II Major Histocompatibility Complex (MHC) protein (see, Stites, et al., *Immunology*, $8^{TH}$ ED., Lange Publishing, Los Altos, Calif. (1994).

An "HLA supertype or family", as used herein, describes sets of HLA molecules grouped on the basis of shared peptide-binding specificities. HLA class I molecules that share somewhat similar binding affinity for peptides bearing certain amino acid motifs are grouped into HLA supertypes. The terms HLA superfamily, HLA supertype family, and HLA xx-like supertype molecules (where xx denotes a particular HLA type) are synonyms.

Throughout this disclosure, results are expressed in terms of "$IC_{50}$'s." $IC_{50}$ is the concentration of peptide in a binding assay at which 50% inhibition of binding of a reference peptide is observed. Given the conditions in which the assays are run (i.e., limiting HLA proteins and labeled peptide concentrations), these values approximate $K_D$ values. It should be noted that $IC_{50}$ values can change, often dramatically, if the assay conditions are varied, and depending on the particular reagents used (e.g., HLA preparation, etc.). For example, excessive concentrations of HLA molecules will increase the apparent measured $IC_{50}$ of a given ligand.

The terms "identical" or percent "identity," in the context of two or more peptide sequences, refer to two or more sequences or subsequences that are the same or have a specified percentage of amino acid residues that are the same, when compared and aligned for maximum correspondence over a comparison window, as measured using a sequence comparison algorithms or by manual alignment and visual inspection.

An "immunogenic peptide" or "peptide epitope" is a peptide which comprises an allele-specific motif or supermotif such that the peptide will bind an HLA molecule and induce a CTL and/or HTL response. Thus, immunogenic peptides of the invention are capable of binding to an appropriate HLA molecule and thereafter inducing a cytotoxic T cell response, or a helper T cell response, to the antigen from which the immunogenic peptide is derived.

The phrases "isolated" or "biologically pure" refer to material which is substantially or essentially free from components which normally accompany the material as it is found in its native state. Thus, isolated peptides in accordance with the invention preferably do not contain materials normally associated with the peptides in their in situ environment.

"Major Histocompatibility Complex" or "MHC" is a cluster of genes that plays a role in control of the cellular interactions responsible for physiologic immune responses. In humans, the MHC complex is also known as the HLA complex. For a detailed description of the MHC and HLA complexes, see, Paul, FUNDAMENTAL IMMUNOLOGY, $3^{RD}$ ED., Raven Press, New York, 1993.

The term "motif" refers to the pattern of residues in a peptide of defined length, usually a peptide of from about 8 to about 13 amino acids for a class I HLA motif and from about 6 to about 25 amino acids for a class II HLA motif, which is recognized by a particular HLA molecule. Peptide motifs are typically different for each protein encoded by each human HLA allele and differ in the pattern of the primary and secondary anchor residues.

A "negative binding residue" is an amino acid which if present at certain positions (typically not primary anchor positions) of peptide epitope results in decreased binding affinity of the peptide for the peptide's corresponding HLA molecule.

The term "peptide" is used interchangeably with "oligopeptide" in the present specification to designate a series of residues, typically L-amino acids, connected one to the other, typically by peptide bonds between the α-amino and carboxyl groups of adjacent amino acids. The preferred CTL-inducing oligopeptides of the invention are fewer than 25 residues in length, or less than 15 residues in length, or 13 residues or less in length and usually consist of between about 8 and about 11 residues, preferably 9 or 10 residues. The preferred HTL-inducing oligopeptides are less than about 50 residues in length and usually consist of between about 6 and about 30 residues, more usually between about 12 and 25, and often between about 15 and 20 residues.

"Pharmaceutically acceptable" refers to a non-toxic, inert, and physiologically compatible composition.

A "primary anchor residue" is an amino acid at a specific position along a peptide sequence which is understood to provide a contact point between the immunogenic peptide and the HLA molecule. One to three, usually two, primary anchor residues within a peptide of defined length generally defines a "motif" for an immunogenic peptide. These residues are understood to fit in close contact with peptide binding grooves of an HLA molecule, with their side chains buried in specific pockets of the binding grooves themselves. In one embodiment, the primary anchor residues are located at position 2 (from the amino terminal position) and at the carboxyl terminal position of a 9 residue peptide in accordance with the invention. The primary anchor positions for each motif and supermotif are set forth in Table I. For example, analog peptides can be created by altering the presence or absence of particular residues in these primary anchor positions. Such analogs are used to finely modulate the binding affinity of a peptide comprising a particular motif or supermotif.

"Promiscuous binding" is where a distinct peptide is recognized by the same T cell clone in the context of various HLA molecules.

A "protective immune response" refers to a CTL and/or an HTL response to an antigen from an infectious agent or a tumor antigen from which an immunogenic peptide is derived, and thereby preventing or at least partially arresting disease symptoms or progression. The immune response may also include an antibody response which has been facilitated by the stimulation of helper T cells.

The term "residue" refers to an amino acid or amino acid mimetic incorporated into an oligopeptide by an amide bond or amide bond mimetic.

A "secondary anchor residue" is an amino acid at a position other than a primary anchor position in a peptide which may influence peptide binding. A secondary anchor residue occurs at a significantly higher frequency amongst bound peptides than would be expected by random distribution of amino acids at one position. The secondary anchor residues are said to occur at "secondary anchor positions." A secondary anchor residue can be identified as a residue which is present at a higher frequency among high affinity binding peptides, or a residue otherwise associated with high affinity binding. For example, analog peptides can be created by altering the presence or absence of particular residues in these secondary anchor positions. Such analogs are used to finely modulate the binding affinity of a peptide comprising a particular motif or supermotif.

A "subdominant epitope" is an epitope which evokes little or no response upon immunization with whole antigens which comprise the epitope, but for which a response can be obtained by immunization with an isolated peptide, and this response (unlike the case of cryptic epitopes) is detected when whole protein is used to recall the response in vitro or in vivo.

A "supermotif" is a peptide binding specificity shared by HLA molecules encoded by two or more HLA alleles. Thus, a preferably is recognized with high or intermediate affinity (as defined herein) by two or more HLA antigens.

"Synthetic peptide" refers to a peptide that is not naturally occurring, but is man-made using such methods as chemical synthesis or recombinant DNA technology.

The nomenclature used to describe peptide compounds follows the conventional practice wherein the amino group is presented to the left (the N-terminus) and the carboxyl group to the right (the C-terminus) of each amino acid residue. When amino acid residue positions are referred to in a peptide epitope they are numbered in an amino to carboxyl direction with position one being the position closest to the amino terminal. In the formulae representing selected specific embodiments of the present invention, the amino- and carboxyl-terminal groups, although not specifically shown, are in the form they would assume at physiologic pH values, unless otherwise specified. In the amino acid structure formulae, each residue is generally represented by standard three letter or single letter designations. The L-form of an amino acid residue is represented by a capital single letter or a capital first letter of a three-letter symbol, and the D-form for those amino acids having D-forms is represented by a lower case single letter or a lower case three letter symbol. Glycine has no asymmetric carbon atom and is simply referred to as "Gly" or G. Symbols for the amino acids are shown below.

| Single Letter Symbol | Three Letter Symbol | Amino Acids |
|---|---|---|
| A | Ala | Alanine |
| C | Cys | Cysteine |
| D | Asp | Aspartic Acid |
| E | Glu | Glutamic Acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

IV.B. Stimulation of CTL and HTL Responses Against HBV

The mechanism by which T cells recognize antigens has been delineated during the past ten years. Based on our new understanding of the immune system we have generated efficacious peptide epitope vaccine compositions that can induce a therapeutic or prophylactic immune response to HBV infection in a broad population. For an understanding of the value and efficacy of the claimed compositions, a brief review of the technology is provided.

A complex of an HLA molecule and a peptidic antigen acts as the ligand recognized by HLA-restricted T cells (Buus, S. et al., *Cell* 47:1071, 1986; Babbitt, B. P. et al., *Nature* 317:359, 1985; Townsend, A., and Bodmer, H., *Annu. Rev. Immunol.* 7:601, 1989; Germain, R. N., *Annu. Rev. Immunol.* 11:403, 1993). Through the study of single amino acid substituted antigen analogs and the sequencing of endogenously bound, naturally processed peptides, critical residues that correspond to motifs required for specific binding to HLA antigen molecules have been identified and are described here and set forth in Tables I, II, and III (see also, e.g., Sette, A. and Grey, H. M., *Curr. Opin. Immunol.* 4:79, 1992; Sinigaglia, F. and Hammer, J., *Curr. Biol.* 6:52, 1994; Engelhard, V. H., *Curr. Opin. Immunol.* 6:13, 1994). Furthermore, x-ray crystallographic analysis of HLA-peptide complexes has revealed pockets within the peptide binding cleft of HLA molecules which accommodate allele-specific residues borne by peptide ligands; these residues in turn determine the HLA binding capacity of the peptides in which they are present (Brown, J. H. et al., *Nature* 364:33, 1993; Guo, H. C. et al., *Proc. Natl. Acad. Sci. USA* 90:8053, 1993; Guo, H. C. et al., *Nature* 360:364, 1992; Silver, M. L. et al., *Nature* 360:367, 1992; Matsumura, M. et al., *Science* 257:927, 1992; Madden et al., *Cell* 70:1035, 1992; Fremont, D. H. et al., *Science* 257:919, 1992; Saper, M. A., Bjorkman, P. J. and Wiley, D. C., *J. Mol. Biol.* 219:277, 1991).

Accordingly, the definition of class I and class II allele-specific HLA binding motifs or class I supermotifs allows identification of regions within a protein that have the potential of binding particular HLA antigens (see also e.g., Sette, A. and Grey, H. M., *Curr. Opin. Immunol.* 4:79, 1992; Sinigaglia, F. and Hammer, J., *Curr. Biol.* 6:52, 1994; Engelhard, V. H., *Curr. Opin. Immunol.* 6:13, 1994Kast, W. M. et al., *J. Immunol.*, 152:3904, 1994).

Furthermore, a variety of assays to detect and quantify the affinity of interaction between peptide and HLA have also been established (Sette, A. and Grey, H. M., *Curr. Opin. Immunol.* 4:79, 1992; Sinigaglia, F. and Hammer, J., *Curr. Biol.* 6:52, 1994; Engelhard, V. H., *Curr. Opin. Immunol.* 6:13, 1994).

We have found that the correlation of binding affinity with immunogenicity is an important factor to be considered when evaluating candidate peptides. Thus, by a combination of motif searches and HLA-peptide binding assays, candidates for epitope-based vaccines have been identified. After determining their binding affinity, additional confirmatory work can be performed to select, amongst these vaccine candidates, epitopes with desired characteristics in terms of antigenicity and immunogenicity. Various strategies can be utilized to evaluate immunogenicity, including:

1) Primary T cell cultures from normal individuals (Wentworth, P. A. et al., *Mol. Immunol.* 32:603, 1995; Celis, E. et al., *Proc. Natl. Acad Sci. USA* 91:2105, 1994; Tsai, V. et al., *J. Immunol.* 158:1796, 1997; Kawashima, I. et al., *Human Immunol.* 59:1, 1998); This procedure involves the stimulation of PBL from normal subjects with a test peptide in the presence of antigen presenting cells in vitro over a period of several weeks. T cells specific for the peptide become activated during this time and are detected using a $^{51}$Cr-release assay involving peptide sensitized target cells.

2) Immunization of HLA transgenic mice (Wentworth, P. A. et al., *J. Immunol.* 26:97, 1996; Wentworth, P. A. et al., *Int. Immunol.* 8:651, 1996; Alexander, J. et al., *J. Immunol.* 159:4753, 1997); In this method, peptides in incomplete Freund's adjuvant are administered subcutaneously to HLA transgenic mice. Several weeks following immunization, splenocytes are removed and cultured in vitro in the presence of test peptide for approximately one week. Peptide-specific T cells are detected using a $^{51}$Cr-release assay involving peptide sensitized target cells and target cells expressing endogenously generated antigen.

3) Demonstration of recall T cell responses from immune individuals who have recovered from infection, and/or from chronically infected patients (Rehermann, B. et al., *J. Exp. Med.* 181:1047, 1995; Doolan, D. L. et al., *Immunity* 7:97, 1997; Bertoni, R. et al., *J. Clin. Invest.* 100:503, 1997; Threlkeld, S. C. et al., *J. Immunol.* 159:1648, 1997; Diepolder, H. M. et al., *J. Virol.* 71:6011, 1997). In applying this strategy, recall responses were detected by culturing PBL from subjects that had been naturally exposed to the antigen, for instance through infection, and thus had generated an immune response "naturally". PBL from subjects were cultured in vitro for 1–2 weeks in the presence of test peptide plus antigen presenting cells (APC) to allow activation of "memory" T cells, as compared to "naive" T cells. At the end of the culture period, T cell activity is detected using assays for T cell activity including $^{51}$Cr release involving peptide-sensitized targets, T cell proliferation or lymphokine release.

The following describes the peptide epitopes and corresponding nucleic acids of the invention.

IV.C. Immune Response Stimulating Peptides

As indicated herein, the large degree of HLA polymorphism is an important factor to be taken into account with the epitope-based approach to vaccine development. To address this factor, epitope selection encompassing identification of peptides capable of binding at high or intermediate affinity to multiple HLA molecules is preferably utilized, most preferably these epitopes bind at high or intermediate affinity to two or more allele specific HLA molecules.

IV.C.1. Binding Affinity of the Peptides for HLA Molecules

CTL-inducing peptides of interest for vaccine compositions preferably include those that have a binding affinity for class I HLA molecules of less than 500 nM. HTL-inducing peptides preferably include those that have a binding affinity for class II HLA molecules of less than 1000 nM. For example, peptide binding is assessed by testing the capacity of a candidate peptide to bind to a purified HLA molecule in vitro. Peptides exhibiting high or intermediate affinity are then considered for further analysis. Selected peptides are tested on other members of the supertype family. In preferred embodiments, peptides that exhibit cross-reactive binding preferably are then used in cellular screening analyses. A peptide is considered to be an epitope if it possesses the molecular features that form the binding site for a particular immunoglobulin or T cell receptor protein.

As disclosed herein, high HLA binding affinity is correlated with greater immunogenicity. Greater immunogenicity can be manifested in several different ways. Immunogenicity corresponds to whether an immune response is elicited at all, and to the vigor of any particular response. For example, a peptide might elicit an immune response in a diverse array of the population, yet in no instance produce a vigorous response. In accordance with these principles, close to 90% of high binding peptides have been found to be immunogenic, as contrasted with about 50% of the peptides which bind with intermediate affinity. Moreover, higher binding affinity peptides leads to more vigorous immunogenic responses. As a result, less peptide is required to elicit a similar biological effect if a high affinity binding peptide is used. Thus, in preferred embodiments of the invention, high binding epitopes are particularly desired.

The relationship between binding affinity for HLA class I molecules and immunogenicity of discrete peptide epitopes on bound antigens has been determined for the first time in the art by the present inventors. The correlation between binding affinity and immunogenicity was analyzed in two different experimental approaches (Sette, et al., *J. Immunol.* 153:5586–5592, 1994). In the first approach, the immunogenicity of potential epitopes ranging in HLA binding affinity over a 10,000-fold range was analyzed in HLA-A*0201 transgenic mice. In the second approach, the antigenicity of approximately 100 different hepatitis B virus (HBV)-derived potential epitopes, all carrying A*0201 binding motifs, was assessed by using PBL (peripheral blood lymphocytes) of acute hepatitis patients. Pursuant to these approaches, it was determined that an affinity threshold of approximately 500 nM (preferably 500 nM or less) determines the capacity of a peptide epitope to elicit a CTL response. These data are true for class I binding affinity measurements for naturally processed peptides and for synthesized T cell epitopes. These data also indicate the important role of determinant selection in the shaping of T cell responses.

An affinity threshold associated with immunogenicity in the context of HLA class II DR molecules has also been delineated (Southwood et al. *J. Immunology* 160:3363–3373,1998, and U.S. Ser. No. 60/087192 filed May 29, 1998). In order to define a biologically significant threshold of DR binding affinity, a database of the binding affinities of 32 DR-restricted epitopes for their restricting element was compiled. In approximately half of the cases (15 of 32 epitopes), DR restriction was associated with high binding affinities, i.e. binding affinities of less than 100 nM. In the other half of the cases (16 of 32), DR restriction was associated with intermediate affinity (binding affinities in the 100–1000 nM range). In only one of 32 cases was DR restriction associated with an $IC_{50}$ of 1000 nM or greater. Thus, 1000 nM can be defined as an affinity threshold associated with immunogenicity in the context of DR molecules.

The binding affinity of peptides for HLA molecules can be determined as described in Example 1, below.

IV.C.2. Peptide Binding Motifs and Supermotifs

In the past few years evidence has accumulated to demonstrate that a large fraction of HLA class I, and possibly class II molecules can be classified into a relatively few supertypes characterized by largely overlapping peptide binding repertoires, and consensus structures of the main peptide binding pockets. Through the study of single amino acid substituted antigen analogs and the sequencing of endogenously bound, naturally processed peptides, critical residues required for allele-specific binding to HLA molecules have been identified. These motifs are relevant since they indicate peptides that have binding affinity for HLA molecules.

For HLA molecule pocket analyses, the residues comprising the B and F pockets of HLA class I molecules as described in crystallographic studies (Guo, H. C. et al., *Nature* 360:364, 1992; Saper, M. A., Bjorkman, P. J. and Wiley, D. C., *J. Mol. Biol.* 219:277, 1991; Madden, D. R., Garboczi, D. N. and Wiley, D. C., *Cell* 75:693, 1993), have been compiled from the database of Parham, et al. (Parham, P., Adams, E. J., and Arnett, K. L., *Immunol. Rev.* 143:141, 1995). In these analyses, residues 9, 45, 63, 66, 67, 70, and 99 were considered to make up the B pocket, and to determine the specificity for the residue in the second position of peptide ligands. Similarly, residues 77, 80, 81, and 116 were considered to determine the specificity of the F pocket, and to determine the specificity for the C-terminal residue of a peptide ligand bound by the HLA molecule.

Peptides of the present invention may also include epitopes that bind to MHC class II DR molecules. A significant difference between class I and class II HLA molecules is that, although a stringent size restriction exists for peptide binding to class I molecules, a greater degree of heterogeneity in both sizes and binding frame positions of the motif, relative to the N and C termini of the peptide, can be demonstrated for class II peptide ligands. This increased heterogeneity is due to the structure of the class II-binding groove which, unlike its class I counterpart, is open at both ends. Crystallographic analysis of DRB!*0101-peptide complexes(see, e.g., Madden, D. R. Ann. Rev. Immunol. 13:587 (1995)) showed that the residues occupying position 1 and position 6 of peptides complexed with DRB*0101 engage two complementary pockets on the DRBa*0101 molecules, with the P1 position corresponding to the most crucial anchor residue and the deepest hydrophobic pocket. Other studies have also pointed to the P6 position as a crucial anchor residue for binding to various other DR molecules.

Thus, peptides of the present invention are identified by any one of several HLA-specific amino acid motifs. If the presence of the motif corresponds to the ability to bind several allele-specific HLA antigens it is referred to as a supermotif. The allele-specific HLA molecules that bind to peptides that possess a particular amino acid supermnotif are collectively referred to as an HLA "supertype."

The peptide motifs and supermotifs described below provide guidance for the identification and use of peptides in accordance with the invention. Examples of peptide epitopes bearing the respective supermotif or motif are included in Tables as designated in the description of each motif or supermotif. The Tables include a binding affinity ratio listing for some of the peptide epitopes. The ratio may be converted to $IC_{50}$ by using the following formula: $IC_{50}$ of the standard peptide/ratio=$IC_{50}$ of the test peptide (i.e. the peptide epitope). The $IC_{50}$ values of standard peptides used to determine binding affinities for Class I peptides are: shown in Table IV. The $IC_{50}$ values of standard peptides used to determine binding affinities for Class II peptides are shown in Table V. The peptides used as standards for the binding assay are examples of standards; alternative standard peptides can also be used when performing such an analysis.

To obtain the peptide epitope sequences listed in each Table, protein sequence data from twenty HBV strains (HPBADR, HPBADR1CG, HPBADRA, HPBADRC, HPBADRCG, HPBCGADR, HPBVADRM, HPBADW, HPBADWI, HPBADW2, HPBADW3, HPBADWZ, HPBHEPB, HPBVADW2, HPBAYR, HPBV, HPBVAYWC, HPBVAYWCI, NAD HPBVAYWE) were evaluated for the presence of the designated supermotif or motif. Peptide epitopes were also selected on the basis of their conservancy. A criterion for conservancy requires that the entire sequence of a peptide be totally conserved in 75% of the sequences available for a specific protein. The percent conservancy of the selected peptide epitopes is indicated on the Tables. The frequency, i.e. the number of strains of the 20 strains in which the peptide sequence was identified, is also shown. The "$1^{st}$ position" column in the Tables designates the amino acid position of the HBV polyprotein that corresponds to the first amino acid residue of the epitope. Preferred peptides are designated by an asterisk.

HLA Class I Motifs Indicative of CTL Inducing Peptide Epitopes:

IV.C.2.a) HLA-A1 Supermotif

The HLA-A1 supermotif is characterized by peptides having a general motif of small (T or S) and hydrophobic (L, I, V, M, or F) primary anchor residues in position 2, and aromatic (Y, F, or W) primary anchor residues at the C-terminal position The corresponding family of HLA molecules that bind to the A1 supermotif (the HLA-A1 supertype) includes A*0101, A*2601, A*2602, A*2501, and A*3201. (DiBrino, M. et al., *J. Immunol.* 151:5930, 1993; DiBrino, M. et al., *J. Immunol.* 152:620, 1994; Kondo, A. et al., *Immunogenetics* 45:249, 1997; Dumrese et al., submitted). Peptides binding to each of the individual HLA proteins can be modulated by substitutions at primary anchor positions.

Representative peptide epitopes that contain the A1 supermotif are set forth on the attached Table VI.

IV.C.2.b) HLA-A2 Supermotif

The HLA-A2 supermotif is characterized by the presence in peptide ligands of small or aliphatic amino acids (L, I, V, M, A, T, or Q) at position 2 and L, I, V, M, A, or T at the C-terminal position. These positions are referred to as primary anchors. The corresponding family of HLA molecules (the HLA-A2 supertype that binds these peptides) is comprised of at least nine HLA-A proteins: A*0201, A*0202, A*0203, A*0204, A*0205, A*0206, A*0207, A*6802, and A*6901. As explained in detail below, binding to each of the individual allele-specific HLA molecules can be modulated by substitutions at the primary anchor and/or secondary anchor positions.

Representative peptide epitopes that contain the A2 supermotif are set forth on the attached Table VII.

IV.C.2.c) HLA-A3 Supermotif

The HLA-A3 supermotif is characterized by peptide ligands having primary anchor residues: A, L, I, V, M, S, or, T at position 2, and positively charged residues, such as R or K at the C-terminal position (in position 9 of 9-mers). Exemplary members of the corresponding HLA family of HLA molecules (the HLA-A3 superfamily) that bind the A3 supermotif include: A3 (A*0301), A11 (A*1101), A31 (A*3101), A*3301, and A*6801. Other allele-encoded HLA molecules predicted to be members of the A3 superfamily include A34, A66, and A*7401. As explained in detail below, peptide binding to each of the individual allele-specific HLA proteins can be modulated by substitutions of amino acids at the primary and/or secondary anchor positions of the peptide.

Representative peptide epitopes that contain the A3 supermotif are set forth on the attached Table VIII.

IV.C.2.d) HLA-A24 Supermotif

The HLA-A24 supermotif is characterized by the presence in peptide ligands of an aromatic (F, W, or Y) residue as a primary anchor in position 2 and a hydrophobic (Y, F, L, I, V, or M) residue as primary anchor at the C-terminal position. The corresponding family of HLA molecules that bind. to the A24 supermotif (the A24 supertype) includes A*2402, A*3001, and A*2301. Peptide binding to each of the allele-specific HLA molecules can be modulated by substitutions at primary anchor positions.

Representative peptide epitopes that contain the A24 supermotif are set forth on the attached Table IX.

IV.C.2.e) HLA-B7 Supermotif

The HLA-B7 supermotif is characterized by peptides bearing proline in position 2 as a primary anchor and hydrophobic or aliphatic amino acids (L, I, V, M, A, F, W, or Y) as the primary anchor at the C-terminal position. The corresponding family of HLA molecules that bind the B7 supermotif (the HLA-B7 supertype) is comprised of at least a dozen HLA-B proteins including B7, B*3501-1, B*3502-2, B*3501-3, B51, B*5301, B*5401, B*5501, B*5401, B*5501, B*5502, B*5601, B*6701, and B*7801 (See, e.g., Sidney, et. al., *J. Immunol.* 154:247 (1995); Barber, et. al., *Curr. Biol.* 5:179 (1995); Hill, et al., *Nature* 360:434 (1992); Rammensee, et al., *Immunogenetics* 41:178 (1995)). As explained in detail below, peptide binding to each of the individual allele-specific HLA proteins can be modulated by substitutions at the primary and/or secondary anchor positions of the peptide.

Representative peptide epitopes that contain the B7 supermotif are set forth on the attached Table X.

IV.C.2.f) HLA-B27 Supermotif

The HLA-B27 supermotif is characterized by the presence in peptide ligands of positively charged (R, H, or K) residues as primary anchors at position 2 and hydrophobic (A, L, I, V, M, Y, F, or W) residues as primary anchors at the C-terminal. Exemplary members of the corresponding HLA molecules that bind to the B27 supermotif (the B27 supertype) include B*14, B*1509, B*38, B*3901, B*3902, B*73, and various B27 subtypes. Peptide binding to each of the allele-specific HLA molecules can be modulated by substitutions at primary anchor positions.

Representative peptide epitopes that contain the B27 supermotif are set forth on the attached Table XI.

IV.C.2.g) HLA-B44 Supermotif

The HLA-B44 supermotif is characterized by the presence in peptide ligands of negatively charged (D or E) residues as a primary anchor in position 2, and hydrophobic residues (F, W, Y, L, I, M V, or A) as a primary anchor at the C-terminal. Exemplary members of the corresponding family of HLA molecules that bind to the B44 supermotif (the B44 supertype) include B*3701, B*4402, B*4403, B60, and B61. Peptide binding to each of the allele-specific HLA molecules can be modulated by substitutions at primary anchor positions.

Representative peptide epitopes that contain the B44 supermotif are set forth on the attached Table XII.

IV.C.2.h) HLA-B58 Supermotif

The HLA-B58 supermotif is characterized by the presence in peptide ligands of small aliphatic residues (A, S, or T) as primary anchor residues at position 2 and aromatic or hydrophobic residues (F, W, Y, L, I, or V) as primary anchor residues at the C-terminal. Exemplary members of the corresponding HLA molecules that bind to the B58 supermotif (the B58 supertype) include B*1516, B*1517, B*5701, B*5702, and B*58. Peptide binding to each of the allele-specific HLA molecules can be modulated by substitutions at primary anchor positions.

Representative peptide epitopes that contain the B58 supermotif are set forth on the attached Table XIII.

IV.C.2.i) HLA-B62 Supermotif

The HLA-B62 supermotif is characterized by the presence in peptide ligands of the polar aliphatic residue Q or the hydrophobic aliphatic residues (L, V, M, or I) as a primary anchor in position 2 and hydrophobic residues (F, W, Y, M, I, or V) as a primary anchor at the C-terminal position. Exemplary members of the corresponding HLA molecules that a bind to the B62 supermotif (the B62 supertype) include B46, B52, B62, B75, and B77. Peptide binding to each of the allele-specific HLA molecules can be modulated by substitutions at primary anchor positions.

Representative peptide epitopes that contain the B62 supermotif are set forth on the attached Table XIV.

IV.C.2.j) HLA-A1 Motif

The allele-specific HLA-A1 motif is characterized by the presence in peptide ligands of T, S, or M as a primary anchor residue at position 2 and the presence of Y as a primary anchor residue at the C-terminal position. Alternatively, a primary anchor residue may be present at position 3 rather than position 2. This motif is characterized by the presence of D, E, A, or S as a primary anchor residue in position 3 and a Y as a primary anchor residue at the C-terminus. Peptide binding to HLA A1 can be modulated by substitutions at primary and/or secondary anchor positions.

Representative peptide epitopes that contain the A1 motif are set forth on the attached Table XV.

IV.C.2.k) HLA-A3 Motif

The allele-specific HLA-A3 motif is characterized by the presence in peptide ligands of L, M, V, I, S, A, T, F, C, G, or D as a primary anchor residue at position 2 and the presence of K, Y, R, H, F, or A as the primary anchor residue at the C-terminal position. Peptide binding to HLA-A3 can be modulated by substitutions at primary and/or secondary anchor positions.

Representative peptide epitopes that contain the A3 motif are set forth on the attached Table XVI.

IV.C.2.l) HLA-A11 Motif

The allele-specific HLA-A11 motif is characterized by the presence in peptide ligands of V, T, M, L, I, S, A, G, N, C, D, or F as a primary anchor residue in position 2 and K, R, Y, or H as a primary anchor residue at the C-terminal position. Peptide binding to HLA-A11 can be modulated by substitutions at primary and/or secondary anchor positions.

Representative peptide epitopes that contain the A11 motif are set forth on the attached Table XVI; peptides bearing the A3 allele-specific motif are also present in Table XVII. The A11 and A3 motifs have a number of anchor residues in common, separate tables would provide a number of redundant entries.

IV.C.2.m) HLA-A24 Motif

The allele-specific HLA-A24 motif is characterized by the presence in peptide ligands of Y, F, W, or M as a primary anchor residue in position 2 and F, L, I, or W as a primary anchor residue at the C-terminal position. Peptide binding to HLA-A24 molecules can be modulated by substitutions at primary and/or secondary anchor positions.

Representative peptide epitopes that contain the A24 motif are set forth on the attached Table XVII.

IV.C.2.n) HLA-A2.1 Motif

The allele-specific HLA-A2.1 motif was first determined to be characterized by the presence in peptide ligands of L, M, V, I, A or T as a primary anchor residue in position 2 and, L, V, I, A, or T as a primary anchor residue at the C-terminal position. The preferred and tolerated residues that characterize the primary anchor positions of the HLA-A2.1 motif are identical to the preferred residue of the A2 supermotif. Secondary anchor residues that characterize the A2.1 motif have additionally been defined as disclosed herein. These are disclosed in Table II. Peptide binding to HLA-A2.1 molecules can be modulated by substitutions at primary and/or secondary anchor positions.

Representative peptide epitopes that contain the A2.1 motif are set forth on the attached Table VII. These peptides, which bear the HLA-A2 supermotif, also contain secondary anchor residues that are characteristic of the HLA-A2.1 motif. In one embodiment, the peptide epitope does not bear an L or M at position 2 and V at the C-terminal position 9 of a 9-amino acid peptide.

The primary anchor residues of the HLA class I peptide epitope supermotifs and motifs delineated above are summarized in Table I. Primary and secondary anchor positions are summarized in Table II.

Motifs Indicative of Class II HTL Inducing Peptide Epitopes

IV.C.2.o) HLA DR-1-4-7 Supermotif

Motifs have also been identified for peptides that bind to three common HLA class II types, HLA DRB1*0401, DRB1*0101, and DRB1*0701. Peptides binding to these DR molecules carry a motif characterized by a large aromatic or hydrophobic residue in position 1 (Y, F, W, L, I, V, or M) and a small, non-charged residue in position 6 (S, T, C, AP, V, I, L, or M). Allele specific secondary effects and secondary anchors for each of these HLA types have also been identified. These are set forth in Table III. Peptide binding to HLA-DR4, DR1, and DR7 can be modulated by substitutions at primary and/or secondary anchor positions.

Representative peptides are set forth in Table XVIII.

IV.C.2.p) HLA DR3 Motifs

Two alternative motifs characterize peptides that bind to HLA-DR3 molecules. In the first motif, a large, hydrophobic residue (I, L, V, M, Y, or F) is present in anchor position 1 and D is present as an anchor at position 4, which is defined as being 3 positions from anchor position 1 towards the carboxyl terminus regardless of the location of anchor position 1 in the peptide. Lack of either the large, hydrophobic residue at anchor position 1, or of the negatively charged or amide-like anchor residue at position 4 may be compensated for by the presence of a positive charge at position 6 (which is defined as being 5 positions from anchor position 1 towards the carboxyl terminus). Thus for the second, alternative motif I, L, V, M, Y, F, or A is present at anchor position 1; D, N, Q, E, S, or T is present at anchor position 4; and K, R, or H is present at anchor position 6. Peptide binding to HLA-DR3 can be modulated by substitutions at primary and/or secondary anchor positions.

Representative peptides are set forth in Table IXX.

IV.C.3. Enhancing Population Coverage of the Vaccine

Vaccines that have broad population coverage are preferred because they are more commercially viable and generally applicable to the most people. Broad population coverage can be obtained using the peptides of the invention (and nucleic acid compositions that encode such peptides) through selecting peptide epitopes that bind to HLA alleles which, when considered in total, are present in most of the population. Table XX lists the overall frequencies of the A2-, A3-, and B7-supertypes in various ethnicities. Coverage in excess of 80% is achieved with these motifs. These results suggest that effective and non-ethnically biased population coverage is achieved upon use of a limited number of cross-reactive peptides. Although the population coverage reached with these three main peptide specificities is high, coverage can be expanded to reach 95% population coverage and above, and more easily achieve truly multispecific responses upon use of additional supermotif or allele-specific motif bearing peptides.

Table XX summarizes the HLA supertypes that have been identified, and indicates an estimate of their combined prevalence in major ethnic groups. The B44-, A1-, and A24-supertypes are present, on average, in over 25% of the world's major ethnic populations. While less prevalent overall, the B27-, B58-, and B62 supertypes are each present with a frequency >25% in at least one major ethnic group. The Table indicates the population coverage achieved by the A2-, A3-, and B7-supertypes, and the incremental coverage obtained by the addition of A1-, A24-, and B44-supertypes, or all of the supertypes described herein. As shown, by including epitopes from the six most frequent supertypes, an average population coverage of 99% is obtained for five major ethnic groups.

The data presented herein, together with the previous definition of the A2-, A3-, and B7-supertypes, indicates that all antigens, with the possible exception of A29, B8, and B46, can be classified into a total of nine HLA supertypes. Focusing on the six most common supertypes affords population coverage greater than 98% for all major ethnic populations.

IV.D. Immune Response Stimulating Peptide Analogs

Although peptides with suitable cross-reactivity among all alleles of a superfamily are identified by the screening procedures described above, cross-reactivity is not always complete and in such cases procedures to further increase cross-reactivity of peptides can be useful; such procedures can also be used to modify other properties of the peptides. Having established the general rules that govern cross-reactivity of peptides for HLA alleles within a given motif or supermotif, modification (i.e., analoging) of the structure of peptides of particular interest in order to achieve broader (or otherwise modified) HLA binding capacity can be performed. More specifically, peptides which exhibit the broadest cross-reactivity patterns, (both amongst the known T cell epitopes, as well as the more extended set of peptides that contain the appropriate supermotifs), can be produced in accordance with the teachings herein.

The strategy employed utilizes the motifs or supermotifs which correlate with binding to certain HLA molecules. The motifs or supermotifs are defined by having primary anchors, though secondary anchors can also be modified. Analog peptides can be created by substituting amino acids residues at primary anchor, secondary anchor, or at primary and secondary anchor positions. Generally, analogs are made for peptides that already bear a motif or supermotif. Preferred secondary anchor residues of supermotifs and motifs that have been defined for HLA class I and class II binding peptides are shown in Tables II and III, respectively.

For a number of the motifs or supermotifs in accordance with the invention, residues are defined which are deleterious to binding to allele-specific HLA molecules or members of HLA supertypes that bind to the respective motif or supermotif (Tables II and III). Accordingly, removal of residues that are detrimental to binding can be performed in accordance with the present invention. For example, in the case of the A3 supertype, when all peptides that have such deleterious residues are removed from the population of analyzed peptides, the incidence of cross-reactivity increases from 22% to 37% (see, e.g., Sidney, J. et al., *Hu. Immunol.* 45:79, 1996). Thus, one strategy to improve the cross-reactivity of peptides within a given supermotif is simply to delete one or more of the deleterious residues present within a peptide and substitute a small "neutral" residue such as Ala (that may not influence T cell recognition of the peptide). An enhanced likelihood of cross-reactivity is expected if, together with elimination of detrimental residues within a peptide, residues associated with high affinity binding to multiple alleles within a superfamily are inserted.

To ensure that changes in the native or original epitope recognized by T cells do not lead to a failure of killing antigen presenting cells presenting the unaltered "wild type" peptide (or, in the case of class II epitopes, a failure to elicit helper T cells that cross-react with the wild type peptides), the variant peptide may be used to immunize T cells in vitro from individuals of the appropriate HLA allele, and the cells' capacity to induce lysis of wild type peptide sensitized target cells is evaluated. In both class I and class II systems it will be desirable to use as targets, cells that have been either infected or transfected with the appropriate genes to establish whether endogenously produced antigen is also recognized by the relevant T cells.

Another embodiment of the invention to ensure adequate numbers of cross-reactive cellular binders is to create analogs of weak binding peptides. Class I peptides exhibiting binding affinities of 500–50000 nM, and carrying an acceptable but suboptimal primary anchor residue at one or both positions can be "fixed" by substituting preferred anchor residues in accordance with the respective supertype. The analog peptides can then be tested for crossbinding activity.

Another embodiment for generating effective peptide analogs involves the substitution of residues that have an adverse impact on peptide stability or solubility in a liquid environment. This substitution may occur at any position of the peptide epitope. For example, a cysteine (C) can be substituted out in favor of α-amino butyric acid. Due to its chemical nature, cysteine has the propensity to form disulfide bridges and sufficiently alter the peptide structurally so as to reduce binding capacity. Substituting α-amino butyric acid for C not only alleviates this problem, but actually improves binding and crossbinding capability in certain instances (Review: A. Sette et al, In: Persistent Viral Infections, Eds. R. Ahmed and I. Chen, John Wiley & Sons, England, in press, 1998). Substitution of cysteine with α-amino butyric acid may occur at any residue of a peptide epitope, i.e. at either anchor or non-anchor positions.

In general, CTL and HTL responses are not directed against all possible epitopes. Rather, they are restricted to a few immunodominant determinants (Zinkemagel, et al., Adv. Immunol. 27:5159, 1979; Bennink, et al., J. Exp. Med. 168:19351939, 1988; Rawle, et al., J. Immunol. 146:3977–3984, 1991). It has been recognized that immunodominance (Benacerraf, et al., Science 175:273–279, 1972) could be explained by either the ability of a given epitope to selectively bind a particular HLA protein (determinant selection theory) (Vitiello, et al., J. Immunol. 131:1635, 1983); Rosenthal, et al., Nature 267:156–158, 1977), or being selectively recognized by the existing TCR (T cell receptor) specificity (repertoire theory) (Klein, J., Immunology, the Science of SelfNonself Discrimination, John Wiley & Sons, New York, pp. 270–310, 1982). It has been demonstrated that additional factors, mostly linked to processing events, can also play a key role in dictating, beyond strict immunogenicity, which of the many potential determinants will be presented as immunodominant (Sercarz, et al., Annu. Rev. Immunol. 11:729–766, 1993).

The concept of dominance and subdominance is relevant to immunotherapy of both infectious diseases and cancer. For example, in the course of chronic viral disease, recruitment of subdominant epitopes can be important for successful clearance of the infection, especially if dominant CTL or HTL specificities have been inactivated by functional tolerance, suppression, mutation of viruses and other mechanisms (Franco, et al., Curr. Opin. Immunol. 7:524–531, (1995)). In the case of cancer and tumor antigens, CTLs recognizing at least some of the highest binding affinity peptides might be functionally inactivated. Lower binding affinity peptides are preferentially recognized at these times.

In particular, it has been noted that a significant number of epitopes derived from known non-viral tumor associated antigens (TAA) bind HLA class I with intermediate affinity ($IC_{50}$ in the 50–500 nM range). For example, it has been found that 8 of 15 known TAA peptides recognized by tumor infiltrating lymphocytes (TIL) or CTL bound in the 50–500 nM range. (These data are in contrast with estimates that 90% of known viral antigens that were recognized as peptides bound HLA with $IC_{50}$ of 50 nM or less, while only approximately 10% bound in the 50–500 nM range (Sette, et al., J. Immunol., 153:558–5592 (1994)). In the cancer setting this phenomenon is probably due to elimination, or functional inhibition of the CTL recognizing several of the highest binding peptides, presumably because of T cell tolerization events.

Without intending to be bound by theory, it is believed that because T cells to dominant epitopes may have been clonally deleted, selecting subdominant epitopes may allow extant T cells to be recruited, which will then lead to a therapeutic response. However, the binding of HLA molecules to subdominant epitopes is often less vigorous than to dominant ones. Accordingly, there is a need to be able to modulate the binding affinity of particular immunogenic epitopes for one or more HLA molecules, and thereby to modulate the immune response elicited by the peptide. Thus a need exists to prepare analog peptides which elicit a more vigorous response. This ability would greatly enhance the usefulness of peptide-based vaccines and therapeutic agents.

Representative analog peptides are set forth in Table XXI. The Table indicates the length and sequence of the analog peptide as well as the motif or supermotif, if appropriate. The information in the "Fixed Nomenclature" column indicates the residues substituted at the indicated position numbers for the respective analog.

IV.E. Computer Screening of Protein Sequences from Disease-Related Antigens for Supermotif or Motif Containing Peptides Computer programs that allow the rapid screening of protein sequences for the occurrence of the subject supermotifs or motifs are encompassed by the present invention; as are programs that permit the generation of analog peptides. These programs are implemented to analyze any identified amino acid sequence or operate on an unknown sequence and simultaneously determine the sequence and identify motif-bearing epitopes thereof; analogs can be simultaneously determined as well. Generally, the identified sequences will be from a pathogenic organism or a tumor-associated peptide. For example, the target molecules considered herein include all of the HBV proteins (e.g. surface, core, polymerase, and X).

In cases where the sequence of multiple variants of the same target protein are available, peptides are also selected on the basis of their conservancy. A presently preferred criterion for conservancy defines that the entire sequence of a peptide be totally conserved in 75% of the sequences evaluated for a specific protein; this definition of conservancy has been employed herein.

It is important that the selection criteria utilized for prediction of peptide binding are as accurate as possible, to correlate most efficiently with actual binding. Prediction of peptides that bind, for example, to HLA-A*0201, on the basis of the presence of the appropriate primary anchors, is positive at about a 30% rate (Ruppert, J. et al. Cell 74:929, 1993). However, by analyzing an extensive peptide-HLA binding database, the present inventors have developed a number of allele specific polynomial algorithms that dramatically increase the predictive value over identification on the basis of the presence of primary anchor residues alone. These algorithms take into account not only the presence or absence of the correct primary anchors, but also consider the positive or deleterious presence of secondary anchor residues (to account for the impact of different amino acids at different positions). The algorithms are essentially based on the premise that the overall affinity (or AG) of peptide-HLA interactions can be approximated as a linear polynomial function of the type:

$$\Delta G = a_{1i} \times a_{2i} \times a_{3i} \ldots \times a_{ni}$$

where $a_{ij}$ is a coefficient that represents the effect of the presence of a given amino acid (j) at a given position (i) along the sequence of a peptide of n amino acids. An important assumption of this method is that the effects at each position are essentially independent of each other. This assumption is justified by studies that demonstrated that peptides are bound to HLA molecules and recognized by T cells in essentially an extended conformation. Derivation of specific algorithm coefficients has been described in Gulukota et al. (Gulukota, K. et al., J.Mol.Biol. 267:1258, 1997).

Additional methods to identify preferred peptide sequences, which also make use of specific motifs, include the use of neural networks and molecular modeling programs (Gulukota, K. et al., J.Mol.Biol. 267:1258, 1997; Milik et al., Nature Biotechnology 16:753, 1998; Altuvia et al., Hum. Immunol. 58:1, 1997; Altuvia et al, J. Mol. Biol. 249:244, 1995).

For example, it has been shown that in sets of A*0201 motif peptides, 69% of the peptides containing at least one preferred secondary anchor residue while avoiding the presence of any deleterious secondary anchor residues, will bind A*0201 with an $IC_{50}$ less than 500 nM (Ruppert, J. et al. *Cell* 74:929, 1993). These algorithms are also flexible in that cut-off scores may be adjusted to select sets of peptides with greater or lower predicted binding properties, as desired.

In utilizing computer screening to identify peptide epitopes, all protein sequence or translated sequence may be analyzed using software developed to search for motifs, for example the "FINDPATTERNS" program (Devereux, et al. *Nucl. Acids Res.* 12:387–395, 1984) or MotifSearch 1.4 software program (D. Brown, San Diego, Calif.) to identify potential peptide sequences containing appropriate HLA binding motifs. As appreciated by one of ordinary skill in the art a large array of software and hardware options are available which can be employed to implement the motifs of the invention relative to known or unknown peptide sequences. The identified peptides will then be scored using customized polynomial algorithms to predict their capacity to bind specific HLA class I or class II alleles.

In accordance with the procedures described above, HBV peptides and analogs thereof that are able to bind HLA supertype groups or allele-specific HLA molecules have been identified (Tables VI–XIX; Table XXI).

IV.F. Assays to Detect T-Cell Responses

Once HLA binding peptides are identified, they can be tested for the ability to elicit a T-cell response. The preparation and evaluation of motif-bearing peptides are described in PCT publications WO 94/20127 and WO 94/03205. Briefly, peptides comprising epitopes from a particular antigen are synthesized and tested for their ability to bind to the appropriate HLA proteins in assays using, for example, purified HLA class I molecules and radioiodonated peptides and/or cells expressing empty class I molecules (which lack peptide in their receptor) by, for instance, immunofluorescent staining and flow microfluorimetry, peptide-dependent class I assembly assays, and inhibition of CTL recognition by peptide competition. Those peptides that bind to the class I molecule are further evaluated for their ability to serve as targets for CTLs derived from infected or immunized individuals, as well as for their capacity to induce primary in vitro or in vivo CTL responses that can give rise to CTL populations capable of reacting with selected target cells associated with a disease. Corresponding assays are used for evaluation of HLA class II binding peptides.

Conventional assays utilized to detect CTL responses include proliferation assays, lymphokine secretion assays, direct cytotoxicity assays, and limiting dilution assays. For example, antigen-presenting cells that have been incubated with a peptide can be assayed for the ability to induce CTL responses in responder cell populations. Antigen-presenting cells can be normal cells such as peripheral blood mononuclear cells or dendritic cells. Alternatively, mutant mammalian cell lines that are deficient in their ability to load class I molecules with internally processed peptides and that have been transfected with the appropriate human class I gene may be used to test for the capacity of the peptide to induce in vitro primary CTL responses.

Peripheral blood lymphocytes may be used as the responder cell source of CTL precursors. The appropriate antigen-presenting cells are incubated with peptide and the peptide-loaded antigen-presenting cells are then incubated with the responder cell population under optimized culture conditions. Positive CTL activation can be determined by assaying the culture for the presence of CTLs that kill radio-labeled target cells, both specific peptide-pulsed targets as well as target cells expressing endogenously processed forms of the HBV antigen from which the peptide sequence was derived.

More recently, a method has also been devised which allows direct quantification of antigen-specific T cells by staining with Fluorescein-labelled HLA tetrameric complexes (Altman, J. D. et al., *Proc. Natl. Acad. Sci. USA* 90:10330, 1993; Altman, J. D. et al., *Science* 274:94, 1996). Other relatively recent technical developments include staining for intracellular lymphokines, and interferon release assays or ELISPOT assays. Tetramer staining, intracellular lymphokine staining and ELISPOT assays all appear to be at least 10-fold more sensitive than more conventional assays (Lalvani, A. et al., *J. Exp. Med.* 186:859, 1997; Dunbar, P. R. et al., *Curr. Biol.* 8:413, 1998; Murali-Krishna, K. et al., *Immunity* 8:177, 1998).

HTL activation may also be assessed using such techniques as T cell proliferation and secretion of lymphokines, e.g. IL-2.

Alternatively, immunization of HLA transgenic mice can be used to determine immunogenicity of peptide epitopes. Several transgenic mouse models including mice with human A2.1, A11, and B7 alleles have been characterized and others (e.g., transgenic mice for HLA-A1 and A24) are being developed. HLA-DR1 and HLA-DR3 mouse models have also been developed. Additional transgenic mouse models with other HLA alleles may be generated as necessary. Mice may be immunized with peptides emulsified in Incomplete Freund's Adjuvant and the resulting T cells tested for their capacity to recognize peptide-pulsed target cells and target cells transfected with appropriate genes. CTL responses may be analyzed using cytotoxicity assays described above. Similarly, HTL responses may be analyzed using such assays as T cell proliferation or secretion of lymphokines.

IV.G. Preparation of Peptides

Peptides in accordance with the invention can be prepared synthetically, by recombinant DNA technology, or from natural sources such as native tumors or pathogenic organisms. Peptide epitopes may be synthesized individually or as polyepitopic peptides. Although the peptide will preferably be substantially free of other naturally occurring host cell proteins and fragments thereof, in some embodiments the peptides may be synthetically conjugated to native fragments or particles.

The peptides in accordance with the invention can be a variety of lengths, and either in their neutral (uncharged) forms or in forms which are salts. Peptides may be synthesized The peptides in accordance with the invention are either free of modifications such as glycosylation, side chain oxidation, or phosphorylation; or they contain these modifications, subject to the condition that modifications do not destroy the biological activity of the peptides as described herein.

Desirably, the peptide will be as small as possible while still maintaining substantially all of the biological activity of the large peptide. When possible, it may be desirable to optimize HLA class I binding peptides of the invention to a length of about 8 to about 13 amino acid residues, preferably 9 to 10. HLA class II binding peptides may be optimized to a length of about 6 to about 25 amino acids in length, preferably to between about 13 and about 20 residues. Preferably, the peptides are commensurate in size with endogenously processed pathogen-derived peptides or tumor cell peptides that are bound to the relevant HLA molecules. Moreover, the identification and preparation of peptides of other lengths can be carried out using the techniques described herein (e.g., the disclosures regarding primary and secondary anchor positions). However, it is also preferred to identify a larger region of a native peptide that encompasses one and preferably two or more epitopes in accordance with the invention. This sequence is selected on the basis that it contains the greatest number of epitopes per amino acid length. It is to be appreciated that epitopes can be present in a frame-shifted manner, e.g. a 10 amino acid long peptide could contain two 9 amino acid long epitopes and one 10 amino acid long epitope; each epitope can be exposed and bound by an HLA molecule upon administration of a plurality of such peptides. This larger, preferably multi-epitopic, peptide can then be generated synthetically, recombinantly, or via cleavage from the native source.

The peptides of the invention can be prepared in a wide variety of ways. For the preferred relatively short size, the peptides can be synthesized in solution or on a solid support in accordance with conventional techniques. Various automatic synthesizers are commercially available and can be used in accordance with known protocols. See, for example, Stewart & Young, *Solid Phase Peptide Synthesis*, 2d. ed., Pierce Chemical Co. (1984). Further, individual peptides may be joined using chemical ligation to produce larger peptides.

Alternatively, recombinant DNA technology may be employed wherein a nucleotide sequence which encodes an immunogenic peptide of interest is inserted into an expression vector, transformed or transfected into an appropriate host cell and cultivated under conditions suitable for expression. These procedures are generally known in the art, as described generally in Sambrook et al., *Molecular Cloning, a Laboratory Manual, Cold Spring Harbor Press*, Cold Spring Harbor, N.Y. (1989). Thus, recombinant polypeptides which comprise one or more peptide sequences of the invention can be used to present the appropriate T cell epitope.

As the nucleotide coding sequence for peptides of the preferred lengths contemplated herein can be synthesized by chemical techniques, for example, the phosphotriester method of Matteucci, et al., *J. Am. Chem. Soc.* 103:3185 (1981) modification can be made simply by substituting the appropriate and desired nucleic acid base(s) for those that encode the native peptide sequence. The coding sequence can then be provided with appropriate linkers and ligated into expression vectors commonly available in the art, and the vectors used to transform suitable hosts to produce the desired fusion protein. A number of such vectors and suitable host systems are now available. For expression of the fusion proteins, the coding sequence will be provided with operably linked start and stop codons, promoter and terminator regions and usually a replication system to provide an expression vector for expression in the desired cellular host. For example, promoter sequences compatible with bacterial hosts are provided in plasmids containing convenient restriction sites for insertion of the desired coding sequence. The resulting expression vectors are transformed into suitable bacterial hosts. Of course, yeast, insect or mammalian cell hosts may also be used, employing suitable vectors and control sequences.

IV.H. Peptide Epitope Reagents to Evaluate Immune Responses

HLA class I and class II binding peptides as described herein can be used, in one embodiment of the invention, as reagents to evaluate an immune response. The immune response to be evaluated may be induced by using as an immunogen any agent that would potentially result in the production of antigen-specific CTLs or HTLs to the peptide epitope(s) to be employed as the reagent. The peptide reagent is not used as the immunogen.

For example, a peptide of the invention may be used in a tetramer staining assay to assess peripheral blood mononuclear cells for the presence of antigen-specific CTLs following exposure to a pathogen or immunogen. The HLA-tetrameric complex is used to directly visualize antigen-specific CTLs (see, e.g., Ogg et al. Science 279:2103–2106, 1998; and Altman et al. Science 174:94–96, 1996) and determine the frequency of the antigen-specific CTL population in a sample of peripheral blood mononuclear cells. A tetramer reagent using a peptide of the invention may be generated as follows: A peptide that binds to an allele-specific HLA molecules, or supertype molecules, is refolded in the presence of the corresponding HLA heavy chain and $\beta_2$-microglobulin to generate a trimolecular complex. The complex is biotinylated at the carboxyl terminal end of the heavy chain at a site that was previously engineered into the protein. Tetramer formation is then induced by the addition of streptavidin. By means of fluorescently labeled streptavidin, the tetramer can be used to stain antigen-specific cells. The cells may then be identified, for example, by flow cytometry. Such an analysis may be used for diagnostic or prognostic purposes.

Peptides of the invention may also be used as reagents to evaluate immune recall responses. (see, e.g., Bertoni et al. *J. Clin. Invest.* 100:503–513, 1997 and Penna et al. *J. Exp. Med.* 174:1565–1570, 1991.) For example, patient PBC samples from individuals with acute hepatitis B or who have recently recovered from acute hepatitis B may be analyzed for the presence of HBV antigen-specific CTLs using HBV-specific peptides. A blood sample containing mononuclear cells may be evaluated by cultivating the PBCs and stimulating the cells with a peptide of the invention. After an appropriate cultivation period, the expanded cell population may be analyzed for cytotoxic activity.

The peptides may also be used as reagents to evaluate the efficacy of a vaccine. PBMCs obtained from a patient vaccinated with an immunogen may be analyzed using, for example, either of the methods described above. A patient is HLA typed, and appropriate peptide reagents that recognize allele-specific molecules present in that patient may be selected for the analysis. The immunogenicity of the vaccine will be indicated by the presence of HBV epitope-specific CTLs in the PBMC sample.

IV.I. Vaccine Compositions

Vaccines that contain as an active ingredient an immunogenically effective amount of one or more peptides as described herein are a further embodiment of the invention. Once appropriately immunogenic epitopes have been defined, they can be sorted and delivered by various means, herein referred to as "vaccine" compositions. Such vaccine compositions can include, for example, lipopeptides (Vitiello, A. et al., *J. Clin. Invest.* 95:341, 1995), peptides compositions encapsulated in poly(DL-lactide-co-glycolide) (PLG) microspheres (see, e.g., Eldridge, et al. *Molec. Immunol.* 28:287–294, 1991: Alonso et al. Vaccine 12:299–306, 1994; Jones et al. *Vaccine* 13:675–681, 1995), peptide compositions encapsulated in immune stimulating complexes (ISCOMS) (see, e.g., Takahashi et al. Nature 344:873–875, 1990; Hu et al. Clin Exp Immunol.

113:235–243, 1998), multiple antigen peptide systems (MAPs) (see e.g., Tam, J. P., Proc. Natl. Acad. Sci. U.S.A. 85:5409–5413, 1988; Tam, J. P., J. Immunol. Methods 196:17–32, 1996), viral delivery vectors (Perkus, M. E. et al., In: *Concepts in vaccine development*, Kaufmann, S. H. E., ed., p. 379, 1996; Chakrabarti, S. et al., *Nature* 320:535, 1986; Hu, S. L. et al., *Nature* 320:537, 1986; Kieny, M.-P. et al., *AIDS Bio/Technology* 4:790, 1986; Top, F. H. et al., *J. Infect. Dis.* 124:148, 1971; Chanda, P. K. et al., *Virology* 175:535, 1990), particles of viral or synthetic origin (Kofler, N. et al., *J. Immunol. Methods*. 192:25, 1996; Eldridge, J. H. et al., *Sem. Hematol.* 30:16, 1993; Falo, L. D., Jr. et al., *Nature Med.* 7:649, 1995), adjuvants (Warren, H. S., Vogel, F. R., and Chedid, L. A. *Annu. Rev. Immunol.* 4:369, 1986; Gupta, R. K. et al., *Vaccine* 11:293, 1993), liposomes (Reddy, R. et al., *J. Immunol.* 148:1585, 1992; Rock, K. L., *Immunol. Today* 17:131, 1996), or, naked or particle absorbed cDNA (Ulmer, J. B. et al., *Science* 259:1745, 1993; Robinson, H. L., Hunt, L. A., and Webster, R. G., *Vaccine* 11:957, 1993; Shiver, J. W. et al., In: *Concepts in vaccine development*, Kaufmann, S. H. E., ed., p. 423, 1996; Cease, K. B., and Berzofsky, J. A., *Annu. Rev. Immunol.* 12:923, 1994 and Eldridge, J. H. et al., *Sem. Hematol.* 30:16, 1993). Toxin-targeted, also know as receptor mediated targeting, delivery technologies also may be used such as those of Avant Immunotherapeutics, Inc. (Needham, Mass.).

Furthermore, vaccines in accordance with the invention encompass compositions of one or more of the claimed peptide(s) that can be introduced into a host, including humans, linked to its own carrier, or as a homopolymer or heteropolymer of active peptide units. Such a polymer has the advantage of increased immunological reaction and, where different peptides are used to make up the polymer, the additional ability to induce antibodies and/or CTLs that react with different antigenic determinants of the pathogenic organism or tumor-related peptide targetted for an immune response.

Furthermore, useful carriers that can be used with vaccines of the invention are well known in the art, and include, e.g., thyroglobulin, albumins such as human serum albumin, tetanus toxoid, polyamino acids such as poly L-lysine, poly L-glutamic acid, influenza, hepatitis B virus core protein, hepatitis B virus recombinant vaccine and the like. The vaccines can contain a physiologically tolerable (i.e., acceptable) diluent such as water, or saline, preferably phosphate buffered saline. The vaccines also typically include an adjuvant. Adjuvants such as incomplete Freund's adjuvant, aluminum phosphate, aluminum hydroxide, or alum are examples of materials well known in the art. Additionally, as disclosed herein, CTL responses can be primed by conjugating peptides of the invention to lipids, such as tripalmitoyl-S-glycerylcysteinlyseryl-serine ($P_3CSS$).

As disclosed in greater detail herein, upon immunization with a peptide composition in accordance with the invention, via injection, aerosol, oral, transdermal, transmucosal, intrapleural, intrathecal, or other suitable routes, the immune system of the host responds to the vaccine by producing large amounts of CTLs specific for the desired antigen, and the host becomes at least partially immune to later infection, or at least partially resistant to developing an ongoing chronic infection.

In some instances it may be desirable to combine the class I peptide vaccines of the invention with vaccines which induce or facilitate neutralizing antibody responses to the target antigen of interest, particularly to viral envelope antigens. A preferred embodiment of such a composition comprises class I and class II epitopes in accordance with the invention. An alternative embodiment of such a composition comprises a class I and/or class II epitope in accordance with the invention, along with a PADRE™ (Epimmune, San Diego, Calif.) molecule (described in the related U.S. Ser. No. 08/485,218, which is a CIP of U.S. Ser. No. 08/305,871, now U.S. Pat. No. 5,736,142, which is a CIP of abandoned application U.S. Ser. No. 08/121,101.) Furthermore, any of these embodiments can be administered as a nucleic acid mediated modality.

For therapeutic or immunization purposes, the peptides of the invention can also be expressed by viral or bacterial vectors. Examples of expression vectors include attenuated viral hosts, such as vaccinia or fowlpox. This approach involves the use of vaccinia virus as a vector to express nucleotide sequences that encode the peptides of the invention. Upon introduction into an acutely or chronically infected host or into a non-infected host, the recombinant vaccinia virus expresses the immunogenic peptide, and thereby elicits a host CTL and/or HTL response. Vaccinia vectors and methods useful in immunization protocols are described in, e.g., U.S. Pat. No. 4,722,848. Another vector is BCG (Bacille Calmette Guerin). BCG vectors are described in Stover, et al. *Nature* 351:456–460 (1991). A wide variety of other vectors useful for therapeutic administration or immunization of the peptides of the invention, e.g. adeno and adeno-associated virus vectors, retroviral vectors, *Salmonella typhi* vectors, detoxified anthrax toxin vectors, and the like, will be apparent to those skilled in the art from the description herein.

Antigenic peptides are used to elicit a CTL and/or HTL response ex vivo, as well. The resulting CTL or HTL cells, can be used to treat chronic infections, or tumors in patients that do not respond to other conventional forms of therapy, or will not respond to a therapeutic vaccine peptide or nucleic acid in accordance with the invention. Ex vivo CTL or HTL responses to a particular pathogen (infectious agent or tumor antigen) are induced by incubating in tissue culture the patient's CTL or HTL precursor cells together with a source of antigen-presenting cells (APC), such as dendritic cells, and the appropriate immunogenic peptide. After an appropriate incubation time (typically about 1–4 weeks), in which the precursor cells are activated, mature and expand into effector cells, the cells are infused back into the patient, where they will destroy (CTL) or facilitate destruction (HTL) of their specific target cell (an infected cell or a tumor cell). Transfected dendritic cells may also be used as antigen presenting cells. Alternatively, dendritic cells are transfected, e.g., with a minigene construct in accordance with the invention, in order to elicit immune responses. Minigenes will be discussed in greater detail in a following section.

DNA or RNA encoding one or more of the peptides of the invention can also be administered to a patient. This approach is described, for instance, in Wolff et. al., *Science* 247:1465 (1990) as well as U.S. Pat. Nos. 5,580,859; 5,589,466; 5,804,566; 5,739,118; 5,736,524; 5,679,647; WO 98/04720; and in more detail below. Examples of DNA-based delivery technologies include "naked DNA", facilitated (bupivicaine, polymers, peptide-mediated) delivery, cationic lipid complexes, and particle-mediated ("gene gun") delivery.

Preferably, the following principles are utilized when selecting an array of epitopes for inclusion in a polyepitopic composition, or for selecting epitopes to be included in a vaccine composition and/or to be encoded by a minigene. It is preferred that each of the following principles are balanced in order to make the selection.

1.) Epitopes are selected which, upon administration, mimic immune responses that have been observed to be correlated with HBV clearance. For HLA Class I this includes 3–4 epitopes that come from at least one antigen of HBV. In other words, it has been observed that in patients who spontaneously clear HBV, that they had generated an immune response to at least 3 epitopes on at least one HBV antigen. For HLA Class II a similar rationale is employed; again 3–4 epitopes are selected from at least one HBV antigen (see e.g., Rosenberg et al. Science 278:1447–1450).

2.) Epitopes are selected that have the requisite binding affinity established to be correlated with imnunogenicity: for HLA Class I an $IC_{50}$ of 500 nM or less, or for Class II an $IC_{50}$ of 1000 nM or less.

3.) Sufficient supermotif bearing peptides, or a sufficient array of allele-specific motif bearing peptides, are selected to give broad population coverage. For example, it is preferable to have at least 80% population coverage. A Monte Carlo analysis, a statistical evaluation known in the art, can be employed to assess population coverage.

4.) When selecting epitopes from cancer-related antigens it is often preferred to select analogs. When selecting epitopes for infectious disease-related antigens it is often preferable to select native epitopes. Therefore, of particular relevance for infectious disease vaccines (but for cancer-related vaccines as well), are epitopes referred to as "nested epitopes." Nested epitopes occur where at least two epitopes overlap in a given peptide sequence. A peptide comprising "transcendent nested epitopes" is a peptide that has both HLA class I and HLA class II epitopes in it.

When providing nested epitopes, it is preferable to provide a sequence that has the greatest number of epitopes per provided sequence. A limitation on this principle is to avoid providing a peptide that is any longer than the amino terminus of the amino terminal epitope and the carboxyl terminus of the carboxyl terminal epitope in the peptide. When providing a longer peptide sequence, such as a sequence comprising nested epitopes, it is important to screen the sequence in order to insure that it does not have pathological or other deleterious biological properties.

5.) When creating a minigene, as disclosed in greater detail in the following section, an objective is to generate the smallest peptide possible that encompasses the epitopes of interest. The principles employed are similar, if not the same as those employed when selecting a peptide comprising nested epitopes. Thus, upon determination of the nucleic acid sequence to be provided as a minigene, the peptide encoded thereby is analyzed to determine whether any "junctional epitopes" have been created. A junctional epitope is an actual binding epitope, as predicted, e.g., by motif analysis. Junctional epitopes are to be avoided because the recipient may generate an immune response to that epitope. Of particular concern is a junctional epitope that is a "dominant epitope." A dominant epitope may lead to such a zealous response that immune responses to other epitopes are diminished or suppressed.

IV.I.1. Minigene Vaccines

A growing body of experimental evidence demonstrates that a number of different approaches are available which allow simultaneous delivery of multiple epitopes. Nucleic acids encoding the peptides of the invention are a particularly useful embodiment of the invention. Epitopes for inclusion in a minigene are preferably selected according to the guidelines above. A preferred means of administering nucleic acids encoding the peptides of the invention uses minigene constructs encoding one or multiple epitopes of the invention. The use of multi-epitope minigenes is described below and in, e.g. An, L. and Whitton, J. L., J. Virol. 71:2292, 1997; Thomson, S. A. et al., J. Immunol. 157:822, 1996; Whitton, J. L. et al., J. Virol. 67:348, 1993; Hanke, R. et al., Vaccine 16:426, 1998. For example, a multi-epitope DNA plasmid encoding nine dominant HLA-A*0201- and A11 -restricted epitopes derived from the polymerase, envelope, and core proteins of HBV and HIV, the PADRE™ universal helper T cell (HTL) epitope, and an ER-translocating signal sequence was engineered. Immunization of HLA transgenic mice with this plasmid construct resulted in strong CTL induction responses against the nine epitopes tested, similar to those observed with a lipopeptide of known immunogenicity in humans, and significantly greater than immunization in oil-based adjuvants. Moreover, the immunogenicity of DNA-encoded epitopes in vivo correlated with the in vitro responses of specific CTL lines against target cells transfected with the DNA plasmid.

For example, to create a DNA sequence encoding the selected epitopes (minigene) for expression in human cells, the amino acid sequences of the epitopes may be reverse translated. A human codon usage table can be used to guide the codon choice for each amino acid. These epitope-encoding DNA sequences may be directly adjoined, so that when translated, a continuous polypeptide sequence is created. To optimize expression and/or immunogenicity, additional elements can be incorporated into the minigene design. Examples of amino acid sequences that could be reverse translated and included in the minigene sequence include: HLA class I epitopes, HLA class II epitopes, a ubiquitination signal sequence, a leader sequence, and/or an endoplasmic reticulum targeting signal. In addition, HLA presentation of CTL and HTL epitopes may be improved by including synthetic (e.g. poly-alanine) or naturally-occurring flanking sequences adjacent to the CTL or HTL epitopes.

The minigene sequence may be converted to DNA by assembling oligonucleotides that encode the plus and minus strands of the minigene. Overlapping oligonucleotides (30–100 bases long) may be synthesized, phosphorylated, purified and annealed under appropriate conditions using well known techniques. The ends of the oligonucleotides can be joined, for example, using T4 DNA ligase. This synthetic minigene, encoding the epitope polypeptide, can then be cloned into a desired expression vector.

Standard regulatory sequences well known to those of skill in the art are preferably included in the vector to ensure expression in the target cells. Several vector elements are desirable: a promoter with a down-stream cloning site for minigene insertion; a polyadenylation signal for efficient transcription termination; an E. coli origin of replication; and an E. coli selectable marker (e.g. ampicillin or kanamycin resistance). Numerous promoters can be used for this purpose, e.g., the human cytomegalovirus (hCMV) promoter. See, e.g., U.S. Pat. Nos. 5,580,859 and 5,589,466 for other suitable promoter sequences.

Additional vector modifications may be desired to optimize minigene expression and immunogenicity. In some cases, introns are required for efficient gene expression, and one or more synthetic or naturally-occurring introns could be incorporated into the transcribed region of the minigene. The inclusion of mRNA stabilization sequences and sequences for replication in mammalian cells may also be considered for increasing minigene expression.

Once an expression vector is selected, the minigene is cloned into the polylinker region downstream of the promoter. This plasmid is transformed into an appropriate E.

*coli* strain, and DNA is prepared using standard techniques. The orientation and DNA sequence of the minigene, as well as all other elements included in the vector, are confirmed using restriction mapping and DNA sequence analysis. Bacterial cells harboring the correct plasmid can be stored as a master cell bank and a working cell bank.

In addition, immunostimulatory sequences (ISSs or CpGs) appear to play a role in the immunogenicity of DNA vaccines. These sequences may be included in the vector, outside the minigene coding sequence, if desired to enhance immunogenicity.

In some embodiments, a bi-cistronic expression vector which allows production of both the minigene-encoded epitopes and a second protein (included to enhance or decrease immunogenicity) can be used. Examples of proteins or polypeptides that could beneficially enhance the immune response if co-expressed include cytokines (e.g., IL-2, IL-12, GM-CSF), cytokine-inducing molecules (e.g., LeIF) or costimulatory molecules. Helper (HTL) epitopes can be joined to intracellular targeting signals and expressed separately from expressed CTL epitopes; this allows direction of the HTL epitopes to a cell compartment different than that of the CTL epitopes. If required, this could facilitate more efficient entry of HTL epitopes into the HLA class II pathway, thereby improving CTL induction. In contrast to HTL or CTL induction, specifically decreasing the immune response by co-expression of immunosuppressive molecules (e.g. TGF-$\beta$) may be beneficial in certain diseases).

Therapeutic quantities of plasmid DNA can be produced for example, by fermentation in *E. coli*, followed by purification. Aliquots from the working cell bank are used to inoculate growth medium, and grown to saturation in shaker flasks or a bioreactor according to well known techniques. Plasmid DNA can be purified using standard bioseparation technologies such as solid phase anion-exchange resins supplied by QIAGEN, Inc. (Valencia, Calif.). If required, supercoiled DNA can be isolated from the open circular and linear forms using gel electrophoresis or other methods.

Purified plasmid DNA can be prepared for injection using a variety of formulations. The simplest of these is reconstitution of lyophilized DNA in sterile phosphate-buffer saline (PBS). This approach, known as "naked DNA," is currently being used for intramuscular (IM) administration in clinical trials. To maximize the immunotherapeutic effects of minigene DNA vaccines, an alternative method for formulating purified plasmid DNA may be desirable. A variety of methods have been described, and new techniques may become available. Cationic lipids can also be used in the formulation (see, e.g., as described by WO 93/24640; Mannino & Gould-Fogerite, *BioTechniques* 6(7): 682 (1988); U.S. Pat. No. 5,279,833; WO 91/06309; and Felgner, et al., *Proc. Nat'l Acad. Sci. USA* 84:7413 (1987). In addition, glycolipids, fusogenic liposomes, peptides and compounds referred to collectively as protective, interactive, non-condensing (PINC) could also be complexed to purified plasmid DNA to influence variables such as stability, intramuscular dispersion, or trafficking to specific organs or cell types.

Target cell sensitization can be used as a functional assay for expression and HLA class I presentation of minigene-encoded CTL epitopes, respectively. For example, the plasmid DNA is introduced into a mammalian cell line that is suitable as a target for standard CTL chromium release assays. The transfection method used will be dependent on the final formulation. Electroporation can be used for "naked" DNA, whereas cationic lipids allow direct in vitro transfection. A plasmid expressing green fluorescent protein (GFP) can be co-transfected to allow enrichment of transfected cells using fluorescence activated cell sorting (FACS). These cells are then chromium-51 ($^{51}$Cr) labeled and used as target cells for epitope-specific CTL lines; cytolysis, detected by $^{51}$Cr release, indicates production of HLA presentation of minigene-encoded CTL epitopes.

In vivo immunogenicity is a second approach for functional testing of minigene DNA formulations. Transgenic mice expressing appropriate human HLA proteins are immunized with the DNA product. The dose and route of administration are formulation dependent (e.g., IM for DNA in PBS, IP for lipid-complexed DNA). Twenty-one days after immunization, splenocytes are harvested and restimulated for 1 week in the presence of peptides encoding each epitope being tested. For CTL effector cells, assays are conducted for cytolysis of peptide-loaded, chromium-51 labeled target cells using standard techniques. Lysis of target cells sensitized by HLA loading of peptides corresponding to minigene-encoded epitopes demonstrates DNA vaccine function for in vivo induction of CTLs.

Alternatively, the nucleic acids can be administered using ballistic delivery as described, for instance, in U.S. Pat. No. 5,204,253. Using this technique, particles comprised solely of DNA are administered. In a further alternative embodiment, DNA can be adhered to particles, such as gold particles.

IV.I.2. Combinations with Helper Peptides

The peptides of the present invention, or analogs thereof, which have immunostimulatory activity may be modified to provide desired attributes, such as improved serum half life, or to enhance immunogenicity.

For instance, the ability of the peptides to induce CTL activity can be enhanced by linking the peptide to a sequence which contains at least one epitope that is capable of inducing a T helper cell response. Particularly preferred immunogenic peptides/T helper conjugates are linked by a spacer molecule. The spacer is typically comprised of relatively small, neutral molecules, such as amino acids or amino acid mimetics, which are substantially uncharged under physiological conditions. The spacers are typically selected from, e.g., Ala, Gly, or other neutral spacers of nonpolar amino acids or neutral polar amino acids. It will be understood that the optionally present spacer need not be comprised of the same residues and thus may be a hetero- or homo-oligomer. When present, the spacer will usually be at least one or two residues, more usually three to six residues. Alternatively, the CTL peptide may be linked to the T helper peptide without a spacer.

The immunogenic peptide may be linked to the T helper peptide either directly or via a spacer either at the amino or carboxy terminus of the CTL peptide. The amino terminus of either the immunogenic peptide or the T helper peptide may be acylated. The T helper peptides used in the invention can be modified in the same manner as CTL peptides. For instance, they may be modified to include D-amino acids or be conjugated to other molecules such as lipids, proteins, sugars and the like. Exemplary T helper peptides include tetanus toxoid 830–843, influenza 307–319, and malarial circumsporozoite 382–398 and 378–389.

In certain embodiments, the T helper peptide is one that is recognized by T helper cells present in the majority of the population. This can be accomplished by selecting amino acid sequences that bind to many, most, or all of the HLA class II molecules. These are known as "loosely HLA-restricted" or "promiscuous" T helper sequences. Examples of amino acid sequences that are promiscuous include sequences from antigens such as tetanus toxoid at positions 830–843 (QYIKANSKFIGITE; SEQ ID NO:2572), *Plasmodium falciparum* CS protein at positions 378–398 (DIEKKIAKMEKASSVFNVVNS; SEQ ID NO:2573), and Streptococcus 18 kD protein at positions 116 (GAVDSILGGVATYGAA; SEQ ID NO:2574). Other examples include peptides bearing a DR 1-4-7 supermotif.

Alternatively, it is possible to prepare synthetic peptides capable of stimulating T helper lymphocytes, in a loosely HLA-restricted fashion, using amino acid sequences not found in nature (see, e.g., PCT publication WO 95/07707). These synthetic compounds called Pan-DR-binding epitopes (e.g., PADRE™, Epimmune, Inc., San Diego, Calif.) are designed on the basis of their binding activity to most HLA-DR (human HLA class II) molecules. For instance, a pan-DR-binding epitope peptide having the formula: aKXVWANTLKAAa, where "X" is either cyclohexvylalanine, phenylalanine, or tyrosine, and a is either D-alanine or L-alanine, (SEQ ID NO:2575) has been found to bind to most HLA-DR alleles, and to stimulate the response of T helper lymphocytes from most individuals, regardless of their HLA type.

T helper epitopes can also be modified to alter their biological properties. For example, peptides presenting T helper epitopes can contain D-amino acids to increase their resistance to proteases and thus extend their serum half-life. Also, the epitope peptides of the invention can be conjugated to other molecules such as lipids, proteins or sugars, or any other synthetic compounds, to increase their biological activity. Specifically, the T helper peptide can be conjugated to one or more palmitic acid chains at either the amino or carboxyl termini.

In some embodiments it may be desirable to include in the pharmaceutical compositions of the invention at least one component which primes cytotoxic T lymphocytes. Lipids have been identified as agents capable of priming CTL in vivo against viral antigens. For example, palmitic acid residues can be attached to the $\epsilon$- and $\alpha$-amino groups of a lysine residue and then linked, e.g., via one or more linking residues such as Gly, Gly-Gly-, Ser, Ser-Ser, or the like, to an immunogenic peptide. The lipidated peptide can then be administered either directly in a micelle or particle, incorporated into a liposome, or emulsified in an adjuvant, e.g., incomplete Freund's adjuvant. In a preferred embodiment, a particularly effective immunogenic comprises palmitic acid attached to $\epsilon$- and $\alpha$-amino groups of Lys, which is attached via linkage, e.g., Ser-Ser, to the amino terminus of the immunogenic peptide.

As another example of lipid priming of CTL responses, *E. coli* lipoproteins, such as tripalmitoyl-S-glycerylcysteinlyseryl-serine ($P_3CSS$) can be used to prime virus specific CTL when covalently attached to an appropriate peptide. See, Deres, et al., *Nature* 342:561 (1989). Peptides of the invention can be coupled to $P_3CSS$, for example, and the lipopeptide administered to an individual to specifically prime a CTL response to the target antigen. Moreover, because the induction of neutralizing antibodies can also be primed with $P_3CSS$-conjugated epitopes, two such compositions can be combined to more effectively elicit both humoral and cell-mediated responses to infection.

In addition, additional amino acids can be added to the termini of a peptide to provide for ease of linking peptides one to another, for coupling to a carrier support, or larger peptide, for modifying the physical or chemical properties of the peptide or oligopeptide, or the like. Amino acids such as tyrosine, cysteine, lysine, glutamic or aspartic acid, or the like, can be introduced at the C- or N-terminus of the peptide or oligopeptide, particularly class I peptides. However, it is to be noted that modification at the carboxyl terminus may, in some cases, alter binding characteristics of the peptide. In addition, the peptide or oligopeptide sequences can differ from the natural sequence by being modified by terminal-$NH_2$ acylation, e.g., by alkanoyl ($C_1$–$C_{20}$) or thioglycolyl acetylation, terminal-carboxyl amidation, e.g., ammonia, methylamine, etc. In some instances these modifications may provide sites for linking to a support or other molecule.

IV.J. Administration of Vaccines for Therapeutic or Prophylactic Purposes

The peptides of the present invention and pharmaceutical and vaccine compositions of the invention are useful for administration to mammals, particularly humans, to treat and/or prevent HBV infection. Vaccine compositions containing the peptides of the invention are administered to a patient susceptible to or otherwise at risk for HBV infection to elicit an immune response against HBV antigens and thus enhance the patient's own immune response capabilities. In therapeutic applications, compositions are administered to a patient in an amount sufficient to elicit an effective CTL response to the virus or tumor antigen and to cure or at least partially arrest or slow symptoms and/or complications. An amount adequate to accomplish this is defined as "therapeutically effective dose." Amounts effective for this use will depend on, e.g., the particular composition administered, the manner of administration, the stage and severity of the disease being treated, the weight and general state of health of the patient, and the judgment of the prescribing physician. Generally the dosage range for an initial immunization (ie., therapeutic or prophylactic administration) is between about 1.0 $\mu$g to about 5000 $\mu$g of peptide, typically between about 10 $\mu$g to about 1000 $\mu$g, for a 70 kg patient, followed by boosting dosages of between about 1.0 $\mu$g to about 5000 $\mu$g of peptide pursuant to a boosting regimen over weeks to months depending upon the patient's response and condition as determined by measuring specific CTL activity in the patient's blood. The peptides and compositions of the present invention may be employed in serious disease states, that is, life-threatening or potentially life threatening situations. In such cases, as a result of the minimal amounts of extraneous substances and the relative nontoxic nature of the peptides in preferred compositions of the invention, it is possible and may be felt desirable by the treating physician to administer substantial excesses of these peptide compositions relative to these stated dosage amounts.

As noted above, the "CTL" peptides of the invention induce immune responses when contacted with a CTL specific to an epitope comprised by the peptide. The manner in which the peptide is contacted with the CTL is not critical to the invention. For instance, the peptide can be contacted with the CTL either in vivo or in vitro. If the contacting occurs in vivo, the peptide itself can be administered to the patient, or other vehicles, e.g., DNA vectors encoding one or more peptides, viral vectors encoding the peptide(s), liposomes and the like, can be used, as described herein.

For pharmaceutical compositions, the immunogenic peptides, or DNA encoding them, are generally administered to an individual already infected with HBV. The peptides or DNA encoding them can be administered individually or as fusions of one or more peptide sequences. Those in the incubation phase or the acute phase of infection can be treated with the immunogenic peptides separately or in conjunction with other treatments, as appropriate.

For therapeutic use, administration should generally begin at the first diagnosis of HBV infection. This is followed by boosting doses until at least symptoms are substantially abated and for a period thereafter. In chronic infection, loading doses followed by boosting doses may be required.

Treatment of an infected individual with the compositions of the invention may hasten resolution of the infection in acutely infected individuals. For those individuals susceptible (or predisposed) to developing chronic infection, the compositions are particularly useful in methods for preventing the evolution from acute to chronic infection. Where susceptible individuals are identified prior to or during infection, the composition can be targeted to them, minimizing need for administration to a larger population.

The peptide or other compositions as used for the treatment of chronic HBV infection and to stimulate the immune system to eliminate pathogen-infected cells in, e.g., persons who have not manifested symptoms of disease but who act as a disease vector. In this context, it is generally important to provide an amount of immuno-potentiating peptide in a formulation and mode of administration sufficient to effectively stimulate a cytotoxic T cell response; compositions which stimulate helper T cell responses can also be given in accordance with this embodiment of the invention. Thus, for treatment of chronic infection, a representative dose is in the range of about 1.0 μg to about 5000 μg, preferably about 10 μg to 1000 μg, per 70 kg patient weight per dose. Immunizing doses followed by boosting doses at established intervals, e.g., from four weeks to six months, may be required, possibly for a prolonged period of time to effectively immunize an individual. In the case of chronic infection, administration should continue until at least clinical symptoms or laboratory tests indicate that the viral infection has been eliminated or substantially abated and for a period thereafter. The dosages, routes of administration, and dose schedules are adjusted in accordance with methodologies known in the art.

The pharmaceutical compositions for therapeutic treatment are intended for parenteral, topical, oral, intrathecal, or local administration. Preferably, the pharmaceutical compositions are administered parentally, e.g., intravenously, subcutaneously, intradermally, or intramuscularly. Thus, the invention provides compositions for parenteral administration which comprise a solution of the immunogenic peptides dissolved or suspended in an acceptable carrier, preferably an aqueous carrier. A variety of aqueous carriers may be used, e.g., water, buffered water, 0.8% saline, 0.3% glycine, hyaluronic acid and the like. These compositions may be sterilized by conventional, well known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as pH-adjusting and buffering agents, tonicity adjusting agents, wetting agents, preservatives, and the like, for example, sodium acetate, sodium lactate, sodium chloride, potassium chloride, calcium chloride, sorbitan monolaurate, triethanolamine oleate, etc.

The concentration of peptides of the invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The peptides of the invention may also be administered via liposomes, which serve to target the peptides to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the peptide to be delivered is incorporated as part of a liposome, alone or in conjunction with a molecule which binds to, e.g., a receptor prevalent among lymphoid cells, such as monoclonal antibodies which bind to the CD45 antigen, or with other therapeutic or immunogenic compositions. Thus, liposomes either filled or decorated with a desired peptide of the invention can be directed to the site of lymphoid cells, where the liposomes then deliver the peptide compositions. Liposomes for use in the invention are formed from standard vesicle-forming lipids, which generally include neutral and negatively charged phospholipids and a sterol, such as cholesterol. The selection of lipids is generally guided by consideration of, e.g., liposome size, acid lability and stability of the liposomes in the blood stream. A variety of methods are available for preparing liposomes, as described in, e.g., Szoka, et al., *Ann. Rev. Biophys. Bioeng.* 9:467 (1980), U.S. Pat. Nos. 4,235,871, 4,501,728, 4,837,028, and 5,019,369.

For targeting cells of the immune system, a ligand to be incorporated into the liposome can include, e.g., antibodies or fragments thereof specific for cell surface determinants of the desired immune system cells. A liposome suspension containing a peptide may be administered intravenously, locally, topically, etc. in a dose which varies according to, inter alia, the manner of administration, the peptide being delivered, and the stage of the disease being treated.

For solid compositions, conventional nontoxic solid carriers may be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10–95% of active ingredient, that is, one or more peptides of the invention, and more preferably at a concentration of 25%–75%.

For aerosol administration, the immunogenic peptides are preferably supplied in finely divided form along with a surfactant and propellant. Typical percentages of peptides are 0.01%–20% by weight, preferably 1%–10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1%–20% by weight of the composition, preferably 0.25–5%. The balance of the composition is ordinarily propellant. A carrier can also be included, as desired, as with, e.g., lecithin for intranasal delivery.

The vaccine compositions of the invention may also be used purely as prophylactic agents. Vaccine compositions containing the peptide epitopes of the invention are administered to a patient susceptible to, or otherwise at risk for, HBV infection to elicit an immune response against HBV antigens and thus enhance the patient's own immune response capabilities following exposure to HBV. Generally the dosage range for an initial prophylactic immunization is between about 1.0 μg to about 5000 μg of peptide, typically between about 10 µg to about 1000 µg, for a 70 kg patient. This is followed by boosting dosages of between about 1.0 µg to about 5000 µg of peptide administered at defined intervals from about four weeks to six months after the initial administration of vaccine. The immunogenicity of the vaccine may be assessed by measuring specific CTL activity in the patient's blood.

IV.K. Kits

The peptide and nucleic acid compositions of this invention can be provided in kit form together with instructions for vaccine administration. Typically the kit would include desired peptide compositions in a container, preferably in unit dosage form and instructions for administration. An alternative kit would include a minigene construct with desired nucleic acids of the invention in a container, preferably in unit dosage form together with instruction for administration. Lymphokines such as IL-2 or IL-12 may also be included in the kit. Other kit components that may also be desirable include, for example, a sterile syringe, booster dosages, and other desired excipients.

The invention will be described in greater detail by way of specific examples. The following examples are offered for illustrative purposes, and are not intended to limit the invention in any manner. Those of skill in the art will readily recognize a variety of non-critical parameters that can be changed or modified to yield alternative embodiments in accordance with the invention.

V. EXAMPLES

Example 1

HLA Class I Binding Assays

The following example of peptide binding to HLA-A3 supertype molecules demonstrates quantification of binding affinities of HLA class I peptides. Analogous binding assays can be performed for other peptides that bind class I or class II HLA molecules. Furthermore, binding assays can be performed with peptides that are not motif-bearing.

For example, the affinity of peptides bearing an HLA-A3 supermotif was determined as follows. Epstein-Barr virus (EBV)-transformed homozygous cell lines were used as sources of class I molecules. Cell lines include, e.g., GM3107 (A3, B7; Human Genetic Mutant Repository); BVR (A11, B35.3, Cw4; Human Genetic Mutant Repository); SPACH (A31, B62, Cw1/3; ASHI Repository Collection); LWAGS (A*3301, B14, and Cw8; ASHI Repository Collection) (Bodmer, et al., *Hum. Immunol.* 43:149, 1995), and a C1R transfectant characterized by Dr. Walter Storkus (University of Pittsburgh) for the isolation of A*6801. Cell lines were maintained as previously described (Sidney, et al., *J. Immunol.* 154:247 (1995); Sette, et al., *Mol. Immunol.* 31:813 (1994)).

Cell lysates were prepared and HLA class I molecules purified in accordance with disclosed protocols (Sidney, et al., *J. Immunol.* 154:247 (1995); Sette, et al., *Mol. Immunol.* 31:813 (1994)). Briefly, cells were lysed at a concentration of $10^8$ cells/ml in 50 mM Tris-HCl, pH 8.5, containing 1% Nonidet P-40 (Fluka Biochemika, Buchs, Switzerland), 150 mM NaCl, 5 mM EDTA, and 2 mM PMSF. The lysates were passed through 0.45 µM filters and cleared of nuclei and debris by centrifugation at 10,000 g for 20 minutes. HLA proteins were then purified by affinity chromatography. Columns of inactivated Sepharose CL 4B and Protein A Sepharose were used as precolumns. The cell lysate was depleted of HLA-B and HLA-C proteins by repeated passage over Protein A Sepharose beads conjugated with the anti-HLA(B,C) antibody B1.23.2 (Rebai, et al., *Tissue Antigens* 22:107 (1983)). Typically two to four passages were required for effective depletion. Subsequently, the anti HLA (A,B,C) antibody W6/32 (Barnstable, et al., *Cell* 14:9 (1978)) was used to capture HLA-A molecules. Protein purity, concentration, and effectiveness of depletion steps were monitored by sodium dodecyl sulfate-polyacrylamide gel electrophoresis (SDS-PAGE).

Binding Assays

Quantitative assays for the binding of peptides to soluble class I molecules on the basis of the inhibition of binding of a radiolabeled standard probe peptide to detergent solubilized HLA molecules were performed as described in the literature (Kubo, et al., *J. Immunol.* 152:3913 (1994); Kast, et al., *J. Immunol.* 152:3904 (1994); Sidney, et al., *J. Immunol.* 154:247 (1995); Sette, et al., *Mol. Immunol.* 31:813 (1994); Ruppert, et al., *Cell* 74:929 (1993)). Briefly, 1–10 nM of radiolabeled probe peptide, iodinated by the Chloramine-T method (Greenwood, et al., *Biochem. J.* 89:114 (1963)), was co-incubated at room temperature with various amounts of HLA in the presence of 1 µM human $\beta_2$-microglobulin (Scripps Laboratories, San Diego, Calif., USA) and a cocktail of protease inhibitors. At the end of a two day incubation period, the percent of HLA-bound radioactivity was determined by size exclusion gel filtration chromatography on a TSK 2000 column.

The A3CON1 peptide (sequence KVFPYALINK; SEQ ID NO:2576) (Kubo, et al., *J. Immunol.* 152:3913 (1994)) was used as the radiolabeled probe for the A3, A11, A31, and A*6801 assays. A T7Y analogue of HBVc $_{141-151}$ (sequence STLPETYVVRR; SEQ ID NO:2577) (Missale, et al., *J. Exp. Med.* 177:751 (1993)) was used as the radiolabeled probe for the A*3301 assay. In the case of competitive assays, the concentration of peptide yielding 50% inhibition of the binding of the radiolabeled probe peptide ($IC_{50}$) was calculated. Peptides were usually tested at one or two high doses, and the $IC_{50}$ of peptides yielding positive inhibition were determined in subsequent experiments, in which two to six further dilutions were tested, as necessary. To achieve a suitable signal, HLA concentrations yielding approximately 15% binding of the radiolabled probe peptide were used for all competitive inhibition assays. Under these conditions the concentration of the labeled peptide is less than the concentration of the HLA molecule and the $IC_{50}$ is less than the concentration of the HLA molecule, therefore the measured $IC_{50}$s are reasonable approximations of the true $K_D$ values. Each competitor peptide was tested in two to four completely independent experiments. As a positive control, in each experiment, the unlabeled version of the relevant radiolabeled probe was tested and its $IC_{50}$ measured. The average $IC_{50}$ of A3CON1 for the A3, A11, A31, and A*6801 assays were 11, 6, 18, and 8 nM, respectively. The average $IC_{50}$ of the HBVc 141–151 peptide in the A*3301 assay was 29 nM.

Example 2

Implementation of the Extended Supermotif to Improve the Binding Capacity of Native Peptides by Creating Analogs HLA motifs and supermotifs (comprising primary and/or secondary residues) are useful in preparing highly cross-reactive native peptides, as demonstrated herein. Moreover, the definition of HLA motifs and supermotifs also allows one to engineer highly cross-reactive epitopes by identifying residues within a native peptide sequence which can be analoged, or "fixed", to confer upon a peptide certain characteristics, e.g., greater cross-reactivity within the group of HLA molecules that make-up the supertype, and/or greater binding affinity for some or all of those HLA molecules Examples of analog peptides that exhibit modulated binding affinity are provided.

Analogs representing primary anchor single amino acid residues substituted with I residues at the C-terminus of two different B7-like peptides (HBV env 313 and HBV pol 541) were synthesized and tested for their B7-supertype binding capacity. It was found that the I substitution had an overall positive effect on binding affinity and/or cross-reactivity in both cases. In the case of HBV env 313 the 19 (I at C-terminal position 9) replacement was effective in increasing cross-reactivity from 4 to 5 alleles bound by virtue of an almost 400-fold increase B*5401 binding affinity. In the case of HBV pol 541, increased cross-reactivity was similarly achieved by a substantial increase in B*5401 binding. Also, significant gains in binding affinity for B*0702, B51, and B*5301 were observed with the HBV pol 541 I9 analog.

Moreover, HLA supermotifs are of value in engineering highly cross-reactive peptides by identifying particular residues at secondary anchor positions that are associated with such cross-reactive properties. Demonstrating this, the capacity of a second set of peptides representing discreet single amino acid substitutions at positions one and three of five different B7-supertype binding peptides were synthesized and tested for their B-7 supertype binding capacity. In 4/4 cases the effect of replacing the native residue at position 1 with the aromatic residue F (an "F1" substitution) resulted in an increase in cross-reactivity, compared to the parent peptide, and, in most instances, binding affinity was increased three-fold or better (Table XXII). More specifically, for HBV env 313, MAGE2 170, and HCV core 168 complete supertype cross-reactivity was achieved with the F1 substitution analogs. These gains were achieved by dramatically increasing B*5401 binding affinity. Also, gains in affinity were noted for other alleles in the cases of HCV core 168 (B*3501 and B*5301) and MAGE2 170 (B*3501, B51 and B*5301). Finally, in the case of MAGE3 196, the F1 replacement was effective in increasing cross-reactivity because of gains in B*0702 binding. An almost 70-fold increase in B51 binding capacity was also noted.

Two analogs were also made using the supermotif positive F substitution at position three (an "F3" substitution). In both instances increases in binding affinity and cross-reactivity were achieved. Specifically, in the case of HBV pol 541, the F3 substitution was effective in increasing cross-reactivity by virtue of its effect on B*5401 binding. In the case of MAGE3 196, complete supertype cross-reactivity was achieved by increasing B*0702 and B*3501 binding capacity. Also, in the case of MAGE3 196, it is notable that increases in binding capacity between 40- and 5000-fold were obtained for B*3501, B51, B*5301, and B*5401.

In conclusion, these data demonstrate that by the use of even single amino acid substitutions, it is possible to increase the binding affinity and/or cross-reactivity of peptide ligands for HLA supertype molecules.

Example 3

Induction of HLA-Restricted CTL By Subcutaneous Priming With HBV Peptide in Incomplete Freund's Adiuvant (IFA)

The immunogenicity of HLA class I binding peptides can be assessed in vivo as described in, e.g., Sette et al. *J. Immunol.* 153:5586–5592 (1994). This example illustrates such a procedure, whereby subcutaneous injection of HBV peptide in Incomplete Freund's Adjuvant (IFA) can be used to induce HBV-specific CTL in mice that are transgenic for a human HLA allele such as the human HLA-A11 allele.

Priming and In Vitro Restimulation: Mice that are transgenic for HLA-A11, (e.g. HLA-A11/$K^b$ strain) are injected with 100 microliters of an emulsion of purified HBV peptide in IFA. The purified peptide comprises an A11 motif, and is selected from the preferred peptides listed in Table XVI or, alternatively, may be an analog peptide. The peptide epitope (50 μg/mouse) and equimolar amounts of the helper epitope HBV core 128–140 (140 μg/mouse) are dissolved in PBS/5% DMSO, emulsified in IFA, and injected subcutaneously at the base of the tail of the transgenic mice. Eleven days after priming, splenocytes ($5\times10^6$ cells/well in a 24-well plate) obtained from these animals are restimulated with syngeneic irradiated LPS blasts ($2\times10^6$/well) coated with peptide.

LPS blasts from unprimed HLA-A11 transgenic mice are prepared 72 hours before use by suspending splenocytes in medium containing LPS (25 μg/ml) and dextran sulfate (7 μg/ml). Coating is achieved by incubating 50 μg of peptide with $1.2\times10^6$ LPS blasts in a volume of 0.4 ml of RPMI medium supplemented with 10% FCS for 1 hour at 37° C. The cells are washed once and then co-cultured with splenocytes. After six days, effector cells are assayed, as outlined for example in Example 5, for cytotoxicity against $^{51}$Cr-labeled 3A4-721.221-A11/$K^b$ target cells in the presence of the peptide.

The effector cells ($2\times10^6$ cells/well) are re-stimulated at weekly intervals. For the first re-stimulation, peptide-coated LPS blasts are used, followed by peptide-coated A11/$K^b$ cells. Six days after re-stimulation, effector cells are assayed for cytotoxicity as above.

Example 4

Recognition of Generation of Endogenous Processed Antigens After Priming

This example determines that CTL induced by in vivo priming with peptide (as disclosed in Example 3) recognize endogenously synthesized antigens.

Effector cells from the procedure disclosed in Example 3 are re-stimulated in vitro using peptide-coated stimulator cells. Six days later, effector cells are assayed for cytotoxicity and the cell lines that contain peptide-specific cytotoxic activity are further re-stimulated. An additional six days later, these cell lines are tested for cytotoxic activity on $^{51}$Cr labeled 3A4-721.221-A11/$K^b$ target cells, in the absence or presence of peptide, and also tested on $^{51}$Cr labeled target cells bearing the endogenously synthesized antigen.

The result will demonstrate that CTL lines obtained from animals primed with peptide epitope recognize endogenously synthesized HBV antigen.

Example 5

Activity of CTL-HTL Conjugated Epitopes in Transgenic Mice

This example illustrates the induction of CTLs in transgenic mice by use of an HBV CTL/HTL peptide conjugate. An analagous study may be found in Oseroff et al. *Vaccine* 16:823–833 (1998). The peptide composition can comprise multiple CTL and/or HTL epitopes. Such a peptide composition can comprise a lipidated HTL epitope conjugated to a preferred CTL epitope containing, for example, an A11 motif or an analog of that epitope.

Lipopeptides are prepared by coupling the appropriate fatty acid to the amino terminus of the resin bound peptide. A typical procedure is as follows: A dichloromethane solution of a four-fold excess of a pre-formed symmetrical anhydride of the appropriate fatty acid is added to the resin and the mixture is allowed to react for two hours. The resin is washed with dichloromethane and dried. The resin is then treated with trifluoroacetic acid in the presence of appropriate scavengers [e.g. 5% (v/v) water] for 60 minutes at 20° C. After evaporation of excess trifluoroacetic acid, the crude peptide is washed with diethyl ether, dissolved in methanol and precipitated by the addition of water. The peptide is collected by filtration and dried.

Preparation of peptides for immunization: Peptide compositions are typically resuspended in DMSO at a concentration of 20 mg/ml. Before use, peptides are prepared at the required concentration by dilution in saline or the appropriate medium.

Immunization procedures: A11/$K^b$ mice, which are transgenic for the human HLA A11 allele, are primed subcutaneously (base of the tail) with 0.1 ml of peptide conjugate formulated in saline, or DMSO/saline. Seven days after priming, splenocytes obtained from these animals are restimulated with syngeneic irradiated LPS-activated lymphoblasts coated with peptide.

Media:
a. RPMI-1640 supplemented with 10% fetal calf serum (FCS) 2 mM Glutamine, 50 µg/ml Gentamicin and $5 \times 10^{-5}$ M 2-mercaptoethanol serves as culture medium
b. RPMI-1640 containing 25 mM HEPES buffer and supplemented with 2% (FCS) is used as cell washing medium.

Cell lines: The 3A4-721.221-A11/$K^b$ cell line is used as target cells. This cell line is an EBV transformed cell line that was mutagenized and selected to be Class I negative which was transfected with an HLA-A11/$K^b$ gene.

LPS-activated lymphoblasts: Splenocytes obtained from transgenic mice are resuspended at a concentration of $1-1.5 \times 10^6$/ml in culture medium supplemented with 25 µg/ml LPS and 7 µg/ml dextran sulfate in 75 cm² tissue culture flasks. After 72 hours at 37° C., the lymphoblasts are collected for use by centrifugation.

Peptide coating of lymphoblasts: Peptide coating of the LPS activated lymphoblasts is achieved by incubating $30 \times 10^6$ irradiated (3000 rads) lymphoblasts with 100 µg of peptide in 1 ml of R10 medium for 1 hr at 37° C. Cells are then washed once and resuspended in culture medium at the desired concentration.

In vitro CTL activation: One week after priming, spleen cells ($30 \times 10^6$ cells/flask) are co-cultured at 37° C. with syngeneic, irradiated (3000 rads), peptide coated lymphoblasts ($10 \times 10^6$ cells/flask) in 10 ml of culture medium/T25 flask. After six days, the effector cells are harvested and assayed for cytotoxic activity.

Assay for cytotoxic activity: Target cells ($1.0-1.5 \times 10^6$) are incubated at 37° C. in the presence of 200 µl of sodium $^{51}$Cr chromate. After 60 minutes, cells are washed three times and resuspended in R10 medium. Peptide is added where required at a concentration of 1 µg/ml. For the assay, 104 $^{51}$Cr-labeled target cells are added to different concentrations of effector cells (final volume of 200 µl) in U-bottom 96-well plates. After a 6 hour incubation period at 37° C., a 0.1 ml aliquot of supernatant is removed from each well and radioactivity is determined in a Micromedic automatic gamma counter. The percent specific lysis is determined by the formula: percent specific release=100×(experimental release−spontaneous release)/(maximum release−spontaneous release). To facilitate comparison between separate CTL assays run under the same conditions, % $^{51}$Cr release data is expressed as lytic units/$10^6$ cells. One lytic unit is arbitrarily defined as the number of effector cells required to achieve 30% lysis of 10,000 target cells in a 6 hour $^{51}$Cr release assay. To obtain specific lytic units/$10^6$, the lytic units/$10^6$ obtained in the absence of peptide is subtracted from the lytic units/$10^6$ obtained in the presence of peptide. For example, if 30% $^{51}$Cr release is obtained at the E:T of 50:1 (i.e., $5 \times 10^5$ effector cells for 10,000 targets) in the absence of peptide and 5:1 (i.e., $5 \times 10^4$ effector cells for 10,000 targets) in the presence of peptide, the specific lytic units would be: $(1 \times 10^6 (5 \times 10^4)) - (1 \times 10^6 (5 \times 10^5)) = 18 LU/10^6$.

The results are analyzed to assess the magnitude of the CTL responses of animals injected with the immunogenic CTL/HTL conjugate vaccine preparation. Analyses similar to this may be performed to evaluate the immunogenicity of peptide conjugates containing multiple CTL epitopes and/or multiple HTL epitopes. In accordance with these procedures it is found that CTL and HTL responses are induced.

Example 7

Induction of Specific CTL Response in Humans

A human clinical trial for an immunogenic composition comprising CTL and HTL epitopes is set up as an IND Phase I, dose escalation study (5, 50 and 500 µg) and carried out as a randomized, double-blind, placebo-controlled trial. Such a trial is designed, for example, as follows:

A total of about 27 subjects are enrolled and divided into 3 groups:
  Group I: 3 subjects are injected with placebo and 6 subjects are injected with 5 µg of peptide composition;
  Group II: 3 subjects are injected with placebo and 6 subjects are injected with 50 µg peptide composition;
  Group III: 3 subjects are injected with placebo and 6 subjects are injected with 500 µg of peptide composition.

After 4 weeks following the first injection, all subjects receive a booster inoculation at the same dosage.

The endpoints measured in this study relate to the safety and tolerability of the peptide composition as well as its immunogenicity. Cellular immune responses to the peptide composition are an index of the intrinsic activity of this the peptide composition, and can therefore be viewed as a measure of biological efficacy. The following summarize the clinical and laboratory data that relate to safety and efficacy endpoints.

Safety: The incidence of adverse events is monitored in the placebo and drug treatment group and assessed in terms of degree and reversibility.

Evaluation of Vaccine Efficacy: For evaluation of vaccine efficacy, subjects are bled before and after injection. Peripheral blood mononuclear cells are isolated from fresh heparinized blood by Ficoll-Hypaque density gradient centrifugation, aliquoted in freezing media and stored frozen. Samples are assayed for CTL and HTL activity.

Thus, the vaccine is found to be both safe and efficacious.

Example 8

Phase II Trials in Patients Infected With HBV

Phase II trials are performed to study the effect of administering the CTL-HTL peptide compositions to patients (male and female) having chronic HBV infection. A main objective of the trials is to determine an effective dose and regimen for inducing CTLs in chronically infected HBV patients, to establish the safety of inducing a CTL response in these patients, and to see to what extent activation of CTLs improves the clinical picture of chronically infected CTL patients, as manifested by a transient flare in alanine aminotransferase (ALT), normalization of ALT, and reduction in HBV DNA. Such a study is designed, for example, as follows:

The studies are performed in multiple centers in the U.S. and Canada. The trial design is an open-label, uncontrolled, dose escalation protocol wherein the peptide composition is administered as a single dose followed six weeks later by a single booster shot of the same dose. The dosages are 50, 500 and 5,000 micrograms per injection. Drug-associated adverse effects are recorded.

There are three patient groupings. The first group is injected with 50 micrograms of the peptide composition and the second and third groups with 500 and 5,000 micrograms of peptide composition, respectively. The patients within each group range in age from 21–65 and include both males and females. The patients represent diverse ethnic backgrounds. All of them are infected with HBV for over five years and are HIV, HCV and HDV negative, but have positive levels of HBe antigen and HBs antigen.

The magnitude and incidence of ALT flares and the levels of HBV DNA in the blood are monitored to assess the effects of administering the peptide compositions. The levels of HBV DNA in the blood are an indirect indication of the progress of treatment. The vaccine composition is found to be both safe and efficacious in the treatment of chronic HBV infection.

Example 9

Selection of CTL and HTL Epitopes for Inclusion in an HBV-specific Vaccine

This example illustrates the procedure for the selection of peptide epitopes for vaccine compositions of the invention.

The following principles are utilized when selecting an array of epitopes for inclusion in a polyepitopic composition, or for selecting epitopes to be included in a vaccine composition and/or to be encoded by a minigene. Each of the following principles are balanced in order to make the selection.

1.) Epitopes are selected which, upon administration, mimic immune responses that have been observed to be correlated with HBV clearance. For HLA Class I this includes 3–4 epitopes that come from at least one antigen of HBV. In other words, it has been observed that in patients who spontaneously clear HBV, that they had generated an immune response to at least 3 epitopes on at least one HBV antigen. For HLA Class II a similar rationale is employed; again 3–4 epitopes are selected from at least one HBV antigen.

2.) Epitopes are selected that have the requisite binding affinity established to be correlated with immunogenicity: for HLA Class I an $IC_{50}$ of 500 nM or less, or for Class II an $IC_{50}$ of 1000 nM or less.

3.) Sufficient supermotif bearing peptides, or a sufficient array of allele-specific motif bearing peptides, are selected to give broad population coverage. For example, epitopes are selected to provide at least 80% population coverage. A Monte Carlo analysis, a statistical evaluation known in the art, is employed to assess population coverage.

4.) When selecting epitopes for HBV antigens it is often preferable to select native epitopes. Therefore, of particular relevance for infectious disease vaccines, are epitopes referred to as "nested epitopes." Nested epitopes occur where at least two epitopes overlap in a given peptide sequence. A peptide comprising "transcendent nested epitopes" is a peptide that has both HLA class I and HLA class II epitopes in it.

When providing nested epitopes, a sequence that has the greatest number of epitopes per provided sequence is provided. A limitation on this principle is to avoid providing a peptide that is any longer than the amino terminus of the amino terminal epitope and the carboxyl terminus of the carboxyl terminal epitope in the peptide. When providing a longer peptide sequence, such as a sequence comprising nested epitopes, the sequence is screened in order to insure that it does not have pathological or other deleterious biological properties.

5.) When creating a minigene, as disclosed in greater detail in the Example 10, an objective is to generate the smallest peptide possible that encompasses the epitopes of interest. The principles employed are similar, if not the same as those employed when selecting a peptide comprising nested epitopes. Thus, upon determination of the nucleic acid sequence to be provided as a minigene, the peptide encoded thereby is analyzed to determine whether any "junctional epitopes" have been created. A junctional epitope is an actual binding epitope, as predicted, e.g., by motif analysis. Junctional epitopes are to be avoided because the recipient may generate an immune response to that epitope. Of particular concern is a junctional epitope that is a "dominant epitope." A dominant epitope may lead to such a zealous response that immune responses to other epitopes are diminished or suppressed.

Peptide epitopes for inclusion in vaccine compositions are, for example, selected from those lsited in Table XXIII. A vaccine composition comprised of selected peptides, when administered, is safe, efficacious, and elicits an immune response similar in magnitude of an immune response that clears an acute HBV infection.

Example 10

Construction of Minigene Multi-Epitope DNA Plasmids

Expression plasmids have been constructed and evaluated as described, for example, in U.S. Ser. No. 60/085,751 filed May 15, 1998 and U.S. Ser. No. 09/078,904 filed May 13, 1998. The binding peptide epitopes and their positions for some of the plasmids described therein are shown in FIG. 1 as example of the orientation of peptide epitopes in minigene constructs. Such a plasmid may, for example, also include multiple CTL and HTL peptide epitopes. In the present example, HLA-A11 motif-bearing peptides are used in conjunction with DR supermotif-bearing peptides. Preferred A11 epitopes are identified, for example, in Table XVI or Table XXI and peptide epitopes recognized by HLA DR molecules (Tables XVIII and XIX). Four class I A11 motif-bearing peptide epitopes or analogs of those peptide epitopes derived from the same HBV antigen, e.g. the envelope protein, are selected as CTL epitopes. Four class II motif-bearing peptide epitopes derived from the same antigen, e.g., the envelope protein, are selected as HTL epitopes. These epitopes are then incorporated into a minigene for expression in an expression vector.

This example illustrates the methods to be used for construction of such a minigene-bearing expression plasmid.

Other expression vectors that may be used for minigene compositions are available and known to those of skill in the art.

A pMin minigene DNA plasmid is constructed from an early generation DNA plasmid designated as pMin.0. This plasmid contains a consensus Kozak sequence and a consensus murine kappa Ig-light chain signal sequence followed by a string of CTL and HTL epitopes selected in accordance with principles disclosed herein. The pMIN sequence encodes an open reading frame fused to the Myc and His antibody epitope tag coded for by the pcDNA 3.1 Myc-His vector.

Overlapping oligonucleotides, for example eight oligonucleotides, averaging approximately 70 nucleotides in length with 15 nucleotide overlaps, are synthesized and HPLC-purified. The oligonucleotides encode the selected peptide epitopes as well as appropriate linker nucleotides. The final multiepitope minigene is assembled by extending the overlapping oligonucleotides in three sets of reactions using PCR. A Perkin/Elmer 9600 PCR machine is used and a total of 30 cycles are performed using the following conditions: 95° C. for 15 sec, annealing temperature (5° below the lowest calculated Tm of each primer pair) for 30 sec, and 72° C. for 1 min.

For the first PCR reaction, 5 μg of each of two oligonucleotides are annealed and extended: Oligonucleotides 1+2, 3+4, 5+6, and 7+8 are combined in 100 μl reactions containing *Pfu* polymerase buffer (1×=10 mM KCL, 10 mM $(NH4)_2SO_4$, 20 mM Tris-chloride, pH 8.75, 2 mM $MgSO_4$, 0.1% Triton X-100, 100 μg/ml BSA), 0.25 mM each dNTP, and 2.5 U of *Pfu* polymerase. The full-length dimer products are gel-purified, and two reactions containing the product of 1+2 and 3+4, and the product of 5+6 and 7+8 are mixed, annealed, and extended for 10 cycles. Half of the two reactions are then mixed, and 5 cycles of annealing and extension carried out before flanking primers are added to amplify the full length product for 25 additional cycles. The full-length product is gel-purified and cloned into pCR-blunt (Invitrogen) and individual clones are screened by sequencing.

Example 11

The Plasmid Construct and the Degree to Which it Induces Immunogenicity

The degree to which the plasmid construct prepared using the methodology outlined in Example 10 is able to induce immunogenicity is evaluated through in vivo injections into mice and in vitro CTL culture and cytotoxicity assays as detailed e.g., in U.S. Ser. No. 60/085,751 filed May 15, 1998. To assess the capacity of the pMin minigene construct to induce CTLs in vivo, HLA-A11/$K^b$ transgenic mice are immunized intramuscularly with 100 μg of naked cDNA. As a means of comparing the level of CTLs induced by cDNA immunization, a control group of animals is also immunized with an actual peptide composition that comprises multiple epitopes synthesized as a single polypeptide.

Splenocytes from immunized animals are stimulated twice with each of the peptide epitopes encoded in the minigene, then assayed for peptide-specific cytotoxic activity in a $^5Cr$ release assay. The results indicate the magnitude of the CTL response directed against each of its A11-restricted epitopes, thus indicating the in vivo immunogenicity of the minigene vaccine. It is, therefore, found that the minigene elicits immune responses directed toward A11-restricted epitopes.

Example 12

Peptide Composition for Prophylactic Uses

Vaccine compositions of the present invention are used to prevent HBV infection in persons who are at risk. For example, a polyepitopic peptide epitope composition containing multiple CTL and HTL epitopes such as those selected in Examples 9 and/or 10, which are also selected to target greater than 80% of the population, is administered to individuals at risk for HBV infection. The composition is provided as a single lipidated polypeptide that encompasses multiple epitopes. The vaccine is administered in an aqueous carrier comprised of Freunds Incomplete Adjuvant. The dose of peptide for the initial immunization is from about 1 to about 5,000 μg for a 70 kg patient. The initial administration of vaccine is followed by booster dosages at 4 weeks followed by evaluation of the magnitude of the immune response in the patient by techniques that determine the presence of epitope-specific CTL populations in a PBMC sample. Additional booster doses are administered as required. The composition is found to be both safe and efficacious as a prophylaxis against HBV infection.

Alternatively, the polyepitopic peptide composition can be administered as a nucleic acid in accordance with methodologies known in the art and disclosed herein.

Example 13

Polyepitopic Vaccine Compositions Derived from Native HBV Sequences

A native HBV polyprotein sequence is screened, preferably using computer algorithms defined for each class I and/or class II supermotif or motif, to identify "relatively short" regions of the polyprotein that comprise multiple epitopes. This relatively short sequence that contains multiple distinct, even overlapping, epitopes is selected and used to generate a minigene construct. The construct is engineered to express the peptide, which corresponds to the native protein sequence. The "relatively short" peptide is less than 100 amino acids in length, preferably less than 75 amino acids in length, and more preferably less than 50 amino acids in length. The protein sequence of the vaccine composition is selected because it has maximal number of epitopes contained within the sequence. As noted herein, epitope motifs may be overlapping (i.e., frame shifted relative to one another) with frame shifted overlapping epitopes, e.g. two 9-mer epitopes can be present in a 10 amino acid peptide. Such a vaccine composition is administered for therapeutic or prophylactic purposes.

The vaccine composition will preferably include, for example, three CTL epitopes and at least one HTL epitope from the source antigen. Junctional sequences will be analyzed to avoid sequences containing a potentially immunodominant epitope. This polyepitopic native sequence is administered either as a peptide or as a nucleic acid sequence which encodes the peptide. Alternatively, an analog can be made of this native sequence.

The embodiment of this example provides for the possibility that an as yet undiscovered aspect of immune system processing will apply to the native nested sequence and thereby facilitate the production of therapeutic or prophylactic immune response-inducing vaccine compositions. Additionally such an embodiment provides for the possibility of motif-bearing epitopes for an HLA makeup that is presently unknown. Furthermore, this embodiment directs the immune response to sequences that are present in native HBV antigens. Lastly, the embodiment provides an economy of scale when producing nucleic acid vaccine compositions.

Related to this embodiment, computer programs can be derived which identify, in a target sequence, the greatest number of epitopes per sequence length.

Example 14

Polyepitopic Vaccine Compositions Directed to Multiple Diseases

The HBV peptide epitopes of the present invention are used in conjunction with peptide epitopes from target antigens related to one or more other diseases, to create a vaccine composition that is useful for the prevention or treatment of HBV as well as another disease. Examples of other diseases include, but are not limited to, HIV, HCV, and HPV.

For example, a polyepitopic peptide composition comprising multiple CTL and HTL epitopes that target greater than 98% of the population may be created for administration to individuals at risk for both HBV and HIV infection. The composition can be provided as a single polypeptide that incorporates the multiple epitopes from the various disease-associated sources.

Example 15

Use of Peptides to Evaluate an Immune Response

Peptides of the invention may be used to analyze an immune response for the presence of specific CTL populations corresponding to HBV. Such an analysis may be performed as described by Ogg et al., *Science* 279:2103–2106, 1998. In the following example, peptides in accordance with the invention are used as a reagent for diagnostic or prognostic purposes, not as an immunogen.

In this example highly sensitive human leukocyte antigen tetrameric complexes ("tetramers") may be used for a cross-sectional analysis of, for example, HBV Env-specific CTL frequencies from untreated HLA A*0201-positive individuals at different stages of infection using an HBV Env peptide containing an A2.1 extended motif. Tetrameric complexes are synthesized as described (Musey et al., *N. Engl. J. Med.* 337:1267, 1997). Briefly, purified HLA heavy chain (A2.1 in this example) and β2-microglobulin are synthesized by means of a prokaryotic expression system. The heavy chain is modified by deletion of the transmembrane-cytosolic tail and COOH-terminal addition of a sequence containing a BirA enzymatic biotinylation site. The heavy chain, β2-microglobulin, and peptide are refolded by dilution. The 45-kD refolded product is isolated by fast protein liquid chromatography and then biotinylated by BirA in the presence of biotin (Sigma, St. Louis, Mo.), adenosine 5'triphosphate and magnesium. Streptavidin-phycoerythrin conjugate is added in a 1:4 molar ratio, and the tetrameric product is concentrated to 1 mg/ml. The resulting product is referred to as tetramer-phycoerythrin.

Approximately one million PBMCs are centrifuged at 300 g for 5 minutes and resuspended in 50 ul of cold phosphate-buffered saline. Tri-color analysis is performed with the tetramer-phycoerythrin, along with anti-CD8-Tricolor, and anti-CD38. The PBMCs are incubated with tetramer and antibodies on ice for 30 to 60 min and then washed twice before formaldehyde fixaation. Gates are applied to contain >99.98% of control samples. Controls for the tetramers include both A*0201-negative individuals and A*0201-positive uninfected donors. The percentage of cells stained with the tetramer is then determined by flow cytometry. The results indicate the number of cells in the PBMC sample that contain epitope-restricted CTLs, thereby readily indicating the stage of infection with HBV or the status of exposure to HBV or to a vaccine that elicits a protective response.

Example 16

Use of Peptide Epitopes to Evaluate Recall Responses

The peptide epitopes of the invention are used as reagents to evaluate T cell responses such as acute or recall responses, in patients. Such an analysis may be performed on patients who have recovered from infection or who are chronically infected with HBV or who have been vaccinated with an HBV vaccine.

For example, the class I restricted CTL response of persons at risk for HBV infection who have been vaccinated may be analyzed. The vaccine may be any HBV vaccine. PBMC are collected from vaccinated individuals and HLA typed. Appropriate peptide reagents that, are highly conserved and, optimally, bear supermotifs to provide cross-reactivity with multiple HLA supertype family members are then used for analysis of samples derived from individuals who bear that HLA type.

PBMC from vaccinated individuals are separated on Ficoll-Histopaque density gradients (Sigma Chemical Co., St. Louis, Mo.), washed three times in HBSS (GIBCO Laboratories), resuspended in RPMI-1640 (GIBCO Laboratories) supplemented with L-glutamine (2 mM), penicillin (50 U/ml), streptomycin (50 µg/ml), and Hepes (10 mM) containing 10% heat-inactivated human AB serum (complete RPMI) and plated using microculture formats. Synthetic peptide is added at 10 µg/ml to each well and recombinant HBc Ag is added at 1 µg/ml to each well as a source of T cell help during the first week of stimulation.

In the microculture format, $4 \times 10^5$ PBMC are stimulated with peptide in 8 replicate cultures in 96-well round bottom plate in 100 µl/well of complete RPMI. On days 3 and 10, 100 ml of complete RPMI and 20 U/ml final concentration of rIL-2 are added to each well. On day 7 the cultures are transferred into a 96-well flat-bottom plate and restimualted with peptide, rIL-2 and $10^5$ irradiated (3,000 rad) autologous feeder cells. The cultures are tested for cytotoxic activity on day 14. A positive CTL response requires two or more of the eight replicate cultures to display greater than 10% specific $^{51}$Cr release, based on comparison with uninfected control subjects as previously described (Rehermann, et al., *Nature Med.* 2:1104,1108, 1996; Rehermann et al., *J. Clin. Invest.* 97:1655–1665, 1996; and Rehermann et al. *J. Clin. Invest.* 98:1432–1440, 1996).

Target cell lines are autologous and allogeneic EBV-transformed B-LCL that are either purchased from the American Society for Histocompatibility and Immunogenetics (ASHI, Boston, Mass.) or established from the pool of patients as described (Guilhot, et al. *J. Virol.* 66:2670–2678, 1992).

Cytotoxicity assays are performed in the following manner. Target cells consist of either allogeneic HLA-matched or autologous EBV-transformed B lymphoblastoid cell line that are incubated overnight with synthetic peptide at 10 µM and labeled with 100 µCi of $^{51}$Cr (Amersham Corp., Arlington Heights, Ill.) for 1 hour after which they are washed four times with HBSS. Cytolytic activity is determined in a standard 4-h, split well $^{51}$Cr release assay using U-bottomed 96 well plates containing 3,000 targets/well. Stimulated PBMC are tested at E/T ratios of 20–50:1 on day 14. Percent cytotoxicity is determined from the formula: 100× [(experimental release-spontaneous release)/maximum release-spontaneous release)]. Maximum release is determined by lysis of targets by detergent (2% Triton X-100; Sigma Chemical Co., St. Louis, Mo.). Spontaneous release is <25% of maximum release for all experiments.

The results of such an analysis will indicate to what extent HLA-restricted CTL populations have been stimulated with the vaccine. Of course, this protocol can also be used to monitor prior HBV exposure.

The above examples are provided to illustrate the invention but not to limit its scope. For example, the humanterminology for the Major Histocompatibility Complex, namely HLA, is used throughout this document. It is to be appreciated that these principles can be extended to other species as well. Moreover, peptide epitopes have been disclosed in the related application U.S. Ser. No. 08/820, 360, which was previously incorporated by reference. Thus, other variants of the invention will be readily apparent to one of ordinary skill in the art and are encompassed by the appended claims. All publications, patents, and patent application cited herein are hereby incorporated by reference for all purposes.

TABLE I

| SUPER-MOTIF | POSITION (Primary Anchor) | POSITION 3 (Primary Anchor) | POSITION C Terminus (Primary Anchor) |
|---|---|---|---|
| A1 | T,I,*L,V,M,S* | | F,W,Y |
| A2 | L,I,V,M,*A,T,Q* | | I,V,*M,A,T,L* |
| A3 | V,S,M,A,*T,L,I* | | R,K |
| A24 | Y,F,*W,I,V,L,M,T* | | F,I,*Y,W,L,M* |
| B7 | P | | V,I,L,F,*M,W,Y,A* |
| B27 | R,H,K | | F,Y,L,*W,M,I* |
| B44 | E,*D* | | F,W,Y,L,I,M,V,A |
| B58 | A,T,S | | F,W,Y,*L,I,V* |
| B62 | Q,L,*I,V,M,P* | | F,W,Y,*M,I,V* |
| MOTIF | | | |
| A1 | T,S,M | | Y |
| A1 | | D,E,*A,S* | Y |
| A2.1 | L,M,*V,Q,I,A,T* | | V,L,I,M,A,T |
| A3 | L,M,V,I,S,A,T,F,*C,G,D* | | K,Y,R,*H,F,A* |
| A11 | V,T,M,L,I,S,A,G,N,*C,D,F* | | K,*R,Y,H* |
| A24 | Y,F,W,*M* | | F,L,I,W |
| A*3101 | M,V,T,*A,L,I,S* | | R,*K* |
| A*3301 | M,V,A,L,F,*I,S,T* | | R,K |
| A*6801 | A,V,T,*M,S,L,I* | | R,K |
| B*0702 | P | | L,M,F,*W,Y,A,I,V* |
| B*3501 | P | | L,M,F,W,Y,*I,V,A* |
| B51 | P | | L,I,V,F,*W,Y,A,M* |
| B*5301 | P | | I,M,F,W,Y,*A,L,V* |
| B*5401 | P | | A,T,I,V,*L,M,F,W,Y* |

Bolded residues are preferred, italicized residues are less preferred: A peptide is considered motif-bearing if it has primary anchors at each primary anchor position for a motif or supermotif as specified in the above table.

TABLE II

| | | 1 | 2 | 3 | 4 | 5 | 6 | 7 | 8 | 9 or C-terminus | C-terminus |
|---|---|---|---|---|---|---|---|---|---|---|---|
| SUPERMOTIFS | | | | | | | | | | | |
| A1 | | | 1° Anchor T,I,L,V,M,S | | | | | | | | 1° Anchor F,W,Y |
| A2 | | | 1° Anchor L,I,V,M,A,T,Q | | | | | | | | 1° Anchor L,I,V,M,A,T |
| A3 | preferred | | 1° Anchor V,S,M,A,T,L,I | Y,F,W (4/5) | | | Y,F,W (3/5) | Y,F,W (4/5) | P (4/5) | 1° Anchor R,K | |
| | deleterious | D,E (3/5); P (5/5) | | D,E (4/5) | | | | | | | |
| A24 | preferred | | 1° Anchor Y,F,W,I,V,L,M,T | | | | | | | | 1° Anchor F,I,Y,W,L,M |
| B7 | preferred | F,W,Y (5/5) L,I,V,M (3/5) | 1° Anchor P | F,W,Y (4/5) | | | | | F,W,Y (3/5) | | 1° Anchor V,I,L,F,M,W,Y,A |
| | deleterious | D,E (3/5); P(5/5); G(4/5); A(3/5); Q,N (3/5) | | | | D,E (3/5) | G (4/5) | Q,N (4/5) | D,E (4/5) | | |
| B27 | | | 1° Anchor R,H,K | | | | | | | | 1° Anchor F,Y,L,W,M,I |
| B44 | | | 1° Anchor E,D | | | | | | | | 1° Anchor F,W,Y,L,I,M,V,A |
| B58 | | | 1° Anchor A,T,S | | | | | | | | 1° Anchor F,W,Y,L,I,V |
| B62 | | | 1° Anchor Q,L,I,V,M,P | | | | | | | | 1° Anchor F,W,Y,M,I,V |
| MOTIFS | | | | | | | | | | | |
| A1 9-mer | preferred | G,F,Y,W | 1° Anchor S,T,M | D,E,A | Y,F,W | | P | D,E,Q,N | Y,F,W | | 1° Anchor Y |
| | deleterious | D,E | | R,H,K,L,I,V,M,P | A | G | A | | | | |
| A1 9-mer | preferred | G,R,H,K | A,S,T,C,L,I,V,M | 1° Anchor D,E,A,S | G,S,T,C | P,Q,N | A,S,T,C | L,I,V,M | D,E | | 1° Anchor Y |
| | deleterious | A | R,H,K,D,E,P,Y,F,W | | D,E | Y,F,W,Q,N | R,H,K | P,G | G,P | | |
| A1 10-mer | preferred | Y,F,W | 1° Anchor S,T,M | D,E,A,Q,N | A | Y,F,W,Q,N | | P,A,S,T,C | G,D,E | P | 1° Anchor Y |
| | deleterious | G,P | | R,H,K,G,L,I,V,M | D,E | R,H,K | Q,N,A | R,H,K,Y,F,W | R,H,K | A | |
| A1 10-mer | preferred | Y,F,W | S,T,C,L,I,V,M | 1° Anchor D,E,A,S | A | Y,F,W | | P,G | G | Y,F,W | 1° Anchor Y |

TABLE II-continued

| | | | | | POSITION | | | | | |
|---|---|---|---|---|---|---|---|---|---|---|
| | | 1 | 2 | 3 | 4 | 5 | 6 | 7 | 8 | 9 or C-terminus | C-terminus |
| A2.1 9-mer | deleterious | R,H,K | R,H,K,D,E, P,Y,F,W | | | P | G | | P,R,H,K | Q,N | |
| | preferred | Y,F,W | 1° Anchor L,M,I,V,Q, A,T | Y,F,W | S,T,C | Y,F,W | | A | P | 1° Anchor V,L,I,M,A,T | |
| A2.1 10-mer | deleterious | D,E,P | 1° Anchor L,M,I,V,Q, A,T | D,E,R,K,H | | | R,K,H | D,E,R,K,H | F,Y,W, L,V,I,M | | 1° Anchor V,L,I,M,A,T |
| | preferred | A,Y,F,W | | L,V,I,M | G | | G | | | | |
| A3 | deleterious | D,E,P | | D,E | R,K,H,A | P | | R,K,H | D,E,R, K,H | R,K,H | |
| | preferred | R,H,K | 1° Anchor L,M,V,I,S, A,T,F,C,G D | Y,F,W | P,R,H,K,Y,F W | | | | | | |
| A11 | deleterious | D,E,P A | 1° Anchor V,T,L,M,I, S,A,G,N,C, D,F | D,E Y,F,W | Y,F,W | A | Y,F,W | Y,F,W | P | 1° Anchor K,Y,R,H,F,A | |
| A24 9-mer | deleterious | D,E,P | 1° Anchor Y,F,W,M | | S,T,C | | | A | G | 1° Anchor K,R,Y,H | |
| | preferred | Y,F,W,R,H,K | | | | | | Y,F,W | Y,F,W | | |
| A24 10-mer | deleterious | D,E,G | 1° Anchor Y,F,W,M | D,E | G P | Q,N,P Y,F,W,P | D,E,R,H,K | G P | A,Q,N | F,L,I,W | 1° Anchor F,L,I,W |
| A3101 | deleterious | R,H,K | 1° Anchor M,V,T,A,L, I,S | G,D,E Y,F,W | Q,N P | R,H,K | D,E Y,F,W | A Y,F,W | Q,N A,P | D,E,A 1° Anchor R,K | |
| A3301 | deleterious | D,E,P | 1° Anchor M,V,A,L,F, I,S,T | D,E Y,F,W | | A,D,E | D,E | D,E A,Y,F,W | D,E | 1° Anchor R,K | |
| A6801 | deleterious | G,P Y,F,W,S,T,C | 1° Anchor A,V,T,M,S, L,I | D,E | Y,F,W,I,L, V,M | | Y,F,W | | P | 1° Anchor R,K | |
| B0702 | deleterious | G,P R,H,K,F,W,Y | 1° Anchor P | D,E,G R,H,K | R,H,K R,H,K | R,H,K | R,H,K | R,H,K | A P,A | 1° Anchor L,M,F,W,Y,A, I,V | |
| B3501 | deleterious | D,E,Q,N,P F,W,Y,L,I,V,M | 1° Anchor P | D,E,P F,W,Y | D,E | G | G,D,E | Q,N F,W,Y | D,E | 1° Anchor L,M,F,W,Y,I, V,A | |
| | deleterious | A,G,P | | | G | G | | | | | |

TABLE II-continued

| | | 1 | 2 | 3 | 4 | 5 | 6 | 7 | 8 | 9 or C-terminus | C-terminus |
|---|---|---|---|---|---|---|---|---|---|---|---|
| B51 | preferred | L,I,V,M,F,W,Y | 1° Anchor P | F,W,Y | S,T,C | F,W,Y | | G | | F,W,Y | 1° Anchor L,I,V,F,W,Y; *A,M* | |
| | deleterious | A,G,P,D,E,R,H,K,S,T,C | | | | | | D,E,Q,N | | G,D,E | | |
| B5301 | preferred | L,I,V,M,F,W,Y | 1° Anchor P | F,W,Y | S,T,C | F,W,Y | G | L,I,V,M,F,W,Y | | F,W,Y | 1° Anchor I,M,F,W,Y,A, *L,V* | |
| | deleterious | A,G,P,Q,N | | | | | | R,H,K,Q,N | | D,E | | |
| B5401 | preferred | F,W,Y | 1° Anchor P | F,W,Y,L,I,V,M | | L,I,V,M | G | A,L,I,V,M | | F,W,Y,A,P | 1° Anchor A,T,I,V,L,M *F,W,Y* | |
| | deleterious | G,P,Q,N,D,E | | G,D,E,S,T,C | | R,H,K,D,E | D,E | Q,N,D,G,E | | D,E | | |

Italicized residues indicate less preferred or "tolerated" residues.
The information in Table II is specific for 9-mers unless otherwise specified.

TABLE III

| MOTIFS | 1° anchor 1 | 2 | 3 | 4 | 1° anchor 4 | 5 | 1° anchor 6 | 7 | 8 | 9 |
|---|---|---|---|---|---|---|---|---|---|---|
| DR4 preferred | F, M, Y, *L, I, V, W* | M | T | | | I | V, S, T, C, P, A, *L, I, M* | M, H | | M, H |
| deleterious | | | | W | | | | R | | W, D, E |
| DR1 preferred | M, F, *L, I, V, W, Y* | | | P, A, M, Q | | | V, M, A, T, *S, P, L, I, C* | M | | A, V, M |
| deleterious | | C | C, H | F, D | | C, W, D | | G, D, E | D | |
| DR7 preferred | M, F, *L, I, V, W, Y* | M | W | A, | | | I, V, M, S, A, C, *T, P, L,* | M | | I, V |
| deleterious | | | C | G, | | | | G, R, D | N | G |
| DR Supermotif | M, F, *L, I, V, W, Y* | | | | | | V, M, S, T, A, C, *P, L, I* | | | |
| DR3 MOTIFS | | | | | | | | | | |
| motif a preferred | L, I, V, M, F, Y | | | | D | | | | | |
| motif b preferred | L, I, V, M, F, A, Y | | | S, T | D, N, Q, E, | | K, R, H | | | |

Italicized residues indicate less preferred or "tolerated" residues.

TABLE IV

HLA Class I Standard Peptide Binding Affinity.

| ALLELE | STANDARD PEPTIDE | SEQUENCE | STANDARD BINDING AFFINITY (nM) | SEQ ID NO: |
|---|---|---|---|---|
| A*0101 | 944.02 | YLEPAIAKY | 25 | 2486 |
| A*0201 | 941.01 | FLPSDYFPSV | 5.0 | 2487 |
| A*0202 | 941.01 | FLPSDYFPSV | 4.3 | 2487 |
| A*0203 | 941.01 | FLPSDYFPSV | 10 | 2487 |
| A*0206 | 941.01 | FLPSDYFPSV | 3.7 | 2487 |
| A*0207 | 941.01 | FLPSDYFPSV | 23 | 2487 |
| A*6802 | 1141.02 | FTQAGYPAL | 40 | 2488 |
| A*0301 | 941.12 | KVFPYALINK | 11 | 2489 |
| A*1101 | 940.06 | AVDLYHFLK | 6.0 | 2490 |
| A*3101 | 941.12 | KVFPYALINK | 18 | 2489 |
| A*3301 | 1083.02 | STLPETYVVRR | 29 | 2491 |
| A*6801 | 941.12 | KVFPYALINK | 8.0 | 2489 |
| A*2401 | 979.02 | AYIDNYNKF | 12 | 2492 |
| B*0702 | 1075.23 | APRTLVYLL | 5.5 | 2493 |
| B*3501 | 1021.05 | FPFKYAAAF | 7.2 | 2494 |
| B51 | 1021.05 | FPFKYAAAF | 5.5 | 2494 |
| B*5301 | 1021.05 | FPFKYAAAF | 9.3 | 2494 |
| B*5401 | 1021.05 | FPFKYAAAF | 10 | 2494 |

TABLE V

HLA Class II Standard Peptide Binding Affinity.

| Allele | Nomenclature | Standard Peptide | Sequence | Binding Affinity (nM) | SEQ ID NO: |
|---|---|---|---|---|---|
| DRB1*0101 | DR1 | 515.01 | PKYVKQNTLKLAT | 5.0 | 2495 |
| DRB1*0301 | DR3 | 829.02 | YKTIAFDEEARR | 300 | 2496 |
| DRB1*0401 | DR4w4 | 515.01 | PKYVKQNTLKLAT | 45 | 2495 |
| DRB1*0404 | DR4w14 | 717.01 | YARFQSQTTLKQKT | 50 | 2497 |
| DRB1*0405 | DR4w15 | 717.01 | YARFQSQTTLKQKT | 38 | 2497 |
| DRB1*0701 | DR7 | 553.01 | QYIKANSKFIGITE | 25 | 2498 |
| DRB1*0802 | DR8w2 | 553.01 | QYIKANSKFIGITE | 49 | 2498 |
| DRB1*0803 | DR8w3 | 553.01 | QYIKANSKFIGITE | 1600 | 2498 |
| DRB1*0901 | DR9 | 553.01 | QYIKANSKFIGITE | 75 | 2498 |
| DRB1*1101 | DR5w11 | 553.01 | QYIKANSKFIGITE | 20 | 2498 |
| DRB1*1201 | DR5w12 | 1200.05 | EALIHQLKINPYVLS | 298 | 2499 |
| DRB1*1302 | DR6w19 | 650.22 | QYIKANAKFIGITE | 3.5 | 2500 |
| DRB1*1501 | DR2w2β1 | 507.02 | GRTQDENPVVHFFKNIVTPRTPPP | 9.1 | 2501 |
| DRB3*0101 | DR52a | 511 | NGQIGNDPNRDIL | 470 | 2502 |
| DRB4*0101 | DRw53 | 717.01 | YARFQSQTTLKQKT | 58 | 2503 |
| DRB5*0101 | DR2w2β2 | 553.01 | QYIKANSKFIGITE | 20 | 2504 |

The "Nomenclature" column lists the allelic designations used in Table XVIII.

TABLE VI

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 95 | 19 | POL | 521 | AICSVVRRAF | XIXXXXXXXF | | | | 1 |
| 95 | 19 | NUC | 54 | ALRQAILCW | XLXXXXXXW | | | | 2 |
| 80 | 16 | ENV | 108 | AMQWNSTTF | XMXXXXXXF | | | | 3 |
| 100 | 20 | POL | 166 | ASFCGSPY | XSXXXXXY | 26.0026 | * | | 4 |
| 100 | 20 | POL | 166 | ASFCGSPYSW | XSXXXXXXXW | | | | 5 |
| 9 | 18 | NUC | 19 | ASKLCLGW | XSXXXXXW | | | | 6 |
| 8 | 17 | NUC | 19 | ASKLCLGWLW | XSXXXXXXXW | | | | 7 |
| 80 | 16 | POL | 822 | ASPLHVAW | XSXXXXXW | | | | 8 |
| 100 | 20 | ENV | 312 | CIPIPSSW | XIXXXXXW | | | | 9 |
| 100 | 20 | ENV | 312 | CIPIPSSWAF | XIXXXXXXXF | | | | 10 |
| 95 | 19 | ENV | 253 | CLIFLLVLLDY | XLXXXXXXXXY | 26.0548 | | | 11 |
| 95 | 19 | ENV | 239 | CLRRFIIF | XLXXXXXF | | | | 12 |
| 75 | 15 | ENV | 239 | CLRRFIIFLF | XLXXXXXXXF | | | | 13 |
| 95 | 19 | POL | 523 | CSVVRRAF | XSXXXXXF | | | | 14 |
| 100 | 20 | ENV | 310 | CTCIPIPSSW | XTXXXXXXXW | | | | 15 |
| 90 | 18 | NUC | 31 | DIDPYKEF | XIXXXXXF | | | | 16 |
| 85 | 17 | NUC | 29 | DLLDTASALY | XLXXXXXXXY | 1.0519 | * | 11.1000 | 17 |
| 95 | 19 | ENV | 196 | DSWWTSLNF | XSXXXXXXF | 20.0120 | | | 18 |
| 95 | 19 | NUC | 43 | ELLSFLPSDF | XLXXXXXXXF | | | | 19 |
| 95 | 19 | NUC | 43 | ELLSFLPSDFF | XLXXXXXXXXF | | | | 20 |
| 95 | 19 | POL | 374 | ESRLWDF | XSXXXXF | | | | 21 |
| 95 | 19 | POL | 374 | ESRLWDFSQF | XSXXXXXXXF | | | | 22 |
| 80 | 16 | ENV | 248 | FILLLCLIF | XIXXXXXXF | | | | 23 |
| 80 | 16 | ENV | 246 | FLFILLLCLIF | XLXXXXXXXXF | | | | 24 |
| 95 | 19 | ENV | 256 | FLLVLLDY | XLXXXXXY | 26.0027 | | | 25 |
| 95 | 19 | POL | 658 | FSPTYKAF | XSXXXXXF | | | | 26 |
| 90 | 18 | X | 63 | FSSAGPCALRF | XSXXXXXXXXF | | | | 27 |
| 100 | 20 | ENV | 333 | FSWLSLLVPF | XSXXXXXXXF | 20.0263 | | | 28 |
| 95 | 19 | POL | 656 | FTFSPTYKAF | XTXXXXXXXF | 20.0262 | | | 29 |
| 95 | 19 | ENV | 346 | FVGLSPTVW | XVXXXXXXW | | | | 30 |
| 95 | 19 | POL | 627 | GLLGFAAPF | XLXXXXXXF | 20.0124 | | | 31 |
| 95 | 19 | POL | 509 | GLSPFLLAQF | XLXXXXXXXF | | | | 32 |
| 85 | 17 | NUC | 29 | GMDIDPYKEF | XMXXXXXXXF | 26.0372 | | | 33 |
| 95 | 19 | NUC | 123 | GVWIRTPPAY | XVXXXXXXXY | 1.0525 | | 0.0017 | 34 |
| 75 | 15 | POL | 569 | HLNPNKTKRW | XLXXXXXXXW | | | | 35 |
| 80 | 16 | POL | 491 | HLYSHPIILGF | XLXXXXXXXXF | | | | 36 |
| 85 | 17 | POL | 715 | HTAELLAACF | XTXXXXXXXF | | | | 37 |
| 95 | 19 | NUC | 52 | HTALRQAILCW | XTXXXXXXXXW | | | | 38 |
| 100 | 20 | POL | 149 | HTLWKAGILY | XTXXXXXXXY | 1.0542 | * | 0.0300 | 39 |
| 100 | 20 | ENV | 249 | ILLLCLIF | XLXXXXXF | | | | 40 |
| 80 | 16 | POL | 760 | ILRGTSFVY | XLXXXXXXY | 1.0205 | * | 0.0017 | 41 |
| 90 | 18 | ENV | 188 | ILTIPQSLDSW | XLXXXXXXXXW | | | | 42 |
| 90 | 18 | POL | 625 | IVGLLGFAAPF | XVXXXXXXXXF | | | | 43 |
| 80 | 16 | POL | 503 | KIPMGVGLSPF | XIXXXXXXXXF | | | | 44 |
| 85 | 17 | NUC | 21 | KLCLGWLW | XLXXXXXW | | | | 45 |
| 75 | 15 | POL | 108 | KLIMPARF | XLXXXXXF | | | | 46 |
| 75 | 15 | POL | 108 | KLIMPARFY | XLXXXXXXY | 1.0171 | | 0.0017 | 47 |
| 80 | 16 | POL | 610 | KLPVNRPIDW | XLXXXXXXXW | | | | 48 |
| 85 | 17 | POL | 574 | KTKRWGYSLNF | XTXXXXXXXXF | | | | 49 |
| 95 | 19 | POL | 55 | KVGNFTGLY | XVXXXXXXY | 1.0166 | * | 0.0680 | 50 |
| 95 | 19 | ENV | 254 | LIFLLVLLDY | XIXXXXXXXY | 1.0899 | | 0.0084 | 51 |
| 100 | 20 | POL | 109 | LIMPARFY | XIXXXXXY | 26.0028 | | | 52 |
| 85 | 17 | NUC | 30 | LLDTASALY | XLXXXXXXY | 1.0155 | * | 25.0000 | 53 |
| 80 | 16 | POL | 752 | LLGCAANW | XLXXXXXW | | | | 54 |
| 95 | 19 | POL | 628 | LLGFAAPF | XLXXXXXF | | | | 55 |
| 100 | 20 | ENV | 378 | LLPIFFCLW | XLXXXXXXW | | | | 56 |
| 100 | 20 | ENV | 378 | LLPIFFCLWVY | XLXXXXXXXXY | 26.0549 | * | | 57 |
| 95 | 19 | NUC | 44 | LLSFLPSDF | XLXXXXXXF | | | | 58 |
| 95 | 19 | NUC | 44 | LLSFLPSDFF | XLXXXXXXXF | | | | 59 |
| 90 | 18 | POL | 407 | LLSSNLSW | XLXXXXXW | | | | 60 |
| 95 | 19 | ENV | 175 | LLVLQAGF | XLXXXXXF | | | | 61 |
| 95 | 19 | ENV | 175 | LLVLQAGFF | XLXXXXXXF | 20.0121 | | | 62 |
| 100 | 20 | ENV | 338 | LLVPFVQW | XLXXXXXW | | | | 63 |
| 100 | 20 | ENV | 338 | LLVPFVQWF | XLXXXXXXF | | | | 64 |
| 85 | 17 | NUC | 100 | LLWFHISCLTF | XLXXXXXXXXF | | | | 65 |
| 95 | 19 | NUC | 46 | LSFLPSDF | XSXXXXXF | | | | 66 |
| 95 | 19 | NUC | 45 | LSFLPSDFF | XSXXXXXXF | 20.0123 | | | 67 |
| 95 | 19 | POL | 415 | LSLDVSAAF | XSXXXXXXF | | | | 68 |
| 95 | 19 | POL | 415 | LSLDVSAAFY | XSXXXXXXXY | 2.0239 | * | 4.2000 | 69 |
| 100 | 20 | ENV | 336 | LSLLVPFVQW | XSXXXXXXXW | | | | 70 |
| 100 | 20 | ENV | 336 | LSLLVPFVQWF | XSXXXXXXXXF | | | | 71 |
| 95 | 19 | X | 53 | LSLRGLPVCAF | XSXXXXXXXXF | | | | 72 |
| 95 | 19 | POL | 510 | LSPFLLAQF | XSXXXXXXF | | | | 73 |
| 75 | 15 | ENV | 349 | LSPTVWLSVIW | XSXXXXXXXXW | | | | 74 |
| 85 | 17 | POL | 742 | LSRKYTSF | XSXXXXXF | | | | 75 |

TABLE VI-continued

HBV A01 SUPER MOTIF (With binding information)

| Conservancy | Freq. | Protein | Position | Sequence | String | Peptide | Filed | A*0101 | SEQ ID NO: |
|---|---|---|---|---|---|---|---|---|---|
| 85 | 17 | POL | 742 | LSRKYTSFPW | XSXXXXXXXW | | | | 76 |
| 75 | 15 | ENV | 16 | LSVPNPLGF | XSXXXXXF | | | | 77 |
| 75 | 15 | NUC | 137 | LTFGRETVLEY | XTXXXXXXXXY | | | | 78 |
| 90 | 18 | ENV | 189 | LTIPDSLDSW | XTXXXXXXXW | | | | 79 |
| 90 | 18 | ENV | 189 | LTIPQSLDSWW | XTXXXXXXXXW | | | | 80 |
| 90 | 18 | POL | 404 | LTNLLSSNLSW | XTXXXXXXXXW | | | | 81 |
| 95 | 19 | ENV | 176 | LVLQAGFF | XVXXXXXF | | | | 82 |
| 100 | 20 | ENV | 339 | LVPFVQWF | XVXXXXXF | | | | 83 |
| 100 | 20 | POL | 377 | LVVDFSQF | XVXXXXXF | | | | 84 |
| 85 | 17 | ENV | 360 | MMWYWGPSLY | XMXXXXXXXY | 1039.01 | * | 0.0810 | 85 |
| 75 | 15 | X | 103 | MSTTDLEAY | XSXXXXXXY | 2.0126 | * | 0.8500 | 86 |
| 75 | 15 | X | 103 | MSTTDLEAYF | XSXXXXXXXF | | | | 87 |
| 95 | 19 | POL | 42 | NLGNLNVSIPW | XLXXXXXXXXW | | | | 88 |
| 90 | 18 | POL | 406 | NLLSSNLSW | XLXXXXXXW | | | | 89 |
| 95 | 19 | POL | 45 | NLNVSIFW | XLXXXXXW | | | | 90 |
| 75 | 15 | ENV | 15 | NLSVPNPLGF | XLXXXXXXXF | | | | 91 |
| 90 | 18 | POL | 738 | NSWLSRKY | XSXXXXXXY | 2.0123 | | 0.0005 | 92 |
| 100 | 20 | ENV | 380 | PIFFCLWVY | XIXXXXXXY | 1.0843 | | 0.0078 | 93 |
| 100 | 20 | ENV | 314 | PIPSSWAF | XIXXXXXF | | | | 94 |
| 100 | 20 | POL | 124 | PLDKGIKPY | XLXXXXXXY | 1.0174 | * | 0.0190 | 95 |
| 100 | 20 | POL | 124 | PLDKGIKPYY | XLXXXXXXXY | 1.0541 | * | 0.1600 | 96 |
| 100 | 20 | ENV | 377 | PLLPIFFCLW | XLXXXXXXXW | | | | 97 |
| 95 | 19 | ENV | 174 | PLLVLQAGF | XLXXXXXXF | | | | 98 |
| 95 | 19 | ENV | 174 | PLLVLQAGFF | XLXXXXXXXF | | | | 99 |
| 80 | 16 | POL | 505 | PMGVGLSPF | XMXXXXXXF | | | | 100 |
| 85 | 17 | POL | 797 | PTTGRTSLY | XTXXXXXXY | 1.0208 | * | 0.7700 | 101 |
| 75 | 15 | ENV | 351 | PTVWLSVIW | XTXXXXXXW | | | | 102 |
| 85 | 17 | POL | 612 | PVNRPIDW | XVXXXXXW | | | | 103 |
| 95 | 19 | POL | 685 | QVFADATPTG | XVXXXXXXXXW | | | | 104 |
| 90 | 18 | POL | 624 | RIVGLLGF | XIXXXXXF | | | | 105 |
| 75 | 15 | POL | 106 | RLKLIMPARF | XLXXXXXXXF | | | | 106 |
| 75 | 15 | POL | 106 | RLKLIMPARFY | XLXXXXXXXXY | | | | 107 |
| 95 | 19 | POL | 376 | RLWDFSQF | XLXXXXXF | 20.0122 | | | 108 |
| 90 | 18 | POL | 353 | RTPARVTGGVF | XTXXXXXXXXF | | | | 109 |
| 100 | 20 | POL | 49 | SIPWTHKVGNF | XIXXXXXXXXF | | | | 110 |
| 95 | 19 | ENV | 194 | SLDSWWTSLNF | XLXXXXXXXXF | | | | 111 |
| 95 | 19 | POL | 416 | SLDVSAAF | XLXXXXXF | | | | 112 |
| 95 | 19 | POL | 416 | SLDVSAAFY | XLXXXXXXY | 1.0186 | * | 17.2000 | 113 |
| 100 | 20 | ENV | 337 | SLLVPFVQW | XLXXXXXXW | | | | 114 |
| 100 | 20 | ENV | 337 | SLLVPFVQWF | XLXXXXXXXF | | | | 115 |
| 95 | 19 | X | 54 | SLRGLPVCAF | XLXXXXXXXF | 20.0259 | | | 116 |
| 90 | 18 | X | 64 | SSAGPCALRF | XSXXXXXXXF | 26.0374 | | | 117 |
| 75 | 15 | X | 104 | STTDLEAY | XTXXXXXY | | | | 118 |
| 75 | 15 | X | 104 | STTDLEAYF | XTXXXXXXF | | | | 119 |
| 75 | 15 | ENV | 17 | SVPNPLGF | XVXXXXXF | | | | 120 |
| 90 | 18 | POL | 739 | SVVLSRKY | XVXXXXXY | 26.0029 | | | 121 |
| 85 | 17 | POL | 739 | SWLSRKYTSF | XVXXXXXXXF | | | | 122 |
| 90 | 18 | ENV | 190 | TIPQSLDSW | XIXXXXXXW | | | | 123 |
| 90 | 18 | ENV | 190 | TIPQSLDSWW | XIXXXXXXXW | | | | 124 |
| 100 | 20 | POL | 150 | TLWKAGILY | XLXXXXXXY | 1.0177 | * | 0.0017 | 125 |
| 75 | 15 | X | 105 | TDDLEAYF | XTXXXXXF | | | | 126 |
| 85 | 17 | POL | 798 | TTGRTSLY | XTXXXXXY | 26.0030 | | | 127 |
| 80 | 16 | NUC | 16 | TVQASKLCLGW | XVXXXXXXXXW | | | | 128 |
| 75 | 15 | ENV | 352 | TVWLSVIW | XVXXXXXW | | | | 129 |
| 85 | 17 | POL | 741 | VLSRKYTSF | XLXXXXXXF | | | | 130 |
| 85 | 17 | POL | 741 | VLSRKYTSFPW | XLXXXXXXXXW | | | | 131 |
| 85 | 17 | POL | 740 | VVLSRKYTSF | XVXXXXXXXF | 20.0261 | | | 132 |
| 80 | 16 | POL | 759 | WILRGTSF | XiXXXXXF | | | | 133 |
| 80 | 16 | POL | 759 | WILRGTSFVY | XIXXXXXXXY | 1.0572 | | 0.0023 | 134 |
| 95 | 19 | NUC | 125 | WIRTPPAY | XIXXXXXY | 26.0031 | | | 135 |
| 80 | 16 | POL | 751 | WLLGCAANW | XLXXXXXXW | | | | 136 |
| 95 | 19 | POL | 414 | WLSLDVSAAF | XLXXXXXXXF | | | | 137 |
| 95 | 19 | POL | 414 | WLSLDVSAAFY | XLXXXXXXXXY | 26.0551 | | | 138 |
| 100 | 20 | ENV | 335 | WLSLLVPF | XLXXXXXF | | | | 139 |
| 100 | 20 | ENV | 335 | WLSLLVPFVQW | XLXXXXXXXXW | | | | 140 |
| 85 | 17 | NUC | 26 | WLWGMDIDPY | XLXXXXXXXY | 1.0774 | * | 0.0810 | 141 |
| 95 | 19 | ENV | 237 | WMCLRRFIIF | XMXXXXXXXF | 20.0266 | | | 142 |
| 85 | 17 | ENV | 359 | WMMWYWGPS | XMXXXXXXXXY | 26.0552 | * | | 143 |
| 100 | 20 | POL | 52 | WTHKVGNF | XTXXXXXF | | | | 144 |
| 100 | 20 | POL | 122 | YLPLDKGIKPY | XLXXXXXXXXY | 26.0553 | | | 145 |
| 90 | 18 | NUC | 118 | YLVSFGVW | XLXXXXXW | | | | 146 |
| 80 | 16 | POL | 493 | YSHPIILGF | XSXXXXXF | | | | 147 |
| 85 | 17 | POL | 580 | YSLNFMGY | XSXXXXXY | 26.0032 | | | 148 |

TABLE VII

HBV A02 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 85 | 17 | POL | 721 | AACFARSRSGA | A | A | | 11 | | | | | | | 149 |
| 85 | 17 | POL | 431 | AAMPHLLV | A | V | | 8 | | | | | | | 150 |
| 80 | 16 | POL | 756 | AANWILRGT | A | T | | 9 | | | | | | | 151 |
| 95 | 19 | POL | 632 | AAPFTQCGYPA | A | A | | 11 | | | | | | | 152 |
| 95 | 19 | POL | 521 | AICSVVRRA | I | A | 5.0025 | 9 | | 0.0001 | | | | | 153 |
| 90 | 18 | NUC | 58 | AILCWGEL | I | L | | 8 | | | | | | | 154 |
| 90 | 18 | NUC | 58 | AILCWGELM | I | M | | 9 | | | | | | | 155 |
| 95 | 19 | POL | 642 | ALMPLYACI | L | I | 927.15 | 9 | * | 0.5000 | 0.0340 | 3.3000 | 0.2500 | 0.0470 | 156 |
| 80 | 16 | ENV | 108 | AMQWNSTT | M | T | | 8 | | | | | | | 157 |
| 75 | 15 | X | 102 | AMSTTDLEA | M | A | 3.0051 | 9 | | 0.0013 | | | | | 158 |
| 95 | 19 | POL | 690 | ATPTGWGL | T | L | | 8 | | | | | | | 159 |
| 80 | 16 | POL | 690 | ATPTGWGLA | T | A | | 9 | | | | | | | 160 |
| 75 | 15 | POL | 690 | AVPTGWGLAI | T | I | | 10 | | | | | | | 161 |
| 95 | 19 | POL | 397 | AVPNLQSL | V | L | | 8 | | | | | | | 162 |
| 95 | 19 | POL | 397 | AVPNLQSLT | V | T | 5.0026 | 9 | | 0.0001 | | | | | 163 |
| 95 | 19 | POL | 397 | AVPNLQSLTNL | V | L | | 11 | | | | | | | 164 |
| 80 | 16 | POL | 755 | CAANWILRGT | A | T | | 10 | | | | | | | 165 |
| 95 | 19 | X | 61 | CAFSSAGPCA | A | A | 5.0090 | 10 | | 0.0001 | | | | | 166 |
| 95 | 19 | X | 61 | CAFSSAGPCAL | A | L | | 11 | | | | | | | 167 |
| 90 | 18 | X | 69 | CALRFTSA | A | A | | 8 | | | | | | | 168 |
| 100 | 20 | ENV | 312 | CIPIPSSWA | I | A | 5.0007 | 9 | | 0.0010 | | | | | 169 |
| 80 | 16 | ENV | 312 | CIPIPSSWAFA | I | A | | 11 | | | | | | | 170 |
| 90 | 18 | POL | 533 | CLAFSYMDDV | L | V | 1.0559 | 10 | | 0.0008 | | | | | 171 |
| 90 | 18 | POL | 533 | CLAFSYMDDVV | L | V | | 11 | | | | | | | 172 |
| 85 | 17 | NUC | 23 | CLGWLWGM | L | M | | 8 | | | | | | | 173 |
| 85 | 17 | NUC | 23 | CLGWLWGMDI | L | I | 3.0210 | 10 | | 0.0093 | | | | | 174 |
| 100 | 20 | ENV | 253 | CLIFLLVL | L | L | Chisari 4.011 | 8 | | 0.0002 | | | | | 175 |
| 100 | 20 | ENV | 253 | CLIFLLVLL | L | L | 1.0836 | 9 | | 0.0006 | | | | | 176 |
| 95 | 19 | ENV | 239 | CLRRFIIFL | L | L | 1.0829 | 9 | | 0.0002 | | | | | 177 |
| 75 | 15 | ENV | 239 | CLRRFIIFLFI | L | I | Chisari 4.055 | 11 | | 0.0004 | | | | | 178 |
| 90 | 18 | NUC | 107 | CLTFGRET | L | T | | 8 | | | | | | | 179 |
| 90 | 18 | NUC | 107 | CLTFGRETV | L | V | 1.0160 | 9 | | 0.0001 | | | | | 180 |
| 100 | 20 | ENV | 310 | CTCIPIPSSWA | T | A | | 11 | | | | | | | 181 |
| 95 | 19 | POL | 689 | DATPTGWGL | A | L | 5.0027 | 9 | | 0.0001 | | | | | 182 |
| 80 | 16 | POL | 689 | DATPTGWGLA | A | A | | 10 | | | | | | | 183 |
| 75 | 15 | POL | 689 | DATPTGWGLAI | A | I | | 11 | | | | | | | 184 |
| 90 | 18 | NUC | 31 | DIDPYKEFGA | I | A | | 10 | | | | | | | 185 |
| 85 | 17 | NUC | 29 | DLLDTASA | L | A | | 8 | | | | | | | 186 |
| 85 | 17 | NUC | 29 | DLLDTASAL | L | L | 1.0154 | 9 | | 0.0001 | | | | | 187 |
| 95 | 19 | POL | 40 | DLNLGNLNV | L | V | 927.30 | 9 | | 0.0004 | | | | | 188 |
| 95 | 19 | POL | 40 | DLNLGNLNVSI | L | I | | 11 | | | | | | | 189 |
| 80 | 16 | NUC | 32 | DTASALYREA | T | A | | 10 | | | | | | | 190 |
| 80 | 16 | NUC | 32 | DTASALYREAL | T | L | | 11 | | | | | | | 191 |
| 95 | 19 | X | 14 | DVLCLRPV | V | V | | 8 | | | | | | | 192 |
| 95 | 19 | X | 14 | DVLCLRPVGA | V | A | 5.0091 | 10 | | 0.0001 | | | | | 193 |
| 90 | 18 | POL | 541 | DVVLGAKSV | V | V | 1.0190 | 9 | | 0.0003 | | | | | 194 |
| 100 | 20 | POL | 17 | EAGPLEEEL | A | L | 5.0028 | 9 | | 0.0001 | | | | | 195 |
| 80 | 16 | X | 122 | ELGEEIRL | L | L | | 8 | | | | | | | 196 |
| 90 | 18 | POL | 718 | ELLAACFA | L | A | | 8 | | | | | | | 197 |
| 75 | 15 | NUC | 142 | ETVLEYLV | T | V | | 8 | | | | | | | 198 |
| 95 | 19 | POL | 687 | FADATPTGWGL | A | L | | 11 | | | | | | | 199 |
| 85 | 17 | POL | 724 | FARSRSGA | A | A | | 8 | | | | | | | 200 |
| 80 | 16 | POL | 821 | FASPLHVA | A | A | | 8 | | | | | | | 201 |
| 95 | 19 | POL | 396 | FAVPNLQSL | A | L | | 9 | | | | | | | 202 |
| 95 | 19 | POL | 396 | FAVPNLQSLT | A | T | 5.0083 | 10 | | 0.0003 | | | | | 203 |
| 80 | 16 | ENV | 243 | FIIFLFIL | I | L | Chisari 4.047 | 8 | | 0.0006 | | | | | 204 |
| 80 | 16 | ENV | 243 | FIIFLFILL | I | L | 1.0830 | 9 | | 0.0002 | | | | | 205 |
| 80 | 16 | ENV | 243 | FIIFLFILLL | I | L | 1.0894 | 10 | | 0.0012 | | | | | 206 |
| 80 | 16 | ENV | 248 | FILLLCLI | I | I | Chisari 4.048 | 8 | | 0.0003 | | | | | 207 |
| 80 | 16 | ENV | 248 | FILLLCLIFL | I | L | 1.0895 | 10 | * | 0.0280 | | | | | 208 |
| 80 | 16 | ENV | 248 | FILLLCLIFLL | I | L | Chisari 4.049 | 11 | | 0.0010 | | | | | 209 |
| 80 | 16 | ENV | 246 | FLFILLLCL | L | L | 1.0832 | 9 | | 0.0002 | | | | | 210 |
| 80 | 16 | ENV | 246 | FLFILLLCLI | L | I | 3.0206 | 10 | | 0.0013 | | | | | 211 |
| 75 | 15 | ENV | 171 | FLGPLLVL | L | L | | 8 | | | | | | | 212 |
| 75 | 15 | ENV | 171 | FLGPLLVLQA | L | A | 3.0205 | 10 | * | 0.0190 | | | | | 213 |
| 95 | 19 | POL | 513 | FLLAQFTSA | L | A | 1069.07 | 9 | * | 0.2400 | | | | | 214 |
| 95 | 19 | POL | 513 | FLLAQFTSAI | L | I | 1147.13 | 10 | * | 0.2100 | 0.0320 | 7.0000 | 0.1100 | 0.0880 | 215 |
| 95 | 19 | POL | 562 | FLLSLGIHL | L | L | 927.11 | 9 | * | 0.6500 | 0.0010 | 0.0100 | 0.1100 | 0.0035 | 216 |

TABLE VII-continued

HBV A02 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 80 | 16 | ENV | 183 | FLLTRILT | L | T | | 8 | | | | | | | 217 |
| 80 | 16 | ENV | 183 | FLLTRILTI | L | I | 777.03 | 9 | * | 0.5100 | 0.0430 | 8.0000 | 0.2000 | 0.0010 | 218 |
| 95 | 19 | ENV | 256 | FLLVLLDYQGM | L | M | | 11 | | | | | | | 219 |
| 100 | 20 | POL | 363 | FLVDKNPHNT | L | T | 5.0084 | 10 | | 0.0012 | | | | | 220 |
| 95 | 19 | POL | 656 | FTFSPTYKA | T | A | 1147.15 | 9 | * | 0.0056 | 0.0150 | 0.0031 | 0.8000 | 7.3000 | 221 |
| 95 | 19 | POL | 656 | FTFSPTYKAFL | T | L | | 11 | | | | | | | 222 |
| 95 | 19 | POL | 59 | FTGLYSST | T | T | | 8 | | | | | | | 223 |
| 90 | 18 | POL | 59 | FTGLYSSTV | T | V | 20.0118 | 9 | | 0.0005 | | | | | 224 |
| 95 | 19 | POL | 635 | FTQCGYPA | T | A | | 8 | | | | | | | 225 |
| 95 | 19 | POL | 635 | FTQCGYPAL | T | L | 5.0031 | 9 | | 0.0009 | | | | | 226 |
| 95 | 19 | POL | 635 | FTQCGYPALM | T | M | 5.0085 | 10 | | 0.0024 | | | | | 227 |
| 95 | 19 | POL | 518 | FTSAICSV | T | V | | 8 | | | | | | | 228 |
| 95 | 19 | POL | 518 | FTSAICSVV | T | V | 5.0032 | 9 | | 0.0090 | | | | | 229 |
| 95 | 19 | ENV | 346 | FVGLSPTV | V | V | | 8 | | | | | | | 230 |
| 95 | 19 | ENV | 346 | FVGLSPTVWL | V | L | 1.0931 | 10 | | 0.0008 | | | | | 231 |
| 90 | 18 | X | 132 | FVLGGCRHKL | V | L | Chisari 4.114 | 10 | | 0.0030 | | | | | 232 |
| 90 | 18 | X | 132 | FVLGGCRHKLV | V | V | | 11 | | | | | | | 233 |
| 95 | 19 | ENV | 342 | FVQWFVGL | V | L | | 8 | | | | | | | 234 |
| 95 | 19 | ENV | 342 | FVQWFVGLSPT | V | T | | 11 | | | | | | | 235 |
| 90 | 18 | POL | 768 | FVYVPSAL | V | L | | 8 | | | | | | | 236 |
| 90 | 18 | POL | 766 | FVYVPSALNPA | V | A | | 11 | | | | | | | 237 |
| 95 | 19 | X | 50 | GAHLSLRGL | A | L | 5.0040 | 9 | | 0.0001 | | | | | 238 |
| 90 | 18 | X | 50 | GAHLSLRGLPV | A | V | | 11 | | | | | | | 239 |
| 85 | 17 | POL | 545 | GAKSVQHL | A | L | | 8 | | | | | | | 240 |
| 85 | 17 | POL | 545 | GAKSVQHLESL | A | L | | 11 | | | | | | | 241 |
| 75 | 15 | POL | 567 | GIHLNPNKT | I | T | | 9 | | | | | | | 242 |
| 90 | 18 | POL | 155 | GILYKRET | I | T | | 8 | | | | | | | 243 |
| 90 | 18 | POL | 155 | GILYKRETT | I | T | | 9 | | | | | | | 244 |
| 85 | 17 | POL | 682 | GLCQVFADA | L | A | 1142.04 | 9 | * | 0.0024 | | | | | 245 |
| 85 | 17 | POL | 682 | GLCQVFADAT | L | T | | 10 | | | | | | | 246 |
| 95 | 19 | POL | 627 | GLLGFAAPFT | L | T | 5.0086 | 10 | | 0.0049 | | | | | 247 |
| 85 | 17 | ENV | 62 | GLLGWSPQA | L | A | 1142.07 | 9 | * | 0.4000 | 0.0003 | 0.0350 | 0.2800 | 0.0005 | 248 |
| 95 | 19 | X | 57 | GLPVCAFSSA | L | A | 5.0092 | 10 | | 0.0008 | | | | | 249 |
| 95 | 19 | POL | 509 | GLSPFLLA | L | A | | 8 | | | | | | | 250 |
| 95 | 19 | POL | 509 | GLSPFLLAQFT | L | T | | 11 | | | | | | | 251 |
| 100 | 20 | ENV | 348 | GLSPTVWL | L | L | Chisari 4.012 | 8 | | 0.0036 | | | | | 252 |
| 75 | 15 | ENV | 348 | GLSPVWLSV | L | V | 1.0518 | 10 | * | 0.2800 | | | | | 253 |
| 75 | 15 | ENV | 348 | GLSPTVWLSVI | L | I | Chisari 4.031 | 11 | | 0.0036 | | | | | 254 |
| 90 | 18 | ENV | 265 | GMLPVCPL | M | L | | 8 | | | | | | | 255 |
| 90 | 18 | POL | 735 | GTDNSVVL | T | L | | 8 | | | | | | | 256 |
| 75 | 15 | ENV | 13 | GTNLSVPNPL | T | L | | 10 | | | | | | | 257 |
| 80 | 16 | POL | 763 | GTSFVYVPSA | T | A | | 10 | | | | | | | 258 |
| 80 | 16 | POL | 763 | GTSFVYVPSAL | T | L | | 11 | | | | | | | 259 |
| 80 | 16 | POL | 507 | GVGLSPFL | V | L | | 8 | | | | | | | 260 |
| 80 | 16 | POL | 507 | GVGLSPFLL | V | L | Chisari 4.082 | 9 | | 0.0002 | | | | | 261 |
| 80 | 16 | POL | 507 | GVGLSPFLLA | V | A | | 10 | | | | | | | 262 |
| 95 | 19 | NUC | 123 | GVWIRTPPA | V | A | 3.0040 | 9 | | 0.0030 | | | | | 263 |
| 90 | 18 | NUC | 104 | HISCLTFGRET | I | T | | 11 | | | | | | | 264 |
| 80 | 16 | POL | 435 | HLLVGSSGL | L | L | 927.43 | 9 | | 0.0031 | | | | | 265 |
| 90 | 18 | X | 52 | HLSLRGLPV | L | V | 927.02 | 9 | | 0.0014 | | | | | 266 |
| 90 | 18 | X | 52 | HLSLRGLPVCA | L | A | | 11 | | | | | | | 267 |
| 80 | 16 | POL | 491 | HLYSHPII | L | I | 17.0256 | 8 | | | | | | | 268 |
| 80 | 16 | POL | 491 | HLYSHPIIL | L | L | 927.47 | 9 | * | 0.2200 | 0.0003 | 0.9300 | 0.1700 | 0.0530 | 269 |
| 85 | 17 | POL | 715 | HTAELLAA | T | A | | 8 | | | | | | | 270 |
| 85 | 17 | POL | 715 | HTAELLAACFA | T | A | | 11 | | | | | | | 271 |
| 100 | 20 | NUC | 52 | HTALRQAI | T | I | | 8 | | | | | | | 272 |
| 95 | 19 | NUC | 52 | HTALRQAIL | T | L | 5.0021 | 9 | | 0.0001 | | | | | 273 |
| 100 | 20 | POL | 149 | HTLWKAGI | T | I | | 8 | | | | | | | 274 |
| 100 | 20 | POL | 149 | HTLWKAGIL | T | L | 5.0033 | 9 | | 0.0001 | | | | | 275 |
| 80 | 16 | ENV | 244 | IIFLFILL | I | L | Chisari 4.051 | 8 | | 0.0004 | | | | | 276 |
| 80 | 16 | ENV | 244 | IIFLFILLL | I | L | 1.0831 | 9 | | 0.0002 | | | | | 277 |
| 80 | 16 | ENV | 244 | IIFLFILLLCL | I | L | Chisari 4.052 | 11 | | 0.0002 | | | | | 278 |
| 80 | 16 | POL | 497 | IILGFRKI | I | I | | 8 | | | | | | | 279 |
| 80 | 16 | POL | 497 | IILGFRKIPM | I | M | | 10 | | | | | | | 280 |
| 90 | 18 | NUC | 59 | ILCWGELM | L | M | | 8 | | | | | | | 281 |
| 80 | 16 | POL | 498 | ILGFRKIPM | L | M | 3.0016 | 9 | | 0.0002 | | | | | 282 |
| 100 | 20 | ENV | 249 | ILLLCLIFL | L | L | 1137.04 | 9 | * | 0.0015 | | | | | 283 |

TABLE VII-continued

HBV A02 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 100 | 20 | ENV | 249 | ILLLCLIFLL | L | L | 1069.08 | 10 | * | 0.0190 | 0.0001 | 0.0002 | 0.1300 | 0.0015 | 284 |
| 100 | 20 | ENV | 249 | ILLLCLIFLLV | L | V | Chisari 4.013 | 11 | | 0.0056 | | | | | 285 |
| 80 | 16 | POL | 760 | ILRGTSFV | L | V | | 8 | | | | | | | 286 |
| 80 | 16 | POL | 760 | ILRGTSFVYV | L | V | 1.0573 | 10 | * | 0.0160 | | | | | 287 |
| 100 | 20 | NUC | 139 | ILSTLPET | L | T | | 8 | | | | | | | 288 |
| 100 | 20 | NUC | 139 | ILSTLPETT | L | T | 5.0022 | 9 | | 0.0001 | | | | | 289 |
| 100 | 20 | NUC | 139 | ILSTLPETTV | L | V | 1069.14 | 10 | * | 0.0210 | 0.0085 | 0.0770 | 0.3100 | 0.0067 | 290 |
| 100 | 20 | NUC | 139 | ILSTLPETTVV | L | V | | 11 | | | | | | | 291 |
| 95 | 19 | ENV | 188 | ILTIPQSL | L | L | | 8 | | | | | | | 292 |
| 90 | 18 | POL | 156 | ILYKRETT | L | T | | 8 | | | | | | | 293 |
| 90 | 18 | POL | 625 | IVGLLGFA | V | A | | 8 | | | | | | | 294 |
| 90 | 18 | POL | 625 | IVGLLGFAA | V | A | 3.0041 | 9 | | 0.0009 | | | | | 295 |
| 90 | 18 | POL | 153 | KAGILYKRET | A | T | | 10 | | | | | | | 296 |
| 90 | 18 | POL | 153 | KAGILYKRETT | A | T | | 11 | | | | | | | 297 |
| 80 | 16 | POL | 503 | KIPMGVGL | I | L | | 8 | | | | | | | 298 |
| 85 | 17 | NUC | 21 | KLCLGWLWGM | L | M | 1142.02 | 10 | * | 0.0001 | | | | | 299 |
| 95 | 19 | POL | 489 | KLHLYSHPI | L | I | 927.46 | 9 | * | 0.0690 | 0.0340 | 2.7000 | 0.5900 | 0.0015 | 300 |
| 80 | 16 | POL | 489 | KLHLYSHPII | L | I | | 10 | | | | | | | 301 |
| 80 | 16 | POL | 489 | KLHLYSHPIIL | L | L | | 11 | | | | | | | 302 |
| 80 | 16 | POL | 610 | KLPVNRPI | L | I | | 8 | | | | | | | 303 |
| 95 | 19 | POL | 574 | KTKRWGYSL | T | L | 5.0034 | 9 | | 0.0001 | | | | | 304 |
| 85 | 17 | POL | 620 | KVCQRIVGL | V | L | 1.0198 | 9 | | 0.0003 | | | | | 305 |
| 85 | 17 | POL | 620 | KVCQRIVGLL | V | L | 1.0567 | 10 | | 0.0001 | | | | | 306 |
| 95 | 19 | POL | 55 | KVGNFTGL | V | L | 17.0116 | 8 | | | | | | | 307 |
| 85 | 17 | X | 91 | KVLHKRTL | V | L | | 6 | | | | | | | 308 |
| 85 | 17 | X | 91 | KVLHKRTLGL | V | L | Chisari 4.115 | 10 | | 0.0004 | | | | | 309 |
| 90 | 18 | POL | 534 | LAFSYMDDV | A | V | 20.0119 | 9 | | 0.0002 | | | | | 310 |
| 90 | 18 | POL | 534 | LAFSYMDDVV | A | V | 20.0257 | 10 | | 0.0003 | | | | | 311 |
| 90 | 18 | POL | 534 | LAFSYMDDVVL | A | L | | 11 | | | | | | | 312 |
| 95 | 19 | POL | 515 | LAQFTSAI | A | I | | 8 | | | | | | | 313 |
| 95 | 19 | POL | 515 | LAQFTSAICSV | A | V | | 11 | | | | | | | 314 |
| 100 | 20 | ENV | 254 | LIFLLVLL | I | L | Chisari 4.014 | 8 | | 0.0025 | | | | | 315 |
| 95 | 19 | POL | 514 | LLAQFTSA | L | A | | 8 | | | | | | | 316 |
| 95 | 19 | POL | 514 | LLAQFTSAI | L | I | 1069.05 | 9 | * | 0.1000 | 0.2700 | 3.7000 | 0.2600 | 0.7900 | 317 |
| 100 | 20 | ENV | 251 | LLCLIFLL | L | L | Chisari 4.015 | 8 | | 0.0004 | | | | | 318 |
| 100 | 20 | ENV | 251 | LLCLIFLLV | L | V | 1137.03 | 9 | * | 0.0048 | | | | | 319 |
| 100 | 20 | ENV | 251 | LLCLIFLLVL | L | L | 1.0898 | 10 | | 0.0075 | | | | | 320 |
| 100 | 20 | ENV | 251 | LLCLIFLLVLL | L | L | Chisari 4.016 | 11 | | 0.0013 | | | | | 321 |
| 85 | 17 | NUC | 30 | LLDTASAL | L | L | | 8 | | | | | | | 322 |
| 95 | 19 | ENV | 260 | LLDYQGML | L | L | Chisari 4.021 | 8 | | 0.0004 | | | | | 323 |
| 90 | 18 | ENV | 260 | LLDYQGMLPV | L | V | 1137.02 | 10 | * | 0.0980 | 0.0001 | 0.0200 | 0.6700 | 0.0009 | 324 |
| 80 | 16 | POL | 752 | LLGCAANWI | L | I | 927.22 | 9 | | 0.0011 | | | | | 325 |
| 80 | 16 | POL | 752 | LLGCAANWIL | L | L | 1.0912 | 10 | * | 0.0140 | | | | | 326 |
| 95 | 19 | POL | 628 | LLGFAAPFT | L | T | 5.0035 | 9 | | 0.0008 | | | | | 327 |
| 85 | 17 | ENV | 63 | LLGWSPQA | L | A | | 8 | | | | | | | 328 |
| 75 | 15 | ENV | 63 | LLGWSPQAQGL | L | I | | 11 | | | | | | | 329 |
| 100 | 20 | ENV | 250 | LLLCLIFL | L | L | Chisari 4.017 | 8 | | 0.0006 | | | | | 330 |
| 100 | 20 | ENV | 250 | LLLCLIFLL | L | L | 1090.05 | 9 | * | 0.0065 | | | | | 331 |
| 100 | 20 | ENV | 250 | LLLCLIFLLV | L | V | 1137.01 | 10 | * | 0.0036 | | | | | 332 |
| 100 | 20 | ENV | 250 | LLLCLIFLLVL | L | L | Chisari 4.018 | 11 | | 0.0005 | | | | | 333 |
| 100 | 20 | ENV | 378 | LLPIFFCL | L | L | Chisari 4.019 | 8 | | 0.0055 | | | | | 334 |
| 100 | 20 | ENV | 378 | LLPIFFCLWV | L | V | 1069.10 | 10 | * | 0.0320 | 0.0008 | 0.0150 | 0.8000 | 0.0005 | 335 |
| 95 | 19 | POL | 563 | LLSLGIHL | L | L | | 8 | | | | | | | 336 |
| 90 | 18 | POL | 407 | LLSSNLSWL | L | L | 927.41 | 9 | * | 0.0110 | 0.0780 | 3.9000 | 0.2700 | 0.0100 | 337 |
| 90 | 18 | POL | 407 | LLSSNLSWLSL | L | L | | 11 | | | | | | | 338 |
| 80 | 16 | ENV | 184 | LLTRILTI | L | I | Chisari 4.053 | 8 | | 0.0026 | | | | | 339 |
| 80 | 16 | POL | 436 | LLVGSSGL | L | L | | 8 | | | | | | | 340 |
| 95 | 19 | ENV | 257 | LLVLLDYQGM | L | M | 3.0207 | 10 | | 0.0050 | | | | | 341 |
| 95 | 19 | ENV | 257 | LLVLLDYQGML | L | L | | 11 | | | | | | | 342 |
| 90 | 18 | ENV | 175 | LLVLQAGFFL | L | L | 1090.06 | 10 | * | 0.0310 | 0.0037 | 0.0045 | 0.1500 | 0.0110 | 343 |
| 90 | 18 | ENV | 175 | LLVLQAGFFLL | L | L | Chisari 4.028 | 11 | | 0.0074 | | | | | 344 |
| 95 | 19 | ENV | 338 | LLVPFVQWFV | L | V | 1069.06 | 10 | * | 0.6700 | 0.3800 | 1.7000 | 0.2900 | 0.1400 | 345 |

TABLE VII-continued

HBV A02 SUPER MOTIF (With binding information)

| Conservancy | Frequency | Protein | Position | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | NUC | 100 | LLWFHISCL | L | L | 1142.01 | 9 | * | 0.0130 | 0.0002 | 0.0420 | 0.3100 | 0.0098 | 346 |
| 85 | 17 | NUC | 100 | LLWFHISCLT | L | T | | 10 | | | | | | | 347 |
| 95 | 19 | POL | 643 | LMPLYACI | M | I | 17.0130 | 8 | | | | | | | 348 |
| 95 | 19 | NUC | 108 | LTFGRETV | T | V | | 8 | | | | | | | 349 |
| 75 | 15 | NUC | 137 | LTFGRETVL | T | L | | 9 | | | | | | | 350 |
| 90 | 18 | POL | 404 | LTNLLSSNL | T | L | | 9 | | | | | | | 351 |
| 80 | 16 | ENV | 185 | LTRILTIPQSL | T | L | | 11 | | | | | | | 352 |
| 85 | 17 | POL | 99 | LTVNEKRRL | T | L | | 9 | | | | | | | 353 |
| 100 | 20 | POL | 364 | LVDKNPHNT | V | T | 5.0036 | 9 | | 0.0001 | | | | | 354 |
| 95 | 19 | ENV | 258 | LVLLDYQGM | V | M | 3.0034 | 9 | | 0.0001 | | | | | 355 |
| 95 | 19 | ENV | 258 | LVLLDYQGML | V | L | 1.0515 | 10 | | 0.0001 | | | | | 356 |
| 90 | 18 | ENV | 176 | LVLQAGFFL | V | L | 1.0827 | 9 | | 0.0096 | | | | | 357 |
| 90 | 18 | ENV | 176 | LVLQAGFFLL | V | L | 1132.17 | 10 | * | 0.0022 | | | | | 358 |
| 90 | 18 | ENV | 176 | LVLQAGFFLLT | V | T | | 11 | | | | | | | 359 |
| 95 | 19 | ENV | 339 | LVPFVQWFV | V | V | 1132.01 | 9 | * | 0.0420 | 0.0150 | 0.0048 | 0.7900 | 2.8000 | 360 |
| 95 | 19 | ENV | 339 | LVPFVQWFVGL | V | L | | 11 | | | | | | | 361 |
| 90 | 18 | NUC | 119 | LVSFGVWI | V | I | Chisari 4.078 | 8 | | 0.0004 | | | | | 362 |
| 90 | 18 | NUC | 119 | LVSFGVWIRT | V | T | | 10 | | | | | | | 363 |
| 85 | 17 | ENV | 360 | MMWYWGPSL | M | L | 1039.03 | 9 | * | 0.6400 | | | | | 364 |
| 100 | 20 | ENV | 136 | NAPILSTL | A | L | | 8 | | | | | | | 365 |
| 100 | 20 | ENV | 136 | NAPILSTLPET | A | T | | 11 | | | | | | | 366 |
| 95 | 19 | POL | 42 | NLGNLNVSI | L | I | 3.0008 | 9 | | 0.0047 | | | | | 367 |
| 90 | 18 | POL | 406 | NLLSSNLSWL | L | L | 1.0549 | 10 | | 0.0016 | | | | | 368 |
| 95 | 19 | POL | 45 | NLNVSIPWT | L | T | 5.0037 | 9 | | 0.0005 | | | | | 369 |
| 100 | 20 | POL | 400 | NLQSLTNL | L | L | | 8 | | | | | | | 370 |
| 100 | 20 | POL | 400 | NLQSLTNLL | L | L | 927.40 | 9 | | 0.0047 | | | | | 371 |
| 75 | 15 | ENV | 15 | NLSVPNPL | L | L | | 8 | | | | | | | 372 |
| 90 | 18 | POL | 411 | NLSWLSLDV | L | V | 927.42 | 9 | * | 0.0650 | 0.0051 | 0.6400 | 0.1600 | 0.0990 | 373 |
| 90 | 18 | POL | 411 | NLSWLSLDVSA | L | A | | 11 | | | | | | | 374 |
| 100 | 20 | POL | 47 | NVSIPWTHKV | V | V | 1.0532 | 10 | | 0.0001 | | | | | 375 |
| 100 | 20 | POL | 430 | PAAMPHLL | A | L | | 8 | | | | | | | 376 |
| 85 | 17 | POL | 430 | PAAMPHLLV | A | V | | 9 | | | | | | | 377 |
| 90 | 18 | POL | 775 | PADDPSRGRL | A | L | | 10 | | | | | | | 378 |
| 90 | 18 | ENV | 131 | PAGGSSSGT | A | T | | 9 | | | | | | | 379 |
| 90 | 18 | ENV | 131 | PAGGSSSGTV | A | V | | 10 | | | | | | | 380 |
| 95 | 19 | POL | 641 | PALMPLYA | A | A | | 8 | | | | | | | 381 |
| 95 | 19 | POL | 641 | PALMPLYACI | A | I | 5.0087 | 10 | | 0.0001 | | | | | 382 |
| 75 | 15 | X | 145 | PAPCNFFT | A | T | | 8 | | | | | | | 383 |
| 75 | 15 | X | 145 | PAPCNFFTSA | A | A | | 10 | | | | | | | 384 |
| 80 | 16 | X | 11 | PARDVLCL | A | L | | 8 | | | | | | | 385 |
| 75 | 15 | X | 11 | PARDVLCLRPV | A | V | | 11 | | | | | | | 386 |
| 90 | 18 | POL | 355 | PARVTGGV | A | V | | 8 | | | | | | | 387 |
| 90 | 18 | POL | 355 | PARVTGGVFL | A | L | | 10 | | | | | | | 388 |
| 90 | 18 | POL | 355 | PARVTGGVFLV | A | V | | 11 | | | | | | | 389 |
| 95 | 19 | NUC | 130 | PAYRPPNA | A | A | | 8 | | | | | | | 390 |
| 95 | 19 | NUC | 130 | PAYRPPNAPI | A | I | 5.0081 | 10 | | 0.0001 | | | | | 391 |
| 95 | 19 | NUC | 130 | PAYRPPNAPIL | A | L | | 11 | | | | | | | 392 |
| 85 | 17 | POL | 616 | PIDWKVCQRI | I | I | Chisari 4.091 | 10 | | 0.0001 | | | | | 393 |
| 85 | 17 | POL | 616 | PIDWKVCQRIV | I | V | | 11 | | | | | | | 394 |
| 100 | 20 | ENV | 380 | PIFFCLWV | I | V | | 8 | | | | | | | 395 |
| 100 | 20 | ENV | 380 | PIFGCLWVYI | I | I | Chisari 3.074 | 10 | | 0.0004 | | | | | 396 |
| 85 | 17 | POL | 713 | PIHTAELL | I | L | | 8 | | | | | | | 397 |
| 85 | 17 | POL | 713 | PIHTAELLA | I | A | | 9 | | | | | | | 398 |
| 85 | 17 | POL | 713 | PIHTAELLAA | I | A | | 10 | | | | | | | 399 |
| 80 | 16 | POL | 496 | PIILGFRKI | I | I | 927.48 | 9 | | 0.0001 | | | | | 400 |
| 80 | 16 | POL | 496 | PIILGFRKIPM | I | M | | 11 | | | | | | | 401 |
| 100 | 20 | NUC | 138 | PILSTLPET | I | T | 5.0023 | 9 | | 0.0001 | | | | | 402 |
| 100 | 20 | NUC | 138 | PILSTLPETT | I | T | 5.0082 | 10 | | 0.0001 | | | | | 403 |
| 100 | 20 | NUC | 138 | PILSTLPETTV | I | V | Chisari 5.125 | 11 | | 0.0001 | | | | | 404 |
| 80 | 16 | ENV | 314 | PIPSSWAFA | I | A | | 9 | | | | | | | 405 |
| 95 | 19 | POL | 20 | PLEEELPRL | L | L | 927.29 | 9 | | 0.0003 | | | | | 406 |
| 90 | 18 | POL | 20 | PLEEELPRLA | L | A | 3.0225 | 10 | | 0.0001 | | | | | 407 |
| 95 | 19 | ENV | 10 | PLGFFPDHQL | L | L | 1.0511 | 10 | | 0.0002 | | | | | 408 |
| 100 | 20 | POL | 427 | PLHPAAMPHL | L | L | 1.0550 | 10 | | 0.0001 | | | | | 409 |
| 100 | 20 | POL | 427 | PLHPAAMPHLL | L | L | | 11 | | | | | | | 410 |
| 100 | 20 | ENV | 377 | PLLPIFFCL | L | L | 1069.13 | 9 | * | 0.0650 | 0.0001 | 0.0018 | 0.1100 | 0.0047 | 411 |
| 100 | 20 | ENV | 377 | PLLPIFFCLWV | L | V | | 11 | | | | | | | 412 |
| 90 | 18 | ENV | 174 | PLLVLQAGFFL | L | L | Chisari 4.029 | 11 | | 0.0008 | | | | | 413 |

TABLE VII-continued

HBV A02 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 80 | 16 | POL | 711 | PLPIHTAEL | L | L | 927.19 | 9 | | 0.0004 | | | | | 414 |
| 80 | 16 | POL | 711 | PLPIHTAELL | L | L | 1.0569 | 10 | | 0.0001 | | | | | 415 |
| 80 | 16 | POL | 711 | PLPIHTAELLA | L | A | | 11 | | | | | | | 416 |
| 75 | 15 | POL | 2 | PLSYQHFRKL | L | L | 1.0527 | 10 | | 0.0001 | | | | | 417 |
| 75 | 15 | POL | 2 | PLSYQHFRKLL | L | L | | 11 | | | | | | | 418 |
| 85 | 17 | POL | 98 | PLTVNEKRRL | L | L | 1.0536 | 10 | | 0.0001 | | | | | 419 |
| 80 | 16 | POL | 505 | PMGVGLSPFL | M | L | 1.0557 | 10 | | 0.0001 | | | | | 420 |
| 80 | 16 | POL | 505 | PMGVGLSPFLL | M | L | | 11 | | | | | | | 421 |
| 75 | 15 | POL | 692 | PTGWGLAI | T | I | | 8 | | | | | | | 422 |
| 80 | 16 | ENV | 219 | PTSNHSPT | T | T | | 8 | | | | | | | 423 |
| 85 | 17 | POL | 797 | PTTGRTSL | T | L | | 8 | | | | | | | 424 |
| 85 | 17 | POL | 797 | PTTGRTSLYA | T | A | | 10 | | | | | | | 425 |
| 80 | 16 | NUC | 15 | PTVQASKL | T | L | | 8 | | | | | | | 426 |
| 80 | 16 | NUC | 15 | PTVOASKLCL | T | L | | 10 | | | | | | | 427 |
| 75 | 15 | ENV | 351 | PTVWLSVI | T | I | | 8 | | | | | | | 428 |
| 75 | 15 | ENV | 351 | PTVWLSVIWM | T | M | | 10 | | | | | | | 429 |
| 95 | 19 | X | 59 | PVCAFSSA | V | A | | 8 | | | | | | | 430 |
| 85 | 17 | POL | 612 | PVNRPIDWKV | V | V | 1.0566 | 10 | | 0.0002 | | | | | 431 |
| 95 | 19 | POL | 654 | QAFTFSPT | A | T | | 8 | | | | | | | 432 |
| 95 | 19 | POL | 654 | QAFTFSPTYKA | A | A | | 11 | | | | | | | 433 |
| 95 | 19 | ENV | 179 | QAGFFLLT | A | T | | 8 | | | | | | | 434 |
| 80 | 16 | ENV | 179 | QAGFFLLTRI | A | I | | 10 | | | | | | | 435 |
| 80 | 16 | ENV | 179 | QAGFFLLTRIL | A | L | | 11 | | | | | | | 436 |
| 90 | 18 | NUC | 57 | QAILCWGEL | A | L | | 9 | | | | | | | 437 |
| 90 | 18 | NUC | 57 | QAILCWGELM | A | M | | 10 | | | | | | | 438 |
| 95 | 19 | ENV | 107 | QAMQWNST | A | T | | 8 | | | | | | | 439 |
| 80 | 16 | ENV | 107 | QAMQWNSTT | A | T | | 9 | | | | | | | 440 |
| 80 | 16 | NUC | 18 | QASKLCLGWL | A | L | | 10 | | | | | | | 441 |
| 80 | 16 | X | 8 | QLDPARDV | L | V | Chisari 4.116 | 8 | | 0.0001 | | | | | 442 |
| 80 | 16 | X | 8 | QLDPARDVL | L | L | 927.01 | 9 | | 0.0001 | | | | | 443 |
| 80 | 16 | X | 8 | QLDPARDVLCL | L | L | Chisari 4.073 | 11 | | 0.0001 | | | | | 444 |
| 90 | 18 | NUC | 99 | QLLWFHISCL | L | L | 1142.03 | 10 | * | 0.0060 | | | | | 445 |
| 85 | 17 | NUC | 99 | QLLWFHISCLT | L | T | | 11 | | | | | | | 446 |
| 95 | 19 | POL | 685 | QVFADATPT | V | T | 5.0038 | 9 | | 0.0001 | | | | | 447 |
| 95 | 19 | POL | 528 | RAFPHCLA | A | A | | 8 | | | | | | | 448 |
| 80 | 16 | ENV | 187 | RILTIPQSL | I | L | Chisari 4.054 | 9 | | 0.0010 | | | | | 449 |
| 90 | 18 | POL | 624 | RIVGLLGFA | I | A | | 9 | | | | | | | 450 |
| 90 | 18 | POL | 624 | RIVGLLGFM | I | A | | 10 | | | | | | | 451 |
| 75 | 15 | POL | 106 | RLKLIMPA | L | A | | 8 | | | | | | | 452 |
| 90 | 18 | POL | 353 | RTPARVTGGV | T | V | | 10 | | | | | | | 453 |
| 95 | 19 | NUC | 127 | RTPPAYRPPNA | T | A | | 11 | | | | | | | 454 |
| 95 | 19 | POL | 36 | RVAEDLNL | V | L | | 8 | | | | | | | 455 |
| 90 | 18 | POL | 36 | RVAEDLNLGNL | V | L | | 11 | | | | | | | 456 |
| 80 | 16 | POL | 818 | RVHFASPL | V | L | | 8 | | | | | | | 457 |
| 75 | 15 | POL | 818 | RVHFASPLHV | V | V | 1.0576 | 10 | | 0.0001 | | | | | 458 |
| 75 | 15 | POL | 818 | RVLIFASPLHVA | V | A | | 11 | | | | | | | 459 |
| 100 | 20 | POL | 357 | RVTGGVFL | V | L | | 8 | | | | | | | 460 |
| 100 | 20 | POL | 357 | RVTGGVFLV | V | V | 1.0181 | 9 | | 0.0041 | | | | | 461 |
| 90 | 18 | X | 65 | SAGPCALRFT | A | T | | 10 | | | | | | | 462 |
| 95 | 19 | POL | 520 | SAICSVVRRA | A | A | 5.0088 | 10 | | 0.0001 | | | | | 463 |
| 90 | 18 | NUC | 35 | SALYREAL | A | L | | 8 | | | | | | | 464 |
| 100 | 20 | POL | 49 | SIPWTHKV | I | V | | 8 | | | | | | | 465 |
| 95 | 19 | ENV | 194 | SLDSWWTSL | L | L | F126.64 | 9 | | | | | | | 466 |
| 75 | 15 | POL | 565 | SLGIHLNPNKT | L | T | | 11 | | | | | | | 467 |
| 95 | 19 | ENV | 337 | SLLVPFVQWFV | L | V | | | | | | | 468 | | |
| 75 | 15 | POL | 581 | SLNFMGYV | L | V | | 8 | | | | | | | 469 |
| 75 | 15 | POL | 581 | SLNFMGYVI | L | I | 927.12 | 9 | | 0.0038 | | | | | 470 |
| 95 | 19 | X | 54 | SLRGLPVCA | L | A | 3.0030 | 9 | | 0.0007 | | | | | 471 |
| 90 | 18 | POL | 403 | SLTNLLSSNL | L | L | 1.0548 | 10 | | 0.0014 | | | | | 472 |
| 75 | 15 | ENV | 280 | STGPCKTCT | T | T | | 9 | | | | | | | 473 |
| 100 | 20 | NUC | 141 | STLPETTV | T | V | | 8 | | | | | | | 474 |
| 100 | 20 | NUC | 141 | STLPETTVV | T | V | 5.0024 | 9 | | 0.0019 | | | | | 475 |
| 80 | 16 | ENV | 85 | STNRQSGRQPT | T | T | | 11 | | | | | | | 476 |
| 85 | 17 | POL | 548 | SVQHLESL | V | L | | 8 | | | | | | | 477 |
| 80 | 16 | ENV | 330 | SVRFSWLSL | V | L | Chisari 4.025 | 9 | | 0.0001 | | | | | 478 |
| 80 | 16 | ENV | 330 | SVRFSWLSLL | V | L | Chisari 4.026 | 10 | | 0.0004 | | | | | 479 |
| 80 | 16 | ENV | 330 | SVRFSWLSLLV | V | V | | 11 | | | | | | | 480 |
| 90 | 18 | POL | 739 | SVVLSRKYT | V | T | | 9 | | | | | | | 481 |

TABLE VII-continued

HBV A02 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 95 | 19 | POL | 524 | SVVRRAFPHCL | V | L | | 11 | | | | | | | 482 |
| 85 | 17 | POL | 716 | TAELLAACFA | A | A | | 10 | | | | | | | 483 |
| 95 | 19 | NUC | 53 | TALRQAIL | A | L | | 8 | | | | | | | 484 |
| 80 | 16 | NUC | 33 | TASALYREA | A | A | | 9 | | | | | | | 485 |
| 80 | 16 | NUC | 33 | TASALYREAL | A | L | | 10 | | | | | | | 486 |
| 90 | 18 | ENV | 190 | TIPQSLDSWWT | I | T | | 11 | | | | | | | 487 |
| 100 | 20 | NUC | 142 | TLPETTVV | L | V | | 8 | | | | | | | 488 |
| 100 | 20 | POL | 150 | TLWKAGIL | L | L | | 8 | | | | | | | 489 |
| 85 | 17 | POL | 798 | TTGRTSLYA | T | A | | 9 | | | | | | | 490 |
| 75 | 15 | ENV | 278 | TTSTGPCKT | T | T | | 9 | | | | | | | 491 |
| 75 | 15 | ENV | 278 | TTSTGPCKTCT | T | T | | 11 | | | | | | | 492 |
| 85 | 17 | POL | 100 | TVNEKRRL | V | L | | 8 | | | | | | | 493 |
| 80 | 16 | NUC | 16 | TVQASKLCL | V | L | 1.0365 | 9 | | 0.0002 | | | | | 494 |
| 75 | 15 | ENV | 352 | TVWLSVIWM | V | M | 3.0035 | 9 | | 0.0002 | | | | | 495 |
| 95 | 19 | POL | 37 | VAEDLNLGNL | A | L | 5.0089 | 10 | | 0.0001 | | | | | 496 |
| 95 | 19 | X | 15 | VLCLRPVGA | L | A | 3.0028 | 9 | | 0.0014 | | | | | 497 |
| 85 | 17 | POL | 543 | VLGAKSVQHL | L | L | 1.0560 | 10 | | 0.0001 | | | | | 498 |
| 90 | 18 | X | 133 | VLGGCRHKL | L | L | 927.08 | 9 | | 0.0009 | | | | | 499 |
| 90 | 18 | X | 133 | VLGGCRHKLV | L | V | 1.0589 | 10 | | 0.0001 | | | | | 500 |
| 85 | 17 | X | 92 | VLHKRTLGL | L | L | 927.03 | 9 | | 0.0012 | | | | | 501 |
| 95 | 19 | ENV | 259 | VLLDYQGM | L | M | 17.0107 | 8 | | | | | | | 502 |
| 95 | 19 | ENV | 259 | VLLDYQGML | L | L | 1069.09 | 9 | * | 0.0440 | 0.0001 | 0.0210 | 0.9000 | 0.0002 | 503 |
| 90 | 18 | ENV | 259 | VLLDYQGMLPV | L | V | 1147.14 | 11 | * | 0.5800 | 0.2200 | 4.9000 | 0.3400 | 0.0170 | 504 |
| 95 | 19 | ENV | 177 | VLQAGFFL | L | L | Chisari 4.027 | 8 | | 0.0019 | | | | | 505 |
| 95 | 19 | ENV | 177 | VLQAGFFLL | L | L | 1013.14 | 9 | * | 0.0660 | | | | | 506 |
| 95 | 19 | ENV | 177 | VLQAGFFLLT | L | T | 5.0066 | 10 | | 0.0011 | | | | | 507 |
| 100 | 20 | POL | 358 | VTGGVFLV | T | V | | 8 | | | | | | | 508 |
| 90 | 18 | POL | 542 | VVLGAKSV | V | V | | 8 | | | | | | | 509 |
| 80 | 16 | POL | 542 | VVLGAKSVQHL | V | L | | 11 | | | | | | | 510 |
| 90 | 18 | POL | 740 | VVLSRKYT | V | T | | 8 | | | | | | | 511 |
| 95 | 19 | POL | 525 | VVRRAFPHCL | V | L | 2.0217 | 10 | | 0.0003 | | | | | 512 |
| 95 | 19 | POL | 525 | VVRRAFPHCLA | V | A | | 11 | | | | | | | 513 |
| 80 | 16 | POL | 759 | WILRGTSFV | I | V | 927.24 | 9 | * | 0.0270 | | | | | 514 |
| 80 | 16 | POL | 759 | WILRGTSFVYV | I | V | 927.24 11 | | | | | | | | 515 |
| 80 | 16 | POL | 751 | WLLGCAANWI | L | I | Chisari 4.104 | 10 | | 0.0053 | | | | | 516 |
| 80 | 16 | POL | 751 | WLLGCAANWIL | L | L | | 11 | | | | | | | 517 |
| 100 | 20 | POL | 414 | WLSLDVSA | L | A | | 8 | | | | | | | |
| 95 | 19 | POL | 414 | WLSLDVSAA | L | A | 3.0023 | 9 | | 0.0059 | | | | | 519 |
| 100 | 20 | ENV | 335 | WLSLLVPFV | L | V | 1013.0102 | 9 | * | 1.1000 | 0.0380 | 7.2000 | 0.3600 | 0.0310 | 520 |
| 95 | 19 | ENV | 237 | WMCLRRFI | M | I | | 8 | | | | | | | 521 |
| 95 | 19 | ENV | 237 | WMCLRRFII | M | I | 1147.10 | 9 | * | 0.0005 | | | | | 522 |
| 95 | 19 | ENV | 237 | WMCLRRFIIFL | M | L | Chisari 4.024 | 11 | | 0.0019 | | | | | 523 |
| 85 | 17 | ENV | 359 | WMMWYWGPSL | M | L | 1137.05 | 10 | * | 0.0009 | | | | | 524 |
| 100 | 20 | POL | 52 | WTHKVGNFT | T | T | 5.0039 | 9 | | 0.0001 | | | | | 525 |
| 95 | 19 | POL | 52 | WTHKVGNFTGL | T | L | | 11 | | | | | | | 526 |
| 100 | 20 | POL | 147 | YLHTLWKA | L | A | | 8 | | | | | | | 527 |
| 100 | 20 | POL | 147 | YLHTLWKAGI | L | I | 1069.11 | 10 | * | 0.0160 | 0.0005 | 0.5600 | 0.1000 | 0.0320 | 528 |
| 100 | 20 | POL | 147 | YLHTLWKAGIL | L | L | | 11 | | | | | | | |
| 100 | 20 | POL | 122 | YLPDKGI | L | I | | 8 | | | | | | | 530 |
| 90 | 18 | NUC | 118 | YLVSFGVWI | L | I | 1090.12 | 9 | * | 0.3800 | | | | | 531 |
| 90 | 18 | NUC | 118 | YLVSFGVWIRT | L | T | | 11 | | | | | | | 532 |
| 90 | 18 | POL | 538 | YMDDVVLGA | M | A | 1090.14 | 9 | * | 0.0250 | 0.0001 | 0.0024 | 0.1000 | 0.0002 | 533 |
| 85 | 17 | POL | 746 | YTSFPWLL | T | L | | 8 | | | | | | | 534 |
| 75 | 15 | POL | 746 | YTSFPWLLGCA | T | A | | 11 | | | | | | | 535 |
| 90 | 18 | POL | 768 | YVPSALNPA 388 | V | A | 3.0042 | 9 | | 0.0039 | | | | | 536 |

TABLE VIII

HBV A03 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 85 | 17 | POL | 721 | AACFARSR | A | R | 26.0003 | 8 | | 0.0004 | 0.0003 | 0.0056 | 0.0035 | 0.0014 | 537 |
| 95 | 19 | POL | 521 | AICSVVRR | I | R | 26.0004 | 8 | | −0.0002 | 0.0003 | 0.0014 | −0.0009 | 0.0006 | 538 |

TABLE VIII-continued

HBV A03 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 90 | 18 | POL | 772 | ALNPADDPSR | L | R | 1.1090 | 10 | | 0.0003 | 0.0001 | | | | 539 |
| 85 | 17 | X | 70 | ALRFTSAR | L | R | 26.0005 | 8 | | 0.0047 | 0.0009 | 0.0450 | 0.0230 | 0.0004 | 540 |
| 80 | 16 | POL | 822 | ASPLHVAWR | S | R | | 9 | | | | | | | 541 |
| 75 | 15 | ENV | 84 | ASTNRQSGR | S | R | 1150.60 | 9 | | 0.0009 | 0.0002 | 0.0088 | 0.0008 | 0.0001 | 542 |
| 80 | 16 | POL | 755 | CAANWILR | A | R | | 8 | | | | | | | 543 |
| 85 | 17 | X | 69 | CALRFTSAR | A | R | 26.0149 | 9 | * | 0.0034 | 0.0230 | 1.5000 | 8.0000 | 0.7300 | 544 |
| 90 | 18 | X | 17 | CLRPVGAESR | L | R | 1.1093 | 10 | | 0.0011 | 0.0001 | | | | 545 |
| 100 | 20 | NUC | 48 | CSPHHTALR | S | R | 5.0055 | 9 | * | 0.0029 | 0.0001 | 0.0520 | 0.0250 | 0.0440 | 546 |
| 85 | 17 | NUC | 29 | DLLDTASALYR | L | R | 26.0530 | 11 | | 0.0042 | −0.0003 | −0.0012 | 3.7000 | 0.0410 | 547 |
| 85 | 17 | NUC | 32 | DTASALYR | T | R | 26.0006 | 8 | | 0.0004 | −0.0002 | −0.0009 | 0.0018 | 0.0009 | 548 |
| 95 | 19 | POL | 17 | EAGFLEEELPR | A | R | 26.0531 | 11 | | −0.0009 | −0.0003 | −0.0012 | 0.0015 | 0.0110 | 549 |
| 90 | 18 | POL | 718 | ELLAACFAR | L | R | 1.0988 | 9 | | 0.0002 | 0.0004 | | | | 550 |
| 85 | 17 | POL | 718 | ELLAACFARSR | L | R | 26.0532 | 11 | | 0.0062 | 0.0016 | 0.0200 | 0.2000 | 0.1600 | 551 |
| 95 | 19 | NUC | 174 | ETTVVRRR | T | R | 26.0007 | 8 | | 0.0003 | −0.0002 | −0.0009 | 0.1400 | 0.0027 | 552 |
| 80 | 16 | NUC | 174 | ETTVVRRRGR | T | R | 1.1073 | 10 | | 0.0003 | 0.0001 | | | | 553 |
| 80 | 16 | POL | 821 | FASPLHVAWR | A | R | | 10 | | | | | | | 554 |
| 90 | 18 | X | 63 | FSSAGPCALR | S | R | | 10 | | | | | | | 555 |
| 95 | 19 | POL | 656 | FTFSPTYK | T | K | 1147.19 | 8 | * | 0.0100 | 0.0100 | 0.0023 | 0.2100 | 0.0590 | 556 |
| 95 | 19 | POL | 518 | FTSAICSVVR | T | R | 1.1085 | 10 | | 0.0003 | 0.0003 | | | | 557 |
| 95 | 19 | POL | 518 | FTSAICSVVRR | T | R | 26.0533 | 11 | | 0.0065 | 0.0092 | 0.0170 | 0.0350 | 1.5000 | 558 |
| 90 | 18 | X | 132 | FVLGGCRHK | V | K | 1090.03 | 9 | * | 0.0430 | 0.0090 | | | | 559 |
| 75 | 15 | POL | 567 | GIHLNPNK | I | K | | 8 | | | | | | | 560 |
| 75 | 15 | POL | 567 | GIHLNPNKTK | I | K | 1.0563 | 10 | | 0.0025 | 0.0011 | 0.0009 | 0.0009 | 0.0003 | 561 |
| 75 | 15 | POL | 567 | GIHLNPNKTKR | I | R | | 11 | | | | | | | 562 |
| 85 | 17 | NUC | 29 | GMDIDPYK | M | K | 26.0009 | 8 | | 0.0006 | 0.0004 | −0.0009 | −0.0009 | 0.0001 | 563 |
| 90 | 18 | POL | 735 | GTDNSVVLSR | T | R | 1090.04 | 10 | * | 0.0010 | 0.0420 | 0.0030 | 0.0019 | 0.0008 | 564 |
| 90 | 18 | POL | 735 | GTDNSVVLSRK | T | K | 1147.17 | 11 | * | 0.0140 | 5.6000 | −0.0002 | −0.0006 | 0.0001 | 565 |
| 95 | 19 | NUC | 123 | GVWIRTPPAYR | V | R | 26.0535 | 11 | * | 0.1900 | 0.1700 | 6.8000 | 0.7300 | 0.6600 | 566 |
| 90 | 18 | NUC | 104 | HISCLTFGR | I | R | 1069.18 | 9 | * | 0.0160 | 0.0065 | | | | 567 |
| 75 | 15 | POL | 569 | HLNPNKTK | L | K | | 8 | | | | | | | 568 |
| 75 | 15 | POL | 569 | HLNPNKTKR | L | R | 1.0983 | 9 | | 0.0025 | 0.0001 | | | | 569 |
| 100 | 20 | POL | 149 | HTLWKAGILYK | T | K | 1147.16 | 11 | * | 0.5400 | 0.4400 | 0.0370 | 0.0720 | 0.1900 | 570 |
| 90 | 18 | NUC | 105 | ISCLTFGR | S | R | 26.0010 | 8 | | 0.0004 | 0.0002 | 0.0017 | −0.0009 | 0.0017 | 571 |
| 100 | 20 | POL | 153 | KAGILYKR | A | R | 26.0011 | 8 | | 0.0002 | −0.0002 | 0.0015 | −0.0009 | 0.0001 | 572 |
| 80 | 16 | POL | 610 | KLPVNRPIDWK | L | K | | 11 | | | | | | | 573 |
| 75 | 15 | X | 130 | KVFVLGGCR | V | R | 1.0993 | 9 | * | 0.0420 | 0.0820 | 0.6000 | 0.0710 | 0.0030 | 574 |
| 85 | 17 | POL | 720 | LAACFARSR | A | R | 20.0129 | 9 | | 0.0058 | 0.0065 | | | | 575 |
| 90 | 18 | POL | 719 | LLAACFAR | L | R | 26.0012 | 8 | | 0.0024 | 0.0003 | 0.0015 | 0.0029 | 0.0064 | 576 |
| 85 | 17 | POL | 719 | LLAACFARSR | L | R | | 10 | | | | | | | 577 |
| 85 | 17 | NUC | 30 | LLDTASALYR | L | R | 1.1070 | 10 | | 0.0050 | 0.0002 | | | | 578 |
| 80 | 16 | POL | 752 | LLGCAANWILR | L | R | | 11 | | | | | | | 579 |
| 75 | 15 | POL | 564 | LSLGIHLNPNK | S | K | | 11 | | | | | | | 580 |
| 95 | 19 | NUC | 169 | LSTLPETTVVR | S | R | 26.0537 | 11 | | −0.0009 | 0.0008 | −0.0012 | −0.0023 | 0.0078 | 581 |
| 75 | 15 | POL | 3 | LSYQHFRK | S | K | | 8 | | | | | | | 582 |
| 85 | 17 | POL | 99 | LTVNEKRR | T | R | 26.0013 | 8 | | −0.0002 | −0.0002 | −0.0009 | −0.0009 | 0.0001 | 583 |
| 90 | 18 | NUC | 119 | LVSFGVWIR | V | R | 1090.08 | 9 | * | 0.0028 | 0.0120 | | | | 584 |
| 100 | 20 | POL | 377 | LVVDFSQFSR | V | R | 1069.20 | 10 | * | 0.0016 | 0.3600 | 0.0260 | 0.2300 | 0.4900 | 585 |
| 75 | 15 | X | 103 | MSTTDLEAYFK | S | K | | 11 | | | | | | | 586 |
| 90 | 18 | NUC | 75 | NLEDPASR | L | R | 26.0014 | 8 | | −0.0002 | −0.0002 | −0.0009 | −0.0009 | 0.0001 | 587 |
| 95 | 19 | POL | 45 | NLNVSIPWTHK | L | K | 26.0538 | 11 | | −0.0009 | 0.0005 | −0.0012 | −0.0023 | 0.0019 | 588 |
| 90 | 18 | POL | 738 | NSVVLSRK | S | K | 26.0015 | 8 | | 0.0006 | 0.0010 | 0.0009 | −0.0009 | 0.0007 | 589 |
| 100 | 20 | POL | 47 | NVSIPWTHK | V | K | 1069.16 | 9 | * | 0.0820 | 0.0570 | 0.0002 | 0.0100 | 0.0320 | 590 |
| 90 | 18 | POL | 775 | PADDPSRGR | A | R | 1150.35 | 9 | | 0.0008 | 0.0002 | 0.0004 | 0.0015 | 0.0002 | 591 |
| 80 | 16 | X | 11 | PARDVLCLR | A | R | 1150.36 | 9 | | 0.0002 | 0.0002 | 0.0100 | 0.0180 | 0.0002 | 592 |
| 75 | 15 | ENV | 83 | PASTNRQSGR | A | R | | 10 | | | | | | | 593 |
| 90 | 18 | POL | 616 | PIDWKVCQR | I | R | 1.0985 | 9 | | 0.0002 | 0.0005 | | | | 594 |
| 80 | 16 | POL | 496 | PIILGFRK | I | K | | 8 | | | | | | | 595 |
| 95 | 19 | POL | 20 | PLEEELPR | L | R | 26.0016 | 8 | | 0.0002 | −0.0002 | −0.0009 | −0.0009 | 0.0001 | 596 |
| 100 | 20 | POL | 2 | PLSYQHFR | L | R | 26.0017 | 8 | | −0.0002 | −0.0002 | −0.0009 | −0.0009 | 0.0001 | 597 |
| 75 | 15 | POL | 2 | PLSYQHFRK | L | K | 1.0161 | 9 | | 0.0011 | 0.0031 | 0.0006 | 0.0008 | 0.0002 | 598 |
| 85 | 17 | POL | 98 | PLTVNEKR | L | R | 26.0018 | 8 | | 0.0002 | −0.0002 | −0.0009 | −0.0009 | 0.0001 | 599 |
| 85 | 17 | POL | 98 | PLTVNEKRR | L | R | 1.0974 | 9 | | 0.0008 | 0.0005 | 0.0004 | 0.0027 | 0.0002 | 600 |
| 90 | 18 | X | 20 | PVGAESRGR | V | R | 1.0950 | 9 | | 0.0002 | 0.0002 | 0.0004 | 0.0043 | 0.0002 | 601 |
| 85 | 17 | POL | 612 | PVNRPIDWK | V | K | 1142.06 | 9 | * | 0.0310 | 0.1400 | 0.0002 | 0.0006 | 0.0009 | 602 |
| 95 | 19 | POL | 654 | QAFTFSPTYK | A | K | 1090.10 | 10 | * | 0.0450 | 0.5400 | 0.0010 | 0.0057 | 1.2000 | 603 |
| 80 | 16 | ENV | 179 | QAGFFLLTR | A | R | | 9 | | | | | | | 604 |
| 75 | 15 | NUC | 169 | QSPRRRRSQSR | S | R | 28.0839 | 11 | | | | | | | 605 |
| 80 | 16 | POL | 189 | QSSGILSR | S | R | | 8 | | | | | | | 606 |
| 75 | 15 | POL | 106 | RLKLIMPAR | L | R | 1.0975 | 9 | * | 0.0950 | 0.0002 | 3.1000 | 0.0490 | 0.0002 | 607 |
| 75 | 15 | X | 128 | RLKVFVLGGCR | L | R | | 11 | | | | | | | 608 |
| 95 | 19 | POL | 376 | FLVVDFSQFSR | L | R | 26.0539 | 11 | * | 0.2800 | 3.8000 | 2.6000 | 1.2000 | 6.1000 | 609 |
| 95 | 19 | NUC | 183 | RSPRRRTPSPR | S | R | 26.0540 | 11 | | −0.0007 | −0.0003 | 0.0190 | −0.0023 | 0.0003 | 610 |
| 75 | 15 | NUC | 167 | RSQSPRRR | S | R | | 8 | | | | | | | 611 |

TABLE VIII-continued

HBV A03 SUPER MOTIF (With binding information)

| Conserv-ancy | Fre-quency | Pro-tein | Posi-tion | Sequence | P2 | C-term | Peptide | AA | Filed | A*0201 | A*0202 | A*0203 | A*0206 | A*6802 | SEQ ID NO: |
|---|---|---|---|---|---|---|---|---|---|---|---|---|---|---|---|
| 75 | 15 | NUC | 167 | RSQSPRRRR | S | R |  | 9 |  |  |  |  |  |  | 612 |
| 95 | 19 | NUC | 188 | RTPSPRRR | T | R | 26.0019 | 8 |  | −0.0002 | −0.0002 | 0.0033 | 0.0014 | 0.0002 | 613 |
| 95 | 19 | NUC | 188 | RTPSPRRRR | T | R | 1.0971 | 9 | * | 0.0054 | 0.0005 | 0.2000 | 0.0016 | 0.0003 | 614 |
| 100 | 20 | POL | 357 | RVTGGVFLVDK | V | K | 1147.18 | 11 | * | 0.0190 | 0.0290 | −0.0002 | −0.0003 | 0.0001 | 615 |
| 90 | 18 | X | 65 | SAGPCALR | A | R | 26.0020 | 8 |  | −0.0002 | 0.0020 | 0.0029 | 0.0024 | 0.0360 | 616 |
| 95 | 19 | POL | 520 | SAICSVVR | A | R | 26.0021 | 8 |  | −0.0002 | 0.0071 | 0.0280 | 0.0081 | 0.0690 | 617 |
| 95 | 19 | POL | 520 | SAICSVVRR | A | R | 1090.11 | 9 | * | 0.0058 | 0.2100 | 0.1500 | 0.0650 | 0.3800 | 618 |
| 90 | 18 | POL | 771 | SALNPADDPSR | A | R | 26.0542 | 11 |  | −0.0004 | −0.0003 | −0.0012 | −0.0023 | 0.0003 | 619 |
| 75 | 15 | POL | 565 | SLGIHLNPNK | L | K | 28.0758 | 10 | * |  |  |  |  |  | 620 |
| 90 | 18 | X | 64 | SSAGPCALR | S | R | 26.0153 | 9 |  | 0.0080 | 0.1400 | 0.3300 | 0.1600 | 0.7500 | 621 |
| 95 | 19 | POL | 170 | STLPETTVVR | T | R | 1069.21 | 10 | * | 0.0007 | 0.0600 | 0.0080 | 0.0240 | 0.0250 | 622 |
| 95 | 19 | NUC | 170 | STLPETTVVRR | T | R | 1083.01 | 11 |  | 0.0150 | 1.4000 | 0.1000 | 0.1600 | 0.3100 | 623 |
| 80 | 16 | ENV | 85 | STNRQSGR | T | R |  | 8 |  |  |  |  |  |  | 624 |
| 75 | 15 | X | 104 | STTDLEAYFK | T | K | 1.0584 | 10 | * | 0.0066 | 2.7000 |  |  |  | 625 |
| 85 | 17 | POL | 716 | TAELLAACFAR | A | R | 26.0544 | 11 |  | 0.0006 | 0.0023 | 0.0066 | 0.1600 | 0.0590 | 626 |
| 95 | 19 | NUC | 171 | TLPETTVVR | L | R | 1.0969 | 9 |  | 0.0008 | 0.0002 | 0.0009 | 0.0024 | 0.0180 | 627 |
| 95 | 19 | NUC | 171 | TLPETTVVRR | L | R | 1069.22 | 10 |  | 0.0007 | 0.0230 | 0.0006 | 0.0120 | 0.0440 | 628 |
| 95 | 19 | NUC | 171 | TLPETTVRRR | L | R | 26.0545 | 11 | * | 0.0005 | 0.0160 | 0.0061 | 0.0710 | 0.6400 | 629 |
| 100 | 20 | POL | 150 | TLWKAGILYK | L | K | 1069.15 | 10 | * | 5.3000 | 0.3600 | 0.0051 | 0.0010 | 0.0130 | 630 |
| 100 | 20 | POL | 150 | TLWKAGILYKR | L | R | 26.0546 | 11 |  | 0.0082 | 0.0095 | 0.1000 | 0.1100 | 0.0640 | 631 |
| 95 | 19 | POL | 519 | TSAICSVVR | S | R | 5.0057 | 9 |  | 0.0005 | 0.0008 | 0.0600 | 0.0200 | 0.0820 | 632 |
| 95 | 19 | POL | 519 | TSAICSVVRR | S | R | 1142.08 | 10 | * | 0.0018 | 0.0006 | 0.0030 | 0.0066 | 0.0048 | 633 |
| 75 | 15 | X | 105 | TTDLEAYFK | T | K | 1.0215 | 9 | * | 0.0006 | 0.9200 | 0.0006 | 0.0012 | 0.0170 | 634 |
| 75 | 15 | ENV | 278 | TTSTGPCK | T | K |  | 8 |  |  |  |  |  |  | 635 |
| 80 | 16 | NUC | 175 | TTVVRRRGR | T | R | 1.0970 | 9 |  | 0.0008 | 0.0005 | 0.2500 | 0.1400 | 0.0095 | 636 |
| 80 | 16 | NUC | 176 | TVVRRRGR | V | R | 3.0324 | 8 |  | 0.0003 | 0.0001 |  |  |  | 637 |
| 80 | 16 | NUC | 176 | TVVRRRGRSPR | V | R | 28.0837 | 11 |  |  |  |  |  |  | 638 |
| 90 | 18 | X | 133 | VLGGCRHK | L | K | 26.0022 | 8 |  | 0.0150 | 0.0002 | −0.0005 | −0.0009 | 0.0001 | 639 |
| 80 | 16 | ENV | 177 | VLQAGFFLLTR | L | R |  | 11 |  |  |  |  |  |  | 640 |
| 90 | 18 | NUC | 120 | VSFGVWIR | S | R | 26.0023 | 8 |  | 0.0040 | 0.0290 | 0.0750 | 0.0270 | 0.0360 | 641 |
| 100 | 20 | POL | 48 | VSIPWTHK | S | K | 26.0024 | 8 | * | 0.0130 | 0.0170 | 0.0031 | 0.0013 | 0.0004 | 642 |
| 100 | 20 | POL | 358 | VTGGVFLVDK | T | K | 1069.17 | 10 | * | 0.0390 | 0.0920 | 0.0002 | 0.0006 | 0.0022 | 643 |
| 100 | 20 | POL | 378 | VVCFSQFSR | V | R | 1069.19 | 9 | * | 0.0015 | 0.0750 | 0.0013 | 0.0170 | 0.0330 | 644 |
| 80 | 16 | NUC | 177 | VVRRRGRSPR | V | R | 1.1074 | 10 |  | 0.0027 | 0.0001 |  |  |  | 645 |
| 80 | 16 | NUC | 177 | VVRRRGRSPRR | V | R | 28.0838 | 11 |  |  |  |  |  |  | 646 |
| 95 | 19 | NUC | 125 | WIRTPPAYR | I | R | 1.0968 | 9 |  | 0.0008 | 0.0005 |  |  |  | 647 |
| 90 | 18 | POL | 314 | WLQFRNSK | L | K | 26.0025 | 8 |  | −0.0002 | 0.0005 | 0.0020 | 0.0052 | 0.0001 | 648 |
| 85 | 17 | NUC | 26 | WLWGMDIDPYK | L | K | 26.0547 | 11 |  | 0.0030 | 0.0013 | −0.0003 | 0.0039 | 0.0490 | 649 |
| 100 | 20 | POL | 122 | YLPLDKGIK | L | K | 1.0173 | 9 |  | 0.0001 | 0.0001 | 0.0006 | 0.0006 | 0.0002 | 650 |
| 90 | 18 | NUC | 118 | YLVSFGVWIR | L | R | 1090.13 | 10 | * | 0.0005 | 0.0002 |  |  |  | 651 |
| 90 | 18 | POL | 538 | YMDDVVLGAK | M | K | 1090.15 | 10 |  | 0.0330 | 0.0043 | 0.0002 | 0.0006 | 0.0001 | 652 |
| 80 | 16 | POL | 493 | YSHPIILGFR | S | R |  | 10 |  |  |  |  |  |  | 653 |
| 80 | 16 | POL | 493 118 | YSHPIILGFRK | S | K |  | 11 |  |  |  |  |  |  | 654 |

TABLE IX

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 95 | 19 | POL | 529 | AFPHCLAF | XFXXXXXF |  |  |  | 655 |
| 95 | 19 | POL | 529 | AFPHCLAFSY | XFXXXXXXXY |  |  |  | 656 |
| 95 | 19 | POL | 529 | AFPHCLAFSYM | XFXXXXXXXXM |  |  |  | 657 |
| 95 | 19 | X | 62 | AFSSAGPCAL | XFXXXXXXXL | 5.0118 |  | 0.0012 | 658 |
| 90 | 18 | POL | 535 | AFSYMDDVVL | XFXXXXXXXL | 13.0130 |  | 0.0009 | 659 |
| 95 | 19 | POL | 655 | AFTFSPTY | XFXXXXXY |  |  |  | 660 |
| 95 | 19 | POL | 655 | AFTFSPTYKAF | XFXXXXXXXXF |  |  |  | 661 |
| 95 | 19 | POL | 521 | AICSVVRRAF | XIXXXXXXXF |  |  |  | 662 |
| 90 | 18 | NUC | 58 | AILCWGEL | XIXXXXXL |  |  |  | 663 |
| 90 | 18 | NUC | 58 | AILCWGELM | XIXXXXXXM |  |  |  | 664 |
| 95 | 19 | POL | 642 | ALMPLYACI | XLXXXXXXI | 3.0012 | * |  | 665 |
| 95 | 19 | NUC | 54 | ALRQAILCW | XLXXXXXXW |  |  |  | 666 |
| 80 | 16 | ENV | 108 | AMQWNSTTF | XMXXXXXXF |  |  |  | 667 |
| 95 | 19 | POL | 690 | ATPTGWGL | XTXXXXXL |  |  |  | 668 |
| 75 | 15 | POL | 690 | ATPTGWGLAI | XTXXXXXXXI |  |  |  | 669 |
| 95 | 19 | POL | 397 | AVPNLQSL | XVXXXXXL |  |  |  | 670 |
| 95 | 19 | POL | 397 | AVPNLQSLTNL | XVXXXXXXXXL |  |  |  | 671 |
| 100 | 20 | NUC | 131 | AYRPPNAPI | XYXXXXXXI | 5.0062 | * | 0.0260 | 672 |
| 100 | 20 | NUC | 131 | AYRPPNAPIL | XYXXXXXXXL | 2.0172 | * | 0.0220 | 673 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 75 | 15 | POL | 607 | CFRKLPVNRPI | XFXXXXXXXXI | | | | 674 |
| 100 | 20 | ENV | 312 | CIPIPSSW | XIXXXXXW | | | | 675 |
| 100 | 20 | ENV | 312 | CIPIPSSWAF | XIXXXXXXXF | | | | 676 |
| 85 | 17 | NUC | 23 | CLGWLWGM | XLXXXXXM | | | | 677 |
| 85 | 17 | NUC | 23 | CLGWLWGMDI | XLXXXXXXXI | 2.0229 | | | 678 |
| 100 | 20 | ENV | 253 | CLIFLLVL | XLXXXXXL | 17.0248 | | | 679 |
| 100 | 20 | ENV | 253 | CLIFLLVLL | XLXXXXXXL | 1.0836 | | | 680 |
| 95 | 19 | ENV | 253 | CLIFLLVLLDY | XLXXXXXXXXY | 26.0548 | | | 681 |
| 95 | 19 | ENV | 239 | CLRRFIF | XLXXXXXF | | | | 682 |
| 95 | 19 | ENV | 239 | CLRRFIFL | XLXXXXXXL | 1.0829 | | | 683 |
| 75 | 15 | ENV | 239 | CLRRFIIFLF | XLXXXXXXXF | | | | 684 |
| 75 | 15 | ENV | 239 | CLRRFIIFLFI | XLXXXXXXXXI | Chisari 4.055 | | | 685 |
| 100 | 20 | ENV | 310 | CTCIPIPSSW | XTXXXXXXXW | | | | 686 |
| 90 | 18 | NUC | 31 | DIDPYKEF | XIXXXXXF | | | | 687 |
| 85 | 17 | NUC | 29 | DLLDTASAL | XLXXXXXXL | 1.0154 | | | 688 |
| 85 | 17 | NUC | 29 | DLLDTASALY | XLXXXXXXXY | 1.0519 | * | | 689 |
| 95 | 19 | POL | 40 | DLNLGNLNVSI | XLXXXXXXXXI | | | | 690 |
| 80 | 16 | NUC | 32 | DTASALYREAL | XTXXXXXXXXL | | | | 691 |
| 85 | 17 | POL | 618 | DWKVCQRI | XWXXXXXI | | | | 692 |
| 85 | 17 | POL | 618 | DWKVCQRIVGL | XWXXXXXXXXL | | | | 693 |
| 90 | 18 | ENV | 262 | DYQGMLPVCPL | XYXXXXXXXXL | 3.0441 | | 0.0002 | 694 |
| 80 | 16 | X | 122 | ELGEEIRL | XLXXXXXL | | | | 695 |
| 95 | 19 | NUC | 43 | ELLSFLPSDF | XLXXXXXXXF | | | | 696 |
| 95 | 19 | NUC | 43 | ELLSFLPSDFF | XLXXXXXXXXF | | | | 697 |
| 90 | 18 | NUC | 117 | EYLVSFGVW | XYXXXXXXW | 26.0150 | | | 698 |
| 90 | 18 | NUC | 117 | EYLVSFGVWI | XYXXXXXXXI | 13.0129 | * | 0.0340 | 699 |
| 100 | 20 | ENV | 382 | FFCLWVYI | XFXXXXXI | | | | 700 |
| 80 | 16 | ENV | 182 | FFLLTRIL | XFXXXXXL | | | | 701 |
| 80 | 16 | ENV | 182 | FFLLTRILTI | XFXXXXXXXI | | | | 702 |
| 85 | 17 | ENV | 13 | FFPDHQLDPAF | XFXXXXXXXXF | | | | 703 |
| 80 | 16 | ENV | 243 | FIIFLFIL | XIXXXXXL | 17.0246 | | | 704 |
| 80 | 16 | ENV | 243 | FILFLFILL | XIXXXXXXL | 1.0830 | | | 705 |
| 80 | 16 | ENV | 243 | FIIFLFILLL | XIXXXXXXXL | 1.0894 | | | 706 |
| 80 | 16 | ENV | 248 | FILLLCLI | XIXXXXXI | Chisari 4.048 | | | 707 |
| 80 | 16 | ENV | 248 | FILLLCLIF | XIXXXXXXF | | | | 708 |
| 80 | 16 | ENV | 248 | FILLLCLIFL | XIXXXXXXXL | 1.0895 | * | | 709 |
| 80 | 16 | ENV | 248 | FILLLCLIFLL | XIXXXXXXXXL | Chisari 4.049 | | | 710 |
| 80 | 16 | ENV | 246 | FLFILLLCL | XLXXXXXXL | 1.0832 | | | 711 |
| 80 | 16 | ENV | 246 | FLFILLLCLI | XLXXXXXXXI | 3.0206 | | | 712 |
| 80 | 16 | ENV | 246 | FLFILLLCLIF | XLXXXXXXXXF | | | | 713 |
| 75 | 15 | ENV | 171 | FLGPLLVL | XLXXXXXL | | | | 714 |
| 95 | 19 | POL | 513 | FLLAQFTSAI | XLXXXXXXXI | 1147.13 | * | | 715 |
| 95 | 19 | POL | 562 | FLLSLGIHL | XLXXXXXXL | 1.0851 | * | | 716 |
| 80 | 16 | ENV | 183 | FLLTRILTI | XLXXXXXXI | 3.0005 | * | | 717 |
| 95 | 19 | ENV | 256 | FLLVLLDY | XLXXXXXY | 26.0027 | | | 718 |
| 95 | 19 | ENV | 256 | FLLVLLDYQGM | XLXXXXXXXXM | | | | 719 |
| 95 | 19 | POL | 656 | FTFSPTYKAF | XTXXXXXXXF | 20.0262 | | | 720 |
| 95 | 19 | POL | 656 | FTFSPTYKAFL | XTXXXXXXXXL | | | | 721 |
| 95 | 19 | POL | 635 | FTQCGYPAL | XTXXXXXXL | 5.0031 | | | 722 |
| 95 | 19 | POL | 635 | FTQCGYPALM | XTXXXXXXXM | 5.0085 | | | 723 |
| 95 | 19 | ENV | 346 | FVGLSPTVW | XVXXXXXXW | | | | 724 |
| 95 | 19 | ENV | 346 | FVGLSPTVWL | XVXXXXXXXL | 1.0931 | | | 725 |
| 90 | 18 | X | 132 | FVLGGCRHKL | XVXXXXXXXL | 1.0588 | | | 726 |
| 95 | 19 | ENV | 342 | FVQWFVGL | XVXXXXXL | 17.0109 | * | | 727 |
| 90 | 18 | POL | 766 | FVYVPSAL | XVXXXXXL | 17.0260 | * | | 728 |
| 95 | 19 | POL | 630 | GFAAPFTQCGY | XFXXXXXXXXY | | | | 729 |
| 80 | 16 | ENV | 181 | GFFLLTRI | XFXXXXXI | | | | 730 |
| 80 | 16 | ENV | 181 | GFFLLTRIL | XFXXXXXXL | | | | 731 |
| 80 | 16 | ENV | 181 | GFFLLTRILTI | XFXXXXXXXXI | | | | 732 |
| 95 | 19 | ENV | 12 | GFFPDHQL | XFXXXXXL | | | | 733 |
| 75 | 15 | ENV | 170 | GFLGPLLVL | XFXXXXXXL | | | | 734 |
| 80 | 16 | POL | 500 | GFRKIPMGVGL | XFXXXXXXXXL | | | | 735 |
| 95 | 19 | POL | 627 | GLLGFAAPF | XLXXXXXXF | 20.0124 | | | 736 |
| 95 | 19 | POL | 509 | GLSPFLLAQF | XLXXXXXXXF | | | | 737 |
| 100 | 20 | ENV | 348 | GLSPTVWL | XLXXXXXL | Chisari 4.012 | | | 738 |
| 75 | 15 | ENV | 348 | GLSPTVWLSVI | XLXXXXXXXXI | Chisari 4.031 | | | 739 |
| 85 | 17 | NUC | 29 | GMDIDPYKEF | XMXXXXXXXF | 26.0372 | | | 740 |
| 90 | 18 | ENV | 265 | GMLPVCPL | XMXXXXXL | | | | 741 |
| 90 | 18 | POL | 735 | GTDNSVVL | XTXXXXXL | | | | 742 |
| 75 | 15 | ENV | 13 | GTNLSVPNPL | XTXXXXXXXL | | | | 743 |
| 80 | 16 | POL | 763 | GTSFVYVPSAL | XTXXXXXXXXL | | | | 744 |
| 80 | 16 | POL | 507 | GVGLSPFL | XVXXXXXL | | | | 745 |
| 80 | 16 | POL | 507 | GVGLSPFLL | XVXXXXXXL | 1.0850 | | | 746 |
| 95 | 19 | NUC | 123 | GVWIRTPPAY | XVXXXXXXXY | 1.0525 | | | 747 |
| 85 | 17 | NUC | 25 | GWLWGMDI | XWXXXXXI | | | | 748 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 85 | 17 | NUC | 25 | GWLWGMDIDPY | XWXXXXXXXXY | | | | 749 |
| 85 | 17 | ENV | 65 | GWSPQAQGI | XWXXXXXXI | 20.0134 | | 0.0024 | 750 |
| 85 | 17 | ENV | 65 | GWSPQAQGIL | XWXXXXXXXL | 20.0268 | | 0.0003 | 751 |
| 95 | 19 | POL | 639 | GYPALMPL | XYXXXXXL | | | | 752 |
| 95 | 19 | POL | 639 | GYPALMPLY | XYXXXXXXY | 2.0060 | * | 0.0490 | 753 |
| 95 | 19 | ENV | 234 | GYRWMCLRRF | XYXXXXXXXF | 2.0171 | * | 0.0110 | 754 |
| 95 | 19 | ENV | 234 | GYRWMCLRRFI | XYXXXXXXXXI | | | | 755 |
| 85 | 17 | POL | 579 | GYSUNFMGY | XYXXXXXXY | 2.0058 | | 0.0002 | 756 |
| 75 | 15 | POL | 579 | GYSLNFMGYVI | XYXXXXXXXXI | | | | 757 |
| 80 | 16 | POL | 820 | HFASPLHVAW | XFXXXXXXXW | | | | 758 |
| 75 | 15 | POL | 7 | HFRKLLLL | XFXXXXXL | | | | 759 |
| 80 | 16 | POL | 435 | HLLVGSSGL | XLXXXXXXL | 1.0187 | | | 760 |
| 75 | 15 | POL | 569 | HLNPNKTKRW | XLXXXXXXXW | | | | 761 |
| 80 | 16 | POL | 491 | HLYSHPII | XLXXXXXI | 17.0256 | | | 762 |
| 80 | 16 | POL | 491 | HLYSHPIIL | XLXXXXXXL | 1.0849 | * | | 763 |
| 80 | 16 | POL | 491 | HLYSHPIILGF | XLXXXXXXXXF | | | | 764 |
| 85 | 17 | POL | 715 | HTAELLAACF | XTXXXXXXXF | | | | 765 |
| 100 | 20 | NUC | 52 | HTALRQAI | XTXXXXXI | | | | 766 |
| 95 | 19 | NUC | 52 | HTALRQAIL | XTXXXXXXL | 5.0021 | | | 767 |
| 95 | 19 | NUC | 52 | HTALRQAILCW | XTXXXXXXXXW | | | | 768 |
| 100 | 20 | POL | 149 | HTLWKAGI | XTXXXXXI | | | | 769 |
| 100 | 20 | POL | 149 | HTLWKAGIL | XTXXXXXXL | 5.0033 | | | 770 |
| 100 | 20 | POL | 149 | HTLWKAGILY | XTXXXXXXXY | 1.0542 | * | | 771 |
| 100 | 20 | POL | 146 | HYLHTLWKAGI | XYXXXXXXXXI | | | | 772 |
| 100 | 20 | ENV | 381 | IFFCLWVY | XFXXXXXY | | | | 773 |
| 100 | 20 | ENV | 381 | IFFCLWVYI | XFXXXXXXI | 5.0058 | | 0.0087 | 774 |
| 80 | 16 | ENV | 245 | IFLFILLL | XFXXXXXL | | | | 775 |
| 80 | 16 | ENV | 245 | IFLFILLLCL | XFXXXXXXXL | | | | 776 |
| 80 | 16 | ENV | 245 | IFLFILLLCLI | XFXXXXXXXXI | | | | 777 |
| 95 | 19 | ENV | 255 | IFLLVLLDY | XFXXXXXXY | | | | 778 |
| 80 | 16 | ENV | 244 | IIFLFILL | XIXXXXXL | 17.0105 | | | 779 |
| 80 | 16 | ENV | 244 | IIFLFILLL | XIXXXXXXL | 1.0831 | | | 780 |
| 80 | 16 | ENV | 244 | IIFLFILLLCL | XIXXXXXXXXL | Chisari 4.052 | | | 781 |
| 80 | 16 | POL | 497 | IILGFRKI | XIXXXXXI | 17.0124 | * | | 782 |
| 80 | 16 | POL | 497 | IILGFRKIPM | XIXXXXXXXM | | | | 783 |
| 90 | 18 | NUC | 59 | ILCWGELM | XLXXXXXM | | | | 784 |
| 80 | 16 | POL | 498 | ILGFRKIPM | XLXXXXXXM | 3.0016 | | | 785 |
| 100 | 20 | ENV | 249 | ILLLCLIF | XLXXXXXF | | | | 786 |
| 100 | 20 | ENV | 249 | ILLLCLIFL | XLXXXXXXL | 1.0833 | * | | 787 |
| 100 | 20 | ENV | 249 | ILLLCLIFLL | XLXXXXXXXL | 1.0896 | * | | 788 |
| 80 | 16 | POL | 760 | ILRGTSFVY | XLXXXXXXY | 1.0205 | * | | 789 |
| 95 | 19 | ENV | 188 | ILTIPQSL | XLXXXXXL | | | | 790 |
| 90 | 18 | ENV | 188 | ILTIPQSLDSW | XLXXXXXXXXW | | | | 791 |
| 90 | 18 | POL | 625 | IVGLLGFAAPF | XVXXXXXXXXF | | | | 792 |
| 85 | 17 | ENV | 358 | IWMMWYWGPS | XWXXXXXXXXL | 1039.07 | | 0.0004 | 793 |
| 95 | 19 | POL | 395 | KFAVPNLQSL | XFXXXXXXXL | 5.0114 | | 0.0020 | 794 |
| 80 | 16 | POL | 503 | KIPMGVGL | XIXXXXXL | | | | 795 |
| 80 | 16 | POL | 503 | KIPMGVGLSPF | XIXXXXXXXXF | | | | 796 |
| 85 | 17 | NUC | 21 | KLCLGWLW | XLXXXXXW | | | | 797 |
| 85 | 17 | NUC | 21 | KLCLGWLWGM | XLXXXXXXXM | 3.0209 | * | | 798 |
| 95 | 19 | POL | 489 | KLHLYSHPI | XLXXXXXXI | 3.0009 | * | | 799 |
| 80 | 16 | POL | 489 | KLHLYSHPII | XLXXXXXXXI | | | | 800 |
| 80 | 16 | POL | 489 | KLHLYSHPIIL | XLXXXXXXXXL | | | | 801 |
| 75 | 15 | POL | 108 | KLIMPARF | XLXXXXXF | | | | 802 |
| 75 | 15 | POL | 108 | KLIMPARFY | XLXXXXXXY | 1.0171 | | | 803 |
| 80 | 16 | POL | 610 | KLPVNRPI | XLXXXXXI | | | | 804 |
| 80 | 16 | POL | 610 | KLPVNRPIDW | XLXXXXXXXW | | | | 805 |
| 95 | 19 | POL | 574 | KTKRWGYSL | XTXXXXXXL | 5.0034 | | | 806 |
| 85 | 17 | POL | 574 | KTKRWGYSLNF | XTXXXXXXXXF | | | | 807 |
| 85 | 17 | POL | 620 | KVCQRIVGL | XVXXXXXXL | 1.0198 | | | 808 |
| 85 | 17 | POL | 620 | KVCQRIVGLL | XVXXXXXXXL | 1.0567 | | | 809 |
| 95 | 19 | POL | 55 | KVGNFTGL | XVXXXXXL | 17.0116 | | | 810 |
| 95 | 19 | POL | 55 | KVGNFTGLY | XVXXXXXXY | 1.0166 | * | | 811 |
| 85 | 17 | X | 91 | KVLHKRTL | XVXXXXXL | | | | 812 |
| 85 | 17 | X | 91 | KVLHKRTLGL | XVXXXXXXXL | 1.0800 | | | 813 |
| 100 | 20 | POL | 121 | KYLPLDKGI | XYXXXXXXI | 5.0063 | * | 0.0028 | 814 |
| 85 | 17 | POL | 745 | KYTSFPWL | XYXXXXXL | 17.0132 | | | 815 |
| 85 | 17 | POL | 745 | KYTSFPWLL | XYXXXXXXL | 2.0061 | * | 3.6000 | 816 |
| 80 | 16 | ENV | 247 | LFILLLCL | XFXXXXXL | 17.0247 | | | 817 |
| 80 | 16 | ENV | 247 | LFILLLCLI | XFXXXXXXI | | | | 818 |
| 80 | 16 | ENV | 247 | LFILLLCLIF | XFXXXXXXXF | | | | 819 |
| 80 | 16 | ENV | 247 | LFILLLCLIFL | XFXXXXXXXXL | | | | 820 |
| 100 | 20 | ENV | 254 | LIFLLVLL | XIXXXXXL | Chisari 4.014 | | | 821 |
| 95 | 19 | ENV | 254 | LIFLLVLLDY | XIXXXXXXXY | 1.0899 | | | 822 |
| 100 | 20 | POL | 109 | LIMPARFY | XIXXXXXY | 26.0028 | | | 823 |

TABLE IX-continued
HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 95 | 19 | POL | 514 | LLAQFTSAI | XLXXXXXXI | 3.0010 | * | | 824 |
| 100 | 20 | ENV | 251 | LLCLIFLL | XLXXXXXL | Chisari 4.015 | | | 825 |
| 100 | 20 | ENV | 251 | LLCLIFLLVL | XLXXXXXXXL | 1.0898 | | | 826 |
| 100 | 20 | ENV | 251 | LLCLIFLLVLL | XLXXXXXXXXL | Chisari 4.016 | | | 827 |
| 85 | 17 | NUC | 30 | LLDTASAL | XLXXXXXL | | | | 828 |
| 85 | 17 | NUC | 30 | LLDTASALY | XLXXXXXXY | 1.0155 | * | | 829 |
| 95 | 19 | ENV | 260 | LLDYQGML | XLXXXXXL | Chisari 4.021 | | | 830 |
| 80 | 16 | POL | 752 | LLGCAANW | XLXXXXXW | | | | 831 |
| 80 | 16 | POL | 752 | LLGCAANWI | XLXXXXXXI | 3.0013 | | | 832 |
| 80 | 16 | POL | 752 | LLGCAANWIL | XLXXXXXXXL | 1.0912 | * | | 833 |
| 95 | 19 | POL | 628 | LLGFAAPF | XLXXXXXF | | | | 834 |
| 75 | 15 | ENV | 63 | LLGWSPQAQGI | XLXXXXXXXXI | | | | 835 |
| 100 | 20 | ENV | 250 | LLLCLIFL | XLXXXXXL | Chisari 4.017 | | | 836 |
| 100 | 20 | ENV | 250 | LLLCLIFLL | XLXXXXXXL | 1.0834 | * | | 837 |
| 100 | 20 | ENV | 250 | LLLCLIFLLVL | XLXXXXXXXXL | Chisari 4.018 | | | 838 |
| 100 | 20 | ENV | 378 | LLPIFFCL | XLXXXXXL | 17.0112 | | | 839 |
| 100 | 20 | ENV | 378 | LLPIFFCLW | XLXXXXXXW | | | | 840 |
| 100 | 20 | ENV | 378 | LLPIFFCLWVY | XLXXXXXXXXY | 26.0549 | * | | 841 |
| 95 | 19 | NUC | 44 | LLSFLPSDF | XLXXXXXXF | | | | 842 |
| 95 | 19 | NUC | 44 | LLSFLPSDFF | XLXXXXXXXF | | | | 843 |
| 95 | 19 | POL | 563 | LLSLGIHL | XLXXXXXL | | | | 844 |
| 90 | 18 | POL | 407 | LLSSNLSW | XLXXXXXW | | | | 845 |
| 90 | 18 | POL | 407 | LLSSNLSWL | XLXXXXXXL | 1.0184 | * | | 846 |
| 90 | 18 | POL | 407 | LLSSNLSWLSL | XLXXXXXXXXL | | | | 847 |
| 80 | 16 | ENV | 184 | LLTRILTI | XLXXXXXI | Chisari 4.053 | | | 848 |
| 80 | 16 | POL | 436 | LLVGSSGL | XLXXXXXL | | | | 849 |
| 95 | 19 | ENV | 257 | LLVLLDYQGM | XLXXXXXXXM | 3.0207 | | | 850 |
| 95 | 19 | ENV | 257 | LLVLLDYQGML | XLXXXXXXXXL | | | | 851 |
| 95 | 19 | ENV | 175 | LLVLQAGF | XLXXXXXF | | | | 852 |
| 95 | 19 | ENV | 175 | LLVLQAGFF | XLXXXXXXF | 20.0121 | | | 853 |
| 90 | 18 | ENV | 175 | LLVLQAGFFL | XLXXXXXXXL | 1.0892 | * | | 854 |
| 90 | 18 | ENV | 175 | LLVLQAGFFLL | XLXXXXXXXXL | Chisari 4.028 | | | 855 |
| 100 | 20 | ENV | 338 | LLVPFVQW | XLXXXXXW | | | | 856 |
| 100 | 20 | ENV | 338 | LLVPFVQWF | XLXXXXXXF | | | | 857 |
| 90 | 18 | NUC | 100 | LLWFHISCL | XLXXXXXXL | 1.0844 | * | | 858 |
| 85 | 17 | NUC | 100 | LLWFHSCLTF | XLXXXXXXXF | | | | 859 |
| 95 | 19 | POL | 643 | LMPLYACI | XMXXXXXI | 17.0130 | | | 860 |
| 75 | 15 | NUC | 137 | LTFGRETVL | XTXXXXXXL | | | | 861 |
| 75 | 15 | NUC | 137 | LTFGRETVLEY | XTXXXXXXXXY | | | | 862 |
| 90 | 18 | ENV | 189 | LTIPQSLDSW | XTXXXXXXXW | | | | 863 |
| 90 | 18 | ENV | 189 | LTIPQSLDSWW | XTXXXXXXXXW | | | | 864 |
| 90 | 18 | POL | 404 | LTNLLSSNL | XTXXXXXXL | | | | 865 |
| 90 | 18 | POL | 404 | LTNLLSSNLSW | XTXXXXXXXXW | | | | 866 |
| 80 | 16 | ENV | 185 | LTRILTIPQSL | XTXXXXXXXXL | | | | 867 |
| 85 | 17 | POL | 99 | LTVNEKRRL | XTXXXXXXL | | | | 868 |
| 95 | 19 | ENV | 258 | LVLLDYQGM | XVXXXXXXM | 3.0034 | | | 869 |
| 95 | 19 | ENV | 258 | LVLLDYQGML | XVXXXXXXXL | 1.0515 | | | 870 |
| 95 | 19 | ENV | 176 | LVLQAGFF | XVXXXXXF | | | | 871 |
| 90 | 18 | ENV | 176 | LVLQAGFFL | XVXXXXXXL | 1.0827 | | | 872 |
| 90 | 18 | ENV | 176 | LVLQAGFFLL | XVXXXXXXXL | 1.0893 | * | | 873 |
| 100 | 20 | ENV | 339 | LVPFVQWF | XVXXXXXF | | | | 874 |
| 95 | 19 | ENV | 339 | LVPFVQWFVGL | XVXXXXXXXXL | | | | 875 |
| 90 | 18 | NUC | 119 | LVSFGVWI | XVXXXXXI | Chisari 4.078 | | | 876 |
| 100 | 20 | POL | 377 | LWDFSQF | XVXXXXXF | | | | 877 |
| 90 | 18 | NUC | 101 | LWFHISCL | XWXXXXXL | | | | 878 |
| 85 | 17 | NUC | 101 | LWFHISCLTF | XWXXXXXXXF | 26.0373 | | | 879 |
| 85 | 17 | NUC | 27 | LWGMDIDPY | XWXXXXXXY | | | | 880 |
| 100 | 20 | POL | 151 | LWKAGILY | XWXXXXXY | | | | 881 |
| 80 | 16 | POL | 492 | LYSHPIIL | XYXXXXXL | | | | 882 |
| 80 | 16 | POL | 492 | LYSHPIILGF | XYXXXXXXXF | 2.0181 | * | 1.1000 | 883 |
| 85 | 17 | ENV | 360 | MMWYWGPSL | XMXXXXXXL | 1.0839 | * | 0.0012 | 884 |
| 85 | 17 | ENV | 360 | MMWYWGPSLY | XMXXXXXXXY | 1039.01 | * | 0.0001 | 885 |
| 85 | 17 | ENV | 361 | MWYWGPSL | XWXXXXXL | 17.0249 | | | 886 |
| 85 | 17 | ENV | 361 | MWYWGPSLY | XWXXXXXXY | 1039.02 | | 0.0027 | 887 |
| 95 | 19 | POL | 561 | NFLLSLGI | XFXXXXXI | | | | 888 |
| 95 | 19 | POL | 561 | NFLLSLGIHL | XFXXXXXXXL | 5.0115 | | 0.0099 | 889 |
| 95 | 19 | POL | 42 | NLGNLNVSI | XLXXXXXXI | 3.0008 | | | 890 |
| 95 | 19 | POL | 42 | NLGNLNVSIPW | XLXXXXXXXXW | | | | 891 |
| 90 | 18 | POL | 406 | NLLSSNLSW | XLXXXXXXW | | | | 892 |
| 90 | 18 | POL | 406 | NLLSSNLSWL | XLXXXXXXXL | 1.0549 | | | 893 |
| 95 | 19 | POL | 45 | NLNVSIPW | XLXXXXXW | | | | 894 |
| 100 | 20 | POL | 400 | NLQSLTNL | XLXXXXXL | | | | 895 |
| 100 | 20 | POL | 400 | NLQSLTNLL | XLXXXXXXL | 1.0183 | | | 896 |
| 75 | 15 | ENV | 15 | NLSVPNPL | XLXXXXXL | | | | 897 |
| 75 | 15 | ENV | 15 | NLSVPNPLGF | XLXXXXXXXF | | | | 898 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 80 | 16 | POL | 758 | NWILRGTSF | XWXXXXXXF | | | | 899 |
| 80 | 16 | POL | 758 | NWILRGTSFVY | XWXXXXXXXXY | | | | 900 |
| 95 | 19 | POL | 512 | PFLLAQFTSAI | XFXXXXXXXXI | | | | 901 |
| 95 | 19 | POL | 634 | PFTQCGYPAL | XFXXXXXXXL | 5.0116 | | 0.0002 | 902 |
| 95 | 19 | POL | 634 | PFTQCGYPALM | XFXXXXXXXXM | | | | 903 |
| 95 | 19 | ENV | 341 | PFVQWFVGL | XFXXXXXXL | 5.0059 | | 0.0003 | 904 |
| 85 | 17 | POL | 616 | PIDWKVCQRI | XIXXXXXXI | Chisari 4.091 | | | 905 |
| 100 | 20 | ENV | 380 | PIFFCLWVY | XIXXXXXXY | 1.0843 | | | 906 |
| 100 | 20 | ENV | 380 | PIFFCLWVYI | XIXXXXXXXI | 20.0258 | | | 907 |
| 85 | 17 | POL | 713 | PIHTAELL | XIXXXXXL | | | | 908 |
| 80 | 16 | POL | 496 | PIILGFRKI | XIXXXXXXI | 927.48 | | | 909 |
| 80 | 16 | POL | 496 | PIILGFRKIPM | XIXXXXXXXXM | | | | 910 |
| 100 | 20 | ENV | 314 | PIPSSWAF | XIXXXXXF | | | | 911 |
| 100 | 20 | POL | 124 | PLDKGIKPY | XLXXXXXXY | 1.0174 | * | | 912 |
| 100 | 20 | POL | 124 | PLDKGIKPYY | XLXXXXXXXY | 1.0541 | * | | 913 |
| 95 | 19 | POL | 20 | PLEEELPRL | XLXXXXXXL | 1.0163 | | | 914 |
| 95 | 19 | ENV | 10 | PLGFFPDHQL | XLXXXXXXXL | 1.0511 | | | 915 |
| 100 | 20 | POL | 427 | PLHPAAMPHL | XLXXXXXXXL | 1.0550 | | | 916 |
| 100 | 20 | POL | 427 | PLHPAAMPHLL | XLXXXXXXXXL | | | | 917 |
| 100 | 20 | ENV | 377 | PLLPIFFCL | XLXXXXXXL | 1.0842 | * | | 918 |
| 100 | 20 | ENV | 377 | PLLPIFFCLW | XLXXXXXXXW | | | | 919 |
| 95 | 19 | ENV | 174 | PLLVLQAGF | XLXXXXXXF | | | | 920 |
| 95 | 19 | ENV | 174 | PLLVLQAGFF | XLXXXXXXXF | | | | 921 |
| 90 | 18 | ENV | 174 | PLLVLQAGFFL | XLXXXXXXXXL | Chisari 4.029 | | | 922 |
| 80 | 16 | POL | 711 | PLPIHTAEL | XLXXXXXXL | 1.0201 | | | 923 |
| 80 | 16 | POL | 711 | PLPIHTAELL | XLXXXXXXXL | 1.0569 | | | 924 |
| 75 | 15 | POL | 2 | PLSYQHFRKL | XLXXXXXXXL | 1.0527 | | | 925 |
| 75 | 15 | POL | 2 | PLSYCHFRKLL | XLXXXXXXXXL | | | | 926 |
| 85 | 17 | POL | 98 | PLTVNEKRRL | XLXXXXXXXL | 1.0536 | | | 927 |
| 80 | 16 | POL | 505 | PMGVGLSPF | XMXXXXXXF | | | | 928 |
| 80 | 16 | POL | 505 | PMGVGLSPFL | XMXXXXXXXL | 1.0557 | | | 929 |
| 80 | 16 | POL | 505 | PMGVGLSPFLL | XMXXXXXXXXL | | | | 930 |
| 75 | 15 | POL | 692 | PTGWGLAI | XTXXXXXI | | | | 931 |
| 85 | 17 | POL | 797 | PTTGRTSL | XTXXXXXL | | | | 932 |
| 85 | 17 | POL | 797 | PTTGRTSLY | XTXXXXXXY | 1.0208 | * | | 933 |
| 80 | 16 | NUC | 15 | PTVQASKL | XTXXXXXL | | | | 934 |
| 80 | 16 | NUC | 15 | PTVQASKLCL | XTXXXXXXXL | | | | 935 |
| 75 | 15 | ENV | 351 | PTVWLSVI | XTXXXXXI | | | | 936 |
| 75 | 15 | ENV | 351 | PTVWLSVIW | XTXXXXXXW | | | | 937 |
| 75 | 15 | ENV | 351 | PTVWLSVIWM | XTXXXXXXXM | | | | 938 |
| 85 | 17 | POL | 612 | PVNRPIDW | XVXXXXXW | | | | 939 |
| 80 | 16 | POL | 750 | PWLLGCAANW | XWXXXXXXXW | | | | 940 |
| 80 | 16 | POL | 750 | PWLLGCAANWI | XWXXXXXXXXI | | | | 941 |
| 100 | 20 | POL | 51 | PWTHKVGNF | XWXXXXXXF | 20.0138 | * | 0.0290 | 942 |
| 80 | 16 | X | 8 | QLDFARDVL | XLXXXXXXL | 1.0210 | | | 943 |
| 80 | 16 | X | 8 | QLDPARDVLCL | XLXXXXXXXXL | Chisari 4.073 | | | 944 |
| 90 | 18 | NUC | 99 | QLLWFHISCL | XLXXXXXXXL | 1.0908 | * | | 945 |
| 95 | 19 | POL | 685 | QVFADATPTGW | XVXXXXXXXXW | | | | 946 |
| 95 | 19 | ENV | 344 | QWFVGLSPTVW | XWXXXXXXXX | | | | 947 |
| 75 | 15 | ENV | 242 | RFIIFLFI | XFXXXXXI | 17.0151 | | | 948 |
| 75 | 15 | ENV | 242 | RFIIFLFIL | XFXXXXXL | | | | 949 |
| 75 | 15 | ENV | 242 | RFIIFLFILL | XFXXXXXXXL | | | | 950 |
| 75 | 15 | ENV | 242 | RFIIFLFILLL | XFXXXXXXXXL | | | | 951 |
| 100 | 20 | ENV | 332 | RFSWLSLL | XFXXXXXL | | | | 952 |
| 100 | 20 | ENV | 332 | RFSWSLLVPF | XFXXXXXXXXF | | | | 953 |
| 80 | 16 | ENV | 187 | RILTIPQSL | XIXXXXXXL | 1.0149 | | | 954 |
| 90 | 18 | POL | 624 | RIVGLLGF | XIXXXXXF | | | | 955 |
| 75 | 15 | POL | 106 | RLKLIMPARF | XLXXXXXXXF | | | | 956 |
| 75 | 15 | POL | 106 | RLKLIMPARFY | XLXXXXXXXXY | | | | 957 |
| 95 | 19 | POL | 376 | RLWDFSQF | XLXXXXXXF | 20.0122 | | | 958 |
| 90 | 18 | POL | 353 | RTPARVTGGVF | XTXXXXXXXXF | | | | 959 |
| 95 | 19 | POL | 36 | RVAEDLNL | XVXXXXXL | | | | 960 |
| 90 | 18 | POL | 36 | RVAEDLNLGNL | XVXXXXXXXXL | | | | 961 |
| 80 | 16 | POL | 818 | RVHFASPL | XVXXXXXL | | | | 962 |
| 100 | 20 | POL | 357 | RVTGGVFL | XVXXXXXL | | | | 963 |
| 85 | 17 | POL | 577 | RWGSYSLNF | XWXXXXXXF | | | | 964 |
| 85 | 17 | POL | 577 | RWGYSLNFM | XWXXXXXXM | | | | 965 |
| 85 | 17 | POL | 577 | RWGYSLNFMGY | XWXXXXXXXXY | | | | 966 |
| 95 | 19 | ENV | 236 | RWMCLRRF | XWXXXXXF | | | | 967 |
| 95 | 19 | ENV | 236 | RWMCLRRFI | XWXXXXXXI | 20.0135 | * | 0.0710 | 968 |
| 95 | 19 | ENV | 236 | RWMCLRRFII | XWXXXXXXXI | 20.0269 | * | 1.1000 | 969 |
| 95 | 19 | ENV | 236 | RWMCLRRFIIF | XWXXXXXXXXF | | | | 970 |
| 100 | 20 | POL | 167 | SFQGSPYSW | XFXXXXXXW | 20.0139 | * | 0.0710 | 971 |
| 95 | 19 | NUC | 46 | SFLPSDFF | XFXXXXXF | | | | 972 |
| 80 | 16 | POL | 765 | SFVYVPSAL | XFXXXXXXL | | | | 973 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 100 | 20 | POL | 49 | SIPWTHKVGNF | XIXXXXXXXXF | | | | 974 |
| 95 | 19 | ENV | 194 | SLDSWWTSL | XLXXXXXXL | 1.0150 | | | 975 |
| 95 | 19 | ENV | 194 | SLDSWWTSLNF | XLXXXXXXXXF | | | | 976 |
| 95 | 19 | POL | 416 | SLDVSAAF | XLXXXXXF | | | | 977 |
| 95 | 19 | POL | 416 | SLDVSAAFY | XLXXXXXXY | 1.0186 | * | | 978 |
| 100 | 20 | ENV | 337 | SLLVPFVQW | XLXXXXXXW | | | | 979 |
| 100 | 20 | ENV | 337 | SLLVPFVQWF | XLXXXXXXXF | | | | 980 |
| 75 | 15 | POL | 581 | SLNFMGYVI | XLXXXXXXI | 3.0011 | | | 981 |
| 95 | 19 | X | 54 | SLRGLPVCAF | XLXXXXXXXF | 20.0259 | | | 982 |
| 90 | 18 | POL | 403 | SLTNLLSSNL | XLXXXXXXXL | 1.0548 | | | 983 |
| 75 | 15 | X | 104 | STTDLEAY | XTXXXXXY | | | | 984 |
| 75 | 15 | X | 104 | STTDLEAYF | XTXXXXXXF | | | | 985 |
| 75 | 15 | ENV | 17 | SVPNPLGF | XVXXXXXF | | | | 986 |
| 85 | 17 | POL | 548 | SVQHLESL | XVXXXXXL | | | | 987 |
| 80 | 16 | ENV | 330 | SVRFSWLSL | XVXXXXXXL | 1.0153 | | | 988 |
| 80 | 16 | ENV | 330 | SVRFSWLSLL | XVXXXXXXXL | 1.0517 | | | 989 |
| 90 | 18 | POL | 739 | SVVLSRKY | XVXXXXXY | 26.0029 | | | 990 |
| 85 | 17 | POL | 739 | SVVLSRKYTSF | XVXXXXXXXXF | | | | 991 |
| 95 | 19 | POL | 524 | SVVRRAFPHCL | XVXXXXXXXXL | | | | 992 |
| 95 | 19 | POL | 413 | SWLSLDVSAAF | XWXXXXXXXXF | | | | 993 |
| 100 | 20 | ENV | 334 | SWLSLLVPF | XWXXXXXXF | 20.0136 | * | 0.3900 | 994 |
| 95 | 19 | POL | 392 | SWPKFAVPNL | XWXXXXXXXL | 20.0271 | * | 5.6000 | 995 |
| 100 | 20 | ENV | 197 | SWWTSLNF | XWXXXXXF | | | | 996 |
| 95 | 19 | ENV | 197 | SWWTSLNFL | XWXXXXXXL | 20.0137 | * | 0.3800 | 997 |
| 90 | 18 | POL | 537 | SYMDDVVL | XYXXXXXL | | | | 998 |
| 75 | 15 | POL | 4 | SYQHFRKL | XYXXXXXL | | | | 999 |
| 75 | 15 | POL | 4 | SYQHFRKLL | XYXXXXXXL | 2.0042 | | 0.0051 | 1000 |
| 75 | 15 | POL | 4 | SYQHFRKLLL | XYXXXXXXXL | 2.0173 | * | 0.0660 | 1001 |
| 75 | 15 | POL | 4 | SYQHFRKLLLL | XYXXXXXXXXL | | | | 1002 |
| 75 | 15 | NUC | 138 | TFGRETVL | XFXXXXXL | | | | 1003 |
| 75 | 15 | NUC | 138 | TFGRETVLEY | XFXXXXXXXY | | | | 1004 |
| 75 | 15 | NUC | 138 | TFGRETVLEYL | XFXXXXXXXXL | | | | 1005 |
| 95 | 19 | POL | 657 | TFSPTYKAF | XFXXXXXXF | 5.0064 | | 0.0060 | 1006 |
| 95 | 19 | POL | 657 | TFSPTYKAFL | XFXXXXXXXL | 5.0117 | | 0.0043 | 1007 |
| 90 | 18 | ENV | 190 | TIPQSLDSW | XIXXXXXXW | | | | 1008 |
| 90 | 18 | ENV | 190 | TIPQSLDSWW | XIXXXXXXXW | | | | 1009 |
| 100 | 20 | POL | 150 | TLWKAGIL | XLXXXXXL | | | | 1010 |
| 100 | 20 | POL | 150 | TLWKAGILY | XLXXXXXXY | 1.0177 | * | | 1011 |
| 75 | 15 | X | 105 | TTDLEAYF | XTXXXXXF | | | | 1012 |
| 85 | 17 | POL | 798 | TTGRTSLY | XTXXXXXY | 26.0030 | | | 1013 |
| 85 | 17 | POL | 100 | TVNEKRRL | XVXXXXXL | | | | 1014 |
| 80 | 16 | NUC | 16 | TVQASKLCL | XVXXXXXXL | 1.0365 | | | 1015 |
| 80 | 16 | NUC | 16 | TVQASKLCLGW | XVXXXXXXXXW | | | | 1016 |
| 75 | 15 | ENV | 352 | TVWLSVIW | XVXXXXXW | | | | 1017 |
| 75 | 15 | ENV | 352 | TVWLSVIWM | XVXXXXXXM | 3.0035 | | | 1016 |
| 95 | 19 | POL | 686 | VFADATPTGW | XFXXXXXXXW | 20.0272 | * | 0.0180 | 1019 |
| 75 | 15 | X | 131 | VFVLGGCRHKL | XFXXXXXXXXL | | | | 1020 |
| 85 | 17 | POL | 543 | VLGAKSVOHL | XLXXXXXXXL | 1.0560 | | | 1021 |
| 90 | 18 | X | 133 | VLGGCRHKL | XLXXXXXXL | 1.0220 | | | 1022 |
| 85 | 17 | X | 92 | VLHKRTLGL | XLXXXXXXL | 1.0391 | | | 1023 |
| 95 | 19 | ENV | 259 | VLLDYOGM | XLXXXXXM | 17.0107 | | | 1024 |
| 95 | 19 | ENV | 259 | VLLDYCGML | XLXXXXXXL | 1.0151 | * | | 1025 |
| 95 | 19 | ENV | 177 | VLQAGFFL | XLXXXXXL | Chisari 4.027 | | | 1026 |
| 95 | 19 | ENV | 177 | VLQAGFFLL | XLXXXXXXL | 1.0828 | | | 1027 |
| 85 | 17 | POL | 741 | VLSRKYTSF | XLXXXXXXF | | | | 1028 |
| 85 | 17 | POL | 741 | VLSRKYTSFPW | XLXXXXXXXXW | | | | 1029 |
| 80 | 16 | POL | 542 | VVLGAKSVQHL | XVXXXXXXXXL | | | | 1030 |
| 85 | 17 | POL | 740 | VVLSRKYTSF | XVXXXXXXXF | 20.0261 | | | 1031 |
| 95 | 19 | POL | 525 | VVRRAFPHCL | XVXXXXXXXL | 1.0558 | | | 1032 |
| 95 | 19 | NUC | 124 | VWIRTPPAY | XWXXXXXXY | | | | 1033 |
| 75 | 15 | ENV | 353 | VWLSVIWM | XWXXXXXM | | | | 1034 |
| 90 | 18 | NUC | 102 | WFHISCLTF | XFXXXXXXF | 13.0073 | * | 0.0300 | 1035 |
| 95 | 19 | ENV | 345 | WFVGLSPTVW | XFXXXXXXXW | 20.0270 | * | 0.0120 | 1036 |
| 95 | 19 | ENV | 345 | WFVGLSPTVWL | XFXXXXXXXXL | | | | 1037 |
| 80 | 16 | POL | 759 | WILRGTSF | XIXXXXXF | | | | 1038 |
| 80 | 16 | POL | 759 | WILRGTSFVY | XIXXXXXXXY | 1.0572 | | | 1039 |
| 95 | 19 | NUC | 125 | WIRTPPAY | XIXXXXXY | 26.0031 | | | 1040 |
| 80 | 16 | POL | 751 | WLLGCAANW | XLXXXXXXW | | | | 1041 |
| 80 | 16 | POL | 751 | WLLGCAANWI | XLXXXXXXXI | Chisari 4.104 | | | 1042 |
| 80 | 16 | POL | 751 | WLLGCAANWIL | XLXXXXXXXXL | | | | 1043 |
| 95 | 19 | POL | 414 | WLSLDVSAAF | XLXXXXXXXF | | | | 1044 |
| 95 | 19 | POL | 414 | WLSLDVSAAFY | XLXXXXXXXXY | 26.0551 | | | 1045 |
| 100 | 20 | ENV | 335 | WLSLLVPF | XLXXXXXF | | | | 1046 |
| 100 | 20 | ENV | 335 | WLSLLVPFVQW | XLXXXXXXXXW | | | | 1047 |
| 85 | 17 | NUC | 26 | WLWGMDIDPY | XLXXXXXXXY | 1.0774 | * | | 1048 |

TABLE IX-continued

HBV A24 SUPER MOTIF (With binding information)

| Conservancy | Freq | Protein | Position | Sequence | String | Peptide | Filed | A*2401 | SEQ ID NO: |
|---|---|---|---|---|---|---|---|---|---|
| 95 | 19 | ENV | 237 | WMCLRRFI | XMXXXXXI | | | | 1049 |
| 95 | 19 | ENV | 237 | WMCLRRFII | XMXXXXXXI | 3.0031 | * | 0.0230 | 1050 |
| 95 | 19 | ENV | 237 | WMCLRRFIIF | XMXXXXXXXF | 20.0266 | | 0.0013 | 1051 |
| 95 | 19 | ENV | 237 | WMCLRRFIFL | XMXXXXXXXXL | Chisari 4.024 | | | 1052 |
| 85 | 17 | ENV | 359 | WMMWYWGPSL | XMXXXXXXXL | 1.0901 | * | 0.0005 | 1053 |
| 85 | 17 | ENV | 359 | WMMWYWGPSL | XMXXXXXXXXY | 26.0552 | * | | 1054 |
| 100 | 20 | POL | 52 | WTHKVGNF | XTXXXXXF | | | | 1055 |
| 95 | 19 | POL | 52 | WTHKVGNFTGL | XTXXXXXXXXL | | | | 1056 |
| 95 | 19 | ENV | 198 | WWTSLNFL | XWXXXXXL | | | | 1057 |
| 85 | 17 | ENV | 362 | WYWGPSLY | XYXXXXXY | 3.0362 | | 0.0001 | 1058 |
| 100 | 20 | POL | 147 | YLHTLWKAGI | XLXXXXXXXI | 7.0066 | * | | 1059 |
| 100 | 20 | POL | 147 | YLHTLWKAGIL | XLXXXXXXXXL | | | | 1060 |
| 100 | 20 | POL | 122 | YLPLDKGI | XLXXXXXI | | | | 1061 |
| 100 | 20 | POL | 122 | YLPLDKGIKPY | XLXXXXXXXXY | 26.0553 | | | 1062 |
| 90 | 18 | NUC | 118 | YLVSFGVW | XLXXXXXW | | | | 1063 |
| 90 | 18 | NUC | 118 | YLVSFGVWI | XLXXXXXXI | 3.0007 | * | | 1064 |
| 85 | 17 | POL | 746 | YTSFPWLL 411 | XTXXXXXL | | | | 1065 |

TABLE X

HBV B07 SUPER MOTIF (With binding information)

| Conservancy | Frequency | Protein | Position | Sequence | P2 | C-term | Peptide | AA | Filed | B*0702 | B*3501 | B*5101 | B*5301 | B*5401 | SEQ ID NO: |
|---|---|---|---|---|---|---|---|---|---|---|---|---|---|---|---|
| 75 | 15 | X | 146 | APCNFFTSA | P | A | | 9 | | 0.0001 | 0.0012 | 0.0019 | 0.0002 | 0.0002 | 1066 |
| 95 | 19 | POL | 633 | APFTQCGY | P | Y | 19.0013 | 8 | | 0.0029 | 0.0001 | | 0.0002 | 1.4000 | 1067 |
| 95 | 19 | POL | 633 | APFTQCGYPA | P | A | 16.0180 | 10 | * | 0.0029 | 0.0001 | | 0.0002 | 1.4000 | 1068 |
| 95 | 19 | POL | 633 | APFTQCGYPAL | P | L | 26.0554 | 11 | * | 0.2300 | 0.0010 | 0.0004 | −0.0003 | 0.0093 | 1069 |
| 100 | 20 | ENV | 232 | CPGYRWMCL | P | L | 1308.21 | 9 | | | | | | | 1070 |
| 80 | 16 | NUC | 14 | CPTVQASKL | P | L | | 9 | | | | | | | 1071 |
| 80 | 16 | NUC | 14 | CPTVQASKLCL | P | L | | 11 | | | | | | | 1072 |
| 80 | 16 | X | 10 | DPARDVLCL | P | L | | 9 | | | | | | | 1073 |
| 80 | 16 | ENV | 122 | DPRVRGLY | P | Y | | 8 | | | | | | | 1074 |
| 90 | 18 | POL | 778 | DPSRGRLGL | P | L | 1147.01 | 9 | * | 0.0120 | 0.0001 | 0.0001 | 0.0001 | 0.0001 | 1075 |
| 90 | 18 | NUC | 33 | DPYKEFGA | P | A | 19.0008 | 8 | | 0.0001 | 0.0001 | 0.0019 | 0.0002 | 0.0019 | 1076 |
| 75 | 15 | ENV | 130 | FPAGGSSSGTV | P | V | | 11 | | | | | | | 1077 |
| 90 | 18 | ENV | 14 | FPDHQLDPA | P | A | 1308.23 | 9 | * | | | | | | 1078 |
| 85 | 17 | ENV | 14 | FPDHQLDPAF | P | F | 20.0274 | 10 | | 0.0002 | 0.0016 | 0.0003 | 0.0011 | 0.0021 | 1079 |
| 95 | 19 | POL | 530 | FPHCLAFSY | P | Y | 1145.08 | 9 | * | 0.0001 | 0.5250 | 0.0665 | 0.5400 | 0.0199 | 1080 |
| 95 | 19 | POL | 530 | FPHCLAFSYM | P | M | 1147.05 | 10 | * | 0.0990 | 0.2200 | 0.0900 | 0.0790 | 0.0480 | 1081 |
| 75 | 15 | POL | 749 | FPWLLGCA | P | A | | 8 | | | | | | | 1082 |
| 75 | 15 | POL | 749 | FPWLLGCAA | P | A | | 9 | | | | | | | 1083 |
| 75 | 15 | POL | 749 | FPWLLGCAANW | P | W | | 11 | | | | | | | 1084 |
| 90 | 18 | X | 67 | GPCALRFTSA | P | A | 16.0182 | 10 | * | 0.0900 | 0.0001 | 0.0001 | 0.0002 | 0.0035 | 1085 |
| 95 | 19 | POL | 19 | GPLEEELPRL | P | L | 15.0208 | 10 | | 0.0001 | 0.0001 | 0.0002 | 0.0001 | 0.0002 | 1086 |
| 90 | 18 | POL | 19 | GPLEEELPRLA | P | A | 26.0555 | 11 | | −0.0002 | 0.0001 | 0.0001 | −0.0003 | 0.0001 | 1087 |
| 95 | 19 | ENV | 173 | GPLLVLQA | P | A | 19.0003 | 8 | * | 0.0003 | 0.0001 | 0.0110 | 0.0002 | 0.0065 | 1088 |
| 95 | 19 | ENV | 173 | GPLLVLQAGF | P | F | 15.0212 | 10 | | 0.0001 | 0.0001 | 0.0002 | 0.0001 | 0.0002 | 1089 |
| 95 | 19 | ENV | 173 | GPLLVLQAGFF | P | F | 26.0556 | 11 | | 0.0011 | 0.0001 | 0.0001 | 0.0008 | 0.0009 | 1090 |
| 85 | 17 | POL | 97 | GPLTVNEKRRL | P | L | 26.0557 | 11 | | 0.0031 | 0.0001 | 0.0001 | −0.0003 | 0.0001 | 1091 |
| 100 | 20 | POL | 429 | HPAAMPHL | P | L | 19.0005 | 8 | * | 0.0650 | 0.0004 | 0.3100 | 0.0037 | 0.0160 | 1092 |
| 100 | 20 | POL | 429 | HPAAMPHLL | P | L | 1147.02 | 9 | * | 0.0980 | 0.0270 | 0.0110 | 0.0500 | 0.0120 | 1093 |
| 85 | 17 | POL | 429 | HPAAMPHLLV | P | V | 20.0273 | 10 | * | 0.0160 | 0.0020 | 0.0078 | 0.0140 | 0.0170 | 1094 |
| 80 | 16 | POL | 495 | HPIILGFRKI | P | I | | 10 | | | | | | | 1095 |
| 100 | 20 | ENV | 313 | IPIPSSWA | P | A | 19.0005 | 8 | * | 0.0004 | 0.0004 | 0.0019 | 0.0002 | 0.0600 | 1096 |
| 100 | 20 | ENV | 313 | IPIPSSWAF | P | F | 1145.04 | 9 | * | 0.1300 | 2.7679 | 2.3500 | 0.7450 | 0.0034 | 1097 |
| 80 | 16 | ENV | 313 | IPIPSSWAFA | P | A | 16.0177 | 10 | * | 0.0013 | 0.0024 | | 0.0014 | 0.4500 | 1098 |
| 80 | 16 | POL | 504 | IPMGVGLSPF | P | F | | 10 | | | | | | | 1099 |
| 80 | 16 | POL | 504 | IPMGVGLSPFL | P | L | | 11 | | | | | | | 1100 |
| 90 | 18 | ENV | 191 | IPQSLDSW | P | W | F126.65 | 8 | | | | | | | 1101 |
| 90 | 18 | ENV | 191 | IPQSLDSWW | P | W | F126.60 | 9 | * | | | | | | 1102 |
| 80 | 16 | ENV | 315 | IPSSWAFA | P | A | | 8 | | | | | | | 1103 |
| 100 | 20 | POL | 50 | IPWTHKVGNF | P | F | 15.0209 | 10 | | 0.0013 | 0.0001 | 0.0007 | 0.0001 | 0.0002 | 1104 |
| 100 | 20 | ENV | 379 | LPIFFCLW | P | W | 19.0007 | 8 | * | 0.0001 | 0.0001 | 0.0360 | 0.1400 | 0.0035 | 1105 |
| 100 | 20 | ENV | 379 | LPIFFCLWV | P | V | 1308.22 | 9 | * | | | | | | 1106 |
| 100 | 20 | ENV | 379 | LPIFFCLWVY | P | Y | 15.0215 | 10 | | 0.0002 | 0.0079 | 0.0002 | 0.0006 | 0.0002 | 1107 |
| 100 | 20 | ENV | 379 | LPIFFCLWVYI | P | I | 26.0558 | 11 | | 0.0002 | 0.0001 | 0.0043 | 0.0139 | 0.0021 | 1108 |
| 85 | 17 | POL | 712 | LPIHTAEL | P | L | 17.0259 | 8 | | | | | | | 1109 |
| 85 | 17 | POL | 712 | LPIHTAELL | P | L | 20.0140 | 9 | * | 0.0040 | 0.0630 | 0.0052 | 0.3100 | 0.0005 | 1110 |

TABLE X-continued

HBV B07 SUPER MOTIF (With binding information)

| Con-servancy | Fre-quency | Pro-tein | Posi-tion | Sequence | P2 | C-term | Peptide | AA | Filed | B*0702 | B*3501 | B*5101 | B*5301 | B*5401 | SEQ ID NO: |
|---|---|---|---|---|---|---|---|---|---|---|---|---|---|---|---|
| 85 | 17 | POL | 712 | LPIHTAELLA | P | A | 16.0181 | 10 | * | 0.0018 | 0.0011 | | 0.0016 | 0.3300 | 1111 |
| 85 | 17 | POL | 712 | LPIHTAELLAA | P | A | 26.0559 | 11 | | 0.0090 | 0.0027 | −0.0003 | 0.0120 | 2.7500 | 1112 |
| 80 | 16 | X | 89 | LPKVLHKRTL | P | L | | 10 | | | | | | | 1113 |
| 100 | 20 | POL | 123 | LPLDKGIKPY | P | Y | 15.0210 | 10 | * | 0.0001 | 0.0290 | 0.0002 | 0.0003 | 0.0002 | 1114 |
| 100 | 20 | POL | 123 | LPLDKGIKPYY | P | Y | 26.0560 | 11 | | −0.0002 | 0.0009 | 0.0001 | 0.0007 | 0.0001 | 1115 |
| 95 | 19 | X | 58 | LPVCAFSSA | P | A | 1147.06 | 9 | * | 0.0480 | 0.0710 | 0.0110 | 0.0009 | 19.0000 | 1116 |
| 80 | 16 | POL | 611 | LPVNRPIDW | P | W | | 9 | | | | | | | 1117 |
| 80 | 16 | POL | 611 | LPVNRPIDWKV | P | V | | 11 | | | | | | | 1118 |
| 80 | 16 | POL | 433 | MPHLLVGSSGL | P | L | | 11 | | | | | | | 1119 |
| 100 | 20 | POL | 1 | MPLSYQHF | P | F | 19.0010 | 8 | * | 0.0001 | 0.0097 | 0.0120 | 0.0370 | 0.0190 | 1120 |
| 75 | 15 | POL | 1 | MPLSYQHFRKL | P | L | | 11 | | | | | | | 1121 |
| 90 | 18 | POL | 774 | NPADDPSRGRL | P | L | 26.0561 | 11 | * | 0.0120 | 0.0001 | 0.0001 | −0.0003 | 0.0001 | 1122 |
| 95 | 19 | ENV | 9 | NPLGFFPDHQL | P | L | 26.0562 | 11 | | 0.0012 | 0.0021 | 0.0001 | 0.0028 | 0.0001 | 1123 |
| 75 | 15 | POL | 571 | NPNKTKRW | P | W | | 8 | | | | | | | 1124 |
| 75 | 15 | POL | 571 | NPNKTKRWGY | P | Y | | 10 | | | | | | | 1125 |
| 95 | 19 | NUC | 129 | PPAYRPPNA | P | A | 16.0007 | 9 | | 0.0001 | 0.0001 | 0.0001 | 0.0002 | 0.0003 | 1126 |
| 95 | 19 | NUC | 129 | PPAYRPPNAPI | P | I | 26.0561 | 11 | | 0.0003 | 0.0001 | 0.0001 | −0.0003 | 0.0001 | 1127 |
| 85 | 17 | ENV | 58 | PPHGGLLGW | P | W | 20.0141 | 9 | | 0.0001 | 0.0002 | 0.0001 | 0.0003 | 0.0002 | 1128 |
| 100 | 20 | NUC | 134 | PPNAPILSTL | P | L | 15.0211 | 10 | | 0.0001 | 0.0001 | 0.0035 | 0.0001 | 0.0002 | 1129 |
| 80 | 16 | POL | 615 | RPIDWKVCQRI | P | I | | 11 | | | | | | | 1130 |
| 100 | 20 | NUC | 133 | RPPNAPIL | P | L | 19.0009 | 8 | * | 0.0076 | 0.0001 | 0.0280 | 0.0002 | 0.0002 | 1131 |
| 100 | 20 | NUC | 133 | RPPNAPILSTL | P | L | 26.0564 | 11 | * | 0.1300 | 0.0001 | 0.0018 | −0.0003 | 0.0001 | 1132 |
| 100 | 20 | NUC | 44 | SPEHCSPHHTA | P | A | 26.0565 | 11 | | −0.0002 | 0.0001 | 0.0001 | 0.0001 | 0.0011 | 1133 |
| 95 | 19 | POL | 511 | SPFLLAQF | P | F | 19.0012 | 8 | * | 0.5500 | 0.0009 | 0.0180 | 0.0009 | 0.0093 | 1134 |
| 95 | 19 | POL | 511 | SPFLLAQFTSA | P | A | 26.0566 | 11 | * | 0.0820 | 0.0001 | 0.0001 | −0.0003 | 12.0500 | 1135 |
| 100 | 20 | NUC | 49 | SPHHTALRQA | P | A | 16.0178 | 10 | | 0.0012 | 0.0001 | | 0.0002 | 0.0035 | 1136 |
| 100 | 20 | NUC | 49 | SPHHTALRQAI | P | I | 26.0567 | 11 | * | 0.5800 | 0.0001 | 0.0004 | 0.0005 | 0.0002 | 1137 |
| 85 | 17 | ENV | 67 | SPQAGIL | P | L | | 8 | | | | | | | 1138 |
| 85 | 17 | POL | 808 | SPSVPSHL | P | L | | 8 | | | | | | | 1139 |
| 75 | 15 | ENV | 350 | SPTVWLSV | P | V | | 8 | | | | | | | 1140 |
| 75 | 15 | ENV | 350 | SPTVWLSVI | P | I | 1308.16 | 9 | | | | | | | 1141 |
| 75 | 15 | ENV | 350 | SPTVWLSVIW | P | W | 1308.17 | 10 | | | | | | | 1142 |
| 75 | 15 | ENV | 350 | SPTVWLSVIWM | P | M | | 11 | | | | | | | 1143 |
| 95 | 19 | POL | 659 | SPTYKAFL | P | L | 19.0015 | 8 | * | 0.3900 | 0.0001 | 0.0019 | 0.0002 | 0.0002 | 1144 |
| 90 | 18 | POL | 354 | TPARVTGGV | P | V | 1147.07 | 9 | * | 0.0078 | 0.0001 | 0.0013 | 0.0001 | 0.0015 | 1145 |
| 90 | 18 | POL | 354 | TPARVTGGVF | P | F | 1147.04 | 10 | * | 0.3200 | 0.1000 | 0.0001 | 0.0099 | 0.0006 | 1146 |
| 90 | 18 | POL | 354 | TPARVTGGVFL | P | L | 26.0568 | 11 | * | 0.0950 | 0.0001 | 0.0001 | 0.0005 | 0.0005 | 1147 |
| 95 | 19 | NUC | 128 | TPPAYRPPNA | P | A | 16.0179 | 10 | * | 0.0001 | 0.0001 | | 0.0002 | 0.0100 | 1148 |
| 75 | 15 | ENV | 57 | TPPHGGLL | P | L | | 8 | | | | | | | 1149 |
| 75 | 15 | ENV | 57 | TPPHGGLLGW | P | W | 1308.04 | 10 | | | | | | | 1150 |
| 80 | 16 | POL | 691 | TPTGWGLA | P | A | | 8 | | | | | | | 1151 |
| 75 | 15 | POL | 691 | TPTGWGLAI | P | I | | 9 | | | | | | | 1152 |
| 95 | 19 | ENV | 340 | VPFVQWFV | P | V | 19.0006 | 8 | * | 0.0010 | 0.0001 | 19.0000 | 0.0002 | 0.1100 | 1153 |
| 95 | 19 | ENV | 340 | VPFVQWFVGL | P | L | 15.0213 | 10 | | 0.0011 | 0.0001 | 0.0100 | 0.0001 | 0.0025 | 1154 |
| 95 | 19 | POL | 398 | VPNLQSLTNL | P | L | 15.0216 | 10 | | 0.0006 | 0.0001 | 0.0004 | 0.0001 | 0.0002 | 1155 |
| 95 | 19 | POL | 398 | VPNLQSLTNLL | P | L | 26.0569 | 11 | | 0.0004 | 0.0001 | 0.0001 | −0.0003 | 0.0002 | 1156 |
| 90 | 18 | POL | 769 | VPSALNPA | P | A | 19.0016 | 8 | * | 0.0011 | 0.0001 | 0.0070 | 0.0002 | 1.0000 | 1157 |
| 95 | 19 | POL | 393 | WPKFAVPNL | P | L | 15.0035 | 9 | | 0.0054 | 0.0002 | 0.0015 | 0.0001 | 0.0015 | 1158 |
| 95 | 19 | POL | 640 | YPALMPLY | P | Y | 19.0014 | 8 | * | 0.0004 | 0.2600 | 0.4100 | 0.0450 | 0.0056 | 1159 |
| 95 | 19 | POL | 640 | YPALMPLYA | P | A | 1147.08 | 9 | * | 0.0180 | 0.0480 | 0.0340 | 0.0140 | 16.0000 | 1160 |
| 95 | 19 | POL | 640 | YPALMPLYACI | P | I | 26.0570 | 11 | * | 0.0040 | 0.0001 | 0.0470 | 0.0320 | 0.0700 | 1161 |

96

TABLE XI

HBV B27 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 95 | 19 | X | 51 | AHLSLRGL | XHXXXXXL | B27s | | | 1162 |
| HBV | 85 | 17 | POL | 546 | AKSVQHLESL | XKXXXXXXXL | B27s | | | 1163 |
| HBV | 90 | 18 | POL | 356 | ARVTGGVF | XRXXXXXF | B27s | | | 1164 |
| HBV | 90 | 18 | POL | 356 | ARVTGGVFL | XRXXXXXXL | B27s | | | 1165 |
| HBV | 95 | 19 | X | 48 | DHGAHLSL | XHXXXXXL | B27s | | | 1166 |
| HBV | 95 | 19 | X | 48 | DHGAHLSLRGL | XHXXXXXXXXL | B27s | | | 1167 |
| HBV | 90 | 18 | ENV | 16 | DHQLDPAF | XHXXXXXF | B27s | | | 1168 |
| HBV | 100 | 20 | POL | 126 | DKGIKPYY | XKXXXXXY | B27s | | | 1169 |
| HBV | 100 | 20 | NUC | 46 | EHCSPHHTAL | XHXXXXXXXL | B27s | | | 1170 |
| HBV | 90 | 18 | NUC | 103 | FHISCLTF | XHXXXXXF | B27s | | | 1171 |

TABLE XI-continued

HBV B27 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 80 | 16 | POL | 501 | FRKIPMGVGL | XRXXXXXXXL | B27s | | 1172 |
| HBV | 80 | 16 | POL | 608 | FRKLPVNRPI | XRXXXXXXXI | B27s | | 1173 |
| HBV | 75 | 15 | NUC | 140 | GRETVLEY | XRXXXXXY | B27s | | 1174 |
| HBV | 75 | 15 | NUC | 140 | GRETVLEYL | XRXXXXXXL | B27s | | 1175 |
| HBV | 100 | 20 | NUC | 51 | HHTALRQAI | XHXXXXXXI | B27s | | 1176 |
| HBV | 95 | 19 | NUC | 51 | HHTALRQAIL | XHXXXXXXXL | B27s | | 1177 |
| HBV | 95 | 19 | POL | 54 | HKVGNFTGL | XKXXXXXXL | B27s | 17.0358 | 1178 |
| HBV | 95 | 19 | POL | 54 | HKVGNFTGLY | XKXXXXXXXY | B27s | | 1179 |
| HBV | 75 | 15 | POL | 568 | IHLNPNKTKRW | XHXXXXXXXXW | B27s | | 1180 |
| HBV | 85 | 17 | POL | 714 | IHTAELLAACF | XHXXXXXXXXF | B27s | | 1181 |
| HBV | 85 | 17 | POL | 576 | KRWGYSLNF | XRXXXXXXF | B27s | | 1182 |
| HBV | 85 | 17 | POL | 576 | KRWGYSLNFM | XRXXXXXXXM | B27s | | 1183 |
| HBV | 90 | 18 | X | 93 | LHKRTLGL | XHXXXXXL | B27s | | 1184 |
| HBV | 95 | 19 | POL | 490 | LHLYSHPI | XHXXXXXI | B27s | | 1185 |
| HBV | 80 | 16 | POL | 490 | LHLYSHPII | XHXXXXXXI | B27s | | 1186 |
| HBV | 80 | 16 | POL | 490 | LHLYSHPIIL | XHXXXXXXXL | B27s | | 1187 |
| HBV | 100 | 20 | POL | 428 | LHPAAMPHL | XHXXXXXXL | B27s | | 1188 |
| HBV | 100 | 20 | POL | 428 | LHPAAMPHLL | XHXXXXXXXL | B27s | | 1189 |
| HBV | 100 | 20 | POL | 148 | LHTLWKAGI | XHXXXXXXI | B27s | | 1190 |
| HBV | 100 | 20 | POL | 148 | LHTLWKAGIL | XHXXXXXXXL | B27s | | 1191 |
| HBV | 100 | 20 | POL | 148 | LHTLWKAGILY | XHXXXXXXXXY | B27s | | 1192 |
| HBV | 75 | 15 | POL | 107 | LKLIMPARF | XKXXXXXXF | B27s | | 1193 |
| HBV | 75 | 15 | POL | 107 | LKLIMPARFY | XKXXXXXXXY | B27s | | 1194 |
| HBV | 95 | 19 | POL | 55 | LRGLPVCAF | XRXXXXXXF | B27s | | 1195 |
| HBV | 80 | 16 | NUC | 761 | LRGTSFVY | XRXXXXXY | B27s | | 1196 |
| HBV | 95 | 19 | NUC | 55 | LRQAILCW | XRXXXXXW | B27s | | 1197 |
| HBV | 90 | 18 | ENV | 55 | LRQAILCWGEL | XRXXXXXXXXL | B27s | | 1198 |
| HBV | 95 | 19 | ENV | 240 | LRRFIFL | XRXXXXL | B27s | | 1199 |
| HBV | 75 | 15 | ENV | 240 | LRRFIFLF | XRXXXXXXF | B27s | | 1200 |
| HBV | 75 | 15 | ENV | 240 | LRRFIIFLFI | XRXXXXXXXI | B27s | | 1201 |
| HBV | 75 | 15 | POL | 240 | LRRFIIFLFIL | XRXXXXXXXXL | B27s | | 1202 |
| HBV | 75 | 15 | POL | 573 | NKTKRWGY | XKXXXXXY | B27s | | 1203 |
| HBV | 75 | 15 | POL | 573 | NKTKRWGYSL | XKXXXXXXXL | B27s | | 1204 |
| HBV | 85 | 17 | POL | 34 | NRRVAEDL | XRXXXXXL | B27s | | 1205 |
| HBV | 85 | 17 | POL | 34 | NRRVAEDLNL | XRXXXXXXXL | B27s | | 1206 |
| HBV | 95 | 19 | POL | 531 | PHCLAFSY | XHXXXXXY | B27s | | 1207 |
| HBV | 95 | 19 | POL | 531 | PHCLAFSYM | XHXXXXXXM | B27s | | 1208 |
| HBV | 85 | 17 | ENV | 59 | PHGGLLGW | XHXXXXXW | B27s | | 1209 |
| HBV | 100 | 20 | NUC | 50 | PHHTALRQAI | XHXXXXXXXI | B27s | | 1210 |
| HBV | 95 | 19 | NUC | 50 | PHHTALRQAIL | XHXXXXXXXXL | B27s | | 1211 |
| HBV | 80 | 16 | POL | 434 | PHLLVGSSGL | XHXXXXXXXL | B27s | | 1212 |
| HBV | 95 | 19 | POL | 394 | PKFAVPNL | XKXXXXXL | B27s | | 1213 |
| HBV | 95 | 19 | POL | 394 | PKFAVPNLQSL | XKXXXXXXXXL | B27s | | 1214 |
| HBV | 85 | 17 | X | 90 | PKVLHKRTL | XKXXXXXXL | B27s | | 1215 |
| HBV | 85 | 17 | X | 90 | PKVLHKRTLGL | XKXXXXXXXXL | B27s | | 1216 |
| HBV | 75 | 15 | POL | 6 | QHFRKLLL | XHXXXXXL | B27s | | 1217 |
| HBV | 75 | 15 | POL | 6 | QHFRNLLLL | XHXXXXXXL | B27s | | 1218 |
| HBV | 90 | 18 | POL | 623 | QRIVGLLGF | XRXXXXXXF | B27s | | 1219 |
| HBV | 100 | 20 | POL | 145 | RHYLHTLW | XHXXXXXW | B27s | | 1220 |
| HBV | 80 | 16 | POL | 502 | RKIPMGVGL | XKXXXXXXL | B27s | | 1221 |
| HBV | 80 | 16 | POL | 609 | RKLPVNRPI | XKXXXXXXI | B27s | | 1222 |
| HBV | 80 | 16 | POL | 609 | RKLPVNRPIDW | XKXXXXXXXXW | B27s | | 1223 |
| HBV | 85 | 17 | POL | 744 | RKYTSFPW | XKXXXXXW | B27s | | 1224 |
| HBV | 85 | 17 | POL | 744 | RKYTSFPWL | XKXXXXXXL | B27s | | 1225 |
| HBV | 85 | 17 | POL | 744 | RKYTSRPWLL | XKXXXXXXXL | B27s | | 1226 |
| HBV | 95 | 19 | POL | 527 | RRAFPHCL | XRXXXXXL | B27s | | 1227 |
| HBV | 95 | 19 | POL | 527 | RRAFPHCLAF | XRXXXXXXXF | B27s | | 1228 |
| HBV | 75 | 15 | ENV | 241 | RRFIIFLF | XRXXXXXXF | B27s | | 1229 |
| HBV | 75 | 15 | ENV | 241 | RRFILFLFI | XRXXXXXXI | B27s | | 1230 |
| HBV | 75 | 15 | ENV | 241 | RRFIIFLFIL | XRXXXXXXXL | B27s | | 1231 |
| HBV | 75 | 15 | ENV | 241 | RRFIIFLFILL | XRXXXXXXXXL | B27s | | 1232 |
| HBV | 75 | 15 | POL | 105 | RRLKLIMPARF | XRXXXXXXXXF | B27s | | 1233 |
| HBV | 90 | 18 | POL | 35 | RRVAEDLNL | XRXXXXXXL | B27s | | 1234 |
| HBV | 80 | 16 | POL | 494 | SHPILGF | XHXXXXXF | B27s | | 1235 |
| HBV | 80 | 16 | POL | 494 | SHPILGFRKI | XHXXXXXXXI | B27s | | 1236 |
| HBV | 90 | 18 | NUC | 20 | SKLCLGWL | XKXXXXXL | B27s | | 1237 |
| HBV | 85 | 17 | NUC | 20 | SKLCLGWLW | XKXXXXXXW | B27s | | 1238 |
| HBV | 85 | 17 | NUC | 20 | SKLCLGWLWGM | XKXXXXXXXXM | B27s | | 1239 |
| HBV | 85 | 17 | POL | 743 | SRKYTSFPW | XRXXXXXXW | B27s | | 1240 |
| HBV | 85 | 17 | POL | 743 | SRKYTSFPWL | XRXXXXXXXL | B27s | | 1241 |
| HBV | 85 | 17 | POL | 743 | SRKYTSFPWLL | XRXXXXXXXXL | B27s | | 1242 |
| HBV | 95 | 19 | POL | 375 | SRLWDFSQF | XRXXXXXXF | B27s | | 1243 |
| HBV | 80 | 16 | POL | 472 | SRNLYVSL | XRXXXXXL | B27s | 17.0123 | 1244 |
| HBV | 95 | 19 | POL | 53 | THKVGNFTGL | XHXXXXXXXL | B27s | | 1245 |

TABLE XI-continued

HBV B27 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 95 | 19 | POL | 53 | THKVGNFTGLY | XHXXXXXXXXY | B27s | | 1246 |
| HBV | 95 | 19 | POL | 575 | TKRWGYSL | XKXXXXXL | B27s | | 1247 |
| HBV | 85 | 17 | POL | 575 | TKRWGYSLNF | XKXXXXXXXF | B27s | | 1248 |
| HBV | 85 | 17 | POL | 575 | TKRWGYSLNFM | XKXXXXXXXXM | B27s | | 1249 |
| HBV | 100 | 20 | POL | 120 | TKYLPLDKGI | XKXXXXXXXI | B27s | | 1250 |
| HBV | 100 | 20 | POL | 144 | TRHYLHTL | XRXXXXXL | B27s | | 1251 |
| HBV | 100 | 20 | POL | 144 | TRHYLHTLW | XRXXXXXXW | B27s | | 1252 |
| HBV | 80 | 16 | ENV | 186 | TRILTIPQSL | XRXXXXXXXL | B27s | | 1253 |
| HBV | 80 | 16 | POL | 819 | VHFASPLHVAW | XHXXXXXXXXW | B27s | | 1254 |
| HBV | 80 | 16 | ENV | 331 | VRFSWLSL | XRXXXXXL | B27s | | 1255 |
| HBV | 80 | 16 | ENV | 331 | VRFSWLSLL | XRXXXXXXL | B27s | | 1256 |
| HBV | 95 | 19 | POL | 526 | VRRAFPHCL | XRXXXXXXL | B27s | | 1257 |
| HBV | 95 | 19 | POL | 526 | VRRAFPHCLAF | XRXXXXXXXXF | B27s | | 1258 |
| HBV | 85 | 17 | POL | 619 | WKVCQRIVGL | XKXXXXXXXL | B27s | | 1259 |
| HBV | 85 | 17 | POL | 619 | WKVCQRIVGLL | XKXXXXXXXXL | B27s | | 1260 |
| HBV | 100 | 20 | NUC | 132 | YRPPNAPI | XRXXXXXI | B27s | | 1261 |
| HBV | 100 | 20 | NUC | 132 | YRPPNAPIL | XRXXXXXXL | B27s | 17.0356 | 1262 |
| HBV | 95 | 19 | ENV | 235 | YRWMCLRRF | XRXXXXXXF | B27s | | 1263 |
| HBV | 95 | 19 | ENV | 235 | YRWMCLRRFI | XRXXXXXXXI | B27s | | 1264 |
| HBV | 95 | 19 | ENV | 235 | YRWMCLRRFII 104 | XRXXXXXXXXI | B27s | | 1265 |

TABLE XII

HBV B44 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 95 | 19 | POL | 688 | ADATPTGW | XDXXXXXW | B44 | | 1266 |
| HBV | 95 | 19 | POL | 688 | ADATPTGWGL | XDXXXXXXXL | B44 | | 1267 |
| HBV | 80 | 16 | POL | 688 | ADATPTGWGL | XDXXXXXXXA | B44 | | 1268 |
| HBV | 90 | 18 | POL | 776 | ADDPSRGRL | XDXXXXXXL | B44 | | 1269 |
| HBV | 90 | 18 | POL | 776 | ADDPSRGRLGL | XDXXXXXXXXL | B44 | | 1270 |
| HBV | 95 | 19 | POL | 38 | AEDLNLGNL | XEXXXXXXL | B44 | 17.0357 | 1271 |
| HBV | 95 | 19 | POL | 38 | AEDLNLGNLNV | XEXXXXXXXXV | B44 | | 1272 |
| HBV | 85 | 17 | POL | 717 | AELLAACF | XEXXXXXF | B44 | | 1273 |
| HBV | 85 | 17 | POL | 717 | AELLAACFA | XEXXXXXXA | B44 | | 1274 |
| HBV | 90 | 18 | POL | 777 | DDPSRGRL | XDXXXXXL | B44 | 17.0010 | 1275 |
| HBV | 90 | 18 | POL | 777 | DDPSRGRLGL | XDXXXXXXXL | B44 | 17.0418 | 1276 |
| HBV | 90 | 18 | POL | 540 | DDVVLGAKSV | XDXXXXXXXV | B44 | | 1277 |
| HBV | 75 | 15 | POL | 16 | DEAGPLEEEL | XEXXXXXXXL | B44 | | 1278 |
| HBV | 95 | 19 | POL | 39 | EDUNLGNL | XDXXXXXL | B44 | | 1279 |
| HBV | 95 | 19 | POL | 39 | EDLNLGNLNV | XDXXXXXXXV | B44 | | 1280 |
| HBV | 90 | 18 | POL | 22 | EEELPRLA | XEXXXXXA | B44 | | 1281 |
| HBV | 80 | 16 | X | 121 | EELGEEIRL | XEXXXXXXL | B44 | | 1282 |
| HBV | 90 | 18 | NUC | 32 | IDPYKEFGA | XDXXXXXXA | B44 | | 1283 |
| HBV | 85 | 17 | POL | 617 | IDWKVCORI | XDXXXXXXI | B44 | | 1284 |
| HBV | 85 | 17 | POL | 617 | IDWKVCORIV | XDXXXXXXXV | B44 | | 1285 |
| HBV | 100 | 20 | POL | 125 | LDKGIKPY | XDXXXXXY | B44 | | 1286 |
| HBV | 100 | 20 | POL | 125 | LDKGIKPYY | XDXXXXXXY | B44 | | 1287 |
| HBV | 80 | 16 | X | 9 | LDPARDVL | XDXXXXXL | B44 | 17.0012 | 1288 |
| HBV | 80 | 16 | X | 9 | LDPARDVLCL | XDXXXXXXXL | B44 | 17.0419 | 1289 |
| HBV | 95 | 19 | ENV | 195 | LDSWWTSL | XDXXXXXL | B44 | | 1290 |
| HBV | 95 | 19 | ENV | 195 | LDSWWTSLNF | XDXXXXXXXF | B44 | | 1291 |
| HBV | 90 | 18 | ENV | 195 | LDSWWTSLNFL | XDXXXXXXXXL | B44 | | 1292 |
| HBV | 85 | 17 | NUC | 31 | LDTASALY | XDXXXXXY | B44 | | 1293 |
| HBV | 80 | 16 | NUC | 31 | LDTASALYREA | XDXXXXXXXXA | B44 | | 1294 |
| HBV | 95 | 19 | POL | 417 | LDVSAAFY | XDXXXXXY | B44 | | 1295 |
| HBV | 90 | 18 | ENV | 261 | LDYQGMLPV | XDXXXXXXV | B44 | | 1296 |
| HBV | 95 | 19 | POL | 21 | LEEELPRL | XEXXXXXL | B44 | | 1297 |
| HBV | 90 | 18 | POL | 21 | LEEEPRLA | XEXXXXXA | B44 | | 1298 |
| HBV | 90 | 18 | POL | 539 | MDDVVLGA | XDXXXXXA | B44 | | 1299 |
| HBV | 90 | 18 | POL | 539 | MDDVVLGAKSV | XDXXXXXXXXV | B44 | | 1300 |
| HBV | 90 | 18 | NUC | 30 | MDIDPYKEF | XDXXXXXXF | B44 | | 1301 |
| HBV | 90 | 18 | NUC | 30 | MDIDPYKEFGA | XDXXXXXXXXA | B44 | | 1302 |
| HBV | 95 | 19 | ENV | 15 | PDHQLDPA | XDXXXXXA | B44 | | 1303 |
| HBV | 90 | 18 | ENV | 15 | PDHQLDPAF | XDXXXXXXF | B44 | | 1304 |
| HBV | 100 | 20 | NUC | 45 | PEHCSPHHTA | XEXXXXXXXA | B44 | | 1305 |
| HBV | 100 | 20 | NUC | 45 | PEHCSPHHTAL | XEXXXXXXXXL | B44 | | 1306 |
| HBV | 85 | 17 | NUC | 28 | RDLLDTASA | XDXXXXXXA | B44 | | 1307 |

TABLE XII-continued
HBV B44 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 85 | 17 | NUC | 28 | RDLLDTASAL | XDXXXXXXXL | B44 | | 1308 |
| HBV | 85 | 17 | NUC | 28 | RDLLDTASALY | XDXXXXXXXXY | B44 | | 1309 |
| HBV | 95 | 19 | X | 13 | RDVCLRPV | XDXXXXXXV | B44 | | 1310 |
| HBV | 95 | 19 | X | 13 | RDVLCLRPVGA | XDXXXXXXXXXA | B44 | | 1311 |
| HBV | 75 | 15 | NUC | 141 | RETVLEYL | XEXXXXXL | B44 | | 1312 |
| HBV | 75 | 15 | NUC | 141 | RETVLEYLV | XEXXXXXXV | B44 | | 1313 |
| HBV | 90 | 18 | POL | 736 | TDNSVVLSRKY | XDXXXXXXXXY | B44 | | 1314 |
| HBV | 95 | 19 | NUC | 42 | VELLSFLPSDF | XEXXXXXXXXF | B44 | | 1315 |
| HBV | 80 | 16 | X | 120 | WEELGEEI | XEXXXXXI | B44 | | 1316 |
| HBV | 80 | 16 | X | 120 | WEELGEEIRL | XEXXXXXXXL | B44 | | 1317 |

TABLE XIII
HBV B58 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 55 | 17 | POL | 431 | AAMPHLLV | XAXXXXXV | B58 | | | 1318 |
| HBV | 95 | 19 | POL | 632 | AAPFTQCGY | XAXXXXXXY | B58 | | | 1319 |
| HBV | 85 | 17 | NUC | 34 | ASALYREAL | XSXXXXXXL | B58 | | | 1320 |
| HBV | 100 | 20 | POL | 166 | ASFCGSPY | XSXXXXXY | B58 | 26.0026 | * | 1321 |
| HBV | 100 | 20 | POL | 168 | ASFQGSPYSW | XSXXXXXXXW | B58 | | | 1322 |
| HBV | 90 | 18 | NUC | 19 | ASKLCLGW | XSXXXXXW | B58 | | | 1323 |
| HBV | 90 | 18 | NUC | 19 | ASKLCLGWL | XSXXXXXXL | B58 | | | 1324 |
| HBV | 85 | 17 | NUC | 19 | ASKLCLGWLW | XSXXXXXXXW | B58 | | | 1325 |
| HBV | 80 | 16 | POL | 822 | ASPLHVAW | XSXXXXXW | B58 | | | 1326 |
| HBV | 80 | 16 | ENV | 329 | ASVRFSWL | XSXXXXXL | B58 | | | 1327 |
| HBV | 80 | 16 | ENV | 329 | ASVRFSWLSL | XSXXXXXXXL | B58 | | | 1328 |
| HBV | 80 | 16 | ENV | 329 | ASVRFSWLSLL | XSXXXXXXXXL | B58 | | | 1329 |
| HBV | 95 | 19 | POL | 690 | ATPTGWGL | XTXXXXXL | B58 | | | 1330 |
| HBV | 75 | 15 | POL | 690 | ATPTGWGLAI | XTXXXXXXXI | B58 | | | 1331 |
| HBV | 95 | 19 | X | 61 | CAFSSAGPCAL | XXXXXXXXXXL | B58 | | | 1332 |
| HBV | 100 | 20 | NUC | 48 | CSPHHTAL | XSXXXXXL | B58 | | | 1333 |
| HRV | 80 | 16 | POL | 471 | CSRNLYVSL | XSXXXXXXL | B58 | | | 1334 |
| HBV | 95 | 19 | POL | 523 | GSVVRRAF | XSXXXXXF | B58 | | | 1335 |
| HBV | 100 | 20 | ENV | 310 | CTCIPIPSSW | XTXXXXXXXW | B58 | | | 1336 |
| HBV | 95 | 19 | POL | 689 | DATPTGWGL | XAXXXXXXL | B58 | 5.0027 | | 1337 |
| HBV | 75 | 15 | POL | 689 | DATPTGWGLAI | XAXXXXXXXXI | B58 | | | 1338 |
| HBV | 95 | 19 | ENV | 196 | DSWWSLNF | XSXXXXXF | B58 | 20.0120 | | 1339 |
| HBV | 90 | 18 | ENV | 196 | DSWWTSLNFL | XSXXXXXXXL | B58 | | | 1340 |
| HBV | 80 | 16 | NUC | 32 | DTASALYREA | XTXXXXXXXA | B58 | | | 1341 |
| HBV | 80 | 18 | NUC | 32 | DTASALYREAL | XTXXXXXXXXL | B58 | | | 1342 |
| HBV | 100 | 20 | POL | 17 | EAGPLEEEL | XAXXXXXXL | B58 | 5.0028 | | 1343 |
| HBV | 95 | 19 | POL | 374 | ESRLWDF | XSXXXXF | B58 | | | 1344 |
| HBV | 95 | 19 | POL | 374 | ESRLWDRSQF | XSXXXXXXXXF | B58 | | | 1345 |
| HBV | 75 | 15 | NUC | 142 | ETVLEYLV | XTXXXXXV | B58 | | | 1346 |
| HBV | 95 | 19 | POL | 631 | FAAPFTQCGY | XAXXXXXXXY | B58 | 20.0254 | * | 1347 |
| HBV | 95 | 19 | POL | 687 | FADATPTGW | XAXXXXXXW | B58 | | | 1348 |
| HBV | 95 | 19 | POL | 687 | FADATPTGWGL | XAXXXXXXXXL | B58 | | | 1349 |
| HBV | 80 | 16 | POL | 821 | FASPLHVAW | XAXXXXXXW | B58 | | | 1350 |
| HBV | 95 | 19 | POL | 396 | FAVPNLQSL | XAXXXXXXL | B58 | 5.0029 | * | 1351 |
| HBV | 95 | 19 | POL | 658 | FSPTYKAF | XSXXXXXF | B58 | | | 1352 |
| HBV | 95 | 19 | POL | 658 | FSPTYKAFL | XSXXXXXXL | B58 | | | 1353 |
| HBV | 95 | 19 | X | 63 | FSSAGPCAL | XSXXXXXXL | B58 | | | 1354 |
| HBV | 90 | 18 | X | 63 | FSSAGPCALRF | XSXXXXXXXXF | B58 | | | 1355 |
| HBV | 100 | 20 | ENV | 333 | FSWLSLLV | XSXXXXXV | B58 | | | 1356 |
| HBV | 100 | 20 | ENV | 333 | FSWLSLLVPF | XSXXXXXXXF | B58 | 20.0263 | | 1357 |
| HBV | 100 | 20 | ENV | 333 | FSWLSLLVPFV | XSXXXXXXXXV | B58 | | | 1358 |
| HBV | 90 | 18 | POL | 536 | FSYMDDW | XSXXXXXV | B58 | 17.0257 | | 1359 |
| HBV | 90 | 18 | POL | 536 | FSYMDDWL | XSXXXXXXL | B58 | | | 1360 |
| HBV | 95 | 19 | POL | 656 | FTFSPTYKAF | XTXXXXXXXF | B58 | 20.0262 | | 1361 |
| HBV | 95 | 19 | POL | 656 | FTFSPTYKAFL | XTXXXXXXXXL | B58 | | | 1362 |
| HBV | 90 | 18 | POL | 59 | FTQLYSSTV | XTXXXXXXV | B58 | 20.0118 | | 1363 |
| HBV | 95 | 19 | POL | 635 | FTQCGYPAL | XTXXXXXXL | B58 | 5.0031 | | 1364 |
| HBV | 190 | 38 | POL | 635 | FTQCGYPALM | XTXXXXXXXM | B58 | 5.0085 | | 1365 |
| HBV | 95 | 19 | POL | 518 | FTSAICSV | XTXXXXXV | B58 | | | 1366 |
| HBV | 95 | 19 | POL | 518 | FTSAICSVV | XTXXXXXXV | B58 | 5.0032 | | 1367 |
| HBV | 95 | 19 | X | 50 | GAHLSLRGL | XAXXXXXXL | B58 | 5.0040 | | 1368 |
| HBV | 90 | 18 | X | 50 | GAHLSLRGLPV | XAXXXXXXXXV | B58 | | | 1369 |
| HBV | 85 | 17 | POL | 545 | GAKSVQHL | XAXXXXXL | B58 | | | 1370 |

TABLE XIII-continued

HBV B58 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 85 | 17 | POL | 545 | GAKSVQHLESL | XAXXXXXXXXL | B58 | | | 1371 |
| HBV | 75 | 15 | ENV | 134 | GSSSGTVNPV | XSXXXXXXXV | B58 | | | 1372 |
| HBV | 90 | 18 | POL | 735 | GTDNSVVL | XTXXXXXL | B58 | | | 1373 |
| HBV | 75 | 15 | ENV | 13 | GTNLSVPNPL | XTXAXXXXXL | B58 | | | 1374 |
| HBV | 80 | 16 | POL | 763 | GTSFVYVPSAL | XTXXXXXXXXL | B58 | | | 1375 |
| HBV | 55 | 17 | POL | 715 | HTAELLAACF | XTXXXXXXF | B58 | | | 1376 |
| HBV | 100 | 20 | NUC | 52 | HTALRQAI | XTXXXXXI | B58 | | | 1377 |
| HBV | 95 | 19 | NUC | 52 | HTALRQAIL | XTXXXXXXL | B58 | 5.0021 | | 1378 |
| HBV | 95 | 19 | NUC | 52 | HTALRQAILCW | XTXXXXXXXXW | B58 | | | 1379 |
| HBV | 100 | 20 | POL | 149 | HTLWKAGI | XTXXXXXI | B58 | | | 1380 |
| HBV | 100 | 20 | POL | 149 | HTLWKAGIL | XTXXXXXXL | B58 | 5.0033 | | 1381 |
| HBV | 100 | 20 | POL | 149 | HTLWKAGILY | XTXXXXXXXY | B58 | 1.0542 | * | 1382 |
| HBV | 90 | 18 | NUC | 105 | ISCLTFGRETV | XSXXXXXXXXV | B58 | | | 1363 |
| HBV | 85 | 17 | POL | 547 | KSVQHLESL | XSXXXXXXL | B58 | | | 1384 |
| HBV | 95 | 19 | POL | 574 | KTKRWGYSL | XTXXXXXXL | B58 | 5.0034 | | 1385 |
| HBV | 85 | 17 | POL | 574 | KTKRWGYSLNF | XTXXXXXXXXF | B58 | | | 1386 |
| HBV | 90 | 18 | POL | 534 | LAFSYMDDV | XAXXXXXXV | B58 | 20.0119 | | 1387 |
| HBV | 90 | 18 | POL | 534 | LAFSYMDDVV | XAXXXXXXXV | B58 | 20.0257 | | 1388 |
| HBV | 90 | 18 | POL | 534 | LAFSYMDDVVL | XAXXXXXXXXL | B58 | | | 1389 |
| HBV | 95 | 19 | POL | 515 | LAQFTSAI | XAXXXXXI | B58 | | | 1390 |
| HBV | 95 | 19 | POL | 515 | LAQFTSAICSV | XAXXXXXXXXV | B58 | | | 1391 |
| HBV | 95 | 19 | NUC | 45 | LSFLPSDF | XSXXXXXF | B58 | | | 1392 |
| HBV | 95 | 19 | NUC | 45 | LSFLPSDFF | XSXXXXXXF | B58 | 20.0123 | | 1393 |
| HBV | 95 | 19 | POL | 415 | LSLDVSAAF | XSXXXXXXF | B58 | | | 1394 |
| HBV | 95 | 19 | POL | 415 | LSLDVSAAFY | XSXXXXXXXY | B58 | 2.0239 | * | 1395 |
| HBV | 100 | 20 | ENV | 336 | LSLLVPFV | XSXXXXXV | B58 | | | 1396 |
| HBV | 100 | 20 | ENV | 336 | LSLLVPFVQW | XSXXXXXXXW | B58 | | | 1397 |
| HBV | 100 | 20 | ENV | 336 | LSLLVPFVQWF | XSXXXXXXXXF | B58 | | | 1398 |
| HBV | 95 | 19 | X | 53 | LSLRGLPV | XSXXXXXV | B58 | | | 1399 |
| HBV | 95 | 19 | X | 53 | LSLRGLPVCAF | XSXXXXXXXXF | B58 | | | 1400 |
| HBV | 95 | 19 | POL | 510 | LSPFLLAQF | XSXXXXXXF | B58 | | | 1401 |
| HBV | 75 | 15 | ENV | 349 | LSPTVWLSV | XSXXXXXXV | B58 | | | 1402 |
| HBV | 75 | 15 | ENV | 349 | LSPTVWLSVI | XSXXXXXXXI | B58 | | | 1403 |
| HBV | 75 | 15 | ENV | 349 | LSPTWLSVIW | XSXXXXXXXXW | B58 | | | 1404 |
| HBV | 85 | 17 | POL | 742 | LSRKYTSF | XSXXXXXF | B58 | | | 1405 |
| HBV | 85 | 17 | POL | 742 | LSRKYTSFPW | XSXXXXXXXW | B58 | | | 1406 |
| HBV | 85 | 17 | POL | 742 | LSRKYTSFPWL | XSXXXXXXXXL | B58 | | | 1407 |
| HBV | 90 | 18 | POL | 408 | LSSNLSWL | XSXXXXXL | B58 | | | 1408 |
| HBV | 90 | 18 | POL | 408 | LSSNLSWLSL | XSXXXXXXXL | B58 | | | 1409 |
| HBV | 100 | 20 | NUC | 140 | LSTLPETTV | XSXXXXXXV | B58 | | | 1410 |
| HBV | 100 | 20 | NUC | 140 | LSTLPETTVV | XSXXXXXXXV | B58 | | | 1411 |
| HBV | 75 | 15 | ENV | 16 | LSVPNPLGF | XSXXXXXXF | B58 | | | 1412 |
| HBV | 100 | 20 | POL | 412 | LSWLSLDV | XSXXXXXV | B58 | | | 1413 |
| HBV | 75 | 15 | POL | 3 | LSYQHFRKL | XSXXXXXXL | B58 | | | 1414 |
| HBV | 75 | 15 | POL | 3 | LSYQHFRKLL | XSXXXXXXXL | B58 | | | 1415 |
| HBV | 75 | 15 | POL | 3 | LSYQHFRKLLL | XSXXXXXXXXL | B58 | | | 1416 |
| HBV | 95 | 19 | NUC | 108 | LTFGRETV | XTXXXXXV | B58 | | | 1417 |
| HBV | 75 | 15 | NUC | 137 | LTFGRETVL | XTXXXXXXL | B58 | | | 1418 |
| HBV | 75 | 15 | NUC | 137 | LTFGRETVL | XTXXXXXXXXY | B58 | | | 1419 |
| HBV | 90 | 18 | ENV | 189 | LTIPQSLDSW | XTXXXXXXXW | B58 | | | 1420 |
| HBV | 90 | 18 | ENV | 189 | LTIPQSLDSWW | XTXXXXXXXXW | B58 | | | 1421 |
| HBV | 90 | 18 | POL | 404 | LTNLLSSNL | XTXXXXXXL | B58 | | | 1422 |
| HBV | 90 | 18 | POL | 404 | LTNLLSSNLSW | XTXXXXXXXXW | B58 | | | 1423 |
| HBV | 80 | 16 | ENV | 185 | LTRILTIPQSL | XTXXXXXXXXL | B58 | | | 1424 |
| HBV | 85 | 17 | POL | 99 | LTVNEKRRL | XTXXXXXXL | B58 | | | 1425 |
| HBV | 75 | 15 | X | 103 | MSTTDLEAY | XSXXXXXXY | B58 | 2.0126 | * | 1426 |
| HBV | 75 | 15 | X | 103 | MSTTDLEAYF | XSXXXXXXXF | B58 | | | 1427 |
| HBV | 100 | 20 | NUC | 136 | NAPILSTL | XAXXXXXL | B58 | | | 1428 |
| HBV | 90 | 18 | POL | 738 | NSVVLSRKY | XSXXXXXXY | B58 | 2.0123 | | 1429 |
| HBV | 100 | 20 | POL | 430 | PAAMPHLL | XAXXXXXL | B58 | | | 1430 |
| HBV | 85 | 17 | POL | 430 | PAAMPHLLV | XAXXXXXXV | B58 | | | 1431 |
| HBV | 90 | 18 | POL | 775 | PADDPSRGRL | XAXXXXXXXL | B58 | | | 1432 |
| HBV | 90 | 18 | ENV | 131 | PAGGSSSGTV | XAXXXXXXXV | B58 | | | 1433 |
| HBV | 95 | 19 | POL | 641 | PALMPLYACI | XAXXXXXXXI | B58 | 5.0087 | | 1434 |
| HBV | 80 | 16 | X | 11 | PARDVLCL | XAXXXXXL | B58 | | | 1435 |
| HBV | 75 | 15 | X | 11 | PARDVLCLRPV | XAXXXXXXXXV | B58 | | | 1436 |
| HBV | 90 | 18 | POL | 355 | PARVTGGV | XAXXXXXV | B58 | | | 1437 |
| HBV | 90 | 18 | POL | 355 | PARVTGGVF | XAXXXXXXF | B58 | | | 1438 |
| HBV | 90 | 18 | POL | 355 | PARVTGGVFL | XAXXXXXXXL | B58 | | | 1439 |
| HBV | 90 | 18 | POL | 355 | PARVTGGVFLV | XAXXXXXXXXV | E58 | | | 1440 |
| HBV | 95 | 19 | NUC | 130 | PAYRPPNAPI | XAXXXXXXXI | B58 | 5.0081 | | 1441 |
| HBV | 95 | 19 | NUC | 130 | PAYRPPNAPIL | XAXXXXXXXXL | B58 | | | 1442 |
| HBV | 90 | 18 | POL | 779 | PSRGRLGL | XSXXXXXL | B58 | | | 1443 |
| HBV | 75 | 15 | POL | 692 | PTGWGLAI | XTXXXXXI | B58 | | | 1444 |

TABLE XIII-continued

HBV B58 SUPER MOTIF

| Source | Conservancy | Freq | Protein | Position | Sequence | String | Supermotif | Peptide Filed | SEQ ID NO: |
|---|---|---|---|---|---|---|---|---|---|
| HBV | 85 | 17 | POL | 797 | PTTGRTSL | XTXXXXXL | B58 | | 1445 |
| HBV | 85 | 17 | POL | 797 | PTTGRTSLY | XTXXXXXXY | B58 | 1.0208 * | 1446 |
| HBV | 80 | 16 | NUC | 15 | PTVQASKL | XTXXXXXL | B58 | | 1447 |
| HBV | 80 | 16 | NUC | 15 | PTVQASKLCL | XTXXXXXXXL | B58 | | 1448 |
| HBV | 75 | 15 | ENV | 351 | PTVWLSVI | XTXXXXXI | B58 | | 1449 |
| HBV | 75 | 15 | ENV | 351 | PTVWLSVIW | XTXXXXXXW | B58 | | 1450 |
| HBV | 150 | 30 | ENV | 351 | PTVWLSVIWM | XTXXXXXXXM | B58 | | 1451 |
| HBV | 95 | 19 | POL | 654 | QAFTFSPTY | XAXXXXXXY | B58 | 20.0127 | 1452 |
| HBV | 80 | 16 | ENV | 179 | QAGFFLLTRIL | XAXXXXXXXXL | B58 | | 1453 |
| HBV | 90 | 18 | NUC | 57 | QAILCWGEL | XXXXXXXXL | B58 | | 1454 |
| HBV | 180 | 36 | NUC | 57 | QALCWGELM | XAXXXXXXXM | B58 | | 1455 |
| HBV | 80 | 16 | ENV | 107 | QAMQWNSTTF | XAXXXXXXXF | B58 | | 1456 |
| HBV | 80 | 16 | NUC | 18 | QASALCLGW | XAXXXXXXW | B58 | | 1457 |
| HBV | 80 | 16 | NUC | 18 | QASKLCLGWL | XAXXXXXXXL | B58 | | 1458 |
| HBV | 75 | 15 | NUC | 18 | QASKLCLGWLW | XAXXXXXXXXW | B58 | | 1459 |
| HBV | 90 | 18 | ENV | 193 | QSLDSWWTSL | XSXXXXXXXL | B58 | F126.63 | 1460 |
| HBV | 90 | 18 | POL | 402 | QSLTNLLSSNL | XSXXXXXXXXL | B58 | | 1461 |
| HBV | 95 | 19 | POL | 528 | RAFPHCLAF | XAXXXXXXF | B58 | 20.0125 | 1482 |
| HBV | 95 | 19 | POL | 528 | RAFPHCLAFSY | XAXXXXXXXXY | B58 | 26.0550 * | 1463 |
| HBV | 90 | 18 | POL | 353 | RTPARVTGGV | XTXXXXXXXV | B56 | | 1464 |
| HBV | 90 | 18 | POL | 353 | RTPARVTGGVF | XTXXXXXXXXF | B58 | | 1465 |
| HBV | 90 | 18 | X | 65 | SAGPCALRF | XAXXXXXXF | B58 | 26.0152 | 1466 |
| HBV | 95 | 19 | POL | 520 | SAICSVVRRAF | XAXXXXXXXXF | B58 | | 1467 |
| HBV | 90 | 18 | NUC | 35 | SALYREAL | XAXXXXXL | B58 | | 1468 |
| HBV | 100 | 20 | POL | 165 | SASFCGSPY | XAXXXXXXY | B58 | 20.0117 * | 1469 |
| HBV | 100 | 20 | POL | 165 | SASFCGSPYSW | XAXXXXXXXXW | B58 | | 1470 |
| HBV | 95 | 19 | X | 64 | SSAGPCAL | XSXXXXXL | B58 | | 1471 |
| HBV | 90 | 18 | X | 64 | SSAGPCALRF | XSXXXXXXXF | B58 | 26.0374 | 1472 |
| HBV | 75 | 15 | ENV | 136 | SSGTVNPV | XSXXXXXV | B58 | | 1473 |
| HBV | 90 | 18 | POL | 409 | SSNLSWLSL | XSXXXXXXL | B58 | | 1474 |
| HBV | 90 | 18 | POL | 409 | SSNLSWLSLDV | XSXXXXXXXXV | B58 | | 1475 |
| HBV | 75 | 15 | ENV | 135 | SSSGTVNPV | XSXXXXXXV | B58 | | 1476 |
| HBV | 100 | 20 | NUC | 141 | STLPETTV | XTXXXXXV | B58 | | 1477 |
| HBV | 100 | 20 | NUC | 141 | STLPETTVV | XTXXXXXXV | B58 | 5.0024 | 1478 |
| HBV | 75 | 15 | X | 104 | STTDLEAY | XTXXXXXY | B58 | | 1479 |
| HBV | 78 | 15 | X | 104 | STTDLEAYF | XTXXXXXXF | B58 | | 1480 |
| HBV | 85 | 17 | POL | 716 | TAELLAACF | XAXXXXXXF | B58 | | 1481 |
| HBV | 95 | 19 | NUC | 53 | TALRQAIL | XAXXXXXL | B58 | | 1482 |
| HBV | 95 | 19 | NUC | 53 | TALRQAILCW | XAXXXXXXXW | B58 | | 1483 |
| HBV | 80 | 16 | NUC | 33 | TASALYREAL | XAXXXXXXXL | B58 | | 1484 |
| HBV | 95 | 19 | POL | 519 | TSAICSVV | XSXXXXXV | B58 | | 1485 |
| HBV | 80 | 16 | POL | 764 | TSFVYVPSAL | XSXXXXXXXL | B58 | | 1486 |
| HBV | 80 | 16 | ENV | 168 | TSGFLGPL | XSXXXXXL | B58 | | 1487 |
| HBV | 75 | 15 | ENV | 168 | TSGFLGPLL | XSXXXXXXL | B58 | | 1488 |
| HBV | 75 | 15 | ENV | 168 | TSGFLGPLLV | XSXXXXXXXV | B58 | | 1489 |
| HBV | 75 | 15 | ENV | 168 | TSGFLGPLLVL | XSXXXXXXXXL | B58 | | 1490 |
| HBV | 75 | 15 | X | 105 | TTDLEAYF | XTXXXXXF | B58 | | 1491 |
| HBV | 85 | 17 | POL | 798 | TTGRTSLY | XTXXXXXY | B58 | 26.0030 | 1492 |
| HBV | 95 | 19 | POL | 37 | VAEDLNLGNL | XAXXXXXXXL | B58 | 5.0089 | 1493 |
| HBV | 100 | 20 | POL | 48 | VSIPWTHKV | XSXXXXXXV | B58 | | 1494 |
| HBV | 95 | 19 | POL | 391 | VSWPKFAV | XSXXXXXV | B58 | | 1495 |
| HBV | 95 | 19 | POL | 391 | VSWPKFAVPNL | XSXXXXXXXXL | B58 | | 1496 |
| HBV | 100 | 20 | POL | 358 | VTGGVFLV | XTXXXXXV | B58 | | 1497 |
| HBV | 85 | 17 | ENV | 66 | WSFQAQGI | XSXXXXXI | B58 | | 1498 |
| HBV | 85 | 17 | ENV | 56 | WSPQAQGIL | XSXXXXXXL | B58 | | 1499 |
| HBV | 100 | 20 | POL | 52 | WTHKVGNF | XTXXXXXF | B58 | | 1500 |
| HBV | 95 | 19 | POL | 52 | WTHKVGNFTGL | XTXXXXXXXXL | B58 | | 1501 |
| HBV | 80 | 16 | POL | 493 | YSHPIILGF | XSXXXXXXF | B58 | | 1502 |
| HBV | 85 | 17 | POL | 580 | YSLNFMGY | XSXXXXXY | B58 | 26.0032 | 1503 |
| HBV | 75 | 15 | POL | 580 | YSLNFMGYV | XSXXXXXXV | B58 | | 1504 |
| HBV | 75 | 15 | POL | 580 | YSLNFMGYVI | XSXXXXXXXI | B58 | | 1505 |
| HBV | 85 | 17 | POL | 746 | YTSFPWLL | XTXXXXXL | B58 | | 1506 |

TABLE XIV

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 95 | 19 | POL | 521 | AICSWRRAF | XIXXXXXXF | B62s | | | 1507 |
| HBV | 90 | 18 | NUC | 58 | AILCVVGELM | XIXXXXXXXM | B62s | | | 1508 |
| HBV | 95 | 19 | POL | 642 | ALMPLYACI | XLXXXXXXI | B62s | 3.0012 | * | 1509 |
| HBV | 95 | 19 | NUC | 54 | ALRQAILCW | XLXXXXXXW | B62s | | | 1510 |
| HBV | 80 | 16 | ENV | 108 | AMQWNSTTF | XMXXXXXXF | B62s | | | 1511 |
| HBV | 95 | 19 | POL | 633 | APFTQCGY | XPXXXXXY | B62s | 19.0013 | | 1512 |
| HBV | 95 | 19 | POL | 516 | AQFTSAICSV | XQXXXXXXXV | B62 | | | 1513 |
| HBV | 95 | 19 | POL | 516 | AQFTSAICSVV | XQXXXXXXXXV | B62s | | | 1514 |
| HBV | 100 | 20 | ENV | 312 | CIPIPSSW | XIXXXXXW | B62s | | | 1515 |
| HBV | 100 | 20 | ENV | 312 | CIPIPSSWAF | XIXXXXXXXF | B62s | | | 1516 |
| HBV | 90 | 18 | POL | 533 | CLAFSYMDDV | XLXXXXXXXV | B62s | 1.0559 | | 1517 |
| HBV | 90 | 18 | POL | 533 | CLAFSYMDDVV | XLXXXXXXXXV | B62s | | | 1518 |
| HBV | 85 | 17 | NUC | 23 | CLGWLWGM | XLXXXXXM | B62s | | | 1519 |
| HBV | 85 | 17 | NUC | 23 | CLGWLWGMDI | XLXXXXXXXI | B62s | 2.0229 | | 1520 |
| HBV | 95 | 19 | ENV | 253 | CLIFLLVLLDY | XLXXXXXXXXY | B62s | 26.0548 | | 1521 |
| HBV | 95 | 19 | ENV | 239 | CLRRFIF | XLXXXXF | B62s | | | 1522 |
| HBV | 75 | 15 | ENV | 239 | CLRRFIIFLF | XLXXXXXXXF | B62s | | | 1523 |
| HBV | 75 | 15 | ENV | 239 | CLRRFIIFLFI | XLXXXXXXXXI | B62s | Chisari | | 1524 |
| HBV | 90 | 18 | NUC | 107 | CLTFGRETV | XLXXXXXXV | B62s | 1.0160 | | 1525 |
| HBV | 80 | 16 | X | 7 | CQLDPARDV | XQXXXXXXV | B62s | | | 1526 |
| HBV | 85 | 17 | POL | 622 | CQRIVGLLGF | XQXXXXXXXF | B62s | | | 1527 |
| HBV | 90 | 18 | NUC | 31 | DIDPYKEF | XIXXXXXF | B62s | | | 1528 |
| HBV | 85 | 17 | NUC | 29 | DLLDTASALY | XLXXXXXXXY | B62s | 1.0519 | * | 1529 |
| HBV | 95 | 19 | POL | 40 | DLNLGNLNV | XLXXXXXXV | B62s | 1.0164 | | 1530 |
| HBV | 95 | 19 | POL | 40 | DLNLGNLNVSI | XLXXXXXXXXI | B62s | | | 1531 |
| HBV | 80 | 16 | ENV | 122 | DPRVRGLY | XPXXXXXY | B62s | | | 1532 |
| HBV | 95 | 19 | X | 14 | DVLCLRPV | XVXXXXXV | B62s | | | 1533 |
| HBV | 90 | 18 | POL | 541 | DVVLGAKSV | XVXXXXXXV | B62s | 1.0190 | | 1534 |
| HBV | 95 | 19 | NUC | 43 | ELLSFLPSDF | XLXXXXXXXF | B62s | | | 1535 |
| HBV | 95 | 19 | NUC | 43 | ELLSFLPSDFF | XLXXXXXXXXF | B62s | | | 1536 |
| HBV | 80 | 16 | ENV | 248 | FILLLCLI | XIXXXXXI | B62s | Chisari | | 1537 |
| HBV | 80 | 16 | ENV | 248 | FILLLCLIF | XIXXXXXXF | B62s | | | 1538 |
| HBV | 80 | 16 | ENV | 246 | FLFILLLCLI | XLXXXXXXXI | B62s | 3.0206 | | 1539 |
| HBV | 80 | 16 | ENV | 246 | FLFILLLCLIF | XLXXXXXXXXF | B62s | | | 1540 |
| HBV | 95 | 19 | POL | 513 | FLLAQFTSAI | XLXXXXXXXI | B62s | 1147.13 | * | 1541 |
| HBV | 80 | 16 | ENV | 183 | FLLTRILTI | XLXXXXXXI | B62s | 3.0005 | * | 1542 |
| HBV | 95 | 19 | ENV | 256 | FLLVLLDY | XLXXXXXY | B62s | 26.0027 | | 1543 |
| HBV | 95 | 19 | ENV | 256 | FLLVLLDYQGM | XLXXXXXXXXM | B62s | | | 1544 |
| HBV | 75 | 15 | ENV | 130 | FPAGGSSSGTV | XPXXXXXXXXV | B62s | | | 1545 |
| HBV | 85 | 17 | ENV | 14 | FPDHQLDPAF | XPXXXXXXXF | B62s | 20.0274 | | 1546 |
| HBV | 95 | 19 | POL | 530 | FPHCLAFSY | XPXXXXXXY | B62s | 15.0037 | * | 1547 |
| HBV | 95 | 19 | POL | 530 | FPHCLAFSYM | XPXXXXXXXM | B62s | 15.0217 | * | 1548 |
| HBV | 75 | 15 | POL | 749 | FPWLLGCAANW | XPXXXXXXXXW | B62s | | | 1549 |
| HBV | 95 | 19 | ENV | 346 | FVGLSPTV | XVXXXXXV | B62s | | | 1550 |
| HBV | 95 | 19 | ENV | 346 | FVGLSPTVW | XVXXXXXXW | B62s | | | 1551 |
| HBV | 90 | 18 | X | 132 | FVLGGCRHKLV | XVXXXXXXXXV | B62s | | | 1552 |
| HBV | 95 | 19 | POL | 627 | GLLGFAAPF | XLXXXXXXF | B62s | 20.0124 | | 1553 |
| HBV | 95 | 19 | POL | 509 | GLSPFLLAQF | XLXXXXXXXF | B62s | | | 1554 |
| HBV | 75 | 15 | ENV | 348 | GLSPTVWLSV | XLXXXXXXXV | B62s | 1.0518 | | 1555 |
| HBV | 75 | 15 | ENV | 348 | GLSPTVWLSVI | XLXXXXXXXXI | B62s | Chisari | | 1556 |
| HBV | 85 | 17 | NUC | 29 | GMDIDPYKEF | XMXXXXXXXF | B62s | 26.0372 | | 1557 |
| HBV | 95 | 19 | ENV | 173 | GPLLVLQAGF | XPXXXXXXXF | B62s | 15.0212 | | 1558 |
| HBV | 95 | 19 | ENV | 173 | GPLLVLQAGFF | XPXXXXXXXXF | B62s | 26.0556 | | 1559 |
| HBV | 95 | 19 | NUC | 123 | GVWIRTPPAY | XVXXXXXXXY | B62s | 1.0525 | | 1560 |
| HBV | 75 | 15 | POL | 569 | HLNPNKTKRW | XLXXXXXXXW | B62s | | | 1561 |
| HBV | 90 | 18 | X | 52 | HLSLRGLPV | XLXXXXXXV | B62s | 1.0212 | | 1562 |
| HBV | 80 | 16 | POL | 491 | HLYSHPII | XLXXXXXI | B62s | 17.0256 | | 1563 |
| HBV | 80 | 16 | POL | 491 | HLYSHPIILGF | XLXXXXXXXXF | B62s | | | 1564 |
| HBV | 85 | 17 | POL | 429 | HPAAMPHLLV | XPXXXXXXXV | B62s | 20.0273 | * | 1565 |
| HBV | 80 | 16 | POL | 495 | HPIILGFRKI | XPXXXXXXXI | B62s | | | 1566 |
| HBV | 80 | 16 | POL | 497 | IILGFRKI | XIXXXXXI | B62s | 17.0124 | * | 1567 |
| HBV | 80 | 16 | POL | 497 | IILGFRKIPM | XIXXXXXXXM | B62s | | | 1568 |
| HBV | 90 | 18 | NUC | 59 | ILCWGELM | XLXXXXXM | B62s | | | 1569 |
| HBV | 80 | 16 | POL | 498 | ILGFRKIPM | XLXXXXXXM | B62s | 3.0016 | | 1570 |
| HBV | 100 | 20 | ENV | 249 | ILLLCLIF | XLXXXXXF | B62s | | | 1571 |
| HBV | 100 | 20 | ENV | 249 | ILLLCLIFLLV | XLXXXXXXXXV | B62s | Chisari | | 1572 |
| HBV | 80 | 16 | POL | 760 | ILRGTSFV | XLXXXXXV | B62s | | | 1573 |
| HBV | 80 | 16 | POL | 760 | ILRGTSFVY | XLXXXXXXY | B62s | 1.0205 | * | 1574 |
| HBV | 80 | 16 | POL | 760 | ILRGTSFVYV | XLXXXXXXXV | B62s | 1.0573 | * | 1575 |
| HBV | 100 | 20 | NUC | 139 | ILSTLPETTV | XLXXXXXXXV | B62 | 1.0526 | | 1576 |
| HBV | 100 | 20 | NUC | 139 | ILSTLPETTVV | XLXXXXXXXXV | B62s | | * | 1577 |
| HBV | 90 | 18 | ENV | 188 | ILTIPQSLDSW | XLXXXXXXXXW | B62s | | | 1578 |
| HBV | 100 | 20 | ENV | 313 | IPIPSSWAF | XPXXXXXXF | B62s | 15.0032 | * | 1579 |
| HBV | 80 | 16 | POL | 504 | IPMGVGLSPF | XPXXXXXXXF | B62s | | | 1580 |

TABLE XIV-continued

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 90 | 18 | ENV | 191 | IPQSLDSW | XPXXXXXW | B62s | 19.0004 |   | 1581 |
| HBV | 90 | 18 | ENV | 191 | IPQSLDSWW | XPXXXXXXW | B62s | 15.0030 | * | 1582 |
| HBV | 100 | 20 | POL | 50 | IPWTHKVGNF | XPXXXXXXXF | B62s | 15.0209 |   | 1583 |
| HBV | 90 | 18 | POL | 625 | IVGLLGFAAPF | XVXXXXXXXXF | B62s |   |   | 1584 |
| HBV | 80 | 16 | POL | 503 | KIPMGVGLSPF | XIXXXXXXXXF | B62s |   |   | 1585 |
| HBV | 85 | 17 | NUC | 21 | KLCLGWLW | XLXXXXXW | B62s |   |   | 1586 |
| HBV | 85 | 17 | NUC | 21 | KLCLGWLWGM | XLXXXXXXXM | B62s | 3.0209 | * | 1587 |
| HBV | 95 | 19 | POL | 489 | KLHLYSHPI | XLXXXXXXI | B62s | 3.0009 | * | 1588 |
| HBV | 80 | 16 | POL | 489 | KLHLYSHPII | XLXXXXXXXI | B62s |   |   | 1589 |
| HBV | 75 | 15 | POL | 108 | KLIMPARF | XLXXXXXF | B62s |   |   | 1590 |
| HBV | 75 | 15 | POL | 108 | KLIMPARFY | XLXXXXXXY | B62s | 1.0171 |   | 1591 |
| HBV | 80 | 16 | POL | 610 | KLPVNRPI | XLXXXXXI | B62s |   |   | 1592 |
| HBV | 80 | 16 | POL | 610 | KLPVNRPIDW | XLXXXXXXXW | B62s |   |   | 1593 |
| HBV | 95 | 19 | POL | 653 | KQAFTFSPTY | XWXXXXXXXY | B62s | 20.0256 |   | 1594 |
| HBV | 95 | 19 | POL | 55 | KVGNFTGLY | XVXXXXXXY | B62s | 1.0166 |   | 1595 |
| HBV | 95 | 19 | ENV | 254 | LIFLLVLLDY | XIXXXXXXXY | B62s | 1.0899 |   | 1596 |
| HBV | 100 | 20 | POL | 109 | LIMPARFY | XIXXXXXY | B62s | 26.0028 |   | 1597 |
| HBV | 95 | 19 | POL | 514 | LLAQFTSAI | XLXXXXXXI | B62s | 3.0010 | * | 1598 |
| HBV | 100 | 20 | ENV | 251 | LLCLIFLLV | XLXXXXXXV | B62s | 1.0835 | * | 1599 |
| HBV | 85 | 17 | NUC | 30 | LLDTASALY | XLXXXXXXY | B62s | 1.0155 | * | 1600 |
| HBV | 90 | 18 | ENV | 260 | LLDYQGMLPV | XLXXXXXXXV | B62s | 1.0516 | * | 1601 |
| HBV | 60 | 18 | POL | 752 | LLGCAAAW | XLXXXXXW | B62s |   |   | 1602 |
| HBV | 80 | 16 | POL | 752 | LLGCAANWI | XLXXXXXXI | B62s | 3.0013 |   | 1603 |
| HBV | 95 | 19 | POL | 628 | LLGFAAPF | XLXXXXXF | B62s |   |   | 1604 |
| HBV | 75 | 15 | ENV | 63 | LLGWSPQAQGI | XLXXXXXXXXI | B62s |   |   | 1605 |
| HBV | 100 | 20 | ENV | 250 | LLLCLIFLLV | XLXXXXXXXV | B62s | 1.0897 | * | 1606 |
| HBV | 100 | 20 | ENV | 378 | LLPIFFCLW | XLXXXXXXW | B62s |   | * | 1607 |
| HBV | 100 | 20 | ENV | 378 | LLPIFFCLWV | XLXXXXXXXV | B62s | 1.0904 | * | 1608 |
| HBV | 100 | 20 | ENV | 378 | LLPIFFCLWVY | XLXXXXXXXXY | B62s | 26.0549 |   | 1609 |
| HBV | 95 | 19 | NUC | 44 | LLSFLPSDF | XLXXXXXXF | B62s |   |   | 1610 |
| HBV | 95 | 19 | NUC | 44 | LLSFLPSDFF | XLXXXXXXXF | B62s |   |   | 1611 |
| HBV | 90 | 18 | POL | 407 | LLSSNLSW | XLXXXXXW | B62s |   |   | 1612 |
| HBV | 80 | 16 | ENV | 184 | LLTRILTI | XLXXXXXI | B62s | Chisari |   | 1613 |
| HBV | 80 | 16 | POL | 436 | LLVGSSGL | XLXXXXXL | B62s |   |   | 1614 |
| HBV | 95 | 19 | ENV | 257 | LLVLLDYQGM | XLXXXXXXXM | B62s | 3.0207 |   | 1615 |
| HBV | 95 | 19 | ENV | 175 | LLVLQAGF | XLXXXXXF | B62s |   |   | 1616 |
| HBV | 95 | 19 | ENV | 175 | LLVLQAGFF | XLXXXXXXF | B62s | 20.0121 |   | 1617 |
| HBV | 100 | 20 | ENV | 338 | LLVPFVQW | XLXXXXXW | B62s |   |   | 1618 |
| HBV | 100 | 20 | ENV | 338 | LLVPFVQWF | XLXXXXXXF | B62s |   |   | 1619 |
| HBV | 95 | 19 | ENV | 338 | LLVPFVQWFV | XLXXXXXXXV | B62s | 1.0930 | * | 1620 |
| HBV | 85 | 17 | NUC | 100 | LLWFHISCLTF | XLXXXXXXXXF | B62s |   |   | 1621 |
| HBV | 95 | 19 | POL | 643 | LMPLYACI | XMXXXXXI | B62s | 17.0130 |   | 1622 |
| HBV | 100 | 20 | ENV | 379 | LPIFFCLW | XPXXXXXW | B62s | 19.0007 |   | 1623 |
| HBV | 100 | 20 | ENV | 379 | LPIFFCLWV | XPXXXXXXV | B62s | 15.0034 |   | 1624 |
| HBV | 100 | 20 | ENV | 379 | LPIFFCLWVY | XPXXXXXXXY | B62s | 15.0215 |   | 1625 |
| HBV | 100 | 20 | ENV | 379 | LPIFFCLWVYI | XPXXXXXXXXI | B62s | 26.0558 |   | 1626 |
| HBV | 100 | 20 | POL | 123 | LPLDKGIKPY | XPXXXXXXXY | B62s | 15.0210 | * | 1627 |
| HBV | 100 | 20 | POL | 123 | LPLDKGIKPYY | XPXXXXXXXXY | B62s | 26.0560 |   | 1628 |
| HBV | 80 | 16 | POL | 611 | LPVNRPIDW | XPXXXXXXW | B62s |   |   | 1629 |
| HBV | 80 | 16 | POL | 611 | LPVNRPIDWKV | XPXXXXXXXXV | B62s |   |   | 1630 |
| HBV | 80 | 16 | ENV | 178 | LQAGFFLLTRI | XQXXXXXXXXI | B62s |   |   | 1631 |
| HBV | 95 | 19 | ENV | 258 | LVLLDYQGM | XVXXXXXXM | B62s | 3.0034 |   | 1632 |
| HBV | 95 | 19 | ENV | 176 | LVLQAGFF | XVXXXXXF | B62s |   |   | 1633 |
| HBV | 100 | 20 | ENV | 339 | LVPFVQWF | XVXXXXXF | B62s |   |   | 1634 |
| HBV | 95 | 19 | ENV | 339 | LVPFVQWFV | XVXXXXXXV | B62s | 1.0877 | * | 1635 |
| HBV | 90 | 18 | NUC | 119 | LVSFGVWI | XVXXXXXI | B62s | Chisari |   | 1636 |
| HBV | 100 | 20 | POL | 377 | LVVDFSQF | XVXXXXXF | B62s |   |   | 1637 |
| HBV | 85 | 17 | ENV | 360 | MMWYWGPSLY | XMXXXXXXXY | B62s | 1039.01 | * | 1638 |
| HBV | 100 | 20 | POL | 1 | MPLSYQHF | XPXXXXXF | B62s | 19.0010 | * | 1639 |
| HBV | 80 | 16 | ENV | 109 | MQWNSTTF | XQXXXXXF | B62s |   |   | 1640 |
| HBV | 95 | 19 | POL | 42 | NLGNLNVSI | XLXXXXXXI | B62s | 3.0008 |   | 1641 |
| HBV | 95 | 19 | POL | 42 | NLGNLNVSIPW | XLXXXXXXXXW | B62s |   |   | 1642 |
| HBV | 90 | 18 | POL | 406 | NLLSSNLSW | XLXXXXXXW | B62s |   |   | 1643 |
| HBV | 95 | 19 | POL | 45 | NLNVSIPW | XLXXXXXW | B62s |   |   | 1644 |
| HBV | 75 | 15 | ENV | 15 | NLSVPNPLGF | XLXXXXXXXF | B62s |   |   | 1645 |
| HBV | 90 | 18 | POL | 411 | NLSWLSLDV | XLXXXXXXV | B62s | 1.0185 | * | 1646 |
| HBV | 75 | 15 | POL | 571 | NPNKTKRW | XPXXXXXW | B62s |   |   | 1647 |
| HBV | 75 | 15 | POL | 571 | NPNKTKRWGY | XPXXXXXXXY | B62s |   |   | 1648 |
| HBV | 100 | 20 | POL | 47 | NVSIPWTHKV | XVXXXXXXXV | B62s | 1.0532 |   | 1649 |
| HBV | 85 | 17 | POL | 616 | PIDWKVCQRI | XIXXXXXXXI | B62s | Chisari |   | 1650 |
| HBV | 85 | 17 | POL | 616 | PIDWKVCQRIV | XIXXXXXXXXV | B62s |   |   | 1651 |
| HBV | 100 | 20 | ENV | 380 | PIFFCLWV | XIXXXXXV | B62s |   |   | 1652 |
| HBV | 100 | 20 | ENV | 380 | PIFFCLWVY | XIXXXXXXY | B62s | 1.0843 |   | 1653 |
| HBV | 100 | 20 | ENV | 380 | PIFFCLWVYI | XIXXXXXXXI | B62s | 20.0258 |   | 1654 |

TABLE XIV-continued
HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 80 | 16 | POL | 496 | PIILGFRKI | XIXXXXXXI | B62s | 927.48 | | 1655 |
| HBV | 80 | 16 | POL | 496 | PIILGFRKIPM | XIXXXXXXXXM | B62s | | | 1656 |
| HBV | 100 | 20 | NUC | 138 | PILSTLPETTV | XIXXXXXXXXV | B62s | Chisari | | 1657 |
| HBV | 100 | 20 | ENV | 314 | PIPSSWAF | XIXXXXXF | B62s | | | 1658 |
| HBV | 100 | 20 | POL | 124 | PLDKGIKPY | XLXXXXXXY | B62s | 1.0174 | * | 1659 |
| HBV | 100 | 20 | POL | 124 | PLDKGIKPYY | XLXXXXXXXY | B62s | 1.0541 | * | 1660 |
| HBV | 100 | 20 | ENV | 377 | PLLPIFFCLW | XLXXXXXXXW | B62s | | | 1661 |
| HBV | 100 | 20 | ENV | 377 | PLLPIFFCLWV | XLXXXXXXXXV | B62s | | | 1662 |
| HBV | 95 | 19 | ENV | 174 | PLLVLQAGF | XLXXXXXXF | B62s | | | 1663 |
| HBV | 95 | 19 | ENV | 174 | PLLVLQAGFF | XLXXXXXXXF | B62s | | | 1664 |
| HBV | 80 | 16 | POL | 505 | PMGVGLSPF | XMXXXXXXF | B62s | | | 1665 |
| HBV | 95 | 19 | NUC | 129 | PPAYRPPNAPI | XPXXXXXXXXI | B62s | 26.0563 | | 1666 |
| HBV | 85 | 17 | ENV | 58 | PPHGGLLGW | XPXXXXXXW | B62s | 20.0141 | | 1667 |
| HBV | 80 | 16 | ENV | 106 | PQAMQWNSTT | XQXXXXXXXF | B62s | | | 1668 |
| HBV | 90 | 18 | ENV | 192 | PQSLDSWW | XQXXXXXW | B62s | | | 1669 |
| HBV | 85 | 17 | POL | 612 | PVNRPIDW | XVXXXXXW | B62s | | | 1670 |
| HBV | 85 | 17 | POL | 612 | PVNRPIDWKV | XVXXXXXXXV | B62s | 1.0566 | | 1671 |
| HBV | 80 | 16 | X | 8 | QLDPARDV | XLXXXXXV | B62s | Chisari | | 1672 |
| HBV | 95 | 19 | POL | 685 | QVFADATPTGW | XVXXXXXXXXW | B62s | | | 1673 |
| HBV | 90 | 18 | POL | 624 | RIVGLLGF | XIXXXXXF | B62s | | | 1674 |
| HBV | 75 | 15 | POL | 106 | RLKLIMPARF | XLXXXXXXXF | B62s | | | 1675 |
| HBV | 75 | 15 | POL | 106 | RLKLIMPARFY | XLXXXXXXXXY | B62s | | | 1676 |
| HBV | 95 | 19 | POL | 376 | RLVVDFSQF | XLXXXXXXF | B62s | 20.0122 | | 1677 |
| HBV | 80 | 16 | POL | 615 | RPIDWKVCORI | XPXXXXXXXXI | B62s | | | 1678 |
| HBV | 90 | 18 | NUC | 56 | RQAILCWGELM | XQXXXXXXXXM | B62s | | | 1679 |
| HBV | 90 | 18 | NUC | 98 | RQLLWFHI | XQXXXXXI | B62s | | | 1680 |
| HBV | 75 | 15 | POL | 818 | RVHFASPLHV | XVXXXXXXXV | B62s | 1.0576 | | 1681 |
| HBV | 100 | 20 | POL | 357 | RVTGGVFLV | XVXXXXXXV | B62s | 1.0181 | | 1682 |
| HBV | 100 | 20 | POL | 49 | SIPWTHKV | XIXXXXXV | B62s | | | 1683 |
| HBV | 100 | 20 | POL | 49 | SIPWTHKVGNF | XIXXXXXXXXF | B62s | | | 1684 |
| HBV | 95 | 19 | ENV | 194 | SLDSWWTSLNF | XLXXXXXXXXF | B62s | | | 1685 |
| HBV | 95 | 19 | POL | 416 | SLDVSAAF | XLXXXXXF | B62s | | | 1686 |
| HBV | 95 | 19 | POL | 416 | SLDVSAAFY | XLXXXXXXY | B62s | 1.0186 | * | 1687 |
| HBV | 100 | 20 | ENV | 337 | SLLVPFVQW | XLXXXXXXW | B62s | | | 1688 |
| HBV | 100 | 20 | ENV | 337 | SLLVPFVQWF | XLXXXXXXXF | B62s | | | 1689 |
| HBV | 95 | 19 | ENV | 337 | SLLVPFVQWFV | XLXXXXXXXXV | B62s | | | 1690 |
| HBV | 75 | 15 | POL | 581 | SLNFMGYV | XLXXXXXV | B62s | | | 1691 |
| HBV | 75 | 15 | POL | 581 | SLNFMGYVI | XLXXXXXXI | B62s | 3.0011 | | 1692 |
| HBV | 95 | 19 | X | 54 | SLRGLPVCAF | XLXXXXXXXF | B62s | 20.0259 | | 1693 |
| HBV | 95 | 19 | POL | 511 | SPFLLAQF | XPXXXXXF | B62s | 19.0012 | * | 1694 |
| HBV | 100 | 20 | NUC | 49 | SPHHTALRQAI | XPXXXXXXXXI | B62s | 26.0567 | * | 1695 |
| HBV | 75 | 15 | ENV | 350 | SPTVWLSV | XPXXXXXV | B62s | | | 1696 |
| HBV | 75 | 15 | ENV | 350 | SPTVWLSVI | XPXXXXXXI | B62s | 1308.16 | | 1697 |
| HBV | 75 | 15 | ENV | 350 | SPTVWLSVIW | XPXXXXXXXW | B62s | 1308.17 | | 1698 |
| HBV | 75 | 15 | ENV | 350 | SPTVWLSVIWM | XPXXXXXXXXM | B62s | | | 1699 |
| HBV | 75 | 15 | ENV | 17 | SVPNPLGF | XVXXXXXF | B62s | | | 1700 |
| HBV | 80 | 16 | ENV | 330 | SVRFSWSLLV | XVXXXXXXXV | B62s | | | 1701 |
| HBV | 90 | 18 | POL | 739 | SVVLSRKY | XVXXXXXY | B62s | 26.0029 | | 1702 |
| HBV | 85 | 17 | POL | 739 | SVVLSRKYTSF | XVXXXXXXXXF | B62s | | | 1703 |
| HBV | 90 | 18 | ENV | 190 | TIPQSLDSW | XIXXXXXXW | B62s | | | 1704 |
| HBV | 90 | 18 | ENV | 190 | TIPQSLDSWW | XIXXXXXXXW | B62s | | | 1705 |
| HBV | 100 | 20 | NUC | 142 | TLPETTVV | XLXXXXXV | B62s | | | 1706 |
| HBV | 100 | 20 | POL | 150 | TLWKAGILY | XLXXXXXXY | B62s | 1.0177 | * | 1707 |
| HBV | 90 | 18 | POL | 354 | TPARVTGGV | XPXXXXXXV | B62s | 15.0033 | * | 1708 |
| HBV | 90 | 18 | POL | 354 | TPARVTGGVF | XPXXXXXXXF | B62s | 15.0214 | * | 1709 |
| HBV | 75 | 15 | ENV | 57 | TPPHGGLLGW | XPXXXXXXXW | B62s | 1308.04 | | 1710 |
| HBV | 75 | 15 | POL | 691 | TPTGWGLAI | XPXXXXXXI | B62s | | | 1711 |
| HBV | 95 | 19 | POL | 636 | TQCGYPALM | XQXXXXXXM | B62s | | | 1712 |
| HBV | 80 | 16 | NUC | 16 | TVQASKLCLGW | XVXXXXXXXXW | B62s | | | 1713 |
| HBV | 75 | 15 | ENV | 352 | TVWLSVIW | XVXXXXXW | B62s | | | 1714 |
| HBV | 75 | 15 | ENV | 352 | TVWLSVIWM | XVXXXXXXM | B62s | 3.0035 | | 1715 |
| HBV | 90 | 18 | X | 133 | VLGGCRHKLV | XLXXXXXXXV | B62s | 1.0589 | | 1716 |
| HBV | 95 | 19 | ENV | 259 | VLLDYQGM | XLXXXXXM | B62s | 17.0107 | | 1717 |
| HBV | 90 | 18 | ENV | 259 | VLLDYQGMLPV | XLXXXXXXXXV | B62s | 1147.14 | * | 1718 |
| HBV | 85 | 17 | POL | 741 | VLSRKYTSF | XLXXXXXXF | B62s | | | 1719 |
| HBV | 85 | 17 | POL | 741 | VLSRKYTSFPW | XLXXXXXXXXW | B62s | | | 1720 |
| HBV | 95 | 19 | ENV | 340 | VPFVQWFV | XPXXXXXV | B62s | 19.0006 | * | 1721 |
| HBV | 80 | 16 | NUC | 17 | VQASKLCLGW | XQXXXXXXXW | B62s | | | 1722 |
| HBV | 95 | 19 | ENV | 343 | VQWFVGLSPTV | XQXXXXXXXXV | B62s | | | 1723 |
| HBV | 90 | 18 | POL | 542 | VVLGAKSV | XVXXXXXV | B62s | | | 1724 |
| HBV | 80 | 16 | POL | 759 | WILRGTSF | XIXXXXXF | B62s | | | 1725 |
| HBV | 80 | 16 | POL | 759 | WILRGTSFV | XIXXXXXXV | B62s | 1.0204 | * | 1726 |
| HBV | 80 | 16 | POL | 759 | WILRGTSFVY | XIXXXXXXXY | B62s | 1.0572 | | 1727 |
| HBV | 80 | 16 | POL | 759 | WILRGTSFVYV | XIXXXXXXXXV | B62s | | | 1728 |

TABLE XIV-continued

HBV B62 SUPER MOTIF

| Source | Conservancy | Freq | Protein | Position | Sequence | String | Supermotif | Peptide | Filed | SEQ ID NO: |
|---|---|---|---|---|---|---|---|---|---|---|
| HBV | 95 | 19 | NUC | 125 | WIRTPPAY | XIXXXXXY | B62s | 26.0031 | | 1729 |
| HBV | 80 | 16 | POL | 751 | WLLGCAANW | XLXXXXXW | B62s | | | 1730 |
| HBV | 80 | 16 | POL | 751 | WLLGCAANWI | XLXXXXXXXI | B62s | Chisari | | 1731 |
| HBV | 95 | 19 | POL | 414 | WLSLDVSAAF | XLXXXXXXXF | B62s | | | 1732 |
| HBV | 95 | 19 | POL | 414 | WLSLDVSAAFY | XLXXXXXXXXY | B62s | 26.0551 | | 1733 |
| HBV | 100 | 20 | ENV | 335 | WLSLLVPF | XLXXXXXF | B62s | | | 1734 |
| HBV | 100 | 20 | ENV | 335 | WLSLLVPFV | XLXXXXXXV | B62s | 1.0838 | * | 1735 |
| HBV | 100 | 20 | ENV | 335 | WLSLLVPFVQW | XLXXXXXXXXW | B62s | | | 1736 |
| HBV | 85 | 17 | NUC | 26 | WLWGMDIDPY | XLXXXXXXXY | B62s | 1.0774 | * | 1737 |
| HBV | 95 | 19 | ENV | 237 | WMCLRRFI | XMXXXXXI | B62s | | | 1738 |
| HBV | 95 | 19 | ENV | 237 | WMCLRRFII | XMXXXXXXI | B62s | 3.0031 | * | 1739 |
| HBV | 95 | 19 | ENV | 237 | WMCLRRFIIF | XMXXXXXXXF | B62s | 20.0266 | | 1740 |
| HBV | 85 | 17 | ENV | 359 | WMMWYWGPSL | XMXXXXXXXL | B62s | 1.0901 | * | 1741 |
| HBV | 100 | 20 | POL | 147 | YLHTLWKAGI | XLXXXXXXXI | B62s | 7.0066 | | 1742 |
| HBV | 100 | 20 | POL | 122 | YLPLDKGI | XLXXXXXI | B62s | | | 1743 |
| HBV | 100 | 20 | POL | 122 | YLPLDKGIKPY | XLXXXXXXXXY | B62s | 26.0553 | | 1744 |
| HBV | 90 | 18 | NUC | 118 | YLVSFGVW | XLXXXXXW | B62s | | | 1745 |
| HBV | 90 | 18 | NUC | 118 | YLVSFGVMI | XLXXXXXXI | B62s | 3.0007 | * | 1746 |
| HBV | 95 | 19 | POL | 640 | YPALMPLY | XPXXXXXY | B62s | 19.0014 | * | 1747 |
| HBV | 95 | 19 | POL | 640 | YPALMPLYACI | XPXXXXXXXXI | B62s | 26.0570 | | 1748 |

TABLE XV

HBV A01 Motif (With Binding Information)

| Conservancy | Frequency | Protein | 1st Pos | Sequence | P2 | C-term | Peptide | Filed | A*0101 | SEQ ID NO: |
|---|---|---|---|---|---|---|---|---|---|---|
| 80 | 16 | ENV | 119 | AMQWNSTTF | M | F | | | | 1749 |
| 90 | 18 | POL | 737 | DNSVVLSRKY | N | Y | 20.0255 | | 0.0001 | 1750 |
| 95 | 19 | POL | 631 | FAAPFTQCGY | A | Y | 20.0254 | * | 0.0680 | 1751 |
| 85 | 17 | POL | 590 | GYSUNFMGY | Y | Y | 2.0058 | | | 1752 |
| 100 | 20 | POL | 149 | HTLWKAGILY | T | Y | 1069.04 | * | 0.1100 | 1753 |
| 95 | 19 | POL | 653 | KQAFTFSPTY | Q | Y | 20.0256 | | 0.0001 | 1754 |
| 85 | 17 | NUC | 30 | LLDTASALY | L | Y | 1069.01 | * | 12.0000 | 1755 |
| 95 | 19 | POL | 415 | LSLDVSAAFY | S | Y | 1090.07 | * | 0.0150 | 1756 |
| 85 | 17 | ENV | 360 | MMWYWGPSLY | M | Y | 1039.01 | * | 0.0810 | 1757 |
| 75 | 15 | X | 103 | MSTTDLEAY | S | Y | 2.0126 | * | 0.8500 | 1758 |
| 90 | 18 | POL | 738 | NSVVLSRKY | S | Y | 2.0123 | | 0.0005 | 1759 |
| 100 | 20 | POL | 124 | PLDKGIKPY | L | Y | 1147.12 | * | | 1760 |
| 100 | 20 | POL | 124 | PLDKGIKPYY | L | Y | 1069.03 | * | 0.1700 | 1761 |
| 85 | 17 | POL | 797 | PTTGRTSLY | T | Y | 1090.09 | * | 0.2100 | 1762 |
| 100 | 20 | POL | 165 | SASFCGSPY | A | Y | | | | 1763 |
| 95 | 19 | POL | 416 | SLDVSAAFY | L | Y | 1069.02 | * | 5.2000 | 1764 |

TABLE XVI

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 85 | 17 | POL | 721 | AACFARSR | A03/A11 | A03 | A | R | 26.0003 | | 0.0004 | 0.0003 | 1765 |
| 95 | 19 | POL | 643 | AAPFTQCGY | A03/A11 | A03 | A | Y | | | | | 1766 |
| 95 | 19 | POL | 540 | AFPHCLAFSY | A03/A11 | A03 | F | Y | | | | | 1767 |
| 95 | 19 | X | 62 | AFSSAGPCA | A03/A11 | A03 | F | A | | | | | 1768 |
| 95 | 19 | POL | 666 | AFTFSPTYK | A03/A11 | A03 | F | K | 20.0130 | * | 0.2600 | 0.0400 | 1769 |
| 95 | 19 | POL | 666 | AFTFSPTYKA | A03/A11 | A03 | F | A | | | | | 1770 |
| 95 | 19 | POL | 18 | AGPLEEELPR | A03/A11 | A03 | G | R | 20.0265 | | 0.0004 | 0.0002 | 1771 |
| 95 | 19 | POL | 521 | AICSVVRR | A03/A11 | A03 | I | R | 26.0004 | | -0.0002 | 0.0003 | 1772 |
| 95 | 19 | POL | 532 | AICSVVRRAF | A03/A11 | A03 | I | F | | | | | 1773 |
| 90 | 18 | POL | 772 | ALNPADDPSR | A03/A11 | A03 | L | R | 1.1090 | | 0.0003 | 0.0001 | 1774 |
| 85 | 17 | X | 70 | ALRFTSAR | A03/A11 | A03 | L | R | 26.0005 | | 0.0047 | 0.0009 | 1775 |
| 80 | 16 | ENV | 119 | AMQWNSTTF | A03/A11 | A03 | M | F | | | | | 1776 |
| 80 | 16 | ENV | 119 | AMQWNSTTF | A03/ | A03 | M | F | | | | | 1777 |
| 80 | 16 | ENV | 119 | AMQWNSTTFH | A03/A11 | A03 | M | H | | | | | 1778 |
| 80 | 16 | POL | 822 | ASPLHVAWR | A03/A11 | A03 | S | R | | | | | 1779 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 75 | 15 | ENV | 84 | ASTNRQSGR | A03/A11 | A03 | S | R | 1150.60 | | 0.0009 | 0.0002 | 1780 |
| 80 | 16 | POL | 755 | CAANWILR | A03/A11 | A03 | A | R | | | | | 1781 |
| 85 | 17 | X | 69 | CALRFTSAR | A03/A11 | A03 | A | R | 26.0149 | * | 0.0034 | 0.0230 | 1782 |
| 85 | 17 | POL | 734 | CFARSRSGA | A03/A11 | A03 | F | A | | | | | 1783 |
| 75 | 15 | POL | 618 | CFRKLPVNR | A03/A11 | A03 | F | R | | | | | 1784 |
| 95 | 19 | POL | 649 | CGYPALMPLY | A03/A11 | A03 | G | Y | | | | | 1785 |
| 100 | 20 | ENV | 323 | CIPIPSSWAF | A03/A11 | A03 | I | F | | | | | 1786 |
| 90 | 18 | X | 17 | CLRPVGAESR | A03/A11 | A03 | L | R | 1.1093 | | 0.0011 | 0.0001 | 1787 |
| 75 | 15 | ENV | 239 | CLRRFIIFLF | A03/A11 | A03 | L | F | | | | | 1788 |
| 100 | 20 | NUC | 48 | CSPHHTALR | A03/A11 | A03 | S | R | 5.0055 | * | 0.0029 | 0.0001 | 1789 |
| 95 | 19 | POL | 534 | CSVVRRAFPH | A03/A11 | A03 | S | H | | | | | 1790 |
| 85 | 17 | NUC | 58 | DLLDTASALY | A03/A11 | A03 | L | Y | 1.0519 | * | 0.0001 | 0.0001 | 1791 |
| 85 | 17 | NUC | 29 | DLLDTASALYR | A03/A11 | A03 | L | R | 26.0530 | | 0.0042 | −0.0003 | 1792 |
| 95 | 19 | ENV | 207 | DSWWTSUNF | A03/A11 | A03 | S | F | 20.0120 | | 0.0006 | 0.0003 | 1793 |
| 85 | 17 | NUC | 32 | DTASALYR | A03/A11 | A03 | T | R | 26.0006 | | 0.0004 | −0.0002 | 1794 |
| 95 | 19 | POL | 17 | EAGPLEEEUPR | A03/A11 | A03 | A | R | 26.0531 | | −0.0009 | −0.0003 | 1795 |
| 90 | 18 | POL | 718 | ELLAACFAR | A03/A11 | A03 | L | R | 1.0988 | | 0.0002 | 0.0004 | 1796 |
| 85 | 17 | POL | 718 | ELLAACFARSR | A03/A11 | A03 | L | R | 26.0532 | | 0.0062 | 0.0016 | 1797 |
| 95 | 19 | NUC | 43 | ELLSFLPSDF | A03/A11 | A03 | L | F | | | | | 1798 |
| 95 | 19 | NUC | 72 | ESPEHCSPH | A03/A11 | A03 | S | H | | | | | 1799 |
| 95 | 19 | NUC | 72 | ESPEHCSPHH | A03/A11 | A03 | S | H | | | | | 1800 |
| 95 | 19 | NUC | 174 | ETTVVRRR | A03/A11 | A03 | T | R | 26.0007 | | 0.0003 | −0.0002 | 1801 |
| 80 | 16 | NUC | 174 | ETTVVRRRGR | A03/A11 | A03 | T | R | 1.1073 | | 0.0003 | 0.0001 | 1802 |
| 95 | 19 | POL | 642 | FAAPFTQCGY | A01/A03/ | A03 | A | Y | 20.0254 | * | | | 1803 |
| 80 | 16 | POL | 821 | FASPLHVAWR | A03/A11 | A03 | A | R | | | | | 1804 |
| 90 | 18 | ENV | 24 | FFPDHQLDPA | A03/A11 | A03 | F | A | | | | | 1805 |
| 75 | 15 | NUC | 139 | FGRETVLEY | A03/A11 | A03 | G | Y | | | | | 1806 |
| 75 | 15 | POL | 255 | FGVEPSGSGH | A03/A11 | A03 | G | H | | | | | 1807 |
| 80 | 16 | ENV | 248 | FILLCLIF | A03/A11 | A03 | I | F | | | | | 1808 |
| 90 | 18 | X | 63 | FSSAGPCALR | A03/A11 | A03 | S | R | | | | | 1809 |
| 100 | 20 | ENV | 344 | FSWLSLLVPF | A03/A11 | A03 | S | F | 20.0263 | | 0.0004 | 0.0002 | 1810 |
| 95 | 19 | POL | 656 | FTFSPTYK | A03/A11 | A03 | T | K | 1147.19 | * | 0.0100 | 0.0100 | 1811 |
| 95 | 19 | POL | 667 | FTFSPTYKAF | A03/A11 | A03 | T | F | 20.0262 | | 0.0004 | 0.0006 | 1812 |
| 95 | 19 | POL | 518 | FTSAICSVVR | A03/A11 | A03 | T | R | 1.1085 | | 0.0003 | 0.0003 | 1813 |
| 95 | 19 | POL | 518 | FTSAICSVVRR | A03/A11 | A03 | T | R | 26.0533 | | 0.0065 | 0.0092 | 1814 |
| 90 | 18 | X | 132 | FVLGGCRHK | A03/A11 | A03 | V | K | 1090.03 | * | 0.0430 | 0.0090 | 1815 |
| 80 | 16 | POL | 765 | GCAANWILR | A03/A11 | A03 | C | R | | | | | 1816 |
| 75 | 15 | POL | 567 | GIHLNPNK | A03/A11 | A03 | I | K | | | | | 1817 |
| 75 | 15 | POL | 567 | GIHLNPNKTK | A03/A11 | A03 | I | K | 1.0563 | | 0.0025 | 0.0011 | 1818 |
| 75 | 15 | POL | 567 | GIHLNPNKTKR | A03/A11 | A03 | I | R | | | | | 1819 |
| 95 | 19 | POL | 638 | GLLGFAAPF | A03/A11 | A03 | L | F | 20.0124 | | 0.0006 | 0.0002 | 1820 |
| 95 | 19 | POL | 520 | GLSPFLLAQF | A03/A11 | A03 | L | F | | | | | 1821 |
| 85 | 17 | NUC | 29 | GMDIDPYK | A03/A11 | A03 | M | K | 26.0009 | | 0.0006 | 0.0004 | 1822 |
| 85 | 17 | NUC | 29 | GMDIDPYKEF | A03/A24 | A03 | M | F | 26.0372 | | −0.0003 | −0.0002 | 1823 |
| 90 | 18 | POL | 735 | GTDNSVVLSR | A03/A11 | A03 | T | R | 1090.04 | * | 0.0010 | 0.0420 | 1824 |
| 90 | 18 | POL | 735 | GTDNSVVLSRK | A03/A11 | A03 | T | K | 1147.17 | * | 0.0140 | 0.5600 | 1825 |
| 80 | 16 | POL | 256 | GVEPSGSGH | A03/A11 | A03 | V | H | | | | | 1826 |
| 100 | 20 | POL | 372 | GVFLVDKNPH | A03/A11 | A03 | V | H | | | | | 1827 |
| 95 | 19 | NUC | 152 | GVWIRTPPAY | A03/A11 | A03 | V | Y | 1.0525 | | 0.0047 | 0.0002 | 1828 |
| 95 | 19 | NUC | 123 | GVWIRTPPAYR | A03/A11 | A03 | V | R | 26.0535 | * | 0.1900 | 0.1700 | 1829 |
| 100 | 20 | NUC | 76 | HCSPHHTALR | A03/A11 | A03 | C | R | | | | | 1830 |
| 80 | 16 | POL | 831 | HFASPLHVA | A03/A11 | A03 | F | A | | | | | 1831 |
| 90 | 18 | NUC | 104 | HISCLTFGR | A03/A11 | A03 | I | R | 1069.18 | * | 0.0160 | 0.0065 | 1832 |
| 75 | 15 | POL | 569 | HLNPNKTK | A03/A11 | A03 | L | K | | | | | 1833 |
| 75 | 15 | POL | 569 | HLNPNKTKR | A03/A11 | A03 | L | R | 1.0983 | | 0.0025 | 0.0001 | 1834 |
| 85 | 17 | POL | 726 | HTAELLAACF | A03/A11 | A03 | T | F | | | | | 1835 |
| 100 | 20 | POL | 149 | HTLWKAGILYK | A03/A11 | A03 | T | K | 1147.16 | * | 0.5400 | 0.4400 | 1836 |
| 95 | 19 | POL | 533 | ICSVVRRAF | A03/A11 | A03 | C | F | | | | | 1837 |
| 95 | 19 | ENV | 266 | IFLLVLLDY | A03/A11 | A03 | F | Y | | | | | 1838 |
| 80 | 16 | POL | 771 | ILRGTSFVY | A03/A11 | A03 | L | Y | 1.0205 | * | 0.0440 | 0.0002 | 1839 |
| 90 | 18 | NUC | 105 | ISCLTFGR | A03/A11 | A03 | S | R | 26.0010 | | 0.0004 | 0.0002 | 1840 |
| 100 | 20 | POL | 153 | KAGILYKR | A03/A11 | A03 | A | R | 26.0011 | | 0.0002 | −0.0002 | 1841 |
| 75 | 15 | POL | 108 | KLIMPARFY | A03/A11 | A03 | L | Y | 1.0171 | | | | 1842 |
| 80 | 16 | POL | 610 | KLPVNRPIDWK | A03/A11 | A03 | L | K | | | | | 1843 |
| 75 | 15 | X | 130 | KVFVLGGCR | A03/A11 | A03 | V | R | 1.0993 | * | 0.0420 | 0.0820 | 1844 |
| 75 | 15 | X | 130 | KVFVLGGCRH | A03/A11 | A03 | V | H | | | | | 1845 |
| 95 | 19 | POL | 55 | KVGNFTGLY | A03/A11 | A03 | V | Y | 1142.05 | * | 0.2100 | 0.0170 | 1846 |
| 85 | 17 | POL | 720 | LAACFARSR | A03/A11 | A03 | A | R | 20.0129 | | 0.0058 | 0.0065 | 1847 |
| 100 | 20 | POL | 125 | LDKGIKPYY | A03/A11 | A03 | D | Y | | | | | 1848 |
| 95 | 19 | ENV | 206 | LDSWWTSLNF | A03/A11 | A03 | D | F | | | | | 1849 |
| 85 | 17 | NUC | 60 | LDTASALYR | A03/A11 | A03 | D | R | 26.0151 | | 0.0004 | −0.0002 | 1850 |
| 95 | 19 | POL | 428 | LDVSAAFYH | A03/A11 | A03 | D | H | | | | | 1851 |
| 80 | 16 | ENV | 247 | LFILLLCLIF | A03/A11 | A03 | F | F | | | | | 1852 |
| 80 | 16 | ENV | 247 | LFILLLCLIF | A03/A24 | A03 | F | F | | | | | 1853 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 80 | 16 | POL | 764 | LGCAANWILR | A03/A11 | A03 | G | R | | | | | 1854 |
| 75 | 15 | POL | 577 | LGIHLNPNK | A03/A11 | A03 | G | K | | | | | 1855 |
| 95 | 19 | ENV | 265 | LIFLLVLLDY | A03/A11 | A03 | I | Y | 1.0899 | | 0.0022 | 0.0004 | 1856 |
| 90 | 18 | POL | 719 | LLAACFAR | A03/A11 | A03 | L | R | 26.0012 | | 0.0024 | 0.0003 | 1857 |
| 85 | 17 | POL | 719 | LLAACFARSR | A03/A11 | A03 | L | R | | | | | 1858 |
| 85 | 17 | NUC | 30 | LLDTASALYR | A03/A11 | A03 | L | R | 1.1070 | | 0.0050 | 0.0002 | 1859 |
| 80 | 16 | POL | 752 | LLGCAANWILR | A03/A11 | A03 | L | R | | | | | 1860 |
| 95 | 19 | NUC | 44 | LLSFLPSDF | A03/A11 | A03 | L | F | | | | | 1861 |
| 95 | 19 | NUC | 44 | LLSFLPSDFF | A03/A11 | A03 | L | F | | | | | 1862 |
| 95 | 19 | ENV | 175 | LLVLQAGFF | A03/A11 | A03 | L | F | 20.0121 | | 0.0006 | 0.0002 | 1863 |
| 100 | 20 | ENV | 349 | LLVPFVQWF | A03/A11 | A03 | L | F | | | | | 1864 |
| 95 | 19 | NUC | 45 | LSFLPSDFF | A03/A11 | A03 | S | F | 20.0123 | | 0.0006 | 0.0002 | 1865 |
| 95 | 19 | POL | 426 | LSLDVSAAF | A03/A11 | A03 | S | F | | | | | 1866 |
| 75 | 15 | POL | 564 | LSLGIHLNPNK | A03/A11 | A03 | S | K | | | | | 1867 |
| 95 | 19 | X | 53 | LSLRGLPVCA | A03/A11 | A03 | S | A | | | | | 1868 |
| 95 | 19 | POL | 521 | LSPFLLAQF | A03/A11 | A03 | S | F | | | | | 1869 |
| 95 | 19 | NUC | 169 | LSTLPETTVVR | A03/A11 | A03 | S | R | 26.0537 | | −0.0009 | 0.0008 | 1870 |
| 75 | 15 | ENV | 16 | LSVPNPLGF | A03/A11 | A03 | S | F | | | | | 1871 |
| 100 | 20 | POL | 423 | LSWLSLDVSA | A03/A11 | A03 | S | A | 20.0260 | | 0.0048 | 0.0035 | 1872 |
| 75 | 15 | POL | 3 | LSYQHFRK | A03/A11 | A03 | S | K | | | | | 1873 |
| 85 | 17 | POL | 99 | LTVNEKRR | A03/A11 | A03 | T | R | 26.0013 | | −0.0002 | −0.0002 | 1874 |
| 90 | 18 | NUC | 119 | LVSFGVWIR | A03/A11 | A03 | V | R | 1090.08 | * | 0.0028 | 0.0120 | 1875 |
| 100 | 20 | POL | 377 | LVVDFSQFSR | A03/A11 | A03 | V | R | 1069.20 | * | 0.0016 | 0.3600 | 1876 |
| 95 | 19 | ENV | 249 | MCLRRFIIF | A03/A11 | A03 | C | F | | | | | 1877 |
| 90 | 18 | POL | 550 | MDDVVLGAK | A03/A11 | A03 | D | K | | | | | 1878 |
| 90 | 18 | NUC | 30 | MDIDPYKEF | A03/A11 | A03 | D | F | | | | | 1879 |
| 85 | 17 | ENV | 360 | MMWYWGPSLY | A01/A03/ | A03 | M | Y | 1039.01 | * | 0.0500 | 0.0008 | 1880 |
| 75 | 15 | X | 103 | MSTTDLEAYF | A03/A11 | A03 | S | F | | | | | 1881 |
| 75 | 15 | X | 103 | MSTTDLEAYFK | A03/A11 | A03 | S | K | | | | | 1882 |
| 95 | 19 | POL | 572 | NFLLSLGIH | A03/A11 | A03 | F | H | | | | | 1883 |
| 90 | 18 | NUC | 75 | NLEDPASR | A03/A11 | A03 | L | R | 26.0014 | | −0.0002 | −0.0002 | 1884 |
| 95 | 19 | POL | 45 | NLNVSIPWTH | A03/A11 | A03 | L | H | | | | | 1885 |
| 95 | 19 | POL | 45 | NLNVSIPWTHK | A03/A11 | A03 | L | K | 26.0538 | | −0.0009 | 0.0005 | 1886 |
| 75 | 15 | ENV | 15 | NLSVPNPLGF | A03/A11 | A03 | L | F | | | | | 1887 |
| 75 | 15 | ENV | 215 | NSQSPTSNH | A03/A11 | A03 | S | H | | | | | 1888 |
| 90 | 18 | POL | 738 | NSVVLSRK | A03/A11 | A03 | S | K | 26.0015 | | 0.0006 | 0.0010 | 1889 |
| 100 | 20 | POL | 47 | NVSIPWTHK | A03/A11 | A03 | V | K | 1069.16 | * | 0.0820 | 0.0570 | 1890 |
| 90 | 18 | POL | 775 | PADDPSRGR | A03/A11 | A03 | A | R | 1150.35 | | 0.0008 | 0.0002 | 1891 |
| 80 | 16 | X | 11 | PARDVLCLR | A03/A11 | A03 | A | R | 1150.36 | | 0.0002 | 0.0002 | 1892 |
| 90 | 18 | POL | 366 | PARVTGGVF | A03/A11 | A03 | A | F | | | | | 1893 |
| 75 | 15 | ENV | 83 | PASTNRQSGR | A03/A11 | A03 | A | R | | | | | 1894 |
| 85 | 17 | X | 68 | PCALRFTSAR | A03/A11 | A03 | C | R | | | | | 1895 |
| 90 | 18 | ENV | 26 | PDHQLDPAF | A03/A11 | A03 | D | F | | | | | 1896 |
| 95 | 19 | POL | 523 | PFLLAQFTSA | A03/A11 | A03 | F | A | | | | | 1897 |
| 95 | 19 | POL | 645 | PFTQCGYPA | A03/A11 | A03 | F | A | | | | | 1898 |
| 100 | 20 | ENV | 244 | PGYRWMCLR | A03/A11 | A03 | G | R | 1.0964 | | 0.0008 | 0.0005 | 1899 |
| 95 | 19 | ENV | 244 | PGYRWMCLRR | A03/A11 | A03 | G | R | 1.1068 | | 0.0048 | 0.0001 | 1900 |
| 90 | 18 | POL | 616 | PIDWKVCQR | A03/A11 | A03 | I | R | 1.0985 | | 0.0002 | 0.0005 | 1901 |
| 100 | 20 | ENV | 391 | PIFFCLWVY | A03/A11 | A03 | I | Y | 1.0843 | | 0.0011 | 0.0002 | 1902 |
| 80 | 16 | POL | 496 | PIILGFRK | A03/A11 | A03 | I | K | | | | | 1903 |
| 95 | 19 | POL | 20 | PLEEELPR | A03/A11 | A03 | L | R | 26.0016 | | 0.0002 | −0.0002 | 1904 |
| 100 | 20 | POL | 438 | PLHPAAMPH | A03/A11 | A03 | L | H | 20.0128 | | 0.0012 | 0.0002 | 1905 |
| 95 | 19 | ENV | 174 | PLLVLQAGF | A03/A11 | A03 | L | F | | | | | 1906 |
| 95 | 19 | ENV | 174 | PLLVLQAGFF | A03/A11 | A03 | L | F | | | | | 1907 |
| 100 | 20 | POL | 2 | PLSYQHFR | A03/A11 | A03 | L | R | 26.0017 | | −0.0002 | −0.0002 | 1908 |
| 75 | 15 | POL | 2 | PLSYQHFRK | A03/A11 | A03 | L | K | 1.0161 | | 0.0011 | 0.0031 | 1909 |
| 85 | 17 | POL | 98 | PLTVNEKR | A03/A11 | A03 | L | R | 26.0018 | | 0.0002 | −0.0002 | 1910 |
| 85 | 17 | POL | 98 | PLTVNEKRR | A03/A11 | A03 | L | R | 1.0974 | | 0.0008 | 0.0005 | 1911 |
| 80 | 16 | POL | 516 | PMGVGLSPF | A03/A11 | A03 | M | F | | | | | 1912 |
| 80 | 16 | POL | 516 | PMGVGLSPF | A03/A24 | A03 | M | F | | | | | 1913 |
| 90 | 18 | X | 20 | PVGAESRGR | A03/A11 | A03 | V | R | 1.0990 | | 0.0002 | 0.0005 | 1914 |
| 85 | 17 | POL | 612 | PVNRPIDWK | A03/A11 | A03 | V | K | 1142.06 | * | 0.0310 | 0.1400 | 1915 |
| 95 | 19 | POL | 665 | QAFTFSPTY | A03/A11 | A03 | A | Y | 20.0127 | | 0.0030 | 0.0017 | 1916 |
| 95 | 19 | POL | 654 | QAFTFSPTYK | A03/A11 | A03 | A | K | 1090.10 | * | 0.0450 | 0.5400 | 1917 |
| 80 | 16 | ENV | 179 | QAGFFLLTR | A03/A11 | A03 | A | R | | | | | 1918 |
| 80 | 16 | ENV | 118 | QAMQWNSTTF | A03/A11 | A03 | A | F | | | | | 1919 |
| 75 | 15 | NUC | 169 | QSPRRRSQSR | A03/A11 | A03 | S | R | 28.0839 | | | | 1920 |
| 80 | 16 | POL | 189 | QSSGILSR | A03/A11 | A03 | S | R | | | | | 1921 |
| 95 | 19 | POL | 539 | RAFPHCLAF | A03/A11 | A03 | A | F | 20.0125 | | 0.0015 | 0.0007 | 1922 |
| 75 | 15 | POL | 106 | RLKLIMPAR | A03/A11 | A03 | L | R | 1.0975 | * | 0.0950 | 0.0002 | 1923 |
| 75 | 15 | POL | 106 | RLKLIMPARF | A03/A11 | A03 | L | F | | | | | 1924 |
| 75 | 15 | X | 128 | RUKVFVLGGCR | A03/A11 | A03 | L | R | | | | | 1925 |
| 95 | 19 | POL | 387 | RLVVDFSQF | A03/A11 | A03 | L | F | 20.0122 | | 0.0006 | 0.0002 | 1926 |
| 95 | 19 | POL | 376 | RLVVDFSQFSR | A03/A11 | A03 | L | R | 26.0539 | * | 0.2800 | 3.8000 | 1927 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 95 | 19 | NUC | 183 | RSPRRATPSPR | A03/A11 | A03 | S | R | 26.0540 | | −0.0007 | −0.0003 | 1928 |
| 75 | 15 | NUC | 167 | RSQSPRRR | A03/A11 | A03 | S | R | | | | | 1929 |
| 75 | 15 | NUC | 167 | RSQSPRRRR | A03/A11 | A03 | S | R | | | | | 1930 |
| 95 | 19 | NUC | 188 | RTPSPRRR | A03/A11 | A03 | T | R | 26.0019 | | −0.0002 | −0.0002 | 1931 |
| 95 | 19 | NUC | 188 | RTPSPRRRR | A03/A11 | A03 | T | R | 1.0971 | * | 0.0054 | 0.0005 | 1932 |
| 80 | 16 | POL | 829 | RVHFASPLH | A03/A11 | A03 | V | H | | | | | 1933 |
| 100 | 20 | POL | 357 | RVTGGVFLVDK | A03/A11 | A03 | V | K | 1147.18 | * | 0.0190 | 0.0290 | 1934 |
| 90 | 18 | X | 65 | SAGPCALR | A03/A11 | A03 | A | R | 26.0020 | | −0.0002 | 0.0020 | 1935 |
| 90 | 18 | X | 65 | SAGPCALRF | A03/A11 | A03 | A | F | 26.0152 | | −0.0003 | 0.0004 | 1936 |
| 95 | 19 | POL | 520 | SAICSVVR | A03/A11 | A03 | A | R | 26.0021 | | −0.0002 | 0.0071 | 1937 |
| 95 | 19 | POL | 520 | SAICSVVRR | A03/A11 | A03 | A | R | 1090.11 | * | 0.0058 | 0.2100 | 1938 |
| 90 | 18 | POL | 771 | SALNPADDPSR | A03/A11 | A03 | A | R | 26.0542 | | −0.0004 | −0.0003 | 1939 |
| 100 | 20 | POL | 165 | SASFCGSPY | A01/A03/ | A03 | A | Y | | | | | 1940 |
| 75 | 15 | POL | 759 | SFPWLLGCA | A03/A11 | A03 | F | A | | | | | 1941 |
| 75 | 15 | POL | 759 | SFPWLLGCAA | A03/A11 | A03 | F | A | | | | | 1942 |
| 95 | 19 | POL | 427 | SLDVSAAFYH | A03/A11 | A03 | L | H | | | | | 1943 |
| 75 | 15 | POL | 565 | SLGIHLNPNK | A03/A11 | A03 | L | K | 28.0758 | * | | | 1944 |
| 100 | 20 | ENV | 348 | SLLVPFVQWF | A03/A11 | A03 | L | F | | | | | 1945 |
| 95 | 19 | X | 54 | SLRGLPVCAF | A03/A11 | A03 | L | F | 20.0259 | | 0.0004 | 0.0002 | 1946 |
| 90 | 18 | X | 64 | SSAGPCALR | A03/A11 | A03 | S | R | 26.0153 | * | 0.0080 | 0.1400 | 1947 |
| 90 | 18 | X | 64 | SSAGPCALRF | A03/A11 | A03 | S | F | 26.0374 | | −0.0003 | −0.0002 | 1948 |
| 95 | 19 | NUC | 170 | STLPETTVVR | A03/A11 | A03 | T | R | 1069.21 | * | 0.0007 | 0.0600 | 1949 |
| 95 | 19 | NUC | 170 | STLPETTVVRR | A03/A11 | A03 | T | R | 1083.01 | | 0.0150 | 1.4000 | 1950 |
| 80 | 16 | ENV | 85 | STNRQSGR | A03/A11 | A03 | T | R | | | | | 1951 |
| 75 | 15 | X | 104 | STTDLEAYF | A03/A11 | A03 | T | F | | | | | 1952 |
| 75 | 15 | X | 104 | STTDLEAYFK | A03/A11 | A03 | T | K | 1.0584 | * | 0.0066 | 2.7000 | 1953 |
| 95 | 19 | POL | 535 | SVVRRAFPH | A03/A11 | A03 | V | H | 20.0131 | * | 0.1100 | 0.6100 | 1954 |
| 85 | 17 | POL | 727 | TAELLAACF | A03/A11 | A03 | A | F | | | | | 1955 |
| 85 | 17 | POL | 716 | TAELLAACFAR | A03/A11 | A03 | A | R | 26.0544 | | 0.0006 | 0.0023 | 1956 |
| 90 | 18 | POL | 747 | TDNSVVLSR | A03/A11 | A03 | D | R | | | | | 1957 |
| 90 | 18 | POL | 747 | TDNSVVLSRK | A03/A11 | A03 | D | K | 20.0264 | | 0.0006 | 0.0017 | 1958 |
| 75 | 15 | NUC | 138 | TFGRETVLEY | A03/A11 | A03 | F | Y | | | | | 1959 |
| 95 | 19 | POL | 668 | TFSPTYKAF | A03/A24 | A03 | F | F | 5.0064 | | | | 1960 |
| 100 | 20 | POL | 370 | TGGVFLVDK | A03/A11 | A03 | G | K | 20.0133 | | 0.0007 | 0.0061 | 1961 |
| 95 | 19 | NUC | 171 | TLPETTVVR | A03/A11 | A03 | L | R | 1.0969 | | 0.0008 | 0.0002 | 1962 |
| 95 | 19 | NUC | 171 | TLPETTVVRR | A03/A11 | A03 | L | R | 1069.22 | * | 0.0007 | 0.0230 | 1963 |
| 95 | 19 | NUC | 171 | TLPETTVVRRR | A03/A11 | A03 | L | R | 26.0545 | * | 0.0005 | 0.0160 | 1964 |
| 100 | 20 | POL | 150 | TLWKAGILY | A03/A11 | A03 | L | Y | 1099.03 | * | 0.1300 | 0.0008 | 1965 |
| 100 | 20 | POL | 150 | TLWKAGILYK | A03/A11 | A03 | L | K | 1069.15 | * | 5.3000 | 0.3600 | 1966 |
| 100 | 20 | POL | 150 | TLWKAGILYKR | A03/A11 | A03 | L | R | 26.0546 | | 0.0082 | 0.0095 | 1967 |
| 95 | 19 | POL | 519 | TSAICSVVR | A03/A11 | A03 | S | R | 5.0057 | | 0.0005 | 0.0008 | 1968 |
| 95 | 19 | POL | 519 | TSAICSVVRR | A03/A11 | A03 | S | R | 1142.08 | * | 0.0018 | 0.0006 | 1969 |
| 75 | 15 | POL | 758 | TSFPWLLGCA | A03/A11 | A03 | S | A | | | | | 1970 |
| 80 | 16 | POL | 775 | TSFVYVPSA | A03/A11 | A03 | S | A | | | | | 1971 |
| 75 | 15 | X | 105 | TTDLEAYFK | A03/A11 | A03 | T | K | 1.0215 | * | 0.0006 | 0.9200 | 1972 |
| 75 | 15 | ENV | 278 | TTSTGPCK | A03/A11 | A03 | T | K | | | | | 1973 |
| 80 | 16 | NUC | 175 | TTVVRRRGR | A03/A11 | A03 | T | R | 1.0970 | | 0.0008 | 0.0005 | 1974 |
| 80 | 16 | NUC | 176 | TVVRRRGR | A03/A11 | A03 | V | R | 3.0324 | | 0.0003 | 0.0001 | 1975 |
| 80 | 16 | NUC | 176 | TVVRRRGRSPR | A03/A11 | A03 | V | R | 28.0837 | | | | 1976 |
| 100 | 20 | POL | 373 | VFLVDKNPH | A03/A11 | A03 | F | H | | | | | 1977 |
| 80 | 16 | X | 131 | VFVLGGCRH | A03/A11 | A03 | F | H | | | | | 1978 |
| 75 | 15 | X | 131 | VFVLGGCRHK | A03/A11 | A03 | F | K | | | | | 1979 |
| 95 | 19 | POL | 637 | VGLLGFAAPF | A03/A11 | A03 | G | F | | | | | 1980 |
| 85 | 17 | POL | 96 | VGPLTVNEK | A03/A11 | A03 | G | K | 20.0132 | | 0.0007 | 0.0078 | 1981 |
| 85 | 17 | POL | 96 | VGPLTVNEKR | A03/A11 | A03 | G | R | | | | | 1982 |
| 95 | 19 | POL | 554 | VLGAKSVQH | A03/A11 | A03 | L | H | | | | | 1983 |
| 90 | 18 | X | 133 | VLGGCRHK | A03/A11 | A03 | L | K | 26.0022 | | 0.0150 | 0.0002 | 1984 |
| 80 | 16 | ENV | 177 | VLQAGFFLLTR | A03/A11 | A03 | L | R | | | | | 1985 |
| 85 | 17 | POL | 752 | VLSRKYTSF | A03/A11 | A03 | L | F | | | | | 1986 |
| 90 | 18 | NUC | 120 | VSFGVWIR | A03/A11 | A03 | S | R | 26.0023 | * | 0.0040 | 0.0290 | 1987 |
| 100 | 20 | POL | 48 | VSIPWTHK | A03/A11 | A03 | S | K | 26.0024 | * | 0.0130 | 0.0170 | 1988 |
| 100 | 20 | POL | 358 | VTGGVFLVDK | A03/A11 | A03 | T | K | 1069.17 | * | 0.0390 | 0.0920 | 1989 |
| 100 | 20 | POL | 378 | VVDFSQFSR | A03/A11 | A03 | V | R | 1069.19 | * | 0.0015 | 0.0750 | 1990 |
| 90 | 18 | POL | 553 | VVLGAKSVQH | A03/A11 | A03 | V | H | | | | | 1991 |
| 85 | 17 | POL | 751 | VVLSRKYTSF | A03/A11 | A03 | V | F | 20.0261 | | 0.0004 | 0.0002 | 1992 |
| 80 | 16 | NUC | 177 | VVRRRGRSPR | A03/A11 | A03 | V | R | 1.1074 | | 0.0027 | 0.0001 | 1993 |
| 80 | 16 | NUC | 177 | VVRRRGRSPRR | A03/A11 | A03 | V | R | 28.0838 | | | | 1994 |
| 90 | 18 | NUC | 131 | WFHISCLTF | A03/A11 | A03 | F | F | 13.0073 | * | | | 1995 |
| 90 | 18 | NUC | 131 | WFHISCLTF | A03/A24 | A03 | F | F | 13.0073 | * | | | 1996 |
| 85 | 17 | NUC | 28 | WGMDIDPYK | A03/A11 | A03 | G | K | 26.0154 | | −0.0003 | 0.0006 | 1997 |
| 85 | 17 | POL | 589 | WGYSLNFMGY | A03/A11 | A03 | G | Y | | | | | 1998 |
| 80 | 16 | POL | 770 | WILRGTSFVY | A03/A11 | A03 | I | Y | 1.0572 | | 0.0076 | 0.0011 | 1999 |
| 95 | 19 | NUC | 125 | WIRTPPAYR | A03/A11 | A03 | I | R | 1.0968 | | 0.0008 | 0.0005 | 2000 |
| 90 | 18 | POL | 314 | WLQFRNSK | A03/A11 | A03 | L | K | 26.0025 | | −0.0002 | 0.0005 | 2001 |

TABLE XVI-continued

HBV A03 and A11 Motif (With binding information)

| Conservancy | Frequency | Protein | 1st Pos | Sequence | Motif | Super Motif | P2 | C-term | Peptide | Filed | A*0301 | A*1101 | SEQ ID NO: |
|---|---|---|---|---|---|---|---|---|---|---|---|---|---|
| 95 | 19 | POL | 425 | WLSLDVSAAF | A03/A11 | A03 | L | F | | | | | 2002 |
| 85 | 17 | NUC | 26 | WLWGMDIDPY | A03/A11 | A03 | L | Y | 1.0774 | * | 0.0002 | 0.0002 | 2003 |
| 85 | 17 | NUC | 26 | WLWGMDIDPYK | A03/A11 | A03 | L | K | 26.0547 | | 0.0030 | 0.0013 | 2004 |
| 95 | 19 | ENV | 248 | WMCLRRFIIF | A03/A11 | A03 | M | F | 20.0266 | | 0.0004 | 0.0011 | 2005 |
| 95 | 19 | ENV | 248 | WMCLRRFIIF | A03/A24 | A03 | M | F | 20.0266 | | 0.0004 | 0.0011 | 2006 |
| 100 | 20 | POL | 122 | YLPLDKGIK | A03/A11 | A03 | L | K | 1.0173 | | 0.0001 | 0.0001 | 2007 |
| 90 | 18 | NUC | 118 | YLVSFGVWIR | A03/A11 | A03 | L | R | 1090.13 | * | 0.0005 | 0.0002 | 2008 |
| 90 | 18 | POL | 538 | YMDDWLGAK | A03/A11 | A03 | M | K | 1090.15 | * | 0.0330 | 0.0043 | 2009 |
| 80 | 16 | POL | 504 | YSHPIILGF | A03/A11 | A03 | S | F | | | | | 2010 |
| 80 | 16 | POL | 493 | YSHPIILGFR | A03/A11 | A03 | S | R | | | | | 2011 |
| 80 | 16 | POL | 493 | YSHPIILGFRK 248 | A03/A11 | A03 | S | K | | | | | 2012 |

TABLE XVII

HBV A24 Motif With Binding Information

| Conservancy | Frequency | Protein | Position | Sequence | P2 | C-term | Peptide | Filed | A*2401 | SEQ ID NO: |
|---|---|---|---|---|---|---|---|---|---|---|
| 95 | 19 | X | 62 | AFSSAGPCAL | F | L | 5.0118 | | 0.0012 | 2013 |
| 90 | 18 | POL | 535 | AFSYMDDVVL | F | L | 13.0130 | | 0.0009 | 2014 |
| 80 | 16 | ENV | 108 | AMQWNSTTF | M | F | | | | 2015 |
| 100 | 20 | NUC | 131 | AYRPPNAPI | Y | I | 1090.02 | * | 0.0310 | 2016 |
| 100 | 20 | NUC | 131 | AYRPPNAPIL | Y | L | 1069.24 | * | 0.0042 | 2017 |
| 90 | 18 | NUC | 117 | EYLVSFGVW | Y | W | 26.0150 | | | 2018 |
| 90 | 18 | NUC | 117 | EYLVSFGVWI | Y | I | 17.0426 | * | | 2019 |
| 80 | 16 | ENV | 182 | FFLLTRILTI | F | I | | | | 2020 |
| 80 | 16 | ENV | 181 | GFFLLTRIL | F | L | | | | 2021 |
| 75 | 15 | ENV | 170 | GFLGPLLVL | F | L | | | | 2022 |
| 85 | 17 | NUC | 29 | GMDIDPYKEF | M | F | 26.0372 | | | 2023 |
| 85 | 17 | ENV | 65 | GWSPQAQGI | W | I | 20.0134 | | 0.0024 | 2024 |
| 85 | 17 | ENV | 65 | GWSPQAQGIL | W | L | 20.0268 | | 0.0003 | 2025 |
| 95 | 19 | ENV | 234 | GYRWMCLRRF | Y | F | 1069.25 | * | 0.0007 | 2026 |
| 80 | 16 | POL | 820 | HFASPLHVAW | F | W | | | | 2027 |
| 100 | 20 | ENV | 381 | IFFCLWVYI | F | I | 5.0058 | | 0.0087 | 2028 |
| 80 | 16 | ENV | 245 | IFLFILLLCL | F | L | | | | 2029 |
| 95 | 19 | POL | 395 | KFAVPNLQSL | F | L | 5.0114 | | 0.0020 | 2030 |
| 100 | 20 | POL | 121 | KYLPLDKGI | Y | I | | | | 2031 |
| 85 | 17 | POL | 745 | KYTSFPWLL | Y | L | 1069.23 | * | 5.3000 | 2032 |
| 80 | 16 | ENV | 247 | LFILLLCLI | F | I | | | | 2033 |
| 80 | 16 | ENV | 247 | LFILLLCLIF | F | F | | | | 2034 |
| 85 | 17 | NUC | 101 | LWFHISCLTF | W | F | 26.0373 | | | 2035 |
| 80 | 16 | POL | 492 | LYSHPIILGF | Y | F | 2.0181 | * | 1.1000 | 2036 |
| 95 | 19 | POL | 561 | NFLLSLGIHL | F | L | 5.0115 | | 0.0099 | 2037 |
| 80 | 16 | POL | 758 | NWILRGTSF | W | F | | | | 2038 |
| 95 | 19 | POL | 634 | PFTQCGYPAL | F | L | 5.0116 | | 0.0002 | 2039 |
| 95 | 19 | ENV | 341 | PFVQWFVGL | F | L | 5.0059 | | 0.0003 | 2040 |
| 80 | 16 | POL | 505 | PMGVGLSPF | M | F | | | | 2041 |
| 80 | 16 | POL | 750 | PWLLGCAANW | W | W | | | | 2042 |
| 100 | 20 | POL | 51 | PWTHKVGNF | W | F | 20.0138 | * | 0.0290 | 2043 |
| 75 | 15 | ENV | 242 | RFIIFLFIL | F | L | | | | 2044 |
| 75 | 15 | ENV | 242 | RFIIFLFILL | F | L | | | | 2045 |
| 95 | 19 | ENV | 236 | RWMCLRRFI | W | I | 20.0135 | * | 0.0710 | 2046 |
| 95 | 19 | ENV | 236 | RWMCLRRFII | W | I | 20.0269 | * | 1.1000 | 2047 |
| 100 | 20 | POL | 167 | SFCGSPYSW | F | W | 20.0139 | * | 0.0710 | 2048 |
| 80 | 16 | POL | 765 | SFVYVPSAL | F | L | | | | 2049 |
| 100 | 20 | ENV | 334 | SWLSLLVPF | W | F | 20.0136 | * | 0.3900 | 2050 |
| 95 | 19 | POL | 392 | SWPKFAVPNL | W | L | 20.0271 | * | 5.6000 | 2051 |
| 95 | 19 | ENV | 197 | SWWTSLNFL | W | L | 20.0137 | * | 0.3800 | 2052 |
| 75 | 15 | POL | 4 | SYQHFRKLL | Y | L | 2.0042 | | 0.0051 | 2053 |
| 75 | 15 | POL | 4 | SYQHFRKLLL | Y | L | 2.0173 | * | 0.0660 | 2054 |
| 95 | 19 | POL | 657 | TFSPTYKAF | F | F | 5.0064 | | 0.0060 | 2055 |
| 95 | 19 | POL | 657 | TFSPTYKAFL | F | L | 5.0117 | | 0.0043 | 2056 |
| 95 | 19 | POL | 686 | VFADATPTGW | F | W | 20.0272 | * | 0.0180 | 2057 |
| 90 | 18 | NUC | 102 | WFHISCLTF | F | F | 13.0073 | * | 0.0300 | 2058 |
| 95 | 19 | ENV | 345 | WFVGLSPTVW | F | W | 20.0270 | * | 0.0120 | 2059 |
| 95 | 19 | ENV | 237 | WMCLRRFIIF 48 | M | F | 20.0266 | | 0.0013 | 2060 |

TABLE XVIII

DR SUPER MOTIF (With binding information)

| SEQ ID NO: | Sequence | Peptide | DR1 | DR2w2β1 | DR2w2β1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2061 | AANWILRGTSFVYVP | 1298.07 | 0.0920 | 0.0240 | 0.0061 | 0.0023 | 0.0510 | 0.0250 | 0.0140 | 0.3700 | 0.0250 | 0.5800 | 0.2500 | 0.2700 | |
| 2062 | AEDLNLGNLNVSIPW | 1186.01 | 0.0001 | | -0.0005 | | -0.0007 | | -0.0002 | | | -0.0003 | | | 0.0170 |
| 2063 | AELLAACFARSRSGA | | | | | | | | | | | | | | |
| 2064 | AFSYMDDVVLGAKSV | 1186.02 | 0.0027 | | -0.0005 | 0.0130 | 2.9000 | | 0.0006 | | | -0.0003 | | | -0.0005 |
| 2065 | AGFFLLTRILTIPQS | 1280.06 | 4.6000 | 0.0420 | 0.0190 | 0.0040 | 5.3000 | 0.1500 | 3.6000 | 0.0700 | 0.3700 | 3.1000 | 0.2600 | 1.3000 | |
| 2066 | AGPLEEELPRLADEG | 35.0091 | | | | 0.0022 | | | | | | | | | |
| 2067 | AKLIGTDNSVVLSRK | | | | | | | | | | | | | | |
| 2068 | ANWILRGTSFVYVPS | | | | | | | | | | | | | | |
| 2069 | ARDVLCLRPVGAESR | | | | | | | | | | | | | | |
| 2070 | ASALYREALESPEHC | | | | | | | | | | | | | | |
| 2071 | ASKLCLGWLWGMDID | 1186.03 | 0.0002 | | -0.0005 | | 0.0017 | | -0.0002 | | | 0.0013 | | | 0.0010 |
| 2072 | CLIFLVLLDYOGML | | | | | | | | | | | | | | |
| 2073 | CLITFGRETVLELYLVS | | | | | | | | | | | | | | |
| 2074 | CPGYRWMCLRRFIIF | | | | | | | | | | | | | | |
| 2075 | CPTVQASKLCLGWLW | | | | | | | | | | | | | | |
| 2076 | CQVFADATPTGWGLA | | | | | | | | | | | | | | |
| 2077 | CSVVRRAFPHCLAFS | 1186.04 | 0.1000 | 0.1024 | 0.0770 | 0.0032 | 0.0016 | -0.0022 | 0.0008 | -0.0013 | 0.0540 | 0.0590 | 0.0250 | 1.2000 | 0.0460 |
| 2078 | CTCIPISSSWAFARF | | | | | | | | | | | | | | |
| 2079 | CWWLQFRNSKPCSDY | | | | | 2.6000 | | | | | | | | | |
| 2080 | DDVVLGAKSVQHLES | | | | | | | | | | | | | | |
| 2081 | DEGLNRRVAEDLNLG | | | | | | | | | | | | | | |
| 2082 | DLNLGNLNVSIPWTH | 1280.07 | 0.0038 | | | | 0.0240 | | | | | 0.0010 | | | |
| 2083 | DVVLGAKSVQHLESL | | | | | | | | | | | | | | |
| 2084 | DWKVCQRIVGLLGFA | 1186.05 | 0.0120 | 0.0150 | -0.0026 | | 0.0030 | | 0.2500 | | | 0.0018 | | | 0.0130 |
| 2085 | EIRLKVFVLGGCRHK | | | | | | | | | | | | | | |
| 2086 | ESRLVDFSQFSRGN | 35.0096 F064.01 | 0.0007 | | | | | | | | | | | | |
| 2087 | FFLLTRILTTPQSLD | | | | | | | | | | | | | | |
| 2088 | FGVWIRTPPAYRPPN | | | | | | | | | | | | | | |
| 2089 | FIIFLFILLLCITILLVL | | | | | | | | | | | | | | |
| 2090 | FLFLLLCLTILLVL | | | | | | | | | | | | | | |
| 2091 | FPWLLGCAANWILRG | | | | | | | | | | | | | | |
| 2092 | FRKLPVNRPIDWKVC | | | | | | | | | | | | | | |
| 2093 | FSWLSLLVPFVQWFV | | | | | | | | | | | | | | |
| 2094 | FSYMDDVVLGAKSVQ | | | | | | | | | | | | | | |
| 2095 | FVQWFVGLSPTVWLS | 1186.06 | 0.4700 | 0.0035 | 0.0160 | -0.0013 | 0.0130 | | 0.0072 | 0.0021 | 0.0190 | 0.0690 | 0.0180 | 0.0410 | 0.0044 |
| 2096 | GAHLSLRGLPVCAFS | 1186.07 | 0.7800 | | 0.0042 | -0.0041 | 0.0011 | | 0.0025 | | 0.0780 | 0.0077 | 1.6000 | 0.5500 | 0.0150 |
| 2097 | GFFLLTRILTIPQSL | 1280.08 | 0.4300 | 0.0150 | 0.0110 | | 3.1000 | 0.4500 | 2.3000 | | | 3.5000 | | | |
| 2098 | GIHLNPNKTKRWGYS | | | | | | | | | | | | | | |
| 2099 | GLPVCAFSSAGPCAL | | | | | | | | | | | | | | |
| 2100 | GLYFPAGGSSSGTVN | | | | | | | | | | | | | | |
| 2101 | GTNLSVPNPLGFFPD | | | | | | | | | | | | | | |
| 2102 | GTSFVYVPSALNPAD | 1280.09 | 0.3500 | 0.0140 | 0.0500 | -0.0006 | 0.3800 | 0.4100 | 0.0470 | -0.0001 | 0.0001 | 0.2700 | 0.0610 | 0.3400 | |
| 2103 | GVFLVDKNPHNTES | | | | | | | | | | | | | | |
| 2104 | GVGLSPFLLAQFTSA | | | | | | | | | | | | | | |
| 2105 | GVWIRTPAYRPPNA | | | | | | | | | | | | | | |
| 2106 | HGGLLGWSPQAQGIL | 27.0280 | 0.3700 | 0.0420 | 7.2000 | 0.0120 | 3.4000 | 0.5700 | 0.4800 | 0.0140 | -0.0004 | 0.2200 | 0.5300 | 0.0450 | |
| 2107 | HLPLHPAAMPHLLVG | | | | | | | | | | | | | | |

TABLE XVIII-continued

DR SUPER MOTIF (With binding information)

| SEQ ID NO: | Sequence | Peptide | DR1 | DR2w2β1 | DR2w2β1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2108 | HLSLRGLPVCAFSSA | 1280.10 | 1.3000 | | | | 0.0028 | | | | | 0.0130 | | | |
| 2109 | HTALRQAILCWGELM | | | | | | | | | | | | | | |
| 2110 | HTLWKAGILYKRETT | | | | | | | | | | | | | | |
| 2111 | IFLFILLLCLIFLLV | 1280.11 | 0.0005 | | | | 0.0041 | | | | | 0.0018 | | | |
| 2112 | HFLFILLLCLIFLL | 1280.12 | | | | | | | | | | | | | | |
| 2113 | ILGFRKIPMGVGLSP | | | | | | | | | | | | | | |
| 2114 | ILLCLIFLLVLLDY | F107.01 | 0.0026 | | 0.0069 | | 0.0320 | | | | | 0.0047 | | | |
| 2115 | IRDLLDTASALYREA | | | | | | | | | | | | | | |
| 2116 | IRQLLWFHISCLTFG | | | | | | | | | | | | | | |
| 2117 | IVGLLGFAAPFTQCG | 1186.09 | 0.0200 | | −0.0005 | | −0.0007 | | −0.0002 | | | 0.0009 | | | |
| 2118 | IWMMWYWGPSLYNIL | | | | | | | | | | | | | | |
| 2119 | KFAVPNLQSLTNLLS | 1280.13 | 0.0180 | 0.0005 | −0.0003 | | 0.1300 | | 0.0043 | | 0.0088 | | | 0.0056 | 0.0067 |
| 2120 | KIPMGVGLSPFLLAQ | | | | | | | | | | | | | | |
| 2121 | KLHLYSHPIILGFRK | | | | | | | | | | | | | | |
| 2122 | KQAFTFSPTYKAFLC | 1298.06 | 0.5300 | 0.2400 | 0.1400 | 0.0090 | 1.1000 | 0.2200 | 0.2400 | 0.0024 | 0.0200 | 0.3300 | 0.1200 | 0.5400 | |
| 2123 | KQCFRKLPVNRPIDW | 1298.04 | 1.5000 | 0.0022 | 0.0210 | −0.0006 | 1.2000 | 0.8500 | 0.0130 | 0.0013 | 0.0043 | 0.4000 | 0.0580 | 0.0250 | |
| 2124 | KRRLKLIMPARFYPN | | | | | | | | | | | | | | |
| 2125 | LAQFTSAICSVVRRA | 1186.10 | 0.0120 | 0.0065 | 0.1500 | −0.0009 | 0.0150 | 0.0280 | 0.0076 | 0.0091 | 0.0010 | 0.0280 | 0.0150 | 0.0880 | 0.0190 |
| 2126 | LCLIFLVLLDYQGM | F107.02 | 0.0016 | | 0.0060 | | 0.0230 | | 0.0017 | | | 0.0044 | | | |
| 2127 | LCQVFADATPTGWGL | 1280.14 | 0.0020 | | | | 0.9600 | | | | | 0.0013 | | | |
| 2128 | LEYLVSFGVWIRTPP | | | | | | | | | | | | | | |
| 2129 | LFILLCLIFLLVLL | | | | | | | | | | | | | | |
| 2130 | LGFFPDHQLDPAFGA | | | | | | | | | | | | | | |
| 2131 | LGNLNVSIPWTHKVG | | | | | | | | | | | | | | |
| 2132 | LGPLLVLQAGFFLLT | | | | | | | | | | | | | | |
| 2133 | LGWLWGMDIDPYKEF | 1186.12 | 0.0004 | 0.0340 | 0.0006 | 0.0200 | 0.0280 | 0.1600 | −0.0002 | 0.0310 | 0.0002 | 0.0004 | 0.0610 | 0.0490 | 0.0430 |
| 2134 | LHLYSHPIILGFRKI | 1280.15 | 0.0220 | | 0.0400 | 0.0040 | 0.6800 | | 0.0410 | | | 0.0006 | | | |
| 2135 | LHTLWKAGILYKRET | | | | | | | | | | | | | | |
| 2136 | LKVFVLGGCRHKLVC | | | | | | | | | | | | | | |
| 2137 | LCLIFLVLLDYQG | 1280.16 | | 0.6900 | | | | 1.4000 | | | | | | | |
| 2138 | LLDYQGMLPVCPLIP | | | | | | | | | | | | | | |
| 2139 | LLGFAAPFTQCGYPA | | | | | | | | | | | | | | |
| 2140 | LLWFHISCLTFGRET | | | | | | | | | | | | | | |
| 2141 | LPKVLHKRTLGLSAM | | | | | | | | | | | | | | |
| 2142 | LPLLPIFFCLWVYTZ | | | | | | | | | | | | | | |
| 2143 | LQSITNLLSSNLSWL | F107.03 | 2.5000 | 0.4400 | 0.0200 | −0.0013 | 4.8000 | 0.8100 | 0.0680 | 0.7500 | 0.0260 | 0.1500 | 0.0880 | 0.1100 | |
| 2144 | ISAMSTTDLEAYFKD | | | | | | | | | | | | | | |
| 2145 | LSTLPETTVVRRRGR | | | | | | | | | | | | | | |
| 2146 | LSWLSLDVSAAFYHI | | | | | | | | | | | | | | |
| 2147 | LTNLLSSNLSWLSLD | 1186.14 | 0.0010 | | 0.0083 | | 0.0160 | | 0.0013 | | | 0.0019 | | | 0.0200 |
| 2148 | LVLLDYQGMLPVCPL | 1280.17 | 0.0034 | | | | −0.0013 | | | | | 0.0011 | | | |
| 2149 | LVPFVQWFVGLSPTV | 1186.15 | 0.0130 | | 0.0140 | | 0.1500 | 1.4000 | 0.3800 | 0.6600 | 0.0018 | 0.0092 | 0.6600 | 2.5000 | 2.6000 |
| 2150 | MQLFHLCLIISCSCP | | | | | | | | | | | | | | |
| 2151 | NAPILSTLPETTVVR | 1186.16 | 0.0009 | | 0.0009 | −0.0041 | −0.0007 | | −0.0002 | | | 0.0005 | | | 0.1600 |
| 2152 | NLNVSIPWTHKVGNF | 1186.17 | 0.0001 | | −0.0005 | 1.3000 | −0.0007 | | −0.0002 | | | 0.0005 | | | 0.0009 |
| 2153 | NLSWLSLDVSAAFYH | | | | 0.0003 | −0.0005 | | 0.2900 | | 0.0033 | 0.0022 | 0.0330 | 0.0041 | 0.0150 | 0.0620 | 2.4000 |
| 2154 | NRPIDWKVCQRIVGL | 1186.18 | 0.1400 | | | | | | | | | | | | |
| 2155 | PAAMPHLLVGSSGLS | | | | | | | | | | | | | | |

TABLE XVIII-continued

DR SUPER MOTIF (With binding information)

| SEQ ID NO: | Sequence | Peptide | DR1 | DR2w2β1 | DR2w2β1 | DR3 | DR4w4 | DR4w15 | DR5w11 | DR5w12 | DR6w19 | DR7 | DR8w2 | DR9 | DRW53 |
|---|---|---|---|---|---|---|---|---|---|---|---|---|---|---|---|
| 2156 | PDRVHFASPLHVAWR | 1298.08 | 0.0510 | 0.0290 | 0.0008 | | 0.0008 | 0.0054 | 0.0008 | | 0.0190 | 0.0810 | 0.0035 | 0.2400 | |
| 2157 | PFLLAQFTSAICSVV | F107.04 | 0.1800 | 0.0270 | 0.0042 | -0.0013 | 0.0800 | 0.1200 | 0.0120 | | 0.0800 | 0.0770 | 0.0580 | 0.0590 | 0.0015 |
| 2158 | PHCLAFSYMDDWLG | | | | | | | | | | | | | | |
| 2159 | PIILGFRKIPMGVGL | | | | | | | | | | | | | | |
| 2160 | PLPIHTAELLAACFA | 1280.18 | 0.0046 | | -0.0005 | | 0.0490 | | | 0.0016 | | -0.0003 | | | |
| 2161 | PAYRPPNAPILSTL | 1186.20 | 0.0056 | | | | 0.0038 | | 0.0022 | | | 0.0024 | | | |
| 2162 | PQAMQWNSTTFHQTL | 1298.01 | 0.0012 | | | | 0.0300 | | | | | 0.1200 | | | |
| 2163 | POSLDWWTSLNFLG | | | | | | | | | | | | | | |
| 2164 | QCGYPALMPLYACIQ | 1186.21 | 0.0062 | | 0.0018 | | 0.0068 | | 0.0023 | | | 0.0006 | | | |
| 2165 | QLLWFHISCLTFGRE | | | | | | | | | | | | | | |
| 2166 | QQYVGPLITVNEKRRL | | | | | | | | | | | | | | |
| 2167 | QWFVGLSPTVWLSVI | | | | | | | | | | | | | | |
| 2168 | RDLLDTASALYREAL | 1280.19 | 0.0001 | | | | 0.0092 | | | | | | | | |
| 2169 | RDVLCLRPVGAESRG | | | | | | | | | | | | 0.0770 | | | |
| 2170 | RFIIFLFLLLCLIF | | | | | | | | | | | | | | |
| 2171 | RFSWLSLLVPFVQWF | 1186.22 | 0.0430 | | 0.0009 | | -0.0007 | 0.0630 | 0.0002 | | | 0.0005 | | | 0.0031 |
| 2172 | RPGLCQVFEADATPTG | | | | | | | | | | | | | | |
| 2173 | RQLIWFHISCLTFGR | 1186.23 | 0.0002 | | 0.0009 | | 0.0140 | | 0.0011 | | | 0.0061 | | | 0.0096 |
| 2174 | RRAFPHCLAFSYMDD | F107.05 | 0.0010 | | 0.0010 | | -0.0009 | | 0.0010 | | | 0.0017 | | | |
| 2175 | RRFIIFLFLLLCLI | | | | | | | | | | | | | | |
| 2176 | RRSFGVEPSGSGHID | | | | | | | | | | | | | | |
| 2177 | RVSWPKEAVPNLQSL | | | | | | | | | | | | | | |
| 2178 | RWGYSLNFMGYVIGS | | | | | | | | | | | | | | |
| 2179 | SFGVWIRTPAYRPP | 1186.25 | 0.0094 | 0.0110 | 0.4300 | -0.0009 | 0.0780 | | 0.0260 | 0.0071 | 0.0002 | 0.0240 | 0.2500 | 0.0800 | 0.0016 |
| 2180 | SFPWLLGCAANWILR | | | | | | | | | | | | | | |
| 2181 | SFVYVPSALNPADDP | | | | | | | | | | | | | | |
| 2182 | SGFLGPLLVLQAGFF | | | | | | | | | | | | | | |
| 2183 | SPFLLAQFTSAICSV | 1186.26 | 0.1200 | 0.0200 | 0.0085 | -0.0013 | 0.0740 | 0.0190 | -0.0002 | -0.0013 | 0.0540 | 0.0330 | 0.0014 | 0.0380 | 0.2000 |
| 2184 | SSNLSWLSLDVSAAF | 1186.27 | 0.1400 | 0.0030 | -0.0005 | 1.5000 | 0.2700 | | 0.0046 | 0.0180 | 0.1000 | 0.0039 | 0.0460 | 0.0110 | 6.2000 |
| 2185 | SVELLSFLPSDFFPS | | | | | | | | | | | | | | |
| 2186 | SVRFSWLSLLVPFVQ | 1280.20 | 0.9000 | | | 0.2100 | 0.0099 | | 0.5300 | | | 0.0037 | | | |
| 2187 | SVVLSRKYTSFPWLL | 27.0282 | 0.0005 | 0.0410 | 0.0057 | | -0.0016 | | 0.0053 | | 0.0160 | 0.0130 | 0.0032 | 0.3800 | 0.0410 |
| 2188 | TNFLLSLGHHLNPNK | 1298.03 | 3.5000 | | 0.1200 | | 0.0220 | | 0.0006 | | | 0.2200 | | | |
| 2189 | TNLLSSNLSWLSLDV | 1186.28 | 0.0016 | | -0.0005 | | 0.1300 | | | | | 0.0019 | | | |
| 2190 | TRILITPQSLDSWWT | | | | | | | | | | | | | | |
| 2191 | TSFVYVPSALNPADD | | | | | | | | | | | | | | |
| 2192 | TSGFLGPLLVLQAGF | | | | | | | | | | | | | | |
| 2193 | VAPLPIHTAELLAAC | | | | | | | | | | | | | | |
| 2194 | VCAFSSAGPCALRFT | 1186.29 | 0.2100 | | 0.2600 | | 0.0023 | | 0.0003 | | | 0.0200 | | | 0.0150 |
| 2195 | VELLSFLPSDFFPSI | | | | | | | | | | | | | | |
| 2196 | VGLLGFAAPFTQCGY | 1280.21 | 0.0470 | | 0.0008 | | -0.0014 | 0.1700 | -0.0004 | | -0.0001 | 0.0014 | 0.0044 | 0.5700 | |
| 2197 | VGNFTGLYSSTVPVF | 1298.02 | 1.7000 | | 0.0016 | | 0.0140 | | 0.0035 | | 0.0580 | 0.5600 | | 0.3100 | |
| 2198 | VLCLRPVGAESRGRP | | | | | | | | | | | | | | |
| 2199 | VQWFVGLSPTVWLSV | | | | | | | | | | | | | | |
| 2200 | WASVRFSWLSLLVPF | | | | | | | | | | | | | | |
| 2201 | WLSLDVSAAFYHIPL | | | | | | | | | | | | | | |
| 2202 | WLSLLVPFVQWFVGL | | | | | | | | | | | | | | |
| 2203 | WMCLRRFIIFLFLL | | | | | | | | | | | | | | |

TABLE XVIII-continued

| | | | DR SUPER MOTIF (With binding information) | | | | | | | | | |
|---|---|---|---|---|---|---|---|---|---|---|---|---|
| SEQ ID NO: Sequence | Peptide | DR1 | DR2w2β1 | DR2w2β1 | DR3 | DR4w4 | DR4w15 | DR5w11 | DR5w12 | DR6w19 | DR7 | DR8w2 | DR9 | DRW53 |
| 2204 WPKFAVPNLQSLTNL | 1186.30 | 0.0007 | | 0.0013 | | 0.0023 | | 0.0002 | | | 0.0008 | | | |
| 2205 YPALMPLYACIQSKQ | 1298.05 | 0.2400 | | | | 0.0014 | | | | | 0.0011 | | | 0.0180 |
| 145 | | | | | | | | | | | | | | |

TABLE XIX

HBV DR3 MOTIF PEPTIDES WITH BINDING DATA

| Total Conservancy | Total | Core Conservancy | Core Freq | Protein | Position | Core Sequence | Core SEQ ID NO: | Sequence | SEQ ID NO: | Peptide | Filed | Binding Data DR3 | Motif |
|---|---|---|---|---|---|---|---|---|---|---|---|---|---|
| 90.00 | 18 | 90.00 | 18 | POL | 535 | YMDDVVLGA | 2228 | AFSYMDDVVLGAKSV | 2206 | 1186.02 | | 0.0130 | DR3 |
| 55.00 | 11 | 95.00 | 19 | POL | 655 | FSPTYKAFL | 2229 | AFTFSPTYKAFLCKQ | 2207 | 35.0099 | | 0.0035 | DR3 |
| 65.00 | 13 | 90.00 | 18 | POL | 18 | LEEELPRLA | 2230 | AGPLEEELPRLADEG | 2208 | 35.0091 | | 0.0022 | DR3 |
| 65.00 | 13 | 80.00 | 16 | POL | 731 | IGTDNSVVL | 2231 | AKLIGTDNSVVLSRK | 2209 | | | | DR3 |
| 85.00 | 17 | 85.00 | 17 | NUC | 34 | LYREALESP | 2232 | ASALYREALESPEHC | 2210 | | | | DR3 |
| 70.00 | 14 | 75.00 | 15 | NUC | 136 | FGRETVLEY | 2233 | CLTFGRETVLEYLVS | 2211 | | | | DR3 |
| 90.00 | 18 | 90.00 | 18 | X | 48 | AHLSLRGLP | 2234 | DHGAHLSLRGLPVCA | 2212 | | | | DR3 |
| 85.00 | 17 | 90.00 | 18 | POL | 737 | VVLSRKYTS | 2235 | DNSVVLSRKYTSFPW | 2213 | | | | DR3 |
| 45.00 | 9 | 100.00 | 20 | POL | 374 | LVVDFSQFS | 2236 | ESRLVVDFSQFSRGN | 2214 | 35.0096 | * | 2.6000 | DR3 |
| 5.00 | 1 | 75.00 | 1 | ENV | 172 | AVLDPRVRG | 2237 | FHQAVLDPRVRGLYL | 2215 | | | | DR3 |
| 90.00 | 18 | 95.00 | 19 | ENV | 256 | VLLDYQGML | 2238 | FLLVLLDYQGMLPVC | 2216 | 35.009 | | 0.0170 | DR3 |
| 55.00 | 11 | 100.00 | 20 | POL | 360 | FLVDKNPHIN | 2239 | GGVFLVDKNPHNTTE | 2217 | 35.0095 | | 0.0790 | DR3 |
| 95.00 | 19 | 95.00 | 19 | POL | 683 | VFADATPTG | 2240 | LCQVFADATPTGWGL | 2218 | 1280.14 | | 0.0000 | DR3 |
| 35.00 | 7 | 95.00 | 19 | X | 18 | VGAESRGRP | 2241 | LRPVGAESRGRPVSG | 2219 | 35.0101 | | −0.0017 | DR3 |
| 55.00 | 11 | 95.00 | 19 | POL | 412 | LSLDVSAAF | 2242 | LSWLSLDVSAAFYHI | 2220 | | | | DR3 |
| 45.00 | 9 | 85.00 | 17 | NUC | 27 | MDIDPYKEF | 2243 | LWGMDIDPYKEFGAS | 2221 | | | | DR3 |
| 85.00 | 17 | 100.00 | 20 | POL | 34 | VAEDLNLGN | 2244 | NRRVAEDLNLGNLNV | 2222 | 35.0092 | | 0.1400 | DR3 |
| 100.00 | 20 | 100.00 | 20 | POL | 47 | IPWTHKVGN | 2245 | NVSIPWTHKVGNFTG | 2223 | | | | DR3 |
| 45.00 | 9 | 95.00 | 19 | ENV | 10 | FFPDHQLDP | 2246 | PLGFFPDHQLDPAFG | 2224 | | | | DR3 |
| 30.00 | 6 | 75.00 | 15 | POL | 241 | FGVEPSGSG | 2247 | RRSFGVEPSGSGHID | 2225 | | | | DR3 |
| 100.00 | 20 | 100.00 | 20 | POL | 120 | LPLDKGIKP | 2248 | TKYLPLDKGIKPYYP | 2226 | 35.0094 | | −0.0017 | DR3 |
| 60.00 | 12 | 85.00 | 17 | POL | 96 | LTVNEKRRL | 2249 22 | VGPLTVNEKRRLKLI | 2227 22 | 35.0093 | * | 2.2000 | DR3 |

TABLE XX

Population coverage with combined HLA Supertypes

| | PHENOTYPIC FREQUENCY | | | | | |
|---|---|---|---|---|---|---|
| HLA-SUPERTYPES | Caucasian | N.A. Black | Japanese | Chinese | Hispanic | Average |
| A2, A3, B7 | 83.0 | 86.1 | 87.5 | 88.4 | 86.3 | 86.2 |
| A2, A3, B7, A24, B44, A1 | 99.5 | 98.1 | 100.0 | 99.5 | 99.4 | 99.3 |
| A2, A3, B7, A24, B44, A1, B27, B62, B58 | 99.9 | 99.6 | 100.0 | 99.8 | 99.9 | 99.8 |

TABLE XXI

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| | ALFKDWEEL | | | | | | | | | 2250 |
| 9 | ALMPLYACV | L2.IV9 | N | Y | N | N | N | 1 | A | 2251 |
| | ALMPLYASI | | | | | | | | | 2252 |
| 9 | ALMPLYAXI | | N | Y | N | N | N | | A | 2253 |
| 10 | ALPSDFFPSV | | N | Y | N | N | N | No | A | 2254 |
| | ALPSDFFPSV-NH2 | | | | | | | | | 2255 |
| | ALSLIVNLL | | | | | | | | | 2256 |
| 9 | AMTFSPTYK | | N | N | Y | N | N | | A | 2257 |
| | ATVELLSFLPSDFFPSV-NH2 | | | | | | | | | 2258 |
| 10 | CILLLCLIFL | | N | Y | N | N | N | No | A | 2259 |
| 11 | CILLLCLIFLL | | N | Y | N | N | N | No | A | 2260 |
| 9 | DPFRGRLGL | | N | N | N | N | Y | | A | 2261 |
| 9 | DPSRGRLGI | | N | N | N | N | Y | | A | 2262 |
| | ELLSFLPSDFFPSV-NH2 | | | | | | | | | 2263 |
| 10 | FAPSDFFPSV | LA2.V10 | N | Y | N | N | N | Rev | A | 2264 |
| 10 | FILLLXLIFL | | N | Y | N | N | N | | A | 2265 |
| 10 | FLASDFFPSV | | N | Y | N | N | N | No | A | 2266 |
| 10 | FLGLSPTVWV | VL2.LV1 | N | Y | N | N | N | 1 | A | 2267 |
| 10 | FLKSDFFPSV | | N | Y | N | N | N | No | A | 2268 |
| 10 | FLLAQFTSAV | L2.IV10 | N | Y | N | N | N | 1 | A | 2269 |
| 9 | FLLAQFTSV | L2.AV9 | N | Y | N | N | N | 1 | A | 2270 |
| 9 | FLLPIFFCL | | N | Y | N | N | N | No | A | 2271 |
| 9 | FLLSLGIHV | L2.LV9 | N | Y | N | N | N | 1 | A | 2272 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 9 | FLLTRILTV | L2.IV9 | N | Y | N | N | N | 1 | A | 2273 |
| 9 | FLLTRILYI | | N | Y | N | N | N | | A | 2274 |
| 9 | FLLTYILTI | | N | Y | N | N | N | | A | 2275 |
| 10 | FLMSDYFPSV | | N | Y | N | N | N | No | A | 2276 |
| 9 | FLMSYFPSV | | N | Y | N | N | N | No | A | 2277 |
| 10 | FLPADFFPSI | L2.SA4 | N | Y | N | N | N | Rev | A | 2278 |
| 10 | FLPADFFPSV | | N | Y | N | N | N | No | A | 2279 |
| 10 | FLPDDFFPSA | L2.SD4 | N | Y | N | N | N | Rev | A | 2280 |
| 10 | FLFDDFFPSV | | N | Y | N | N | N | No | A | 2281 |
| 10 | FLPNDFFPSA | L2.SN4 | N | Y | N | N | N | Rev | A | 2282 |
| 10 | FLPNDFFPSV | | N | Y | N | N | N | No | A | 2283 |
| 10 | FLPS(X)YFPSV | | N | N | N | N | N | | A | 2284 |
| 10 | FLPSAFFPSV | | N | Y | N | N | N | No | A | 2285 |
| 10 | FLPSD(X)FPSV | | N | N | N | N | N | | A | 2286 |
| 10 | FLPSDAFPSV | | N | Y | N | N | N | No | A | 2287 |
| 10 | FLPSDFAPSV | | N | Y | N | N | N | No | A | 2288 |
| | FLPSDFF-NH2 | | | | | | | | | 2289 |
| 10 | FLPSDFFASV | | N | Y | N | N | N | No | A | 2290 |
| 10 | FLPSDFFKSV | | N | Y | N | N | N | No | A | 2291 |
| 8 | FLPSDFFP | | N | N | N | N | N | | A | 2292 |
| | FLPSDFFP-NH2 | | | | | | | | | 2293 |
| 10 | FLPSDFFPAV | | N | Y | N | N | N | No | A | 2294 |
| 10 | FLPSDFFPKV | | N | Y | N | N | N | No | A | 2295 |
| 9 | FLPSDFFPS | | N | N | N | N | N | | A | 2296 |
| | FLPSDFFPS-NH2 | | | | | | | | | 2297 |
| 10 | FLPSDFFPSA | L2.VA10 | N | Y | N | N | N | Rev | A | 2298 |
| 10 | FLPSDFFPSI | L2.VI10 | N | Y | N | N | N | Rev | A | 2299 |
| | FLPSDFFPSV(CONH2) | | | | | | | | | 2300 |
| | FLPSDFFPSV-NH2 | | | | | | | | | 2301 |
| 11 | FLPSDFFPSVR | | N | N | Y | N | N | | A | 2302 |
| | FLPSDFFPSVR-NH2 | | | | | | | | | 2303 |
| 12 | FLPSDFFPSVRD | | N | N | N | N | N | | A | 2304 |
| 10 | FLPSDFYPSV | | N | Y | N | N | N | No | A | 2305 |
| 11 | FLPSDLLPSVR | | N | N | Y | N | N | | A | 2306 |
| 10 | FLPSDYFPSV | | N | Y | N | N | N | No | A | 2307 |
| 10 | FLPSEFFPSV | | N | Y | N | N | N | No | A | 2308 |
| 9 | FLPSYFPSA | L2.FY5. | N | Y | N | N | N | Rev3 | A | 2309 |
| 9 | FLPSYFPSV | L2.FY5. | N | Y | N | N | N | 3 | A | 2310 |
| 10 | FLPSZFFPSV | | N | Y | N | N | N | No | A | 2311 |
| 10 | FLPSZFFPSV | | N | Y | N | N | N | No | A | 2312 |
| 10 | FLPVDFFPSI | L2.SV4. | N | Y | N | N | N | Rev | A | 2313 |
| 10 | FLPVDFFPSV | | N | Y | N | N | N | No | A | 2314 |
| | FLSKQYLNL | | | | | | | | | 2315 |
| 9 | FLYTRILTI | | N | Y | N | N | N | | A | 2316 |
| 8 | FMFSPTYK | | N | N | Y | N | N | | A | 2317 |
| 10 | FMLLLCLIFL | IM2.L10 | N | Y | N | Y | N | 1 | A | 2318 |
| 10 | FMPSDFFPSV | LM2.V1 | N | Y | N | N | N | 1 | A | 2319 |
| 8 | FPAAMPHL | | N | N | N | N | Y | | A | 2320 |
| 9 | FPAAPHLL | | N | N | N | N | Y | | A | 2321 |
| 10 | FPAAMPHLLV | | N | N | N | N | Y | | A | 2322 |
| 9 | FPALMPLYA | | N | N | N | N | Y | | A | 2323 |
| 10 | FPARVTGGVF | | N | N | N | N | Y | | A | 2324 |
| 10 | FPCALRFTSA | | N | N | N | N | Y | | A | 2325 |
| 9 | FPFCLAFSY | | N | N | N | N | Y | | A | 2326 |
| 10 | FPFCLAFSYM | | N | N | N | N | Y | | A | 2327 |
| 9 | FPHCLAFAL | | N | N | N | N | Y | | A | 2328 |
| 9 | FPHCLAFAY | | N | N | N | N | Y | | A | 2329 |
| 9 | FPHCLAFSA | | N | N | N | N | Y | | A | 2330 |
| 9 | FPHCLAFSI | | N | N | N | N | Y | | A | 2331 |
| 9 | FPHCLAFSL | | N | N | N | N | Y | | A | 2332 |
| 10 | FPHCLAFSYI | | N | N | N | N | Y | | A | 2333 |
| 10 | FPHXLAFSYM | | N | N | N | N | Y | | A | 2334 |
| 9 | FPIPSSWAF | | N | N | N | N | Y | | A | 2335 |
| 9 | FPSRGRLGL | | N | N | N | N | Y | | A | 2336 |
| 9 | FPVCAFSSA | | N | N | N | N | Y | | A | 2337 |
| 9 | FPVCLAFSY | | N | N | N | N | Y | | A | 2338 |
| 10 | FQPSDYFPSV | | N | Y | N | N | N | Rev | A | 2339 |
| 8 | FVFSPTYK | | N | N | Y | N | N | | A | 2340 |
| 9 | FVLGGXRHK | | N | N | Y | N | N | | A | 2341 |
| 9 | GLCQVFADV | L2.AV9 | N | Y | N | N | N | 1 | A | 2342 |
| 9 | GLLGWSPQV | L2.AV9 | N | Y | N | N | N | 1 | A | 2343 |
| 9 | GLWIRTPPV | VL2.AV9 | N | Y | N | N | N | 1 | A | 2344 |
| 9 | GLXQVFADA | | N | Y | N | N | N | | A | 2345 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 10 | GMDNSVVLSR | | N | N | Y | N | N | | A | 2346 |
| 11 | GMDNSVVLSRK | | N | N | Y | N | N | | A | 2347 |
| 10 | GPCALRFTSI | | N | N | N | N | Y | | A | 2348 |
| 10 | GPFALRFTSA | | N | N | N | N | Y | | A | 2349 |
| 10 | GPXALRFTSA | | N | N | N | N | Y | | A | 2350 |
| 10 | GTFNSVVLSR | | N | N | Y | N | N | | A | 2351 |
| 11 | GTFNSVVLSRK | | N | N | Y | N | N | | A | 2352 |
| 10 | GVDNSVVLSR | | N | N | Y | N | N | | A | 2353 |
| 11 | GVDNSVVLSRK | | N | N | Y | N | N | | A | 2354 |
| 10 | GYRWMXLRRF | | N | N | N | Y | N | | A | 2355 |
| 9 | HISXLTFGR | | N | N | Y | N | N | | A | 2356 |
| 10 | HMLWKAGILY | | Y | N | Y | N | N | | A | 2357 |
| 11 | HMLWKAGILYK | | N | N | Y | N | N | | A | 2358 |
| 8 | HPAAMPHI | | N | N | N | N | Y | | A | 2359 |
| 9 | HPAAMPHLI | | N | N | N | N | Y | | A | 2360 |
| 10 | HPAAMPHLLI | | N | N | N | N | Y | | A | 2361 |
| 8 | HPFAMPHL | | N | N | N | N | Y | | A | 2362 |
| 9 | HPFAMPHLL | | N | N | N | N | Y | | A | 2363 |
| 10 | HPFAMPHLLV | | N | N | N | N | Y | | A | 2364 |
| 10 | HTLWKAGILK | | N | N | Y | N | N | | A | 2365 |
| 10 | HTLWKAGILR | | N | N | Y | N | N | | A | 2366 |
| 10 | HVLWKAGILY | | N | N | Y | N | N | | A | 2367 |
| 11 | HVLWKAGILYK | | N | N | Y | N | N | | A | 2368 |
| | IIKKSEQFV | | | | | | | | | 2369 |
| 9 | ILGLLGFAV | VL2.AV9 | N | Y | N | N | N | 1 | A | 2370 |
| 10 | ILLLCLIFLV | L2.LV10 | N | Y | N | N | N | 1 | A | 2371 |
| 9 | ILLLXLIFL | | N | Y | N | N | N | | A | 2372 |
| 10 | ILLLXLIFLL | | N | Y | N | N | N | | A | 2373 |
| 9 | IPFPSSWAF | | N | N | N | N | Y | | A | 2374 |
| 9 | IPILSSWAF | | N | N | N | N | Y | | A | 2375 |
| 9 | IPIPMSWAF | | N | N | N | N | Y | | A | 2376 |
| 9 | IPIPSSWAI | | N | N | N | N | Y | | A | 2377 |
| 9 | IPITSSWAF | | N | N | N | N | Y | | A | 2378 |
| | KIKESFRKL | | | | | | | | | 2379 |
| 9 | KLFLYSHPI | | N | Y | N | N | N | No | A | 2380 |
| 9 | KLHLYSHPV | L2.IV9 | N | Y | N | N | N | 1 | A | 2381 |
| 9 | KVGNFTGLK | | N | N | Y | N | N | | A | 2382 |
| 9 | KVGNFTGLR | | N | N | Y | N | N | | A | 2383 |
| 9 | LLAQFTSAV | L2.IV9 | N | Y | N | N | N | 1 | A | 2384 |
| 10 | LLFYQGMLPV | | N | Y | N | N | N | No | A | 2385 |
| | LLGSAANWI | | | | | | | | | 2386 |
| 10 | LLGXAANWIL | | N | Y | N | N | N | | A | 2387 |
| 9 | LLLXLIFLL | | N | Y | N | N | N | | A | 2388 |
| 10 | LLLXLIFLLV | | N | Y | N | N | N | | A | 2389 |
| 10 | LLLYQGMLPV | | N | Y | N | N | N | No | A | 2390 |
| 9 | LLPFVQWFV | VL2.V9 | N | Y | N | N | N | 1 | A | 2391 |
| 10 | LLPIFFXLWV | | N | Y | N | N | N | | A | 2392 |
| | LLSFLPSDFFPSV-NH2 | | | | | | | | | 2393 |
| 9 | LLSSNLSWV | L2.LV9 | N | Y | N | N | N | 1 | A | 2394 |
| 10 | LLVLQAGFFV | L2.LV10 | N | Y | N | N | N | 1 | A | 2395 |
| 9 | LLXLIFLLV | | N | Y | N | N | N | | A | 2396 |
| 10 | LMLLDYQGMV | VM2.LV | N | Y | N | N | N | 1 | A | 2397 |
| 10 | LMLQAGFFLV | VM2.LV | N | Y | N | N | N | 1 | A | 2398 |
| 9 | LMPFVQWFV | VM2.V9 | N | Y | N | N | N | 1 | A | 2399 |
| 9 | LPFCAFSSA | | N | N | N | N | Y | | A | 2400 |
| 8 | LPIFFCLI | | N | N | N | N | Y | | A | 2401 |
| 9 | LPIFFCLWI | | N | N | N | N | Y | | A | 2402 |
| 9 | LPIHTAELI | | N | N | N | N | Y | | A | 2403 |
| 11 | LPIHTAELLAI | | N | N | N | N | Y | | A | 2404 |
| | LPSDFFPSV-NH2 | | | | | | | | | 2405 |
| 9 | LPVCAFSSI | | N | N | N | N | Y | | A | 2406 |
| 9 | LPVXAFSSA | | N | N | N | N | Y | | A | 2407 |
| 12 | LSFLPSDFFPSV | | N | N | N | N | N | | A | 2408 |
| | LSFLPSDFFPSV-NH2 | | | | | | | | | 2409 |
| 10 | MMWYWGPSLK | | N | N | Y | N | N | | A | 2410 |
| 10 | MMWYWGPSLR | | N | N | Y | N | N | | A | 2411 |
| 9 | MMWYWGPSV | M2.LV9 | N | Y | N | N | N | 1 | A | 2412 |
| 8 | MPLSYQHI | | N | N | N | N | Y | | A | 2413 |
| 9 | NLGNLNVSV | L2.IV9 | N | Y | N | N | N | 1 | A | 2414 |
| | NLNNLNVSI | | | | | | | | | 2415 |
| 9 | NMGLKYROL | | N | Y | N | Y | N | No | A | 2416 |
| 11 | NPLGFFPDHQI | | N | N | N | N | Y | | A | 2417 |
| 9 | PLLPIFFCV | L2.LV9 | N | Y | N | N | N | 1 | A | 2418 |

TABLE XXI-continued

HBV ANALOGS

| AA | Sequence | Fixed Nomen. | A1 Motif | A2 Super Motif | A3 Super Motif | A24 Motif | B7 Super Motif | 1° Anchor Fixer | Analog | SEQ ID NO: |
|---|---|---|---|---|---|---|---|---|---|---|
| 9 | PLLPIFFXL | | N | Y | N | N | N | | A | 2419 |
| 8 | PSDFFPSV | | N | N | N | N | N | | A | 2420 |
| | PSDFFPSV-NH2 | | | | | | | | | 2421 |
| 10 | QLLWFHISXL | | N | Y | N | N | N | | A | 2422 |
| 10 | QMFTFSPTYK | | N | N | Y | N | N | | A | 2423 |
| 10 | QVFTFSPTYK | | N | N | Y | N | N | | A | 2424 |
| | RIPRTPRSV | | | | | | | | | 2425 |
| 9 | RLSWPKFAV | VL2.V9 | N | Y | N | N | N | 1 | A | 2426 |
| 9 | RLTGGVFLV | VL2.V9 | N | Y | N | N | N | 1 | A | 2427 |
| 9 | RMLTIPQSV | IM2.LV9 | N | Y | N | N | N | 1 | A | 2428 |
| 9 | RMTGGVFLV | VM2.V9 | N | Y | N | N | N | 1 | A | 2429 |
| 9 | RMYLHTLWK | | N | N | Y | N | N | | A | 2430 |
| 9 | RVYLHTLWK | | N | N | Y | N | N | | A | 2431 |
| 9 | SAIXSVVRR | | N | N | Y | N | N | | A | 2432 |
| 11 | SFLPSDFFPSV | | N | N | N | N | N | | A | 2433 |
| | SFLPSDFFPSV-NH2 | | | | | | | | | 2434 |
| 9 | SLDSWWTSV | L2.LV9 | N | Y | N | N | N | 1 | A | 2435 |
| | SLNFLGGTTV(NH2) | | | | | | | | | 2436 |
| 9 | SMICSVVRR | | N | N | Y | N | N | | A | 2437 |
| 10 | SMLPETTVVR | | N | N | Y | N | N | | A | 2438 |
| 11 | SMLPETTVVRR | | N | N | Y | N | N | | A | 2439 |
| 10 | SMLSPFLPLV | IM2.LV1 | N | Y | N | N | N | 1 | A | 2440 |
| 8 | SPFLLAQI | | N | N | N | N | Y | | A | 2441 |
| 11 | STLPETYVVRR | | N | N | Y | N | N | | A | 2442 |
| 9 | SVICSVVRR | | N | N | Y | N | N | | A | 2443 |
| 10 | SVLPETTVVR | | N | N | Y | N | N | | A | 2444 |
| 11 | SVLPETTVVRR | | N | N | Y | N | N | | A | 2445 |
| 9 | SVNRPIDWK | | N | N | Y | N | N | | A | 2446 |
| 9 | SVVRRAFPK | | N | N | Y | N | N | | A | 2447 |
| 9 | SVVRRAFPR | | N | N | Y | N | N | | A | 2448 |
| 9 | TLWKAGILK | | N | N | Y | N | N | | A | 2449 |
| 9 | TLWKAGILR | | N | N | Y | N | N | | A | 2450 |
| 10 | TMPETTVVRR | | N | N | Y | N | N | | A | 2451 |
| 9 | TMWKAGILY | | Y | N | Y | N | N | | A | 2452 |
| 10 | TMWKAGILYK | | N | N | Y | N | N | | A | 2453 |
| 10 | TPARVTGGVI | | N | N | N | N | Y | | A | 2454 |
| 10 | TPFRVTGGVF | | N | N | N | N | Y | | A | 2455 |
| 10 | TSAIXSVVRR | | N | N | Y | N | N | | A | 2456 |
| | TVELLSFLPSDFFPSV-NH2 | | | | | | | | | 2457 |
| 10 | TVPETTVVRR | | N | N | Y | N | N | | A | 2458 |
| 9 | TVWKAGILY | | N | N | Y | N | N | | A | 2459 |
| 10 | TVWKAGILYK | | N | N | Y | N | N | | A | 2460 |
| | VELLSFLPSDFFPSV-NH2 | | | | | | | | | 2461 |
| | VLEYLVSFGV(NH2) | | | | | | | | | 2462 |
| | VLGGSRHKL | | | | | | | | | 2463 |
| 9 | VLLDYQGMV | L2.LV9 | N | Y | N | N | N | 1 | A | 2464 |
| 9 | VLQAGFFLV | L2.LV9 | N | Y | N | N | N | 1 | A | 2465 |
| 10 | VMGGVFLVDK | | N | N | Y | N | N | | A | 2466 |
| 10 | VPFVQWFVGI | | N | N | N | N | Y | | A | 2467 |
| 8 | VPSALNPI | | N | N | N | N | Y | | Analog | 2468 |
| 9 | VVFFSQFSR | | N | N | Y | N | N | | A | 2469 |
| 10 | VVGGVFLVDK | | N | N | Y | N | N | | A | 2470 |
| 9 | WLLRGTSFV | IL2.V9 | N | Y | N | N | N | 1 | A | 2471 |
| 10 | YLFTLWKAGI | | N | Y | N | N | N | No | A | 2472 |
| 10 | YLHTLWKAGV | L2.IV10 | N | Y | N | N | N | 1 | A | 2473 |
| 10 | YLLTLWKAGI | | N | Y | N | N | N | No | A | 2474 |
| 9 | YLLTRILTI | | N | Y | N | N | N | | A | 2475 |
| 9 | YLPSALNPV | VL2.AV9 | N | Y | N | N | N | 1 | A | 2476 |
| 10 | YLPSDFFPSV | | N | Y | N | N | N | No | A | 2477 |
| 9 | YMDDVVLGV | M2.AV9 | N | Y | N | N | N | 1 | A | 2478 |
| 9 | YMFDVVLGA | | N | Y | N | N | N | No | A | 2479 |
| 10 | YMFDVVLGAK | | N | N | Y | N | N | | A | 2480 |
| 10 | YNMGLKFRQL | | N | N | N | N | N | | A | 2481 |
| 8 | YPALMPLI | | N | N | N | N | Y | | A | 2482 |
| 9 | YPALMPLYI | | N | N | N | N | Y | | A | 2483 |
| 9 | YPFLMPLYA | | N | N | N | N | Y | | A | 2484 |
| 12 | YSFLPSDFFPSV | | N | N | N | N | N | | A | 2485 |
| 236 | | | | | | | | | | |

TABLE XXII

Discreet substitutions improve the B7 supertype binding capacity and degeneracy of peptide ligands.

| Source | 1 | 2 | 3 | 4 | 5 | 6 | 7 | 8 | 9 | Binding (IC₅₀ nM) B*0701 | B*3501 | B*5101 | B*5301 | B*5401 | x-rxn | SEQ ID NO: |
|---|---|---|---|---|---|---|---|---|---|---|---|---|---|---|---|---|
| HBV ENV 313 | I | P | I | P | S | S |   | A | F | 42 | 2.6 | 2.3 | 12 | 2970 | 4 | 2505 |
|  | ■ | P | I | P | S | S |   | A | F | 24 | 1.2 | 305 | 1.7 | 105 | 5 | 2506 |
|  | I | P | I | P | S | S |   | A | ■ | 31 | 54 | 15 | 24 | 7.7 | 5 | 2507 |
| HBV POL 541 | F | P | H | C | L | A | F | S | Y | — | 14 | 83 | 17 | 503 | 3 | 2508 |
|  | F | P | H | C | L | A | F | ■ | ■ | 25 | 2.7 | 28 | 5.0 | 24 | 5 | 2509 |
|  | F | P | H | C | L | A | F | S | ■ | 74 | 2.4 | 4.5 | 15 | 7.7 | 5 | 2510 |
|  | F | P | ■ | C | L | A | F | S | Y | — | 6.5 | 27 | 4.8 | 5.1 | 4 | 2511 |
|  | F | P | H | C | L | A | F | S | ■ | 675 | 29 | 6.3 | 3.8 | 1.0 | 4 | 2512 |
|  | F | P | H | C | L | A | F | S | ■ | 3667 | 6.5 | 250 | 137 | 0.6 | 4 | 2513 |
| HCV Core 168 | L | P | G | C | S | F | S | I | F | 28 | 90 | 100 | 114 | 6897 | 4 | 2514 |
|  | ■ | P | G | C | S | F | S | I | F | 19 | 1.6 | 132 | 3.2 | 67 | 5 | 2515 |
| MAGE2 170 | V | P | I | S | H | L | Y | I | L | 22 | 171 | 96 | 238 | 3175 | 4 | 2516 |
|  | ■ | P | I | S | H | L | Y | I | L | 16 | 7.3 | 6.4 | 7.0 | 28 | 5 | 2517 |
| MAGE3 196 |   | P | K | A | G | L | L | I | I | 940 | 5039 | 393 | 90 | 248 | 3 | 2518 |
|  | ■ | P | K | A | G | L | L | I | I | 162 | 1303 | 5.8 | 60 | 150 | 4 | 2519 |
|  |   | P | ■ | A | G | L | L | I | I | 229 | 1.0 | 0.9 | 2.3 | 0.27 | 5 | 2520 |

TABLE XXIII

Sets of preferred epitopes restricted by class I and class II molecules can be selected for inclusion in an HBV-specific vaccine. Table XXIII lists as a matter of example one such set of epitopes.

| Peptide | Sequence | Protein | restriction | SEQ ID NO: |
|---|---|---|---|---|
| A) Class I restricted epitopes | | | | |
| 924.07 | FLPSDFFPSV | core 18 | A2 | 2521 |
| 777.03 | FLLTRILTI | env 183 | A2 | 2522 |
| 927.15 | ALMPLYACI | pol 642 | A2 | 2523 |
| 1013.01 | WLSLLVPFV | env 335 | A2 | 2524 |
| 1090.14 | YMDDVVLGA | pol 538 | A2/A1 | 2525 |
| 1168.02 | GLSRYVARL | pol 455 | A2 | 2526 |
| 927.11 | FLLSLGIHL | pol 562 | A2 | 2527 |
| 1069.10 | LLPIFFCLWV | env 378 | A2 | 2528 |
| 1069.06 | LLVPFVQWFV | env 338 | A2 | 2529 |
| 1147.16 | HTLWKAGILYK | pol 149 | A3/A1 | 2530 |
| 1083.01 | STLPETTVVRR | core 141 | A3 | 2531 |
| 1069.16 | NVSIPWTHK | pol 47 | A3 | 2532 |
| 1069.20 | LVVDFSQFSR | pol 388 | A3 | 2533 |
| 1090.10 | QAFTFSPTYK | pol 665 | A3 | 2534 |
| 1090.11 | SAICSVVRR | pol 531 | A3 | 2535 |
| 1142.05 | KVGNFTGLY | pol 629 | A3/A1 | 2536 |
| 1147.05 | FPHCLAFSYM | pol 530 | B7 | 2537 |
| 988.05 | LPSDFFPSV | core 19 | B7 | 2538 |
| 1145.04 | IPIPSSWAF | env 313 | B7 | 2539 |
| 1147.02 | HPAAMPHLL | pol 429 | B7 | 2540 |
| 26.0570 | YPALMPLYACI | pol 640 | B7 | 2541 |
| 1147.04 | TPARVTGGVF | pol 354 | B7 | 2542 |
| 1.0519 | DLLDTASALY | core 419 | A1 | 2543 |
| 2.0239 | LSLDVSAAFY | pol 1000 | A1 | 2544 |
| 1039.06 | WMMWYWGPSLY | env 359 | A1 | 2545 |
| 20.0269 | RWMCLRRFII | env 236 | A24 | 2546 |
| 20.0136 | SWLSLLVPF | env 334 | A24 | 2547 |
| 20.0137 | SWWTSLNFL | env 197 | A24 | 2548 |
| 13.0129 | EYLVSFGVWI | core 117 | A24 | 2549 |
| 1090.02 | AYRPPNAPI | core 131 | A24 | 2550 |
| 13.0073 | WFHISCLTF | core 102 | A24 | 2551 |
| 20.0271 | SWPKFAVPNL | pol 392 | A24 | 2552 |
| 1069.23 | KYTSFPWLL | pol 745 | A24 | 2553 |
| 2.0181 | LYSHPIILGF | pol 492 | A24 | 2554 |
| B) Class II restricted epitopes | | | | |
| F107.03 | LQSLTNLLSSNLSWL | pol 412 | DR supermotif | 2555 |
| 1298.06 | KQAFTFSPTYKAFLC | pol 664 | | 2556 |
| 1280.06 | AGFFLLTRILTIPQS | env 180 | | 2557 |
| 1280.09 | GTSFVYVPSALNPAD | pol 774 | | 2558 |
| CF-08 | VSFGVWIRTPPAYRPPNAPI | core 120 | | 2559 |
| 27.0281 | RHYLHTLWKAGILYK | pol 145 | | 2560 |
| 1186.15 | LVPFVQWFVGLSPTV | env 339 | | 2561 |
| 1280.15 | LHLYSHPIILGFRKI | pol 501 | | 2562 |
| F107.04 | PFLLAQFTSAICSVV | pol 523 | | 2563 |
| 1298.04 | KQCFRKLPVNRPIDW | pol 618 | | 2564 |
| 1298.07 | AANWILRGTSFVYVP | pol 767 | | 2565 |
| 857.02 | PHHTALRQAILCWGELMTLA | core 50 | | 2566 |
| 1280.14 | LCQVPADATPTGWGL | pol 694 | DR3 motif | 2567 |
| 35.0096 | ESRLVVDFSQFSRGN | pol 385 | | 2568 |
| 35.0093 | VGPLTVNEKRRLKLI | pol 96 | | 2569 |
| 1186.27 | SSNLSWLSLDVSAAF | pol 420 | | 2570 |
| 1186.18 | NLSWLSLDVSAAFYH | pol 442 | | 2571 |

SEQUENCE LISTING

The patent contains a lengthy "Sequence Listing" section. A copy of the "Sequence Listing" is available in electronic form from the USPTO web site (http://seqdata.uspto.gov/sequence.html?DocID=6689363B1). An electronic copy of the "Sequence Listing" will also be available from the USPTO upon request and payment of the fee set forth in 37 CFR 1.19(b)(3).

What is claimed is:

1. A hepatitis B virus (HBV) vaccine composition comprising a pharmaceutically acceptable carrier and an isolated peptide less than 25 amino acids in length which comprises an oligopeptide selected from the group consisting of:
LLVPFVQWFV (SEQ ID NO:2529) and
WLSLLVPFV (SEQ ID NO:2524).

2. The vaccine composition of claim 1, wherein said peptide is 10 amino acids in length.

3. The vaccine composition of claim 2, wherein said peptide consists of the oligopeptide LLVPFVQWFV (SEQ ID NO:2529).

4. The vaccine composition of claim 1, wherein said peptide consists of the oligopeptide WLSLLVPFV (SEQ ID NO:2524).

5. The vaccine composition of claim 1, wherein said peptide is fused to a T helper peptide.

6. The vaccine composition of claim 1, wherein said peptide is fused to spacer or linker amino acids.

7. The vaccine composition of claim 1, wherein said peptide is fused to a carrier.

8. The vaccine composition of claim 1, wherein said peptide is linked to a lipid.

9. The vaccine composition of claim 1, which comprises a homopolymer of said peptide.

10. The vaccine composition of claim 1, which comprises a heteropolymer of said peptide and a different peptide.

11. The vaccine composition of claim 1, which comprises a liposome.

12. The vaccine composition of claim 1, which comprises one or more other peptides.

13. The vaccine composition of claim 12, wherein said peptides form a fusion protein.

14. The vaccine composition of claim 12, which comprises a carrier.

15. The vaccine composition of claim 12, wherein said peptides are fused by spacer or linker amino acids.

16. The vaccine composition of claim 1, wherein said peptide comprises the oligopeptide LLVPFVQWFV (SEQ ID NO:2529).

17. The vaccine composition of claim 16, wherein said peptide is 10 amino acids in length.

18. The vaccine composition of claim 16, wherein said peptide is fused to a T helper peptide.

19. The vaccine composition of claim 16, wherein said peptide is fused to spacer or linker amino acids.

20. The vaccine composition of claim 16, wherein said peptide is fused to a carrier.

21. The vaccine composition of claim 16, wherein said peptide is linked to a lipid.

22. The vaccine composition of claim 16, which comprises a homopolymer of said peptide.

23. The vaccine composition of claim 16, which comprises a heteropolymer of said peptide and a different peptide.

24. The vaccine composition of claim 16, which comprises a liposome.

25. The vaccine composition of claim 16, which comprises one or more other peptides.

26. The vaccine composition of claim 25, wherein said peptides form a fusion protein.

27. The vaccine composition of claim 25, which comprises a carrier.

28. The vaccine composition of claim 25, wherein said peptides are fused by spacer or linker amino acids.

29. The vaccine composition of claim 1, wherein said peptide comprises of the oligopeptide WLSLLVPFV (SEQ ID NO:2524).

30. The vaccine composition of claim 29, wherein said peptide is 10 amino acids in length.

31. The vaccine composition of claim 29, wherein said peptide is fused to a T helper peptide.

32. The vaccine composition of claim 29, wherein said peptide is fused to spacer or linker amino acids.

33. The vaccine composition of claim 29, wherein said peptide is fused to a carrier.

34. The vaccine composition of claim 29, wherein said peptide is linked to a lipid.

35. The vaccine composition of claim 29, which comprises a homopolymer of said peptide.

36. The vaccine composition of claim 29, which comprises a heteropolymer of said peptide and a different peptide.

37. The vaccine composition of claim 29, which comprises a liposome.

38. The vaccine composition of claim 29, which comprises one or more second peptides.

39. The vaccine composition of claim 29, which comprises one or more other peptides.

40. The vaccine composition of claim 38, which comprises a carrier.

41. The vaccine composition of claim 38, wherein said peptides are fused by spacer or linker amino acids.

42. An IBV vaccine composition comprising a pharmaceutically acceptable carrier and an isolated peptide less than 15 amino acids in length which comprises the oligopeptide LYSHPIILGF (SEQ ID NO:2554).

43. The vaccine composition of claim 42, wherein said peptide is 11 amino acids in length.

44. The vaccine composition of claim 42, wherein said peptide is 10 amino acids in length.

45. The vaccine composition of claim 42, wherein said peptide is fused to a T helper peptide.

46. The vaccine composition of claim 42, wherein said peptide is fused to spacer or linker amino acids.

47. The vaccine composition of claim 42, wherein said peptide is fused to a carrier.

48. The vaccine composition of claim 42, wherein said peptide is linked to a lipid.

49. The vaccine composition of claim 42, which comprises a homopolymer of said peptide.

50. The vaccine composition of claim 42, which comprises a heteropolymer of said peptide and a different peptide.

51. The vaccine composition of claim 42, which comprises a liposome.

52. The vaccine composition of claim 42, which comprises one or more other peptides.

53. The vaccine composition of claim 52, wherein said peptides form a fusion protein.

54. The vaccine composition of claim 52, which comprises a carrier.

55. The vaccine composition of claim 52, wherein said peptides are fused by spacer or linker amino acids.

\* \* \* \* \*

UNITED STATES PATENT AND TRADEMARK OFFICE
CERTIFICATE OF CORRECTION

PATENT NO. : 6,689,363 B1
DATED : February 10, 2003
INVENTOR(S) : Sette et al.

It is certified that error appears in the above-identified patent and that said Letters Patent is hereby corrected as shown below:

<u>Columns 57-58,</u>
In Table III,
Line 3, please insert -- <u>SEQ ID NO:</u> -- before the term "MOTIFS."
Line 10, please insert -- 2578 -- before the phrase "DR7 preferred."
Line 12, please insert -- 2579 -- beneath the number -- 2578 -- inserted as noted above and before the phrase "deleterious."

<u>Column 138,</u>
Line 52, please delete "IBV" and insert therein -- HBV --

Signed and Sealed this

Twenty-second Day of June, 2004

JON W. DUDAS
*Acting Director of the United States Patent and Trademark Office*